United States Patent
Sano et al.

(10) Patent No.: US 10,471,254 B2
(45) Date of Patent: Nov. 12, 2019

(54) SELECTIVE MODULATION OF INTRACELLULAR EFFECTS OF CELLS USING PULSED ELECTRIC FIELDS

(71) Applicants: Virginia Tech Intellectual Properties, Inc., Blacksburg, VA (US); Michael B. Sano, Durham, NC (US); Christopher B. Arena, Burlington, NC (US); Scott S. Verbridge, Blacksburg, VA (US); Rafael V. Davalos, Blacksburg, VA (US)

(72) Inventors: Michael B. Sano, Durham, NC (US); Christopher B. Arena, Burlington, NC (US); Scott S. Verbridge, Blacksburg, VA (US); Rafael V. Davalos, Blacksburg, VA (US)

(73) Assignee: Virginia Tech Intellectual Properties, Inc., Blacksburg, VA (US)

(*) Notice: Subject to any disclaimer, the term of this patent is extended or adjusted under 35 U.S.C. 154(b) by 335 days.

(21) Appl. No.: 15/310,114

(22) PCT Filed: May 12, 2015

(86) PCT No.: PCT/US2015/030429
§ 371 (c)(1),
(2) Date: Nov. 10, 2016

(87) PCT Pub. No.: WO2015/175570
PCT Pub. Date: Nov. 19, 2015

(65) Prior Publication Data
US 2017/0266438 A1    Sep. 21, 2017

Related U.S. Application Data

(60) Provisional application No. 61/992,023, filed on May 12, 2014.

(51) Int. Cl.
*A61B 18/14* (2006.01)
*A61N 1/32* (2006.01)
(Continued)

(52) U.S. Cl.
CPC .......... *A61N 1/327* (2013.01); *A61B 18/1206* (2013.01); *A61B 18/1477* (2013.01);
(Continued)

(58) Field of Classification Search
CPC ...... A61B 18/1477; A61B 2018/00613; A61B 18/1206; A61B 18/14; A61B 2018/00577;
(Continued)

(56) References Cited

U.S. PATENT DOCUMENTS

| 1,653,819 A | 12/1927 | Northcott |
| 3,730,238 A | 5/1973 | Butler |

(Continued)

FOREIGN PATENT DOCUMENTS

| AU | 2002315095 A1 | 12/2002 |
| AU | 2003227960 A1 | 12/2003 |

(Continued)

OTHER PUBLICATIONS

A.I. Daud et al., "Phase I Trial of Interleukin-12 Plasmid Electroporation in Patients With Metastatic Melanoma," Journal of Clinical Oncology, 26, pp. 5896-5903, 2008.

(Continued)

*Primary Examiner* — Michael F Peffley
*Assistant Examiner* — Amanda L Zink
(74) *Attorney, Agent, or Firm* — New River Valley IP Law, PC; Michele L. Mayberry

(57) ABSTRACT

A system and method for selectively treating aberrant cells such as cancer cells through administration of a train of electrical pulses is described. The pulse length and delay between successive pulses is optimized to produce effects on (Continued)

intracellular membrane potentials. Therapies based on the system and method produce two treatment zones: an ablation zone surrounding the electrodes within which aberrant cells are non-selectively killed and a selective treatment zone surrounding the ablation zone within which target cells are selectively killed through effects on intracellular membrane potentials. As a result, infiltrating tumor cells within a tumor margin can be effectively treated while sparing healthy tissue. The system and method are useful for treating various cancers in which solid tumors form and have a chance of recurrence from microscopic disease surrounding the tumor.

35 Claims, 55 Drawing Sheets

(51) Int. Cl.
A61N 1/40 (2006.01)
A61B 90/00 (2016.01)
A61B 18/12 (2006.01)
A61N 1/06 (2006.01)
A61N 1/08 (2006.01)
A61B 18/00 (2006.01)
A61B 17/00 (2006.01)

(52) U.S. Cl.
CPC ........... *A61B 90/37* (2016.02); *A61N 1/06* (2013.01); *A61N 1/08* (2013.01); *A61N 1/40* (2013.01); *A61B 2017/00172* (2013.01); *A61B 2018/00577* (2013.01); *A61B 2018/126* (2013.01); *A61B 2018/143* (2013.01)

(58) Field of Classification Search
CPC .............. A61B 2034/104; A61B 90/37; A61B 18/1492; A61B 2017/00172; A61B 2018/0016; A61B 2018/00446; A61B 2018/00779; A61B 2018/00875; A61B 2018/00886; A61B 2018/00892; A61B 2018/126; A61B 2018/1425; A61B 2018/143; A61B 2018/1472; A61B 2034/256; A61B 2218/002; A61B 34/10; A61B 34/25; A61N 1/327; A61N 1/05; A61N 1/06; A61N 1/08; A61N 1/40
See application file for complete search history.

(56) References Cited

U.S. PATENT DOCUMENTS

| | | |
|---|---|---|
| 3,746,004 A | 7/1973 | Jankelson |
| 3,871,359 A | 3/1975 | Pacela |
| 4,016,886 A | 4/1977 | Doss et al. |
| 4,037,341 A | 7/1977 | Odle et al. |
| 4,216,860 A | 8/1980 | Heimann |
| 4,226,246 A | 10/1980 | Fragnet |
| 4,262,672 A | 4/1981 | Kief |
| 4,267,047 A | 5/1981 | Henne et al. |
| 4,278,092 A | 7/1981 | Borsanyi et al. |
| 4,299,217 A | 11/1981 | Sagae et al. |
| 4,311,148 A | 1/1982 | Courtney et al. |
| 4,336,881 A | 6/1982 | Babb et al. |
| 4,344,436 A | 8/1982 | Kubota |
| 4,392,855 A | 7/1983 | Oreopoulos et al. |
| 4,406,827 A | 9/1983 | Carim |
| 4,407,943 A | 10/1983 | Cole et al. |
| 4,416,276 A | 11/1983 | Newton et al. |
| 4,447,235 A | 5/1984 | Clarke |
| 4,469,098 A | 9/1984 | Davi |
| 4,489,535 A | 12/1984 | Veltman |
| 4,512,765 A | 4/1985 | Muto |
| 4,580,572 A | 4/1986 | Granek et al. |
| 4,636,199 A | 1/1987 | Victor |
| 4,672,969 A | 6/1987 | Dew |
| 4,676,258 A | 6/1987 | Inokuchi et al. |
| 4,676,782 A | 6/1987 | Yamamoto et al. |
| 4,687,471 A | 8/1987 | Twardowski et al. |
| 4,716,896 A | 1/1988 | Ackerman |
| 4,723,549 A | 2/1988 | Wholey et al. |
| D294,519 S | 3/1988 | Hardy |
| 4,756,838 A | 7/1988 | Veltman |
| 4,772,269 A | 9/1988 | Twardowski et al. |
| 4,798,585 A | 1/1989 | Inoue et al. |
| 4,810,963 A | 3/1989 | Blake-Coleman et al. |
| 4,813,929 A | 3/1989 | Semrad |
| 4,819,637 A | 4/1989 | Dormandy et al. |
| 4,822,470 A | 4/1989 | Chang |
| 4,836,204 A | 6/1989 | Landymore et al. |
| 4,840,172 A | 6/1989 | Augustine et al. |
| 4,863,426 A | 9/1989 | Ferragamo et al. |
| 4,885,003 A | 12/1989 | Hillstead |
| 4,886,496 A | 12/1989 | Conoscenti et al. |
| 4,886,502 A | 12/1989 | Poirier et al. |
| 4,889,634 A | 12/1989 | El-Rashidy |
| 4,907,601 A | 3/1990 | Frick |
| 4,919,148 A | 4/1990 | Muccio |
| 4,920,978 A | 5/1990 | Colvin |
| 4,921,484 A | 5/1990 | Hillstead |
| 4,946,793 A | 8/1990 | Marshall, III |
| 4,976,709 A | 12/1990 | Sand |
| 4,981,477 A | 1/1991 | Schon et al. |
| 4,986,810 A | 1/1991 | Semrad |
| 4,987,895 A | 1/1991 | Heimlich |
| 5,019,034 A | 5/1991 | Weaver et al. |
| 5,031,775 A | 7/1991 | Kane |
| 5,052,391 A | 10/1991 | Silberstone et al. |
| 5,053,013 A | 10/1991 | Ensminger et al. |
| 5,058,605 A | 10/1991 | Slovak |
| 5,071,558 A | 12/1991 | Itoh |
| 5,098,843 A | 3/1992 | Calvin |
| 5,122,137 A | 6/1992 | Lennox |
| 5,134,070 A | 7/1992 | Casnig |
| 5,137,517 A | 8/1992 | Loney et al. |
| 5,141,499 A | 8/1992 | Zappacosta |
| D329,496 S | 9/1992 | Wotton |
| 5,156,597 A | 10/1992 | Verreet et al. |
| 5,173,158 A | 12/1992 | Schmukler |
| 5,186,715 A | 2/1993 | Phillips et al. |
| 5,186,800 A | 2/1993 | Dower |
| 5,188,592 A | 2/1993 | Hakki |
| 5,190,541 A | 3/1993 | Abele et al. |
| 5,192,312 A | 3/1993 | Orton |
| 5,193,537 A | 3/1993 | Freeman |
| 5,209,723 A | 5/1993 | Twardowski et al. |
| 5,215,530 A | 6/1993 | Hogan |
| 5,224,933 A | 7/1993 | Bromander |
| 5,227,730 A | 7/1993 | King et al. |
| 5,242,415 A | 9/1993 | Kantrowitz et al. |
| 5,273,525 A | 12/1993 | Hofmann |
| D343,687 S | 1/1994 | Houghton et al. |
| 5,277,201 A | 1/1994 | Stern |
| 5,279,564 A | 1/1994 | Taylor |
| 5,281,213 A | 1/1994 | Milder |
| 5,283,194 A | 2/1994 | Schmukler |
| 5,290,263 A | 3/1994 | Wigness et al. |
| 5,308,325 A | 5/1994 | Quinn et al. |
| 5,308,338 A | 5/1994 | Helfrich |
| 5,318,543 A | 6/1994 | Ross et al. |
| 5,318,563 A | 6/1994 | Malis et al. |
| 5,328,451 A | 7/1994 | Davis et al. |
| 5,334,167 A | 8/1994 | Cocanower |
| 5,348,554 A | 9/1994 | Imran et al. |
| D351,661 S | 10/1994 | Fischer |
| 5,383,917 A | 1/1995 | Desai et al. |
| 5,389,069 A | 2/1995 | Weaver |
| 5,391,158 A | 2/1995 | Peters |
| 5,403,311 A | 4/1995 | Abele et al. |
| 5,405,320 A | 4/1995 | Twardowski et al. |
| 5,425,752 A | 6/1995 | Vu Nguyen |
| 5,439,440 A | 8/1995 | Hofmann |

(56) References Cited

U.S. PATENT DOCUMENTS

| | | |
|---|---|---|
| 5,458,625 A | 10/1995 | Kendall |
| 5,484,400 A | 1/1996 | Edwards et al. |
| 5,484,401 A | 1/1996 | Rodriguez et al. |
| 5,533,999 A | 7/1996 | Hood et al. |
| 5,536,240 A | 7/1996 | Edwards et al. |
| 5,536,267 A | 7/1996 | Edwards et al. |
| 5,540,737 A | 7/1996 | Fenn |
| 5,546,940 A | 8/1996 | Panescu et al. |
| 5,562,720 A | 10/1996 | Stern et al. |
| 5,575,811 A | 11/1996 | Reid et al. |
| D376,652 S | 12/1996 | Hunt et al. |
| 5,582,588 A | 12/1996 | Sakurai et al. |
| 5,586,982 A | 12/1996 | Abela |
| 5,588,424 A | 12/1996 | Insler et al. |
| 5,588,960 A | 12/1996 | Edwards et al. |
| 5,599,294 A | 2/1997 | Edwards et al. |
| 5,599,311 A | 2/1997 | Raulerson |
| 5,616,126 A | 4/1997 | Malekmehr et al. |
| 5,620,479 A | 4/1997 | Diederich |
| 5,626,146 A | 5/1997 | Barber et al. |
| D380,272 S | 6/1997 | Partika et al. |
| 5,634,899 A | 6/1997 | Shapland et al. |
| 5,643,197 A | 7/1997 | Brucker et al. |
| 5,645,855 A | 7/1997 | Lorenz |
| 5,672,173 A | 9/1997 | Gough et al. |
| 5,674,267 A | 10/1997 | Mir et al. |
| 5,683,384 A | 11/1997 | Gough et al. |
| 5,687,723 A | 11/1997 | Avitall |
| 5,690,620 A | 11/1997 | Knott |
| 5,697,905 A | 12/1997 | d'Ambrosio |
| 5,700,252 A | 12/1997 | Klingenstein |
| 5,702,359 A | 12/1997 | Hofmann et al. |
| 5,718,246 A | 2/1998 | Vona |
| 5,720,921 A | 2/1998 | Meserol |
| 5,735,847 A | 4/1998 | Gough et al. |
| 5,752,939 A | 5/1998 | Makoto |
| 5,778,894 A | 7/1998 | Dorogi et al. |
| 5,782,882 A | 7/1998 | Lerman et al. |
| 5,800,378 A | 9/1998 | Edwards et al. |
| 5,800,484 A | 9/1998 | Gough et al. |
| 5,807,272 A | 9/1998 | Kun et al. |
| 5,807,306 A | 9/1998 | Shapland et al. |
| 5,807,395 A | 9/1998 | Mulier et al. |
| 5,810,742 A | 9/1998 | Pearlman |
| 5,810,762 A | 9/1998 | Hofmann |
| 5,830,184 A | 11/1998 | Basta |
| 5,836,897 A | 11/1998 | Sakurai et al. |
| 5,836,905 A | 11/1998 | Lemelson et al. |
| 5,843,026 A | 12/1998 | Edwards et al. |
| 5,843,182 A | 12/1998 | Goldstein |
| 5,865,787 A | 2/1999 | Shapland et al. |
| 5,868,708 A | 2/1999 | Hart et al. |
| 5,873,849 A | 2/1999 | Bernard |
| 5,904,648 A | 5/1999 | Arndt et al. |
| 5,919,142 A | 7/1999 | Boone et al. |
| 5,919,191 A | 7/1999 | Lennox et al. |
| 5,921,982 A | 7/1999 | Lesh et al. |
| 5,944,710 A | 8/1999 | Dev et al. |
| 5,947,284 A | 9/1999 | Foster |
| 5,947,889 A | 9/1999 | Hehrlein |
| 5,951,546 A | 9/1999 | Lorentzen |
| 5,954,745 A | 9/1999 | Gertler et al. |
| 5,957,919 A | 9/1999 | Laufer |
| 5,957,963 A | 9/1999 | Dobak |
| 5,968,006 A | 10/1999 | Hofmann |
| 5,983,131 A | 11/1999 | Weaver et al. |
| 5,984,896 A | 11/1999 | Boyd |
| 5,991,697 A | 11/1999 | Nelson et al. |
| 5,999,847 A | 12/1999 | Elstrom |
| 6,004,339 A | 12/1999 | Wijay |
| 6,009,347 A | 12/1999 | Hofmann |
| 6,009,877 A | 1/2000 | Edwards |
| 6,010,613 A | 1/2000 | Walters et al. |
| 6,016,452 A | 1/2000 | Kasevich |
| 6,029,090 A | 2/2000 | Herbst |
| 6,041,252 A | 3/2000 | Walker et al. |
| 6,043,066 A | 3/2000 | Mangano et al. |
| 6,050,994 A | 4/2000 | Sherman |
| 6,055,453 A | 4/2000 | Hofmann et al. |
| 6,059,780 A | 5/2000 | Gough et al. |
| 6,066,134 A | 5/2000 | Eggers et al. |
| 6,068,121 A | 5/2000 | McGlinch |
| 6,068,650 A | 5/2000 | Hofmann et al. |
| 6,071,281 A | 6/2000 | Burnside et al. |
| 6,074,374 A | 6/2000 | Fulton |
| 6,074,389 A | 6/2000 | Levine et al. |
| 6,085,115 A | 7/2000 | Weaver et al. |
| 6,090,016 A | 7/2000 | Kuo |
| 6,090,105 A | 7/2000 | Zepeda et al. |
| 6,090,106 A | 7/2000 | Goble et al. |
| D430,015 S | 8/2000 | Himbert et al. |
| 6,096,035 A | 8/2000 | Sodhi et al. |
| 6,102,885 A | 8/2000 | Bass |
| 6,106,521 A | 8/2000 | Blewett et al. |
| 6,109,270 A | 8/2000 | Mah et al. |
| 6,110,192 A | 8/2000 | Ravenscroft et al. |
| 6,113,593 A | 9/2000 | Tu et al. |
| 6,116,330 A | 9/2000 | Salyer |
| 6,120,493 A | 9/2000 | Hofmann |
| 6,122,599 A | 9/2000 | Mehta |
| 6,123,701 A | 9/2000 | Nezhat |
| 6,132,397 A | 10/2000 | Davis et al. |
| 6,132,419 A | 10/2000 | Hofmann |
| 6,134,460 A | 10/2000 | Chance |
| 6,139,545 A | 10/2000 | Utley et al. |
| 6,150,148 A | 11/2000 | Nanda et al. |
| 6,159,163 A | 12/2000 | Strauss et al. |
| 6,178,354 B1 | 1/2001 | Gibson |
| D437,941 S | 2/2001 | Frattini |
| 6,193,715 B1 | 2/2001 | Wrublewski et al. |
| 6,198,970 B1 | 3/2001 | Freed et al. |
| 6,200,314 B1 | 3/2001 | Sherman |
| 6,208,893 B1 | 3/2001 | Hofmann |
| 6,210,402 B1 | 4/2001 | Olsen et al. |
| 6,212,433 B1 | 4/2001 | Behl |
| 6,216,034 B1 | 4/2001 | Hofmann et al. |
| 6,219,577 B1 | 4/2001 | Brown, III et al. |
| D442,697 S | 5/2001 | Hajianpour |
| 6,233,490 B1 | 5/2001 | Kasevich |
| 6,235,023 B1 | 5/2001 | Lee et al. |
| D443,360 S | 6/2001 | Haberland |
| 6,241,702 B1 | 6/2001 | Lundquist et al. |
| 6,241,725 B1 | 6/2001 | Cosman |
| D445,198 S | 7/2001 | Frattini |
| 6,258,100 B1 | 7/2001 | Alferness et al. |
| 6,261,831 B1 | 7/2001 | Agee |
| 6,277,114 B1 | 8/2001 | Bullivant et al. |
| 6,278,895 B1 | 8/2001 | Bernard |
| 6,280,441 B1 | 8/2001 | Ryan |
| 6,283,988 B1 | 9/2001 | Laufer et al. |
| 6,283,989 B1 | 9/2001 | Laufer et al. |
| 6,284,140 B1 | 9/2001 | Sommermeyer et al. |
| 6,287,293 B1 | 9/2001 | Jones et al. |
| 6,287,304 B1 | 9/2001 | Eggers et al. |
| 6,296,636 B1 | 10/2001 | Cheng et al. |
| 6,298,726 B1 | 10/2001 | Adachi et al. |
| 6,299,633 B1 | 10/2001 | Laufer |
| 6,300,108 B1 | 10/2001 | Rubinsky et al. |
| D450,391 S | 11/2001 | Hunt et al. |
| 6,312,428 B1 | 11/2001 | Eggers et al. |
| 6,326,177 B1 | 12/2001 | Schoenbach et al. |
| 6,327,505 B1 | 12/2001 | Medhkour et al. |
| 6,328,689 B1 | 12/2001 | Gonzalez et al. |
| 6,347,247 B1 | 2/2002 | Dev et al. |
| 6,349,233 B1 | 2/2002 | Adams |
| 6,351,674 B2 | 2/2002 | Silverstone |
| 6,375,634 B1 | 4/2002 | Carroll et al. |
| 6,387,671 B1 | 5/2002 | Rubinsky et al. |
| 6,398,779 B1 | 6/2002 | Buysse et al. |
| 6,403,348 B1 | 6/2002 | Rubinsky et al. |
| 6,405,732 B1 | 6/2002 | Edwards et al. |
| 6,411,852 B1 | 6/2002 | Danek et al. |
| 6,419,674 B1 | 7/2002 | Bowser et al. |
| 6,428,802 B1 | 8/2002 | Atala |

(56) References Cited

U.S. PATENT DOCUMENTS

| | | |
|---|---|---|
| 6,443,952 B1 | 9/2002 | Mulier et al. |
| 6,463,331 B1 | 10/2002 | Edwards |
| 6,470,211 B1 | 10/2002 | Ideker et al. |
| 6,482,221 B1 | 11/2002 | Hebert et al. |
| 6,482,619 B1 | 11/2002 | Rubinsky et al. |
| 6,485,487 B1 | 11/2002 | Sherman |
| 6,488,673 B1 | 12/2002 | Laufer et al. |
| 6,488,678 B2 | 12/2002 | Sherman |
| 6,488,680 B1 | 12/2002 | Francischelli et al. |
| 6,491,706 B1 | 12/2002 | Alferness et al. |
| 6,493,589 B1 | 12/2002 | Medhkour et al. |
| 6,493,592 B1 | 12/2002 | Leonard et al. |
| 6,500,173 B2 | 12/2002 | Underwood et al. |
| 6,503,248 B1 | 1/2003 | Levine |
| 6,506,189 B1 | 1/2003 | Rittman et al. |
| 6,514,248 B1 | 2/2003 | Eggers et al. |
| 6,520,183 B2 | 2/2003 | Amar |
| 6,526,320 B2 | 2/2003 | Mitchell |
| D471,640 S | 3/2003 | McMichael et al. |
| D471,641 S | 3/2003 | McMichael et al. |
| 6,530,922 B2 | 3/2003 | Cosman et al. |
| 6,533,784 B2 | 3/2003 | Truckai et al. |
| 6,537,976 B1 | 3/2003 | Gupta |
| 6,540,695 B1 | 4/2003 | Burbank et al. |
| 6,558,378 B2 | 5/2003 | Sherman et al. |
| 6,562,604 B2 | 5/2003 | Rubinsky et al. |
| 6,569,162 B2 | 5/2003 | He |
| 6,575,969 B1 | 6/2003 | Rittman et al. |
| 6,589,161 B2 | 7/2003 | Corcoran |
| 6,592,594 B2 | 7/2003 | Rimbaugh et al. |
| 6,607,529 B1 | 8/2003 | Jones et al. |
| 6,610,054 B1 | 8/2003 | Edwards et al. |
| 6,611,706 B2 | 8/2003 | Avrahami et al. |
| 6,613,211 B1 | 9/2003 | Mccormick et al. |
| 6,616,657 B2 | 9/2003 | Simpson et al. |
| 6,627,421 B1 | 9/2003 | Unger et al. |
| D480,816 S | 10/2003 | McMichael et al. |
| 6,634,363 B1 | 10/2003 | Danek et al. |
| 6,638,253 B2 | 10/2003 | Breznock |
| 6,653,091 B1 | 11/2003 | Dunn et al. |
| 6,666,858 B2 | 12/2003 | Lafontaine |
| 6,669,691 B1 | 12/2003 | Taimisto |
| 6,673,070 B2 | 1/2004 | Edwards et al. |
| 6,678,558 B1 | 1/2004 | Dimmer et al. |
| 6,689,096 B1 | 2/2004 | Loubens et al. |
| 6,692,493 B2 | 2/2004 | Mcgovern et al. |
| 6,694,979 B2 | 2/2004 | Deem et al. |
| 6,694,984 B2 | 2/2004 | Habib |
| 6,695,861 B1 | 2/2004 | Rosenberg et al. |
| 6,697,669 B2 | 2/2004 | Dev et al. |
| 6,697,670 B2 | 2/2004 | Chomenky et al. |
| 6,702,808 B1 | 3/2004 | Kreindel |
| 6,712,811 B2 | 3/2004 | Underwood et al. |
| D489,973 S | 5/2004 | Root et al. |
| 6,753,171 B2 | 6/2004 | Karube et al. |
| 6,761,716 B2 | 7/2004 | Kadhiresan et al. |
| D495,807 S | 9/2004 | Agbodoe et al. |
| 6,795,728 B2 | 9/2004 | Chornenky et al. |
| 6,801,804 B2 | 10/2004 | Miller et al. |
| 6,812,204 B1 | 11/2004 | McHale et al. |
| 6,837,886 B2 | 1/2005 | Collins et al. |
| 6,847,848 B2 | 1/2005 | Sterzer et al. |
| 6,860,847 B2 | 3/2005 | Alferness et al. |
| 6,865,416 B2 | 3/2005 | Dev et al. |
| 6,881,213 B2 | 4/2005 | Ryan et al. |
| 6,892,099 B2 | 5/2005 | Jaafar et al. |
| 6,895,267 B2 | 5/2005 | Panescu et al. |
| 6,905,480 B2 | 6/2005 | McGuckin et al. |
| 6,912,417 B1 | 6/2005 | Bernard et al. |
| 6,927,049 B2 | 8/2005 | Rubinsky et al. |
| 6,941,950 B2 | 9/2005 | Wilson et al. |
| 6,942,681 B2 | 9/2005 | Johnson |
| 6,958,062 B1 | 10/2005 | Gough et al. |
| 6,960,189 B2 | 11/2005 | Bates et al. |
| 6,962,587 B2 | 11/2005 | Johnson et al. |
| 6,972,013 B1 | 12/2005 | Zhang et al. |
| 6,972,014 B2 | 12/2005 | Eum et al. |
| 6,989,010 B2 | 1/2006 | Francischelli et al. |
| 6,994,689 B1 | 2/2006 | Zadno-Azizi et al. |
| 6,994,706 B2 | 2/2006 | Chornenky et al. |
| 7,011,094 B2 | 3/2006 | Rapacki et al. |
| 7,012,061 B1 | 3/2006 | Reiss et al. |
| 7,027,869 B2 | 4/2006 | Danek et al. |
| 7,036,510 B2 | 5/2006 | Zgoda et al. |
| 7,053,063 B2 | 5/2006 | Rubinsky et al. |
| 7,054,685 B2 | 5/2006 | Dimmer et al. |
| 7,063,698 B2 | 6/2006 | Whayne et al. |
| 7,087,040 B2 | 8/2006 | McGuckin et al. |
| 7,097,612 B2 | 8/2006 | Bertolero et al. |
| 7,100,616 B2 | 9/2006 | Springmeyer |
| 7,113,821 B1 | 9/2006 | Sun et al. |
| 7,130,697 B2 | 10/2006 | Chornenky et al. |
| 7,211,083 B2 | 5/2007 | Chornenky et al. |
| 7,232,437 B2 | 6/2007 | Berman et al. |
| 7,250,048 B2 | 7/2007 | Francischelli et al. |
| D549,332 S | 8/2007 | Matsumoto et al. |
| 7,257,450 B2 | 8/2007 | Auth et al. |
| 7,264,002 B2 | 9/2007 | Danek et al. |
| 7,267,676 B2 | 9/2007 | Chornenky et al. |
| 7,273,055 B2 | 9/2007 | Danek et al. |
| 7,291,146 B2 | 11/2007 | Steinke et al. |
| 7,331,940 B2 | 2/2008 | Sommerich |
| 7,331,949 B2 | 2/2008 | Marisi |
| 7,341,558 B2 | 3/2008 | Torre et al. |
| 7,344,533 B2 | 3/2008 | Pearson et al. |
| D565,743 S | 4/2008 | Phillips et al. |
| D571,478 S | 6/2008 | Horacek |
| 7,387,626 B2 | 6/2008 | Edwards et al. |
| 7,399,747 B1 | 7/2008 | Clair et al. |
| D575,399 S | 8/2008 | Matsumoto et al. |
| D575,402 S | 8/2008 | Sandor |
| 7,419,487 B2 | 9/2008 | Johnson et al. |
| 7,434,578 B2 | 10/2008 | Dillard et al. |
| 7,449,019 B2 | 11/2008 | Uchida et al. |
| 7,451,765 B2 | 11/2008 | Adler |
| 7,455,675 B2 | 11/2008 | Schur et al. |
| 7,476,203 B2 | 1/2009 | DeVore et al. |
| 7,520,877 B2 | 4/2009 | Lee et al. |
| 7,533,671 B2 | 5/2009 | Gonzalez et al. |
| D595,422 S | 6/2009 | Mustapha |
| 7,544,301 B2 | 6/2009 | Shah et al. |
| 7,549,984 B2 | 6/2009 | Mathis |
| 7,565,208 B2 | 7/2009 | Harris et al. |
| 7,571,729 B2 | 8/2009 | Saadat et al. |
| 7,632,291 B2 | 12/2009 | Stephens et al. |
| 7,655,004 B2 | 2/2010 | Long |
| 7,674,249 B2 | 3/2010 | Ivorra et al. |
| 7,680,543 B2 | 3/2010 | Azure |
| D613,418 S | 4/2010 | Ryan et al. |
| 7,718,409 B2 | 5/2010 | Rubinsky et al. |
| 7,722,606 B2 | 5/2010 | Azure |
| 7,742,795 B2 | 6/2010 | Stone et al. |
| 7,765,010 B2 | 7/2010 | Chornenky et al. |
| 7,771,401 B2 | 8/2010 | Hekmat et al. |
| RE42,016 E | 12/2010 | Chornenky et al. |
| D630,321 S | 1/2011 | Hamilton |
| D631,154 S | 1/2011 | Hamilton |
| RE42,277 E | 4/2011 | Jaafar et al. |
| 7,918,852 B2 | 4/2011 | Tullis et al. |
| 7,937,143 B2 | 5/2011 | Demarais et al. |
| 7,938,824 B2 | 5/2011 | Chornenky et al. |
| 7,951,582 B2 | 5/2011 | Gazit et al. |
| 7,955,827 B2 | 6/2011 | Rubinsky et al. |
| RE42,835 E | 10/2011 | Chornenky et al. |
| D647,628 S | 10/2011 | Helfteren |
| 8,048,067 B2 | 11/2011 | Davalos et al. |
| RE43,009 E | 12/2011 | Chornenky et al. |
| 8,109,926 B2 | 2/2012 | Azure |
| 8,114,070 B2 | 2/2012 | Rubinsky et al. |
| 8,162,918 B2 | 4/2012 | Ivorra et al. |
| 8,187,269 B2 | 5/2012 | Shadduck et al. |
| 8,221,411 B2 | 7/2012 | Francischelli et al. |
| 8,231,603 B2 | 7/2012 | Hobbs et al. |
| 8,240,468 B2 | 8/2012 | Wilkinson et al. |

(56) References Cited

U.S. PATENT DOCUMENTS

| | | |
|---|---|---|
| 8,251,986 B2 | 8/2012 | Chornenky et al. |
| 8,267,927 B2 | 9/2012 | Dalal et al. |
| 8,267,936 B2 | 9/2012 | Hushka et al. |
| 8,282,631 B2 | 10/2012 | Davalos et al. |
| 8,298,222 B2 | 10/2012 | Rubinsky et al. |
| 8,348,921 B2 | 1/2013 | Ivorra et al. |
| 8,361,066 B2 | 1/2013 | Long et al. |
| D677,798 S | 3/2013 | Hart et al. |
| 8,425,455 B2 | 4/2013 | Nentwick |
| 8,425,505 B2 | 4/2013 | Long |
| 8,454,594 B2 | 6/2013 | Demarais et al. |
| 8,465,464 B2 | 6/2013 | Travis et al. |
| 8,465,484 B2 | 6/2013 | Davalos et al. |
| 8,511,317 B2 | 8/2013 | Thapliyal et al. |
| 8,518,031 B2 | 8/2013 | Boyden et al. |
| 8,562,588 B2 | 10/2013 | Hobbs et al. |
| 8,603,087 B2 | 12/2013 | Rubinsky et al. |
| 8,632,534 B2 | 1/2014 | Pearson et al. |
| 8,634,929 B2 | 1/2014 | Chornenky et al. |
| 8,647,338 B2 | 2/2014 | Chornenky et al. |
| 8,715,276 B2 | 5/2014 | Thompson et al. |
| 8,753,335 B2 | 6/2014 | Moshe et al. |
| 8,814,860 B2 | 8/2014 | Davalos et al. |
| 8,835,166 B2 | 9/2014 | Phillips et al. |
| 8,845,635 B2 | 9/2014 | Daniel et al. |
| 8,880,195 B2 | 11/2014 | Azure |
| 8,903,488 B2 | 12/2014 | Callas et al. |
| 8,906,006 B2 | 12/2014 | Chornenky et al. |
| 8,926,606 B2 | 1/2015 | Davalos et al. |
| 8,958,888 B2 | 2/2015 | Chornenky et al. |
| 8,968,542 B2 | 3/2015 | Davalos et al. |
| 8,992,517 B2 | 3/2015 | Davalos et al. |
| 9,005,189 B2 | 4/2015 | Davalos et al. |
| 9,078,665 B2 | 7/2015 | Moss et al. |
| 9,149,331 B2 | 10/2015 | Deem et al. |
| 9,173,704 B2 | 11/2015 | Hobbs et al. |
| 9,198,733 B2 | 12/2015 | Neal, II et al. |
| 9,283,051 B2 | 3/2016 | Garcia et al. |
| 9,414,881 B2 * | 8/2016 | Callas .................. A61B 18/14 |
| 9,598,691 B2 | 3/2017 | Davalos |
| 9,867,652 B2 | 1/2018 | Sano et al. |
| 10,117,701 B2 | 11/2018 | Davalos et al. |
| 10,117,707 B2 | 11/2018 | Garcia et al. |
| 10,154,874 B2 | 12/2018 | Davalos et al. |
| 10,238,447 B2 | 3/2019 | Neal et al. |
| 10,245,098 B2 | 4/2019 | Davalos et al. |
| 10,245,105 B2 | 4/2019 | Davalos et al. |
| 10,272,178 B2 | 4/2019 | Davalos et al. |
| 10,286,108 B2 | 5/2019 | Davalos et al. |
| 10,292,755 B2 | 5/2019 | Davalos et al. |
| 2001/0039393 A1 | 11/2001 | Mori et al. |
| 2001/0044596 A1 | 11/2001 | Jaafar |
| 2001/0046706 A1 | 11/2001 | Rubinsky et al. |
| 2001/0047167 A1 | 11/2001 | Heggeness |
| 2001/0051366 A1 | 12/2001 | Rubinsky et al. |
| 2002/0002393 A1 | 1/2002 | Mitchell |
| 2002/0010491 A1 | 1/2002 | Schoenbach et al. |
| 2002/0022864 A1 | 2/2002 | Mahvi et al. |
| 2002/0040204 A1 | 4/2002 | Dev et al. |
| 2002/0049370 A1 | 4/2002 | Laufer et al. |
| 2002/0052601 A1 | 5/2002 | Goldberg et al. |
| 2002/0055731 A1 | 5/2002 | Atala et al. |
| 2002/0065541 A1 | 5/2002 | Fredricks et al. |
| 2002/0072742 A1 | 6/2002 | Schaefer et al. |
| 2002/0077314 A1 | 6/2002 | Falk et al. |
| 2002/0077676 A1 | 6/2002 | Schroeppel et al. |
| 2002/0082543 A1 | 6/2002 | Park et al. |
| 2002/0099323 A1 | 7/2002 | Dev et al. |
| 2002/0111615 A1 | 8/2002 | Cosman et al. |
| 2002/0112729 A1 | 8/2002 | DeVore et al. |
| 2002/0115208 A1 | 8/2002 | Mitchell et al. |
| 2002/0119437 A1 | 8/2002 | Grooms et al. |
| 2002/0133324 A1 | 9/2002 | Weaver et al. |
| 2002/0137121 A1 | 9/2002 | Rubinsky et al. |
| 2002/0138075 A1 | 9/2002 | Edwards et al. |
| 2002/0138117 A1 | 9/2002 | Son |
| 2002/0143365 A1 | 10/2002 | Herbst |
| 2002/0147462 A1 | 10/2002 | Mair et al. |
| 2002/0156472 A1 | 10/2002 | Lee et al. |
| 2002/0161361 A1 | 10/2002 | Sherman et al. |
| 2002/0183684 A1 | 12/2002 | Dev et al. |
| 2002/0183735 A1 | 12/2002 | Edwards et al. |
| 2002/0183740 A1 | 12/2002 | Edwards et al. |
| 2002/0188242 A1 | 12/2002 | Wu |
| 2002/0193784 A1 | 12/2002 | McHale et al. |
| 2002/0193831 A1 | 12/2002 | Smith |
| 2003/0009110 A1 | 1/2003 | Tu et al. |
| 2003/0016168 A1 | 1/2003 | Jandrell |
| 2003/0055220 A1 | 3/2003 | Legrain |
| 2003/0055420 A1 | 3/2003 | Kadhiresan et al. |
| 2003/0059945 A1 | 3/2003 | Dzekunov et al. |
| 2003/0060856 A1 | 3/2003 | Chornenky et al. |
| 2003/0078490 A1 | 4/2003 | Damasco et al. |
| 2003/0088189 A1 | 5/2003 | Tu et al. |
| 2003/0088199 A1 | 5/2003 | Kawaji |
| 2003/0096407 A1 | 5/2003 | Atala et al. |
| 2003/0105454 A1 | 6/2003 | Cucin |
| 2003/0109871 A1 | 6/2003 | Johnson et al. |
| 2003/0127090 A1 | 7/2003 | Gifford et al. |
| 2003/0130711 A1 | 7/2003 | Pearson et al. |
| 2003/0135242 A1 | 7/2003 | Mongeon et al. |
| 2003/0149451 A1 | 8/2003 | Chomenky et al. |
| 2003/0154988 A1 | 8/2003 | DeVore et al. |
| 2003/0159700 A1 | 8/2003 | Laufer et al. |
| 2003/0166181 A1 | 9/2003 | Rubinsky et al. |
| 2003/0170898 A1 | 9/2003 | Gundersen et al. |
| 2003/0194808 A1 | 10/2003 | Rubinsky et al. |
| 2003/0195385 A1 | 10/2003 | DeVore |
| 2003/0195406 A1 | 10/2003 | Jenkins et al. |
| 2003/0199050 A1 | 10/2003 | Mangano et al. |
| 2003/0208200 A1 | 11/2003 | Palanker et al. |
| 2003/0208236 A1 | 11/2003 | Heil et al. |
| 2003/0212394 A1 | 11/2003 | Pearson et al. |
| 2003/0212412 A1 | 11/2003 | Dillard et al. |
| 2003/0225360 A1 | 12/2003 | Eppstein et al. |
| 2003/0228344 A1 | 12/2003 | Fields et al. |
| 2004/0009459 A1 | 1/2004 | Anderson et al. |
| 2004/0019371 A1 | 1/2004 | Jaafar et al. |
| 2004/0055606 A1 | 3/2004 | Hendricksen et al. |
| 2004/0059328 A1 | 3/2004 | Daniel et al. |
| 2004/0059389 A1 | 3/2004 | Chornenky et al. |
| 2004/0068228 A1 | 4/2004 | Cunningham |
| 2004/0116965 A1 | 6/2004 | Falkenberg |
| 2004/0133194 A1 | 7/2004 | Eum et al. |
| 2004/0138715 A1 | 7/2004 | Groeningen et al. |
| 2004/0146877 A1 | 7/2004 | Diss et al. |
| 2004/0153057 A1 | 8/2004 | Davison |
| 2004/0176855 A1 | 9/2004 | Badylak |
| 2004/0193097 A1 | 9/2004 | Hofmann et al. |
| 2004/0199159 A1 | 10/2004 | Lee et al. |
| 2004/0200484 A1 | 10/2004 | Springmeyer |
| 2004/0206349 A1 | 10/2004 | Alferness et al. |
| 2004/0210248 A1 | 10/2004 | Gordon et al. |
| 2004/0230187 A1 | 11/2004 | Lee et al. |
| 2004/0236376 A1 | 11/2004 | Miklavcic et al. |
| 2004/0243107 A1 | 12/2004 | Macoviak et al. |
| 2004/0267189 A1 | 12/2004 | Mavor et al. |
| 2004/0267340 A1 | 12/2004 | Cioanta et al. |
| 2005/0010209 A1 | 1/2005 | Lee et al. |
| 2005/0010259 A1 | 1/2005 | Gerber |
| 2005/0013870 A1 | 1/2005 | Freyman et al. |
| 2005/0020965 A1 | 1/2005 | Rioux et al. |
| 2005/0043726 A1 | 2/2005 | Mchale et al. |
| 2005/0048651 A1 * | 3/2005 | Ryttsen .................. A61N 1/306 435/459 |
| 2005/0049541 A1 | 3/2005 | Behar et al. |
| 2005/0061322 A1 | 3/2005 | Freitag |
| 2005/0066974 A1 | 3/2005 | Fields et al. |
| 2005/0143817 A1 | 6/2005 | Hunter et al. |
| 2005/0165393 A1 | 7/2005 | Eppstein |
| 2005/0171522 A1 | 8/2005 | Christopherson |
| 2005/0171523 A1 | 8/2005 | Rubinsky et al. |
| 2005/0171574 A1 | 8/2005 | Rubinsky et al. |
| 2005/0182462 A1 | 8/2005 | Chornenky et al. |

(56) References Cited

U.S. PATENT DOCUMENTS

| | | |
|---|---|---|
| 2005/0197619 A1 | 9/2005 | Rule et al. |
| 2005/0261672 A1 | 11/2005 | Deem et al. |
| 2005/0267407 A1 | 12/2005 | Goldman |
| 2005/0282284 A1 | 12/2005 | Rubinsky et al. |
| 2005/0283149 A1 | 12/2005 | Thorne et al. |
| 2005/0288684 A1 | 12/2005 | Aronson et al. |
| 2005/0288702 A1 | 12/2005 | McGurk et al. |
| 2005/0288730 A1 | 12/2005 | Deem et al. |
| 2006/0004356 A1 | 1/2006 | Bilski et al. |
| 2006/0004400 A1 | 1/2006 | McGurk et al. |
| 2006/0009748 A1 | 1/2006 | Mathis |
| 2006/0015147 A1 | 1/2006 | Persson et al. |
| 2006/0020347 A1 | 1/2006 | Barrett et al. |
| 2006/0024359 A1 | 2/2006 | Walker et al. |
| 2006/0025760 A1 | 2/2006 | Podhajsky |
| 2006/0074413 A1 | 4/2006 | Behzadian |
| 2006/0079838 A1 | 4/2006 | Walker et al. |
| 2006/0079845 A1 | 4/2006 | Howard et al. |
| 2006/0079883 A1 | 4/2006 | Elmouelhi et al. |
| 2006/0085054 A1 | 4/2006 | Zikorus et al. |
| 2006/0089635 A1 | 4/2006 | Young et al. |
| 2006/0121610 A1 | 6/2006 | Rubinsky et al. |
| 2006/0142801 A1 | 6/2006 | Demarais et al. |
| 2006/0149123 A1 | 7/2006 | Vidlund et al. |
| 2006/0173490 A1 | 8/2006 | Lafontaine et al. |
| 2006/0182684 A1 | 8/2006 | Beliveau |
| 2006/0195146 A1 | 8/2006 | Tracey et al. |
| 2006/0212032 A1 | 9/2006 | Daniel et al. |
| 2006/0212078 A1 | 9/2006 | Demarais et al. |
| 2006/0217703 A1 | 9/2006 | Chornenky et al. |
| 2006/0224188 A1 | 10/2006 | Libbus et al. |
| 2006/0235474 A1 | 10/2006 | Demarais |
| 2006/0247619 A1 | 11/2006 | Kaplan et al. |
| 2006/0264752 A1* | 11/2006 | Rubinsky ............ A61B 5/0536 600/439 |
| 2006/0264807 A1 | 11/2006 | Westersten et al. |
| 2006/0269531 A1 | 11/2006 | Beebe et al. |
| 2006/0276710 A1 | 12/2006 | Krishnan |
| 2006/0283462 A1 | 12/2006 | Fields et al. |
| 2006/0293713 A1 | 12/2006 | Rubinsky et al. |
| 2006/0293725 A1 | 12/2006 | Rubinsky et al. |
| 2006/0293730 A1 | 12/2006 | Rubinsky et al. |
| 2006/0293731 A1 | 12/2006 | Rubinsky et al. |
| 2006/0293734 A1 | 12/2006 | Scott et al. |
| 2007/0010805 A1 | 1/2007 | Fedewa et al. |
| 2007/0016183 A1 | 1/2007 | Lee et al. |
| 2007/0016185 A1 | 1/2007 | Tullis et al. |
| 2007/0021803 A1 | 1/2007 | Deem et al. |
| 2007/0025919 A1 | 2/2007 | Deem et al. |
| 2007/0043345 A1 | 2/2007 | Davalos et al. |
| 2007/0060989 A1 | 3/2007 | Deem et al. |
| 2007/0078391 A1 | 4/2007 | Wortley et al. |
| 2007/0088347 A1 | 4/2007 | Young et al. |
| 2007/0093789 A1 | 4/2007 | Smith |
| 2007/0096048 A1 | 5/2007 | Clerc |
| 2007/0118069 A1 | 5/2007 | Persson et al. |
| 2007/0129711 A1 | 6/2007 | Altshuler et al. |
| 2007/0129760 A1 | 6/2007 | Demarais et al. |
| 2007/0156135 A1 | 7/2007 | Rubinsky et al. |
| 2007/0191889 A1 | 8/2007 | Lang |
| 2007/0203486 A1 | 8/2007 | Young |
| 2007/0230757 A1 | 10/2007 | Trachtenberg et al. |
| 2007/0239099 A1 | 10/2007 | Goldfarb et al. |
| 2007/0244521 A1 | 10/2007 | Bornzin et al. |
| 2007/0287950 A1 | 12/2007 | Kjeken et al. |
| 2007/0295336 A1 | 12/2007 | Nelson et al. |
| 2007/0295337 A1 | 12/2007 | Nelson et al. |
| 2008/0015571 A1 | 1/2008 | Rubinsky et al. |
| 2008/0021371 A1 | 1/2008 | Rubinsky et al. |
| 2008/0027314 A1 | 1/2008 | Miyazaki et al. |
| 2008/0027343 A1 | 1/2008 | Fields et al. |
| 2008/0033340 A1 | 2/2008 | Heller et al. |
| 2008/0033417 A1 | 2/2008 | Nields et al. |
| 2008/0045880 A1 | 2/2008 | Kjeken et al. |
| 2008/0052786 A1 | 2/2008 | Lin et al. |
| 2008/0071262 A1 | 3/2008 | Azure |
| 2008/0097139 A1 | 4/2008 | Clerc et al. |
| 2008/0097422 A1 | 4/2008 | Edwards et al. |
| 2008/0103529 A1 | 5/2008 | Schoenbach et al. |
| 2008/0121375 A1 | 5/2008 | Richason et al. |
| 2008/0125772 A1 | 5/2008 | Stone et al. |
| 2008/0132826 A1 | 6/2008 | Shadduck et al. |
| 2008/0132884 A1* | 6/2008 | Rubinsky ............ A61B 18/1477 606/34 |
| 2008/0132885 A1 | 6/2008 | Rubinsky et al. |
| 2008/0140064 A1 | 6/2008 | Vegesna |
| 2008/0146934 A1 | 6/2008 | Czygan et al. |
| 2008/0154259 A1 | 6/2008 | Gough et al. |
| 2008/0167649 A1 | 7/2008 | Edwards et al. |
| 2008/0171985 A1 | 7/2008 | Karakoca |
| 2008/0190434 A1 | 8/2008 | Wai |
| 2008/0200911 A1 | 8/2008 | Long |
| 2008/0200912 A1 | 8/2008 | Long |
| 2008/0208052 A1 | 8/2008 | LePivert et al. |
| 2008/0210243 A1 | 9/2008 | Clayton et al. |
| 2008/0214986 A1 | 9/2008 | Ivorra et al. |
| 2008/0236593 A1 | 10/2008 | Nelson et al. |
| 2008/0249503 A1 | 10/2008 | Fields et al. |
| 2008/0262489 A1 | 10/2008 | Steinke |
| 2008/0269586 A1 | 10/2008 | Rubinsky et al. |
| 2008/0269838 A1 | 10/2008 | Brighton et al. |
| 2008/0275465 A1 | 11/2008 | Paul et al. |
| 2008/0281319 A1 | 11/2008 | Paul et al. |
| 2008/0283065 A1 | 11/2008 | Chang et al. |
| 2008/0288038 A1 | 11/2008 | Paul et al. |
| 2008/0300589 A1 | 12/2008 | Paul et al. |
| 2008/0306427 A1 | 12/2008 | Bailey |
| 2008/0312599 A1 | 12/2008 | Rosenberg |
| 2009/0018206 A1 | 1/2009 | Barkan et al. |
| 2009/0024075 A1 | 1/2009 | Schroeppel et al. |
| 2009/0029407 A1 | 1/2009 | Gazit et al. |
| 2009/0038752 A1 | 2/2009 | Weng et al. |
| 2009/0062788 A1 | 3/2009 | Long et al. |
| 2009/0062792 A1 | 3/2009 | Vakharia et al. |
| 2009/0081272 A1 | 3/2009 | Clarke et al. |
| 2009/0105703 A1 | 4/2009 | Shadduck |
| 2009/0114226 A1 | 5/2009 | Deem et al. |
| 2009/0125009 A1 | 5/2009 | Zikorus et al. |
| 2009/0138014 A1 | 5/2009 | Bonutti |
| 2009/0143705 A1 | 6/2009 | Danek et al. |
| 2009/0157166 A1 | 6/2009 | Singhal et al. |
| 2009/0163904 A1 | 6/2009 | Miller et al. |
| 2009/0171280 A1 | 7/2009 | Samuel et al. |
| 2009/0177111 A1 | 7/2009 | Miller et al. |
| 2009/0186850 A1 | 7/2009 | Kiribayashi et al. |
| 2009/0192508 A1 | 7/2009 | Laufer et al. |
| 2009/0198231 A1 | 8/2009 | Esser et al. |
| 2009/0228001 A1 | 9/2009 | Pacey |
| 2009/0247933 A1 | 10/2009 | Maor et al. |
| 2009/0248012 A1 | 10/2009 | Maor et al. |
| 2009/0269317 A1 | 10/2009 | Davalos |
| 2009/0275827 A1 | 11/2009 | Aiken et al. |
| 2009/0281477 A1 | 11/2009 | Mikus et al. |
| 2009/0292342 A1 | 11/2009 | Rubinsky et al. |
| 2009/0301480 A1 | 12/2009 | Elsakka et al. |
| 2009/0306544 A1 | 12/2009 | Ng et al. |
| 2009/0306545 A1 | 12/2009 | Elsakka et al. |
| 2009/0318905 A1 | 12/2009 | Bhargav et al. |
| 2009/0326436 A1 | 12/2009 | Rubinsky et al. |
| 2009/0326570 A1 | 12/2009 | Brown |
| 2010/0004623 A1 | 1/2010 | Hamilton et al. |
| 2010/0023004 A1 | 1/2010 | Francischelli et al. |
| 2010/0030211 A1* | 2/2010 | Davalos ................ A61N 1/327 606/41 |
| 2010/0049190 A1 | 2/2010 | Long et al. |
| 2010/0057074 A1 | 3/2010 | Roman et al. |
| 2010/0069921 A1 | 3/2010 | Miller et al. |
| 2010/0087813 A1 | 4/2010 | Long |
| 2010/0130975 A1 | 5/2010 | Long |
| 2010/0147701 A1 | 6/2010 | Field |
| 2010/0152725 A1 | 6/2010 | Pearson et al. |
| 2010/0160850 A1 | 6/2010 | Ivorra et al. |
| 2010/0168735 A1 | 7/2010 | Deno et al. |
| 2010/0174282 A1 | 7/2010 | Demarais et al. |

(56) References Cited

U.S. PATENT DOCUMENTS

| | | |
|---|---|---|
| 2010/0179530 A1 | 7/2010 | Long et al. |
| 2010/0196984 A1 | 8/2010 | Rubinsky et al. |
| 2010/0204560 A1 | 8/2010 | Salahieh et al. |
| 2010/0204638 A1 | 8/2010 | Hobbs et al. |
| 2010/0222677 A1 | 9/2010 | Placek et al. |
| 2010/0228234 A1 | 9/2010 | Hyde et al. |
| 2010/0228247 A1 | 9/2010 | Paul et al. |
| 2010/0241117 A1 | 9/2010 | Paul et al. |
| 2010/0249771 A1 | 9/2010 | Pearson et al. |
| 2010/0250209 A1 | 9/2010 | Pearson et al. |
| 2010/0255795 A1 | 10/2010 | Rubinsky et al. |
| 2010/0256628 A1 | 10/2010 | Pearson et al. |
| 2010/0256630 A1 | 10/2010 | Hamilton, Jr. et al. |
| 2010/0261994 A1* | 10/2010 | Davalos .............. A61B 18/1477 600/411 |
| 2010/0286690 A1 | 11/2010 | Paul et al. |
| 2010/0298823 A1 | 11/2010 | Cao et al. |
| 2010/0331758 A1 | 12/2010 | Davalos et al. |
| 2011/0017207 A1 | 1/2011 | Hendricksen et al. |
| 2011/0034209 A1 | 2/2011 | Rubinsky et al. |
| 2011/0064671 A1 | 3/2011 | Bynoe |
| 2011/0106221 A1 | 5/2011 | Robert et al. |
| 2011/0112531 A1 | 5/2011 | Landis et al. |
| 2011/0118727 A1 | 5/2011 | Fish et al. |
| 2011/0118732 A1 | 5/2011 | Rubinsky et al. |
| 2011/0130834 A1 | 6/2011 | Wilson et al. |
| 2011/0144524 A1 | 6/2011 | Fish et al. |
| 2011/0144635 A1 | 6/2011 | Harper et al. |
| 2011/0144657 A1 | 6/2011 | Fish et al. |
| 2011/0152678 A1 | 6/2011 | Aljuri et al. |
| 2011/0202053 A1 | 8/2011 | Moss et al. |
| 2011/0217730 A1 | 9/2011 | Gazit et al. |
| 2011/0251607 A1 | 10/2011 | Kruecker et al. |
| 2011/0301587 A1 | 12/2011 | Deem et al. |
| 2012/0034131 A1 | 2/2012 | Rubinsky et al. |
| 2012/0059255 A1 | 3/2012 | Paul et al. |
| 2012/0071872 A1 | 3/2012 | Rubinsky et al. |
| 2012/0071874 A1 | 3/2012 | Davalos et al. |
| 2012/0085649 A1 | 4/2012 | Sane et al. |
| 2012/0089009 A1 | 4/2012 | Omary et al. |
| 2012/0090646 A1 | 4/2012 | Tanaka et al. |
| 2012/0095459 A1 | 4/2012 | Callas et al. |
| 2012/0109122 A1 | 5/2012 | Arena et al. |
| 2012/0130289 A1 | 5/2012 | Demarais et al. |
| 2012/0150172 A1 | 6/2012 | Ortiz et al. |
| 2012/0165813 A1 | 6/2012 | Lee et al. |
| 2012/0179091 A1 | 7/2012 | Ivorra et al. |
| 2012/0226218 A1 | 9/2012 | Phillips et al. |
| 2012/0226271 A1 | 9/2012 | Callas et al. |
| 2012/0265186 A1 | 10/2012 | Burger et al. |
| 2012/0277741 A1 | 11/2012 | Davalos et al. |
| 2012/0303020 A1 | 11/2012 | Chornenky et al. |
| 2012/0310236 A1 | 12/2012 | Placek et al. |
| 2013/0090646 A1* | 4/2013 | Moss .............. A61B 18/1487 606/41 |
| 2013/0108667 A1 | 5/2013 | Soikum et al. |
| 2013/0110106 A1 | 5/2013 | Richardson |
| 2013/0184702 A1 | 7/2013 | Neal, II et al. |
| 2013/0196441 A1 | 8/2013 | Rubinsky et al. |
| 2013/0197425 A1 | 8/2013 | Golberg et al. |
| 2013/0202766 A1 | 8/2013 | Rubinsky et al. |
| 2013/0218157 A1* | 8/2013 | Callas .............. A61B 18/14 606/41 |
| 2013/0253415 A1 | 9/2013 | Sane et al. |
| 2013/0281968 A1 | 10/2013 | Davalos et al. |
| 2013/0345697 A1 | 12/2013 | Garcia et al. |
| 2013/0345779 A1 | 12/2013 | Maor et al. |
| 2014/0039489 A1 | 2/2014 | Davalos et al. |
| 2014/0046322 A1 | 2/2014 | Callas et al. |
| 2014/0066913 A1 | 3/2014 | Sherman |
| 2014/0081255 A1 | 3/2014 | Johnson et al. |
| 2014/0088578 A1 | 3/2014 | Rubinsky et al. |
| 2014/0121663 A1 | 5/2014 | Pearson et al. |
| 2014/0121728 A1 | 5/2014 | Dhillon et al. |
| 2014/0163551 A1 | 6/2014 | Maor et al. |
| 2014/0207133 A1 | 7/2014 | Model et al. |
| 2014/0296844 A1 | 10/2014 | Kevin et al. |
| 2014/0309579 A1 | 10/2014 | Rubinsky et al. |
| 2014/0378964 A1 | 12/2014 | Pearson |
| 2015/0088120 A1 | 3/2015 | Garcia et al. |
| 2015/0088220 A1 | 3/2015 | Callas et al. |
| 2015/0112333 A1 | 4/2015 | Chorenky et al. |
| 2015/0126922 A1 | 5/2015 | Willis |
| 2015/0164584 A1 | 6/2015 | Davalos et al. |
| 2015/0173824 A1 | 6/2015 | Davalos et al. |
| 2015/0201996 A1 | 7/2015 | Rubinsky et al. |
| 2015/0265349 A1 | 9/2015 | Moss et al. |
| 2015/0289923 A1 | 10/2015 | Davalos et al. |
| 2015/0320488 A1 | 11/2015 | Moshe et al. |
| 2015/0327944 A1 | 11/2015 | Davalos et al. |
| 2016/0022957 A1 | 1/2016 | Hobbs et al. |
| 2016/0066977 A1 | 3/2016 | Neal et al. |
| 2016/0074114 A1 | 3/2016 | Pearson et al. |
| 2016/0113708 A1 | 4/2016 | Moss et al. |
| 2016/0143698 A1 | 5/2016 | Garcia et al. |
| 2016/0235470 A1 | 8/2016 | Callas et al. |
| 2016/0287313 A1 | 10/2016 | Rubinsky et al. |
| 2016/0287314 A1 | 10/2016 | Arena et al. |
| 2016/0338761 A1 | 11/2016 | Chornenky et al. |
| 2016/0354142 A1 | 12/2016 | Pearson et al. |
| 2017/0035501 A1 | 2/2017 | Chornenky et al. |
| 2017/0189579 A1 | 7/2017 | Davalos |
| 2017/0209620 A1 | 7/2017 | Davalos et al. |
| 2017/0360326 A1 | 12/2017 | Davalos |
| 2018/0125565 A1 | 5/2018 | Sano et al. |
| 2018/0161086 A1 | 6/2018 | Davalos et al. |
| 2019/0029749 A1 | 1/2019 | Garcia |
| 2019/0046255 A1 | 2/2019 | Davalos et al. |
| 2019/0069945 A1 | 3/2019 | Davalos et al. |
| 2019/0133671 A1 | 5/2019 | Davalos et al. |

FOREIGN PATENT DOCUMENTS

| | | |
|---|---|---|
| AU | 2005271471 A2 | 2/2006 |
| AU | 2006321570 A1 | 6/2007 |
| AU | 2006321574 A1 | 6/2007 |
| AU | 2006321918 A1 | 6/2007 |
| CA | 2297846 A1 | 2/1999 |
| CA | 2378110 A1 | 2/2001 |
| CA | 2445392 A1 | 11/2002 |
| CA | 2458676 A1 | 3/2003 |
| CA | 2487284 A1 | 12/2003 |
| CA | 2575792 A1 | 2/2006 |
| CA | 2631940 A1 | 6/2007 |
| CA | 2631946 A1 | 6/2007 |
| CA | 2632604 A1 | 6/2007 |
| CA | 2751462 A1 | 11/2010 |
| CN | 1525839 A | 9/2004 |
| CN | 101534736 A | 9/2009 |
| CN | 102238921 A | 11/2011 |
| CN | 102421386 A | 4/2012 |
| DE | 863111 | 1/1953 |
| DE | 4000893 | 7/1991 |
| DE | 60038026 | 2/2009 |
| EP | 0218275 A1 | 4/1987 |
| EP | 0339501 A2 | 11/1989 |
| EP | 0378132 A | 7/1990 |
| EP | 0533511 A1 | 3/1993 |
| EP | 0998235 A1 | 5/2000 |
| EP | 0528891 B1 | 7/2000 |
| EP | 1196550 A2 | 4/2002 |
| EP | 1439792 A1 | 7/2004 |
| EP | 1442765 A1 | 8/2004 |
| EP | 1462065 A2 | 9/2004 |
| EP | 1061983 B1 | 11/2004 |
| EP | 1493397 A1 | 1/2005 |
| EP | 1506039 A1 | 2/2005 |
| EP | 0935482 B1 | 5/2005 |
| EP | 1011495 B1 | 11/2005 |
| EP | 1796568 A1 | 6/2007 |
| EP | 1207797 B1 | 2/2008 |
| EP | 1406685 B1 | 6/2008 |
| EP | 1424970 B1 | 12/2008 |
| EP | 2381829 A1 | 11/2011 |

(56) References Cited

FOREIGN PATENT DOCUMENTS

| | | |
|---|---|---|
| EP | 2413833 A1 | 2/2012 |
| EP | 1791485 B1 | 12/2014 |
| EP | 2373241 B1 | 1/2015 |
| EP | 1962710 B1 | 8/2015 |
| EP | 1962708 B1 | 9/2015 |
| EP | 1962945 B1 | 4/2016 |
| ES | 2300272 | 6/2008 |
| ES | 2315493 | 4/2009 |
| JP | 2001510702 A | 8/2001 |
| JP | 2003505072 A | 2/2003 |
| JP | 2003506064 A | 2/2003 |
| JP | 2004203224 A | 7/2004 |
| JP | 2004525726 A | 8/2004 |
| JP | 2004303590 A | 10/2004 |
| JP | 2005501596 A | 1/2005 |
| JP | 2005526579 A | 9/2005 |
| JP | 2008508946 A | 3/2008 |
| JP | 4252316 B2 | 4/2009 |
| JP | 2009518130 A | 5/2009 |
| JP | 2009518150 A | 5/2009 |
| JP | 2009518151 A | 5/2009 |
| JP | 2009532077 A | 9/2009 |
| JP | 2010503496 A | 2/2010 |
| JP | 2011137025 | 7/2011 |
| JP | 2011137025 A | 7/2011 |
| JP | 2012510332 A | 5/2012 |
| JP | 2012515018 A | 7/2012 |
| JP | 2012521863 A | 9/2012 |
| KR | 101034682 A | 5/2011 |
| WO | 9104014 | 4/1991 |
| WO | 9634571 | 11/1996 |
| WO | 9639531 A | 12/1996 |
| WO | 9810745 | 3/1998 |
| WO | 9614238 A | 4/1998 |
| WO | 9901076 | 1/1999 |
| WO | 9904710 | 2/1999 |
| WO | 0020554 A | 4/2000 |
| WO | 0107583 A | 2/2001 |
| WO | 0107584 A | 2/2001 |
| WO | 0107585 A | 2/2001 |
| WO | 0110319 A | 2/2001 |
| WO | 2001048153 A1 | 7/2001 |
| WO | 0170114 A1 | 9/2001 |
| WO | 0181533 A | 11/2001 |
| WO | 02078527 A | 10/2002 |
| WO | 02089686 A | 11/2002 |
| WO | 02100459 A | 12/2002 |
| WO | 2003020144 A1 | 3/2003 |
| WO | 2003047684 A2 | 6/2003 |
| WO | 03099382 A | 12/2003 |
| WO | 2004037341 A2 | 5/2004 |
| WO | 2004080347 A2 | 9/2004 |
| WO | 2005065284 A | 7/2005 |
| WO | 2006017666 A2 | 2/2006 |
| WO | 2006031541 A1 | 3/2006 |
| WO | 2006130194 A2 | 12/2006 |
| WO | 2007067628 A1 | 6/2007 |
| WO | 2007067937 A2 | 6/2007 |
| WO | 2007067938 A2 | 6/2007 |
| WO | 2007067939 A2 | 6/2007 |
| WO | 2007067940 A2 | 6/2007 |
| WO | 2007067941 A2 | 6/2007 |
| WO | 2007067943 A2 | 6/2007 |
| WO | 2007070361 A2 | 6/2007 |
| WO | 2007100727 A2 | 9/2007 |
| WO | 2007123690 A2 | 11/2007 |
| WO | 2008063195 A1 | 5/2008 |
| WO | 2008034103 A3 | 11/2008 |
| WO | 2009046176 A1 | 4/2009 |
| WO | 2007137303 | 7/2009 |
| WO | 2009134876 A | 11/2009 |
| WO | 2009135070 A1 | 11/2009 |
| WO | 2009137800 A2 | 11/2009 |
| WO | 2010064154 A1 | 6/2010 |
| WO | 2010080974 A1 | 7/2010 |
| WO | 2010117806 A1 | 10/2010 |
| WO | 2010118387 A | 10/2010 |
| WO | 2010132472 A1 | 11/2010 |
| WO | 2010151277 A | 12/2010 |
| WO | 2011047387 A | 4/2011 |
| WO | 2011062653 A1 | 5/2011 |
| WO | 2011072221 A1 | 6/2011 |
| WO | 2012051433 A2 | 4/2012 |
| WO | 2012071526 A | 5/2012 |
| WO | 2012088149 A | 6/2012 |
| WO | 2015175570 A1 | 11/2015 |
| WO | 2016100325 A1 | 6/2016 |
| WO | 2016164930 A1 | 10/2016 |

OTHER PUBLICATIONS

Agerholm-Larsen, B., et al., "Preclinical Validation of Electrochemotherapy as an Effective Treatment for Brain Tumors", Cancer Research 71: 3753-3762 (2011).

Alberts et al., "Molecular Biology of the Cell," 3rd edition, Garland Science, New York, 1994, 1 page.

Al-Sakere et al., "Tumor ablation with irreversible electroporation." PLoS One, Issue 11, e1135, 8 pages, 2007.

Amasha, et al., Quantitative Assessment of Impedance Tomography for Temperature Measurements in Microwave Hyperthermia, Clin. Phys. Physiol. Meas., 1998, Suppl. A, 49-53.

Andreason, Electroporation as a Technique for the Transfer of Macromolecules into Mammalian Cell Lines, J. Tiss. Cult. Meth., 15:56-62, 1993.

Appelbaum et al., "US Findings after Irreversible Electroporation Ablation: Radiologic-Pathologic Correlation," Radiology, 262, pp. 117-125, Jan. 1, 2012.

Arena et al. "High-Frequency Irreversible Electroporation (H-FIRE) for Non-thermal Ablation without Muscle Contraction." Biomed. Eng. Online, vol. 10, 20 pages (2011).

Arena, C.B., et al., "A three-dimensional in vitro tumor platform for modeling therapeutic irreversible electroporation." Biophysical Journal, 2012.103(9): p. 2033-2042.

Arena, Christopher B., et al., "Towards the development of latent heat storage electrodes for electroporation-based therapies", Applied Physics Letters, 101, 083902 (2012).

Arena, Christopher B., et al.,"Phase Change Electrodes for Reducing Joule Heating During Irreversible Electroporation". Proceedings of the ASME 2012 Summer Bioengineering Conference, SBC2012, Jun. 20-23, 2012, Fajardo, Puerto Rico.

Asami et al., "Dielectric properties of mouse lymphocytes and erythrocytes." Biochimica et Biophysica Acta (BBA)—Molecular Cell Research, 1010 (1989) pp. 49-55.

Bagla, S. and Papadouris, D., "Percutaneous Irreversible Electroporation of Surgically Unresectable Pancreatic Cancer: A Case Report" J. Vascular Int. Radiol. 23(1), 142-145 (2012).

Baker, et al., Calcium-Dependent Exocytosis in Bovine Adrenal Medullary Cells with Leaky Plasma Membranes, Nature, vol. 276, pp. 620-622, 1978.

Ball, C., K.R. Thomson, and H. Kavnoudias, "Irreversible electroporation: a new challenge in "out of-operating theater" anesthesia." Anesth Analg, 2010. 110(5): p. 1305-9.

Bancroft, et al. Design of a Flow Perfusion Bioreactor System for Bone Tissue-Engineering Applications, Tissue Engineering, vol. 9, No. 3, 2003, p. 549-554.

Baptista et al., "The Use of Whole Organ Decellularization for the Generation of a Vascularized Liver Organoid," Heptatology, vol. 53, No. 2, pp. 604-617 (2011).

Barber, Electrical Impedance Tomography Applied Potential Tomography, Advances in Biomedical Engineering, Beneken and Thevenin, eds., IOS Press, pp. 165-173, 1993.

Beebe, S.J., et al., "Diverse effects of nanosecond pulsed electric fields on cells and tissues", DNA and Cell Biology, 22(12): 785-796 (2003).

Beebe, S.J., et al., Nanosecond pulsed electric field (nsPEF) effects on cells and tissues: apoptosis induction and tumor growth inhibition. PPPS-2001 Pulsed Power Plasma Science 2001, 28th IEEE International Conference on Plasma Science and 13th IEEE Inter-

(56) References Cited

OTHER PUBLICATIONS national Pulsed Power Conference, Digest of Technical Papers (Cat. No. 01CH37251). IEEE, Part vol. 1, 2001, pp. 211-215, vol. I, Piscataway, NJ, USA.
Ben-David, et al., "Characterization of Irreversible Electroporation Ablation in Vivo Porcine Liver," Am J Roentgenol, vol. 198, pp. W62-W68, 2012.
Blad, et al., Impedance Spectra of Tumour Tissue in Comparison with Normal Tissue; a Possible Clinical Application for Electrical or Electrical Impedance Tomography, Physiol. Meas. 17 (1996) A105-A115.
Bolland, F., et al., "Development and characterisation of a full-thickness acellular porcine bladder matrix for tissue engineering", Biomaterials, Elsevier Science Publishers, Barking, GB, vol. 28, No. 6, Nov. 28, 2006, pp. 1061-1070.
Boone, K., Barber, D. & Brown, B. Review—Imaging with electricity: report of the European Concerted Action on Impedance Tomography. J. Med. Eng. Technol. 21, 201-232 (1997).
Bower et al., "Irreversible electroporation of the pancreas: definitive local therapy without systemic effects." Journal of surgical oncology, 2011. 104(1): p. 22-28.
BPH Management Strategies: Improving Patient Satisfaction, Urology Times, May 2001, vol. 29, Supplement 1.
Brown, et al., Blood Flow Imaging Using Electrical Impedance Tomography, Clin. Phys. Physiol. Meas., 1992, vol. 13, Suppl. A, 175-179.
Brown, S.G., Phototherapy of tumors. World J. Surgery, 1983. 7: p. 700-9.
Cannon et al., "Safety and early efficacy of irreversible electroporation for hepatic tumors in proximity to vital structures." Journal of Surgical Oncology, 6 pages (2012).
Carpenter A.E. et al., "CellProfiler: image analysis software for identifying and quantifying cell phenotypes." Genome Biol. 2006; 7(10): R100. Published online Oct. 31, 2006, 11 pages.
Cemazar M, Parkins CS, Holder AL, Chaplin DJ, Tozer GM, et al., "Electroporation of human microvascular endothelial cells: evidence for an anti-vascular mechanism of electrochemotherapy", Br J Cancer 84: 565-570 (2001).
Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.
Chang, D.C., "Cell Poration and Cell-Fusion Using an Oscillating Electric-Field". Biophysical Journal, 56(4): p. 641-652 (1989).
Charpentier, K.P., et al., "Irreversible electroporation of the pancreas in swine: a pilot study." HPB: the official journal of the International Hepato Pancreato Biliary Association, 2010. 12(5): p. 348-351.
Chen et al., "Classification of cell types using a microfluidic device for mechanical and electrical measurement on single cells." Lab on a Chip, vol. 11, pp. 3174-3181 (2011).
Chen, M.T., et al., "Two-dimensional nanosecond electric field mapping based on cell electropermeabilization", PMC Biophys, 2(1):9 (2009).
Clark et al., "The electrical properties of resting and secreting pancreas." The Journal of Physiology, vol. 189, pp. 247-260 (1967).
Coates, C.W.,et al., "The Electrical Discharge of the Electric Eel, *Electrophorous electricus*," Zoologica, 1937, 22(1), p. 1-32.
Cook, et al., ACT3: A High-Speed, High-Precision Electrical Impedance Tomograph, IEEE Transactions on Biomedical Engineering, vol. 41, No. 8, Aug. 1994.
Co-Pending U.S. Appl. No. 10/571,162, filed Oct. 18, 2006 (published as 2007/0043345 on Feb. 22, 2007).
Co-Pending U.S. Appl. No. 12/432,295, filed Apr. 29, 2009.
Co-Pending U.S. Appl. No. 12/609,779, filed Oct. 30, 2009.
Co-Pending U.S. Appl. No. 12/751,826, filed Mar. 31, 2010 (published as 2010/0250209 on Sep. 30, 2010).
Co-Pending U.S. Appl. No. 12/751,854, filed Mar. 31, 2010 (published as 2010/0249771 on Sep. 30, 2010).
Co-Pending U.S. Appl. No. 12/757,901, filed Apr. 9, 2010.
Co-Pending U.S. Appl. No. 12/906,923, filed Oct. 18, 2010.
Co-Pending U.S. Appl. No. 14/558,631, filed Dec. 2, 2014.
Co-Pending U.S. Appl. No. 14/686,380, filed Apr. 14, 2015 and Published as US 2015/0289923 on Oct. 15, 2015.
Co-Pending U.S. Appl. No. 14/808,679, filed Jul. 24, 2015 and Published as U.S. Publication No. 2015/0327944 on Nov. 19, 2015.
Co-Pending U.S. Appl. No. 15/011,752, filed Feb. 1, 2016.
Jarm et al., "Antivascular effects of electrochemotherapy: implications in treatment of bleeding metastases." Expert Rev Anticancer Ther. vol. 10, pp. 729-746 (2010).
Jaroszeski, et al., In Vivo Gene Delivery by Electroporation, Advanced Drug Delivery Review, vol. 35, pp. 131-137, 1999.
Jensen et al., "Tumor volume in subcutaneous mouse xenografts measured by microCT is more accurate and reproducible than determined by 18FFDG-microPET or external caliper." BMC medical Imaging vol. 8:16, 9 Pages (2008).
Jossinet et al., Electrical Impedance Endo-Tomography: Imaging Tissue From Inside, IEEE Transactions on Medical Imaging, vol. 21, No. 6, Jun. 2002, pp. 560-565.
Kingham et al., "Ablation of perivascular hepatic malignant tumors with irreversible electroporation." Journal of the American College of Surgeons, 2012. 215(3), p. 379-387.
Kinosita and Tsong, "Formation and resealing of pores of controlled sizes in human erythrocyte membrane." Nature, vol. 268 (1977) pp. 438-441.
Kinosita and Tsong, "Voltage-induced pore formation and hemolysis of human erythrocytes." Biochimica et Biophysica Acta (BBA)—Biomembranes, 471 (1977) pp. 227-242.
Kinosita et al., "Electroporation of cell membrane visualized under a pulsed-laser fluorescence microscope." Biophysical Journal, vol. 53, pp. 1015-1019 (1988).
Kinosita, et al., Hemolysis of Human Erythrocytes by a Transient Electric Field, Proc. Natl. Acad. Sci. USA, vol. 74, No. 5, pp. 1923-1927, 1977.
Kirson et al., "Alternating electric fields arrest cell proliferation in animal tumor models and human brain tumors." Proceedings of the National Academy of Sciences vol. 104, pp. 10152-10157 (2007).
Kotnik and Miklavcic, "Theoretical evaluation of voltage inducement on internal membranes of biological cells exposed to electric fields." Biophysical Journal, vol. 90(2), pp. 480-491 (2006).
Kotnik, T. and D. Miklavcic, "Theoretical evaluation of the distributed power dissipation in biological cells exposed to electric fields", Bioelectromagnetics, 21(5): p. 385-394 (2000).
Kotnik, T., et al., "Cell membrane electropermeabilization by symmetrical bipolar rectangular pulses. Part II. Reduced electrolytic contamination", Bioelectrochemistry, 54(1): p. 91-5 (2001).
Kotnik, T., et al., "Role of pulse shape in cell membrane electropermeabilization", Biochimica Et Biophysica Acta-Biomembranes, 1614(2): p. 193-200 (2003).
Labeed et al., "Differences in the biophysical properties of membrane and cytoplasm of apoptotic cells revealed using dielectrophoresis." Biochimica et Biophysica Acta (BBA)—General Subjects, vol. 1760, pp. 922-929 (2006).
Lackovic, I., et al., "Three-dimensional Finite-element Analysis of Joule Heating in Electrochemotherapy and in vivo Gene Electrotransfer", Ieee Transactions on Dielectrics and Electrical Insulation, 16(5): p. 1338-1347 (2009).
Laufer et al., "Electrical impedance characterization of normal and cancerous human hepatic tissue." Physiological Measurement, vol. 31, pp. 995-1009 (2010).
Lebar et al., "Inter-pulse interval between rectangular voltage pulses affects electroporation threshold of artificial lipid bilayers." IEEE Transactions on NanoBioscience, vol. 1 (2002) pp. 116-120.
Lee, E. W. et al. Advanced Hepatic Ablation Technique for Creating Complete Cell Death : Irreversible Electroporation. Radiology 255, 426-433, doi:10.1148/radiol.10090337 (2010).
Lee, E.W., et al., "Imaging guided percutaneous irreversible electroporation: ultrasound and immunohistological correlation", Technol Cancer Res Treat 6: 287-294 (2007).
Li, W., et al., "The Effects of Irreversible Electroporation (IRE) on Nerves" PloS One, Apr. 2011, 6(4), e18831.
Liu, et al., Measurement of Pharyngeal Transit Time by Electrical Impedance Tomography, Clin. Phys. Physiol. Meas., 1992, vol. 13, Suppl. A, pp. 197-200.

(56) References Cited

OTHER PUBLICATIONS

Long, G., et al., "Targeted Tissue Ablation With Nanosecond Pulses". Ieee Transactions on Biomedical Engineering, 58(8) (2011).
Lundqvist et al. Altering the Biochemical State of Individual Cultured Cells and Organelles with Ultramicroelectrodes, Proc. Natl. Acad. Sci. USA, vol. 95, pp. 10356-10360, Sep. 1998.
Lurquin, Gene Transfer by Electroporation, Molecular Biotechnology, vol. 7, 1997.
Lynn et al., A New Method for the Generation and Use of Focused Ultrasound in Experimental Biology, The Journal of General Physiology, vol. 26, 179-193, 1942.
M. Marty et al., "Electrochemotherapy—an easy, highly effective and safe treatment of cutaneous and subcutaneous metastases: Results of ESOPE (European Standard Operating Procedures of Electrochemotherapy) study," European Journal of Cancer Supplements, 4, pp. 3-13, 2006.
Maček Lebar and Miklavčič, "Cell electropermeabilization to small molecules in vitro: control by pulse parameters." Radiology and Oncology, vol. 35(3), pp. 193-202 (2001).
Mahmood, F., et al., "Diffusion-Weighted MRI for Verification of Electroporation-Based Treatments", Journal of Membrane Biology 240: 131-138 (2011).
Mahnic-Kalamiza, et al., "Educational application for visualization and analysis of electric field strength in multiple electrode electroporation," BMC Med Educ, vol. 12:102, 13 pages, 2012.
Malpica et al., "Grading ovarian serous carcinoma using a two-tier system." The American Journal of Surgical Pathology, vol. 28, pp. 496-504 (2004).
Maor et al., The Effect of Irreversible Electroporation on Blood Vessels, Tech. in Cancer Res. and Treatment, vol. 6, No. 4, Aug. 2007, pp. 307-312.
Maor, E., A. Ivorra, and B. Rubinsky, Non Thermal Irreversible Electroporation: Novel Technology for Vascular Smooth Muscle Cells Ablation, PLoS One, 2009, 4(3): p. e4757.
Maor, E., A. Ivorra, J. Leor, and B. Rubinsky, Irreversible electroporation attenuates neointimal formation after angioplasty, IEEE Trans Biomed Eng, Sep. 2008, 55(9): p. 2268-74.
Marszalek et al., "Schwan equation and transmembrane potential induced by alternating electric field." Biophysical Journal, vol. 58, pp. 1053-1058 (1990).
Martin, n.R.C.G., et al., "Irreversible electroporation therapy in the management of locally advanced pancreatic adenocarcinoma." Journal of the American College of Surgeons, 2012. 215(3): p. 361-369.
Miklavcic et al., "A validated model of in vivo electric field distribution in tissues for electrochemotherapy and for DNA electrotransfer for gene therapy," Biochimica et Biophysica Acta, 1523, pp. 73-83, 2000.
Miklavčič, et al., The Importance of Electric Field Distribution for Effective in Vivo Electroporation of Tissues, Biophysical Journal, vol. 74, May 1998, pp. 2152-2158.
Miller, L., et al., Cancer cells ablation with irreversible electroporation, Technology in Cancer Research and Treatment 4 (2005) 699-706.
Mir et al., "Mechanisms of Electrochemotherapy" Advanced Drug Delivery Reviews 35:107-118 (1999).
Mir, et al., Effective Treatment of Cutaneous and Subcutaneous Malignant Tumours by Electrochemotherapy, British Journal of Cancer, vol. 77, No. 12, pp. 2336-2342, 1998.
Mir, et al., Electrochemotherapy Potentiation of Antitumour Effect of Bleomycin by Local Electric Pulses, European Journal of Cancer, vol. 27, No. 1, pp. 68-72, 1991.
Mir, et al., Electrochemotherapy, a Novel Antitumor Treatment: First Clinical Trial, C.R. Acad. Sci. Paris, Ser. III, vol. 313, pp. 613-618, 1991.
Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.

Mir, L.M., et al., Electric Pulse-Mediated Gene Delivery to Various Animal Tissues, in Advances in Genetics, Academic Press, 2005, p. 83-114.
Mir, Therapeutic Perspectives of in Vivo Cell Electropermeabilization, Bioelectrochemistry, vol. 53, pp. 1-10, 2000.
Mulhall et al., "Cancer, pre-cancer and normal oral cells distinguished by dielectrophoresis." Analytical and Bioanalytical Chemistry, vol. 401, pp. 2455-2463 (2011).
Narayan, et al., Establishment and Characterization of a Human Primary Prostatic Adenocarcinoma Cell Line (ND-1), The Journal of Urology, vol. 148, 1600-1604, Nov. 1992.
Naslund, Cost-Effectiveness of Minimally Invasive Treatments and Transurethral Resection (TURP) in Benign Prostatic Hyperplasia (BPH), (Abstract), Presented at 2001 AUA National Meeting,, Anaheim, CA, Jun. 5, 2001.
Naslund, Michael J., Transurethral Needle Ablation of the Prostate, Urology, vol. 50, No. 2, Aug. 1997.
Salmanzadeh et al., "Sphingolipid Metabolites Modulate Dielectric Characteristics of Cells in a Mouse Ovarian Cancer Progression Model." Integr. Biol., 5(6), pp. 843-852 (2013).
Sano et al., "Contactless Dielectrophoretic Spectroscopy: Examination of the Dielectric Properties of Cells Found in Blood." Electrophoresis, 32, pp. 3164-3171, 2011.
Sano et al., "In-vitro bipolar nano- and microsecond electro-pulse bursts for irreversible electroporation therapies." Bioelectrochemistry vol. 100, pp. 69-79 (2014).
Sano et al., "Modeling and Development of a Low Frequency Contactless Dielectrophoresis (cDEP) Platform to Sort Cancer Cells from Dilute Whole Blood Samples." Biosensors & Bioelectronics, 8 pages (2011).
Sano, M. B., et al., "Towards the creation of decellularized organ constructs using irreversible electroporation and active mechanical perfusion", Biomedical Engineering Online, Biomed Central LTD, London, GB, vol. 9, No. 1, Dec. 10, 2010, p. 83.
Saur et al., "CXCR4 expression increases liver and lung metastasis in a mouse model of pancreatic cancer." Gastroenterology, vol. 129, pp. 1237-1250 (2005).
Schmukler, Impedance Spectroscopy of Biological Cells, Engineering in Medicine and Biology Society, Engineering Advances: New Opportunities for Biomedical Engineers, Proceedings of the 16th Annual Internal Conference of the IEEE, vol. 1, p. A74, downloaded from IEEE Xplore website, 1994.
Schoenbach et al., "Intracellular effect of ultrashort electrical pulses." Bioelectromagnetics, 22 (2001) pp. 440-448.
Seibert et al., "Clonal variation of MCF-7 breast cancer cells in vitro and in athymic nude mice." Cancer Research, vol. 43, pp. 2223-2239 (1983).
Seidler et al., "A Cre-loxP-based mouse model for conditional somatic gene expression and knockdown in vivo by using avian retroviral vectors." Proceedings of the National Academy of Sciences, vol. 105, pp. 10137-10142 (2008).
Set, D., Lebar, A. M. & Miklavcic, D. Feasibility of employing model-based optimization of pulse amplitude and electrode distance for effective tumor electropermeabilization. IEEE Trans Biomed Eng 54, 773-781 (2007).
Sel, et al., "Sequential finite element model of tissue electropermeabilization," IEEE Trans Biomed Eng, vol. 52, pp. 816-827, 2005.
Sersa, et al., Reduced Blood Flow and Oxygenation in SA-1 Tumours after Electrochemotherapy with Cisplatin, British Journal of Cancer, 87, 1047-1054, 2002.
Sersa, et al., Tumour Blood Flow Modifying Effects of Electrochemotherapy: a Potential Vascular Targeted Mechanism, Radiol. Oncol., 37(1): 43-8, 2003.
Sharma, A., et al., "Review on Thermal Energy Storage with Phase Change Materials and Applications", Renewable Sustainable Energy Rev. 13(2), 318-345 (2009).
Sharma, et al., Poloxamer 188 Decreases Susceptibility of Artificial Lipid Membranes to Electroporation, Biophysical Journal, vol. 71, No. 6, pp. 3229-3241, Dec. 1996.
Shiina, S., et al, Percutaneous ethanol injection therapy for hepatocellular carcinoma: results in 146 patients. AJR, 1993, 160: p. 1023-8.
Szot et al., "3D in vitro bioengineered tumors based on collagen I hydrogels." Biomaterials vol. 32, pp. 7905-7912 (2011).

(56) References Cited

OTHER PUBLICATIONS

Talele, S., et al., "Modelling single cell electroporation with bipolar pulse parameters and dynamic pore radii". Journal of Electrostatics, 68(3): p. 261-274 (2010).
Tekle, Ephrem, R. Dean Astumian, and P. Boon Chock, Electroporation by using bipolar oscillating electric field: An Improved method for DNA transfection of NIH 3T3 cells, Proc. Natl. Acad. Sci., vol. 88, pp. 4230-4234, May 1991, Biochemistry.
Thompson, et al., To determine whether the temperature of 2% lignocaine gel affects the initial discomfort which may be associated with its instillation into the male urethra, BJU International (1999), 84, 1035-1037.
Thomson et al., "Investigation of the safety of irreversible electroporation in humans," J Vasc Interv Radiol, 22, pp. 611-621, 2011.
TUNA—Suggested Local Anesthesia Guidelines, no date available.
Verbridge et al., "Oxygen-Controlled Three-Dimensional Cultures to Analyze Tumor Angiogenesis." Tissue Engineering, Part A vol. 16, pp. 2133-2141 (2010).
Vernier, P.T., et al., "Nanoelectropulse-driven membrane perturbation and small molecule permeabilization", Bmc Cell Biology, 7 (2006).
Vidamed, Inc., Transurethral Needle Ablation (TUNA): Highlights from Worldwide Clinical Studies, Vidamed's Office TUNA System, 2001.
Weaver et al., "A brief overview of electroporation pulse strength-duration space: A region where additional Intracellular effects are expected." Bioelectrochemistry vol. 87, pp. 236-243 (2012).
Weaver, Electroporation: A General Phenomenon for Manipulating Cells and Tissues, Journal of Cellular Biochemistry, 51: 426-435, 1993.
Weaver, et al., Theory of Electroporation: A Review, Bioelectrochemistry and Bioenergetics, vol. 41, pp. 136-160, 1996.
Weaver, J. C., Electroporation of biological membranes from multicellular to nano scales, IEEE Tms. Dielectr. Electr. Insul. 10, 754-768 (2003).
Weaver, J.C., "Electroporation of cells and tissues", IEEE Transactions on Plasma Science, 28(1): p. 24-33 (2000).
Weisstein: Cassini Ovals. From MathWorld—A. Wolfram Web Resource; Apr. 30, 2010; http://mathworld.wolfram.com/ (updated May 18, 2011).
Yang et al., "Dielectric properties of human leukocyte subpopulations determined by electrorotation as a cell separation criterion." Biophysical Journal, vol. 76, pp. 3307-3314 (1999).
Yao et al., "Study of transmembrane potentials of inner and outer membranes induced by pulsed-electric-field model and simulation." IEEE Trans Plasma Sci, 2007. 35(5): p. 1541-1549.
Zhang, Y., et al., MR imaging to assess immediate response to irreversible electroporation for targeted ablation of liver tissues: preclinical feasibility studies in a rodent model. Radiology, 2010. 256(2): p. 424-32.
Zimmermann, et al., Dielectric Breakdown of Cell Membranes, Biophysical Journal, vol. 14, No. 11, pp. 881-899, 1974.
Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.
Zlotta, et al., Possible Mechanisms of Action of Transurethral Needle Ablation of the Prostate on Benign Prostatic Hyperplasia Symptoms: a Neurohistochemical Study, Reprinted from Journal of Urology, vol. 157, No. 3, Mar. 1997, pp. 894-899.
Co-Pending Application No. AU 2015259303, filed Oct. 24, 2016.
Co-Pending Application No. CN 201580025135.6, filed Nov. 14, 2016.
Co-Pending Application No. EP 15793361.5, filed Dec. 12, 2016.
Co-Pending Application No. JP 2016-567747, filed Nov. 10, 2016.
Neal II et al., "A Case Report on the Successful Treatment of a Large Soft-Tissue Sarcoma with Irreversible Electroporation," Journal of Clinical Oncology, 29, pp. 1-6, 2011.
Neal II et al., "Experimental Characterization and Numerical Modeling of Tissue Electrical Conductivity during Pulsed Electric Fields for Irreversible Electroporation Treatment Planning," Biomedical Engineering, IEEE Transactions on Biomedical Engineering, vol. 59, pp. 1076-1085, 2012.
Neal II, R. E., et al., "Successful Treatment of a Large Soft Tissue Sarcoma with Irreversible Electroporation", Journal of Clinical Oncology, 29:13, e372-e377 (2011).
Neal II, R.E., et al., "Treatment of breast cancer through the application of irreversible electroporation using a novel minimally invasive single needle electrode." Breast Cancer Research and Treatment, 2010. 123(1): p. 295-301.
Neal II, Robert E. and R.V. Davalos, The Feasibility of Irreversible Electroporation for the Treatment of Breast Cancer and Other Heterogeneous Systems, Ann Biomed Eng, 2009, 37(12): p. 2615-2625.
Nesin et al., "Manipulation of cell volume and membrane pore comparison following single cell permeabilization with 60- and 600-ns electric pulses." Biochimica et Biophysica Acta (BBA)—Biomembranes, vol. 1808, pp. 792-801 (2011).
Neumann, et al., Gene Transfer into Mouse Lyoma Cells by Electroporation in High Electric Fields, J. Embo., vol. 1, No. 7, pp. 841-845, 1982.
Neumann, et al., Permeability Changes Induced by Electric Impulses in Vesicular Membranes, J. Membrane Biol., vol. 10, pp. 279-290, 1972.
Nikolova, B., et al., "Treatment of Melanoma by Electroporation of Bacillus Calmette-Guerin". Biotechnology & Biotechnological Equipment, 25(3): p. 2522-2524 (2011).
Nuccitelli, R., et al., "A new pulsed electric field therapy for melanoma disrupts the tumor's blood supply and causes complete remission without recurrence", Int J Cancer, 125(2): p. 438-45 (2009).
O'Brien et al., "Investigation of the Alamar Blue (resazurin) fluorescent dye for the assessment of mammalian cell cytotoxicity." European Journal of Biochemistry, vol. 267, pp. 5421-5426 (2000).
Okino, et al., Effects of High-Voltage Electrical Impulse and an Anticancer Drug on in Vivo Growing Tumors, Japanese Journal of Cancer Research, vol. 78, pp. 1319-1321, 1987.
Onik, et al., Sonographic Monitoring of Hepatic Cryosurgery in an Experimental Animal Model, AJR American J. of Roentgenology, vol. 144, pp. 1043-1047, May 1985.
Onik, et al., Ultrasonic Characteristics of Frozen Liver, Cryobiology, vol. 21, pp. 321-328, 1984.
Onik, G. and B. Rubinsky, eds. "Irreversible Electroporation: First Patient Experience Focal Therapy of Prostate Cancer. Irreversible Electroporation", ed. B. Rubinsky 2010, Springer Berlin Heidelberg, pp. 235-247.
Onik, G., P. Mikus, and B. Rubinsky, "Irreversible electroporation: implications for prostate ablation." Technol Cancer Res Treat, 2007. 6(4): p. 295-300.
Organ, L.W., Electrophysiological principles of radiofrequency lesion making, Apply. Neurophysiol., 1976. 39: p. 69-76.
Ott, H. C., et al., "Perfusion-decellularized matrix: using nature's platform to engineer a bioartificial heart", Nature Medicine, Nature Publishing Group, New York, NY, US, vol. 14, No. 2, Feb. 1, 2008, pp. 213-221.
Paszek et al., "Tensional homeostasis and the malignant phenotype." Cancer Cell, vol. 8, pp. 241-254 (2005).
Payselj, et al., "The course of tissue permeabilization studied on a mathematical model of a subcutaneous tumor in small animals," IEEE Trans Biomed Eng, vol. 52, pp. 1373-1381, 2005.
PCT International Preliminary Report on Patentability of Corresponding International Application No. PCT/2011/062067, dated May 28, 2013.
PCT International Preliminary Report on Patentability of Corresponding International Application No. PCT/2011/066239, dated Jun. 25, 2013.
PCT International Search Report (dated Aug. 2, 2011), Written Opinion (dated Aug. 2, 2011), and International Preliminary Report on Patentability (dated Apr. 17, 2012) of PCT/US10/53077.
PCT International Search Report (dated Aug. 22, 2012), and Written Opinion (dated Aug. 22, 2012) of PCT/US11/66239.

(56) References Cited

OTHER PUBLICATIONS

PCT International Search Report (dated Aug. 26, 2005), Written Opinion (dated Aug. 26, 2005), and International Preliminary Report on Patentability (dated Jun. 26, 2006) of PCT/US2004/043477.
PCT International Search Report (dated Jan. 19, 2010), Written Opinion (dated Jan. 19, 2010), and International Preliminary Report on Patentability (dated Jan. 4, 2010) of PCT/US09/62806, 15 pgs.
PCT International Search Report (dated Jul. 15, 2010), Written Opinion (dated Jul. 15, 2010), and International Preliminary Report on Patentability (dated Oct. 11, 2011) from PCT/US2010/030629.
PCT International Search Report (dated Jul. 9, 2009), Written Opinion (dated Jul. 9, 2009), and International Preliminary Report on Patentability (dated Nov. 2, 2010) of PCT/US2009/042100.
PCT International Search Report and Written Opinion (dated Jul. 25, 2012) of PCT/US2011/062067.
PCT International Search Report, 4 pgs, (dated Jul. 30, 2010), Written Opinion, 7 pgs, (dated Jul. 30, 2010), and International Preliminary Report on Patentability, 8 pgs, (dated Oct. 4, 2011) from PCT/US2010/029243.
PCT IPRP for PCT/US15/30429 (WO2015175570), dated Nov. 15, 2016.
Phillips, M., Maor, E. & Rubinsky, B. Non-Thermal Irreversible Electroporation for Tissue Decellularization. J. Biomech. Eng, doi:10.1115/1.4001882 (2010).
Piñero, et al., Apoptotic and Necrotic Cell Death Are Both Induced by Electroporation in HL60 Human Promyeloid Leukaemia Cells, Apoptosis, vol. 2, No. 3, 330-336, Aug. 1997.
Polak et al., "On the Electroporation Thresholds of Lipid Bilayers: Molecular Dynamics Simulation Investigations." The Journal of Membrane Biology, vol. 246, pp. 843-850 (2013).
Precision Office TUNA System, When Patient Satisfaction is Your Goal, VidaMed 2001.
Pucihar et al., "Numerical determination of transmembrane voltage induced on irregularly shaped cells." Annals of Biomedical Engineering, vol. 34, pp. 642-652 (2006).
Rajagopal, V. and S.G. Rockson, Coronary restenosis: a review of mechanisms and management, The American Journal of Medicine, 2003, 115(7): p. 547-553.
Rebersek, M. and D. Miklavčič, "Advantages and Disadvantages of Different Concepts of Electroporation Pulse Generation," Automatika 52(2011) 1, 12-19.
Rols, M.P., et al., Highly Efficient Transfection of Mammalian Cells by Electric Field Pulses: Application to Large Volumes of Cell Culture by Using a Flow System, Eur. J. Biochem. 1992, 206, pp. 115-121.
Ron et al., "Cell-based screening for membranal and cytoplasmatic markers using dielectric spectroscopy." Biophysical chemistry, 135 (2008) pp. 59-68.
Rossmeisl et al., "Pathology of non-thermal irreversible electroporation (N-TIRE)-induced ablation of the canine brain." Journal of Veterinary Science vol. 14, pp. 433-440 (2013).
Rossmeisl, "New Treatment Modalities for Brain Tumors in Dogs and Cats." Veterinary Clinics of North America: Small Animal Practice 44, pp. 1013-1038 (2014).
Rubinsky et al., "Optimal Parameters for the Destruction of Prostate Cancer Using Irreversible Electroporation." The Journal of Urology, 180 (2008) pp. 2668-2674.
Rubinsky, B., "Irreversible Electroporation in Medicine", Technology in Cancer Research and Treatment, vol. 6, No. 4, Aug. 1, 2007, pp. 255-259.
Rubinsky, B., ed, Cryosurgery. Annu Rev. Biomed. Eng. vol. 2 2000. 157-187.
Rubinsky, B., et al., "Irreversible Electroporation: A New Ablation Modality—Clinical Implications" Technol. Cancer Res. Treatment 6(1), 37-48 (2007).
Sabuncu et al., "Dielectrophoretic separation of mouse melanoma clones." Biomicrofluidics, vol. 4, 7 pages (2010).
Salford, L.G., et al., "A new brain tumour therapy combining bleomycin with in vivo electropermeabilization", Biochem. Biophys. Res. Commun., 194(2): 938-943 (1993).

Salmanzadeh et al., "Investigating dielectric properties of different stages of syngeneic murine ovarian cancer cells" Biomicrofluidics 7, 011809 (2013), 12 pages.
Salmanzadeh et al., "Dielectrophoretic differentiation of mouse ovarian surface epithelial cells, macrophages, and fibroblasts using contactless dielectrophoresis." Biomicrofluidics, vol. 6, 13 Pages (2012).
Co-pending U.S. Appl. No. 15/186,653, filed Jun. 20, 2016.
Co-Pending Application No. PCT/US04/43477, filed Dec. 21, 2004.
Co-Pending Application No. PCT/US09/42100, filed Apr. 29, 2009.
Co-Pending Application No. PCT/US09/62806, filed Oct. 30, 2009.
Co-Pending Application No. PCT/US10/30629, filed Apr. 9, 2010.
Co-Pending Application No. PCT/US10/53077, filed Oct. 18, 2010.
Co-Pending Application No. PCT/US11/62067, filed Nov. 23, 2011.
Co-Pending Application No. PCT/US11/66239, filed Dec. 20, 2011.
Co-Pending Application No. PCT/US15/30429, filed May 12, 2015.
Co-Pending Application No. PCT/US15/30429, International Search Report and Written Opinion dated Oct. 16, 2015, 19 pages.
Co-pending Application No. PCT/US2010/029243, filed Mar. 30, 2010, published as WO 2010/117806 on Oct. 14, 2010.
Co-Pending Application No. PCT/US2015/030429, Published on Nov. 19, 2015 as WO 2015/175570.
Co-Pending U.S. Appl. No. 12/491,151, filed Jun. 24, 2009.
Co-Pending U.S. Appl. No. 13/332,133, filed Dec. 20, 2011.
Co-Pending U.S. Appl. No. 13/550,307, filed Jul. 16, 2012.
Co-Pending U.S. Appl. No. 13/919,640, filed Jun. 17, 2013.
Co-Pending U.S. Appl. No. 13/958,152, filed Aug. 2, 2013.
Co-Pending U.S. Appl. No. 13/989,175, filed May 23, 2013.
Co-Pending U.S. Appl. No. 14/012,832, filed Aug. 28, 2013.
Co-Pending U.S. Appl. No. 14/017,210, filed Sep. 3, 2013.
Co-Pending U.S. Appl. No. 14/627,046, filed Feb. 20, 2015.
Co-Pending U.S. Appl. No. 14/686,380, filed Apr. 14, 2015.
Co-Pending U.S. Appl. No. 14/940,863, filed Nov. 13, 2015 and Published as US 2016/0066977 on Mar. 10, 2016.
Corovic et al., "Analytical and numerical quantification and comparison of the local electric field in the tissue for different electrode configurations," Biomed Eng Online, 6, 14 pages, 2007.
Cowley, Good News for Boomers, Newsweek, Dec. 30, 1996/Jan. 6, 1997.
Cox, et al., Surgical Treatment of Atrial Fibrillation: A Review, Europace (2004) 5, S20-S-29.
Crowley, Electrical Breakdown of Biomolecular Lipid Membranes as an Electromechanical Instability, Biophysical Journal, vol. 13, pp. 711-724, 1973.
Dahl et al., "Nuclear shape, mechanics, and mechanotransduction." Circulation Research vol. 102, pp. 1307-1318 (2008).
Daud, A.I., et al., "Phase I Trial of Interleukin-12 Plasmid Electroporation in Patients With Metastatic Melanoma," Journal of Clinical Oncology, 26, 5896-5903, Dec. 20, 2008.
Davalos et al., "Electrical impedance tomography for imaging tissue electroporation," IEEE Transactions on Biomedical Engineering, 51, pp. 761-767, 2004.
Davalos et al., "Theoretical analysis of the thermal effects during in vivo tissue electroporation." Bioelectrochemistry, vol. 61(1-2): pp. 99-107, 2003.
Davalos et al., "Tissue ablation with irreversible electroporation." Annals of Biomedical Engineering, vol. 33, No. 2, pp. 223-231 (Feb. 2005).
Davalos, et al., A Feasibility Study for Electrical Impedance Tomography as a Means to Monitor Tissue Electroporation for Molecular Medicine, IEEE Transactions on Biomedical Engineering, vol. 49, No. 4, Apr. 2002.
Davalos, R. V. & Rubinsky, B. Temperature considerations during irreversible electroporation. International Journal of Heat and Mass Transfer 51, 5617-5622, doi:10.1016/j.ijheatmasstransfer.2008.04.046 (2008).
Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002.
De Vuyst, E., et al., "In situ bipolar Electroporation for localized cell loading with reporter dyes and investigating gap functional coupling", Biophysical Journal, 94(2): p. 469-479 (2008).

(56) References Cited

OTHER PUBLICATIONS

Dean, Nonviral Gene Transfer to Skeletal, Smooth, and Cardiac Muscle in Living Animals, Am J. Physiol Cell Physiol 289: 233-245, 2005.

Demirbas, M. F., "Thermal Energy Storage and Phase Change Materials: An Overview" Energy Sources Part B 1(1), 85-95 (2006).

Dev, et al., Medical Applications of Electroporation, IEEE Transactions of Plasma Science, vol. 28, No. 1, pp. 206-223, Feb. 2000.

Dev, et al., Sustained Local Delivery of Heparin to the Rabbit Arterial Wall with an Electroporation Catheter, Catheterization and Cardiovascular Diagnosis, Nov. 1998, vol. 45, No. 3, pp. 337-343.

Duraiswami, et al., Boundary Element Techniques for Efficient 2-D and 3-D Electrical Impedance Tomography, Chemical Engineering Science, vol. 52, No. 13, pp. 2185-2196, 1997.

Duraiswami, et al., Efficient 2D and 3D Electrical Impedance Tomography Using Dual Reciprocity Boundary Element Techniques, Engineering Analysis with Boundary Elements 22, (1998) 13-31.

Duraiswami, et al., Solution of Electrical Impedance Tomography Equations Using Boundary Element Methods, Boundary Element Technology XII, 1997, pp. 226-237.

Edd et al., "Mathematical modeling of irreversible electroporation for treatment planning." Technology in Cancer Research and Treatment, vol. 6, No. 4, pp. 275-286 (2007).

Edd, J. et al., In-Vivo Results of a New Focal Tissue Ablation Technique: Irreversible Electroporaton, IEEE Trans. Biomed. Eng. 53 (2006) p. 1409-1415.

Ellis TL, Garcia PA, Rossmeisl JH, Jr., Henao-Guerrero N, Robertson J, et al., "Nonthermal irreversible electroporation for intracranial surgical applications. Laboratory investigation", J Neurosurg 114: 681-688 (2011).

Eppich et al., "Pulsed electric fields for selection of hematopoietic cells and depletion of tumor cell contaminants." Nature Biotechnology 18, pp. 882-887 (2000).

Erez, et al., Controlled Destruction and Temperature Distributions in Biological Tissues Subjected to Monoactive Electrocoagulation, Transactions of the ASME: Journal of Mechanical Design, vol. 102, Feb. 1980.

Ermolina et al., "Study of normal and malignant white blood cells by time domain dielectric spectroscopy." IEEE Transactions on Dielectrics and Electrical Insulation, 8 (2001) pp. 253-261.

Esser, A.T., et al., "Towards solid tumor treatment by irreversible electroporation: intrinsic redistribution of fields and currents in tissue". Technol Cancer Res Treat, 6(4): p. 261-74 (2007).

Esser, A.T., et al., "Towards Solid Tumor Treatment by Nanosecond Pulsed Electric Fields". Technology in Cancer Research & Treatment, 8(4): p. 289-306 (2009).

Faroja, M., et al., "Irreversible Electroporation Ablation: Is the entire Damage Nonthermal?", Radiology, 266(2), 462-470 (2013).

Fischbach et al., "Engineering tumors with 3D scaffolds." Nat Meth 4, pp. 855-860 (2007).

Flanagan et al., "Unique dielectric properties distinguish stem cells and their differentiated progeny." Stem Cells, vol. 26, pp. 656-665 (2008).

Fong et al., "Modeling Ewing sarcoma tumors in vitro with 3D scaffolds." Proceedings of the National Academy of Sciences vol. 110, pp. 6500-6505 (2013).

Foster RS, "High-intensity focused ultrasound in the treatment of prostatic disease", European Urology, 1993, vol. 23 Suppl 1, pp. 29-33.

Foster, R.S., et al., Production of Prostatic Lesions in Canines Using Transrectally Administered High-Intensity Focused Ultrasound. Eur. Urol., 1993; 23: 330-336.

Fox, et al., Sampling Conductivity Images via MCMC, Mathematics Department, Auckland University, New Zealand, May 1997.

Freeman, S.A., et al., Theory of Electroporation of Planar Bilayer-Membranes—Predictions of the Aqueous Area, Change in Capacitance, and Pore-Pore Separation. Biophysical Journal, 67(1): p. 42-56 (1994).

Garcia et al., "Irreversible electroporation (IRE) to treat brain cancer." ASME Summer Bioengineering Conference, Marco Island, FL, Jun. 25-29, 2008, 2 pages.

Garcia et al., "Non-thermal irreversible electroporation (N-TIRE) and adjuvant fractionated radiotherapeutic multimodal therapy for intracranial malignant glioma in a canine patient," Technol Cancer Res Treat, 10, pp. 73-83, 2011.

Garcia et al., "Towards a Predictive Model of Electroporation-Based Therapies using Pre-Pulse Electrical Measurements" Abstract presented in the IEEE Engineering in Medicine and Biology Conference in Aug. 28, 2012 in San Diego, California, 4 pages.

Garcia P.A., et al., "7.0-T Magnetic Resonance Imaging Characterization of Acute Blood-Brain-Barrier Disruption Achieved with Intracranial Irreversible Electroporation", PLOS One, Nov. 2012, 7:11, e50482.

Garcia P.A., et al., "Pilot study of irreversible electroporation for intracranial surgery", Conf Proc IEEE Eng Med Biol Soc, 2009:6513-6516, 2009.

Garcia, et al., "A Parametric Study Delineating Irreversible Electroporation from Thermal Damage Based on a Minimally Invasive Intracranial Procedure," Biomed Eng Online, vol. 10:34, 22 pages, 2011.

Garcia, P. et al. Intracranial nonthermal irreversible electroporation: in vivo analysis. J Membr Biol 236, 127-136 (2010).

Gascoyne et al., "Membrane changes accompanying the induced differentiation of Friend murine erythroleukemia cells studied by dielectrophoresis." Biochimica et Biophysica Acta (BBA)—Biomembranes, vol. 1149, pp. 119-126 (1993).

Gauger, et al., A Study of Dielectric Membrane Breakdown in the Fucus Egg, J. Membrane Biol., vol. 48, No. 3, pp. 249-264, 1979.

Gehl, et al., In Vivo Electroporation of Skeletal Muscle: Threshold, Efficacy and Relation to Electric Field Distribution, Biochimica et Biphysica Acta 1428, 1999, pp. 233-240.

Gençer, et al., Electrical Impedance Tomography: Induced-Current Imaging Achieved with a Multiple Coil System, IEEE Transactions on Biomedical Engineering, vol. 43, No. 2, Feb. 1996.

Gilbert, et al., Novel Electrode Designs for Electrochemotherapy, Biochimica et Biophysica Acta 1334, 1997, pp. 9-14.

Gilbert, et al., The Use of Ultrasound Imaging for Monitoring Cryosurgery, Proceedings 6th Annual Conference, IEEE Engineering in Medicine and Biology, 107-111, 1984.

Gilbert, T. W., et al., "Decellularization of tissues and organs", Biomaterials, Elsevier Science Publishers, Barking, GB, vol. 27, No. 19, Jul. 1, 2006, pp. 3675-3683.

Gimsa et al., "Dielectric spectroscopy of single human erythrocytes at physiological ionic strength: dispersion of the cytoplasm." Biophysical Journal, vol. 71, pp. 495-506 (1996).

Glidewell, et al., The Use of Magnetic Resonance Imaging Data and the Inclusion of Anisotropic Regions in Electrical Impedance Tomography, Biomed. Sci. Instrum. 1993; 29: 251-7.

Solberg, A. and Rubinsky, B., "A statistical model for multidimensional irreversible electroporation cell death in tissue." Biomed Eng Online, 9, 13 pages, 2010.

Gothelf, et al., Electrochemotherapy: Results of Cancer Treatment Using Enhanced Delivery of Bleomycin by Electroporation, Cancer Treatment Reviews 2003: 29: 371-387.

Gowrishankar T.R., et al., "Microdosimetry for conventional and supra-electroporation in cells with organelles". Biochem Biophys Res Commun, 341(4): p. 1266-76 (2006).

Griffiths, et al., A Dual-Frequency Electrical Impedance Tomography System, Phys. Med. Biol., 1989, vol. 34, No. 10, pp. 1465-1476.

Griffiths, The Importance of Phase Measurement in Electrical Impedance Tomography, Phys. Med. Biol., 1987, vol. 32, No. 11, pp. 1435-1444.

Griffiths, Tissue Spectroscopy with Electrical Impedance Tomography: Computer Simulations, IEEE Transactions on Biomedical Engineering, vol. 42, No. 9, Sep. 1995.

Gumerov, et al., The Dipole Approximation Method and Its Coupling with the Regular Boundary Element Method for Efficient Electrical Impedance Tomography, Boundary Element Technology XIII, 1999.

Hapala, Breaking the Barrier: Methods for Reversible Permeabilization of Cellular Membranes, Critical Reviews in Biotechnology, 17(2): 105-122, 1997.

(56) References Cited

OTHER PUBLICATIONS

Helczynska et al., "Hypoxia promotes a dedifferentiated phenotype in ductal breast carcinoma in situ." Cancer Research, vol. 63, pp. 1441-1444 (2003).
Heller, et al., Clinical Applications of Electrochemotherapy, Advanced Drug Delivery Reviews, vol. 35, pp. 119-129, 1999.
Hjouj, M., et al., "Electroporation-Induced BBB Disruption and Tissue Damage Depicted by MRI", Neuro-Oncology 13: Issue suppl 3, abstract ET-32 (2011).
Hjouj, M., et al., "MRI Study on Reversible and Irreversible Electroporation Induced Blood Brain Barrier Disruption", PLOS One, Aug. 2012, 7:8, e42817.
Hjouj, Mohammad et al., "Electroporation-Induced BBB Disruption and Tissue Damage Depicted by MRI," Abstracts from 16th Annual Scientific Meeting of the Society for Neuro-Oncology in Conjunction with the AANS/CNS Section on Tumors, Nov. 17-20, 2011, Orange County California, Neuro-Oncology Supplement, vol. 13, Supplement 3, p. iii114.
Ho, et al., Electroporation of Cell Membranes: A Review, Critical Reviews in Biotechnology, 16(4): 349-362, 1996.
Holder, et al., Assessment and Calibration of a Low-Frequency System for Electrical Impedance Tomography (EIT), Optimized for Use in Imaging Brain Function in Ambulant Human Subjects, Annals of the New York Academy of Science, vol. 873, Issue 1, Electrical BI, pp. 512-519, 1999.
Huang, et al., Micro-Electroporation: Improving the Efficiency and Understanding of Electrical Permeabilization of Cells, Biomedical Microdevices, vol. 2, pp. 145-150, 1999.
Hughes, et al., An Analysis of Studies Comparing Electrical Impedance Tomography with X-Ray Videofluoroscopy in the Assessment of Swallowing, Physiol. Meas. 15, 1994, pp. A199-A209.
Ibey et al., "Selective cytotoxicity of intense nanosecond-duration electric pulses in mammalian cells." Biochimica Et Biophysica Acta-General Subjects, vol. 1800, pp. 1210-1219 (2010).
Issa, et al., The TUNA Procedure for BPH: Review of the Technology: The TUNA Procedure for BPH: Basic Procedure and Clinical Results, Reprinted from Infections in Urology, Jul./Aug. 1998 and Sep./Oct. 1998.
Ivanuša, et al., MRI Macromolecular Contrast Agents as Indicators of Changed Tumor Blood Flow, Radiol. Oncol. 2001; 35(2): 139-47.
Ivorra et al., "In vivo electric impedance measurements during and after electroporation of rat live." Bioelectrochemistry, vol. 70, pp. 287-295 (2007).
Ivorra et al., "In vivo electrical conductivity measurements during and after tumor electroporation: conductivity changes reflect the treatment outcome." Physics in Medicine and Biology, vol. 54, pp. 5949-5963 (2009).
Ivorra, "Bioimpedance monitoring for physicians: an overview." Biomedical Applications Group, 35 pages (2002).
Co-pending U.S. Appl. No. 15/423,986, filed Feb. 3, 2017.
Co-pending U.S. Appl. No. 15/424,335, filed Feb. 3, 2017.
Co-pending U.S. Appl. No. 16/404,392, Petition for Priority, filed Jun. 4, 2019, 2 pages.
Co-pending U.S. Appl. No. 16/404,392, Preliminary Amendment, filed Jun. 4, 2019, 9 pages.
Co-Pending Application No. JP 2016-567747, First Office Action (Translation) dated Feb. 21, 2019, 4 pages.
Co-Pending Application No. JP 2016-567747, First Office Action dated Feb. 21, 2019, 4 pages.
Co-Pending U.S. Appl. No. 13/332,133, Amendment with RCE after Board Decision, dated Mar. 29, 2019, 16 pages.
Co-Pending U.S. Appl. No. 13/332,133, Board Decision dated Jan. 29, 2019, 13 pages.
Co-Pending U.S. Appl. No. 13/332,133, Notice of Allowance, dated May 31, 2019, 5 pages.
Co-Pending U.S. Appl. No. 13/332,133, Office Actions and Responses through Mar. 2018, 221 pages.
Co-Pending U.S. Appl. No. 14/017,210, Acceptance of 312 Amendment dated Sep. 12, 2018, 1 page.
Co-Pending U.S. Appl. No. 14/017,210, AFCP dated Aug. 13, 2018, 9 pages.
Co-Pending U.S. Appl. No. 14/017,210, Final Office Action dated Aug. 30, 2016, 11 pages.
Co-Pending U.S. Appl. No. 14/017,210, Notice of Allowance (dated Dec. 12, 2018 RCE) dated Jan. 9, 2019, 5 pages.
Co-Pending U.S. Appl. No. 14/017,210, Notice of Allowance dated Sep. 12, 2018, 7 pages.
Co-Pending U.S. Appl. No. 14/017,210, Petition dated Dec. 11, 2015, 5 pages.
Co-Pending U.S. Appl. No. 14/017,210, Petition Decision dated Aug. 12, 2016, 9 pages.
Co-Pending U.S. Appl. No. 14/017,210, Petition Decision dated Aug. 2, 2016, 5 pages.
Co-Pending U.S. Appl. No. 14/017,210, RCE dated Aug. 1, 2017, 13 pages.
Co-Pending U.S. Appl. No. 14/017,210, RCE dated Nov. 30, 2016, 13 pages.
Co-Pending U.S. Appl. No. 14/017,210, Response to Dec. 15, 2016 Non-Final Office Action dated Mar. 20, 2017, 9 pages.
Co-Pending U.S. Appl. No. 14/017,210, Response to May 1, 2017 Final Office Action dated Aug. 1, 2017, 10 pages.
Co-Pending U.S. Appl. No. 14/017,210, Response to Non-Final Office Action dated Mar. 8, 2016, 16 pages.
Co-Pending U.S. Appl. No. 14/627,046, Amendment dated Jun. 29, 2017, 8 pages.
Co-Pending U.S. Appl. No. 14/627,046, Final Office Action dated Sep. 14, 2017, 11 pages.
Co-Pending U.S. Appl. No. 14/627,046, Interview Summary dated dated Apr. 27, 2018, 3 pages.
Co-Pending U.S. Appl. No. 14/627,046, Non-Final Office Action dated Feb. 15, 2018, 12 pages.
Co-Pending U.S. Appl. No. 14/627,046, Non-Final Office Action dated Mar. 29, 2017, 9 pages.
Co-Pending U.S. Appl. No. 14/627,046, Notice of Allowance dated Sep. 19, 2018, 7 pages.
Co-Pending U.S. Appl. No. 14/627,046, Response to Sep. 14, 2017 Final Office Action dated Dec. 14, 2017, 7 pages.
Co-Pending U.S. Appl. No. 14/627,046, Rule 132 Affidavit and Response to Feb. 15, 2018 Non-Final Office Action, dated Jun. 15, 2018, 13 pages.
Co-Pending U.S. Appl. No. 16/152,743, filed Oct. 5, 2018.
Co-Pending U.S. Appl. No. 16/232,962, filed Dec. 26, 2018.
Co-pending U.S. Appl. No. 16/404,392, Preliminary Amendment, filed Jun. 6, 2019, 5 pages.
Co-Pending U.S. Appl. No. 14/686,380, Final Office Action dated May 9, 2018, 14 pages.
Co-Pending U.S. Appl. No. 14/686,380, Non-Final Office Action dated May 1, 2019, 26 pages.
Co-Pending U.S. Appl. No. 14/686,380, Non-Final Office Action dated Nov. 22, 2017, 11 pages.
Co-Pending U.S. Appl. No. 14/686,380, Response to Jul. 19, 2017 Restriction Requirement, dated Sep. 15, 2017, 2 pages.
Co-Pending U.S. Appl. No. 14/686,380, Response to May 9, 2018 Final Office Action with RCE, dated Aug. 30, 2018, 14 pages.
Co-Pending U.S. Appl. No. 14/686,380, Response to Nov. 22, 2017 Non-Final Office Action dated Mar. 28, 2018, 11 pages.
Co-Pending U.S. Appl. No. 14/686,380, Restriction Requirement Jul. 19, 2017, 7 pages.
Co-pending U.S. Appl. No. 15/843,888, filed Dec. 15, 2017.
Co-pending U.S. Appl. No. 15/881,414, filed Jan. 26, 2018.
Co-Pending U.S. Appl. No. 14/017,210, Final Office Action dated Apr. 11, 2018, 10 pages.
Co-Pending U.S. Appl. No. 14/017,210, Final Office Action dated May 1, 2017, 11 pages.
Co-Pending U.S. Appl. No. 14/017,210, Non-Final Office Action dated Dec. 15, 2016, 8 pages.
Co-Pending U.S. Appl. No. 14/017,210, Non-Final Office Action dated Oct. 25, 2017, 9 pages.
Co-Pending U.S. Appl. No. 14/017,210, Non-Final Office Action, dated Sep. 8, 2015, 8 pages.
Co-Pending U.S. Appl. No. 14/017,210, Priority Petition Dec. 11, 2015, 5 pages.

(56) References Cited

OTHER PUBLICATIONS

Co-Pending U.S. Appl. No. 14/017,210, RCE filed Aug. 1, 2017, 13 pages.
Co-Pending U.S. Appl. No. 14/017,210, Response to Aug. 30, 2016 Final Office Action, dated Nov. 30, 2016, 10 pages.
Co-Pending U.S. Appl. No. 14/017,210, Response to Oct. 25, 2017 Non-Final Office Action dated Jan. 25, 2018, 11 pages.
Co-Pending U.S. Appl. No. 14/017,210, Response to Sep. 8, 2015 Non-Final Office Action, dated Mar. 8, 2016, 57 pages.
Garcia, Paulo A., Robert E. Neal II and Rafael V. Davalos, Chapter 3, Non-Thermal Irreversible Electroporation for Tissue Ablation, In: Electroporation in Laboratory and Clinical Investigations ISBN 978-1-61668-327-6 Editors: Enrico P. Spugnini and Alfonso Baldi, 2010, 22 pages.
Kotnik et al., "Sensitivity of transmembrane voltage induced by applied electric fields—a theoretical analysis", Bioelectrochemistry and Bioenergetics,vol. 43, Issue 2, 1997, pp. 285-291.
Neal RE II, et al. (2013) Improved Local and Systemic Anti-Tumor Efficacy for Irreversible Electroporation in Immunocompetent versus Immunodeficient Mice. PLoS One 8(5): e64559. https://doi.org/10.1371/journal.pone.0064559.
Tibbitt et al., "Hydrogels as Extracellular Matrix Mimics for 3D Cell Culture", Jul. 2009, Biotechnol Bioeng, 103(4),655-663.
Wimmer, Thomas, et al., "Planning Irreversible Electroporation (IRE) in the Porcine Kidney: Are Numerical Simulations Reliable for Predicting Empiric Ablation Outcomes?", Cardiovasc Intervent Radiol. Feb. 2015; 38(1): 182-190. doi:10.1007/s00270-014-0905-2.
Co-Pending U.S. Appl. No. 12/491,151, Final Rejection dated Apr. 20, 2012, 8 pages.
Co-Pending U.S. Appl. No. 12/491,151, Non-Final Rejection dated Apr. 4, 2014, 12 pages.
Co-Pending U.S. Appl. No. 12/491,151, Non-Final Rejection dated Dec. 28, 2011, 7 pages.
Co-Pending U.S. Appl. No. 12/491,151, Official Notice of Allowance dated Feb. 12, 2015, 2 pages.
Co-Pending U.S. Appl. No. 12/491,151, Official Notice of Allowance dated Nov. 6, 2014, 15 pages.
Co-Pending U.S. Appl. No. 12/491,151, Official Notice of Allowance dated Oct. 15, 2014, 5 pages.
Co-Pending U.S. Appl. No. 12/491,151, Requirement for Restriction/Election dated Dec. 2, 2011, 6 pages.
Co-Pending U.S. Appl. No. 12/491,151, Response to Apr. 4, 2014 Non-Final Rejection dated Aug. 22, 2014, 12 pages.
Co-Pending U.S. Appl. No. 12/491,151, Response to Non-Final Rejection dated Mar. 28, 2012, 10 pages.
Co-Pending U.S. Appl. No. 12/491,151, Response to Requirement for Restriction/Election dated Dec. 13, 2011, 2 pages.
Co-Pending U.S. Appl. No. 12/491,151, Response with RCE to Final Rejection dated Aug. 20, 2012, 14 pages.
Co-Pending U.S. Appl. No. 12/491,151, Supplemental Amendment dated Dec. 17, 2012, 6 pages.
Co-Pending U.S. Appl. No. 12/757,901, File History 2018.
Co-Pending U.S. Appl. No. 12/906,923, Office Actions and Responses Jul. 2017, 55 pages.
Co-Pending U.S. Appl. No. 14/558,631, Final Office Action dated Sep. 1, 2017, 9 pages.
Co-Pending U.S. Appl. No. 14/558,631, Non-Final Office Action dated Jan. 8, 2018, 5 pages.
Co-Pending U.S. Appl. No. 14/558,631, Non-Final Office Action dated Mar. 13, 2017, 10 pages.
Co-Pending U.S. Appl. No. 14/558,631, Notice of Allowance dated Jul. 17, 2018, 2 pages.
Co-Pending U.S. Appl. No. 14/558,631, Notice of Allowance dated Jun. 21, 2018, 7 pages.
Co-Pending U.S. Appl. No. 14/558,631, Response to Jan. 8, 2018 Non-Final Office Action dated Apr. 9, 2018, 8 pages.
Co-Pending U.S. Appl. No. 14/558,631, Response to Mar. 13, 2017 Non-Final Office Action dated Jul. 13, 2017, 10 pages.
Co-Pending U.S. Appl. No. 14/558,631, Response to Sep. 1, 2017 Final Office Action dated Dec. 1, 2017, 7 pages.
Co-Pending U.S. Appl. No. 14/808,679, Restriction Requirement dated Mar. 19, 2018, 7 pages.
Co-Pending U.S. Appl. No. 14/808,679, Final Office Action dated Jan. 11, 2019, 12 pages.
Co-Pending U.S. Appl. No. 14/808,679, Interview Summary dated Apr. 26, 2019, 3 pages.
Co-Pending U.S. Appl. No. 14/808,679, Non-Final Office Action dated Sep. 10, 2018, 12 pages.
Co-Pending U.S. Appl. No. 14/808,679, Petition for Priority and Supplemental Response, filed May 8, 2019, 25 pages.
Co-Pending U.S. Appl. No. 14/808,679, Preliminary Amendment, filed Jul. 27, 2015, 9 pages.
Co-Pending U.S. Appl. No. 14/808,679, RCE filed Apr. 11, 2019, 8 pages.
Co-Pending U.S. Appl. No. 14/808,679, Response to Mar. 19, 2018 Restriction Requirement dated May 21, 2018, 2 pages.
Co-Pending U.S. Appl. No. 14/808,679, Response to Sep. 10, 2018 Non-Final Office Action dated Dec. 10, 2018, 9 pages.
Co-pending U.S. Appl. No. 15/186,653, Notice of Allowance dated Aug 1, 2018, 7 pages.
Co-pending U.S. Appl. No. 15/186,653, Notice of Allowance dated Mar. 20, 2019, 9 pages.
Co-pending U.S. Appl. No. 15/424,335 Examiner Interview Request (date Jul. 2, 2018), 1 page.
Co-pending U.S. Appl. No. 15/424,335 Examiner Interview Summary (dated Jul. 20, 2018), 3 pages.
Co-pending U.S. Appl. No. 15/424,335 Non-Final Office Action dated Apr. 26, 2018, 9 pages.
Co-pending U.S. Appl. No. 15/424,335 Notice of Allowance dated Sep. 21, 2018, 7 pages.
Co-pending U.S. Appl. No. 15/424,335 Preliminary Amendment filed Apr. 17, 2017, 17 pages.
Co-pending U.S. Appl. No. 15/424,335 Response to Non-Final Office Action dated Jul. 26, 2018, 13 pages.
Co-pending U.S. Appl. No. 15/881,414 Amendment and Petition for Priority Claim dated Jul. 26, 2018, 26 pages.
Co-pending U.S. Appl. No. 15/881,414 Apr. 26, 2018 Non-Final Office Action, 8 pages.
Co-pending U.S. Appl. No. 15/881,414 Notice of Allowance dated Oct. 24, 2018, 7 pages.
Co-pending U.S. Appl. No. 15/881,414 Petition Decision dated Oct. 9, 2018, 9 pages.
Co-pending U.S. Appl. No. 16/177,745, filed Nov. 1, 2018.
Co-pending U.S. Appl. No. 16/177,745, Preliminary Amendment dated Dec. 19, 2018, 7 pages.
Co-pending U.S. Appl. No. 16/275,429, filed Feb. 14, 2019.
Co-pending U.S. Appl. No. 16/280,511, filed Feb. 20, 2019.
Co-pending U.S. Appl. No. 16/372,520, filed Apr. 2, 2019.
Co-pending U.S. Appl. No. 16/375,878, filed Apr. 5, 2019.
Co-pending U.S. Appl. No. 16/404,392, filed May 6, 2019.
Co-pending Application No. JP 2016-567747 Amendment filed Jul. 18, 2019, 7 pgs.
Co-pending Application No. JP 2016-567747 English version of amended claims filed Jul. 18, 2019, 6 pgs.
Co-pending Application No. JP 2019-133057 filed Jul. 18, 2019, 155 pgs.
Co-pending Application No. JP 2019-133057 Filing receipt for application filed Jul. 18, 2019, 2 pg.

* cited by examiner

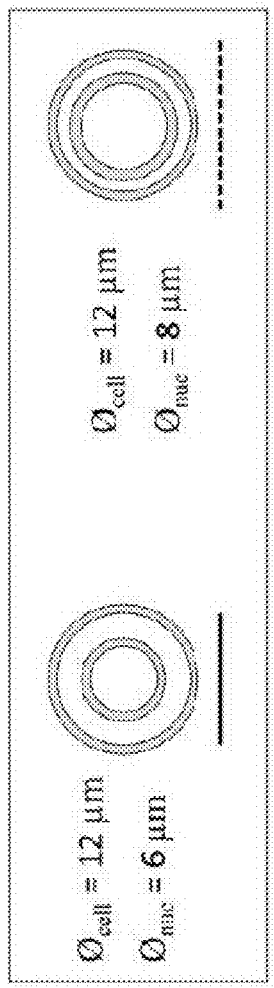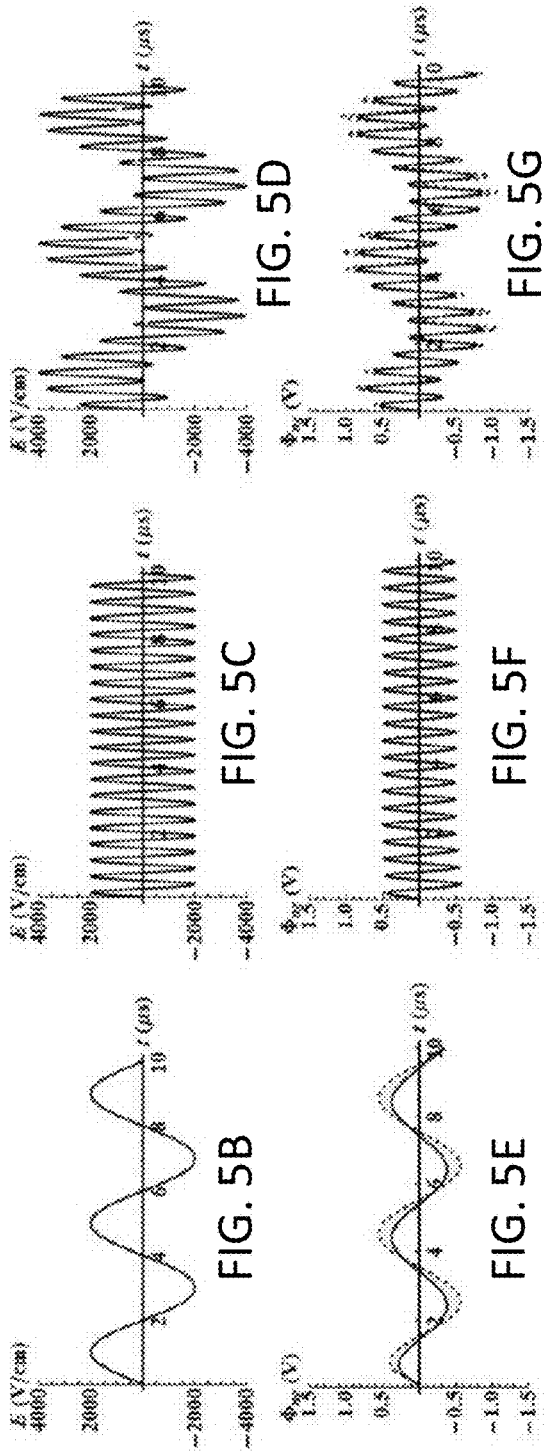

Table: Parameter values used in parametric studies on the TMP

| Parameter | Value | Units | Reference |
|---|---|---|---|
| membrane thickness | 5 | [nm] | Alberts 1994 'Mollecular Biology of the cell' |
| cell radius | 8.88 | [μm] | Sano 2011 |
| membrane conductivity | 3e-7 | [S/m] | Miklavcic 2006 / Gascoyne 1993 |
| membrane capacitance | 0.01518 | [F/m²] | MDA-MB231 Sano 2011 |
| cytoplasmic conductivity | 0.3 | [S/m] | Miklavcic 2006 / Hozel 1992 |
| cytoplasmic permittivity | 50 | | Sano 2011 |
| nucleus-cytoplasm ratio | 0.5 | | |

FIG. 10

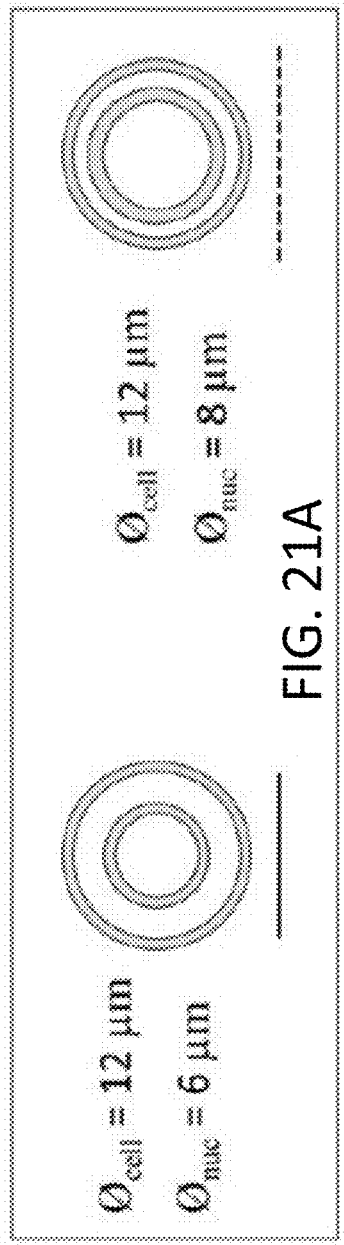
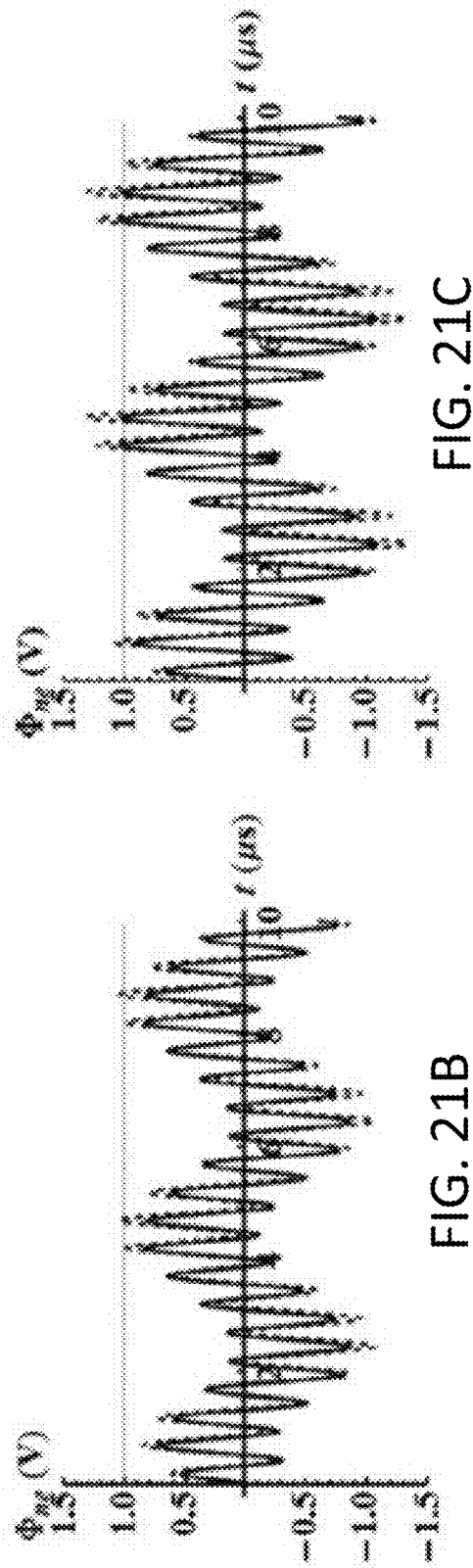
FIG. 21A
FIG. 21B
FIG. 21C

| Parameter | Value |
|---|---|
| $\varepsilon_0 / (m^{-3} kg^{-1} s^4 A^2)$ | $8.85 \times 10^{-12}$ |
| $\sigma_m / (S^1 m^{-1})$ | 0.2 |
| $\varepsilon_m$ | $80\varepsilon_0$ |
| $d_{mem} / m$ | $5 \times 10^{-9}$ |
| $r_c / m$ | $6.55 \times 10^{-6}$ |
| $\sigma_{mem} / (S^1 m^{-1})$ | $3 \times 10^{-7}$ |
| $\varepsilon_{mem}$ | $8.57\varepsilon_0$ |
| $\sigma_c / (S^1 m^{-1})$ | 0.3 |
| $\varepsilon_c$ | $154.4\varepsilon_0$ |
| NCR | 0.8 |
| $d_{ne} / m$ | $40 \times 10^{-9}$ |
| $\sigma_{ne} / (S^1 m^{-1})$ | $6 \times 10^{-3}$ |
| $\varepsilon_{ne}$ | $28\varepsilon_0$ |
| $\sigma_{np} / (S^1 m^{-1})$ | 1.35 |
| $\varepsilon_{np}$ | $52\varepsilon_0$ |

FIG. 28

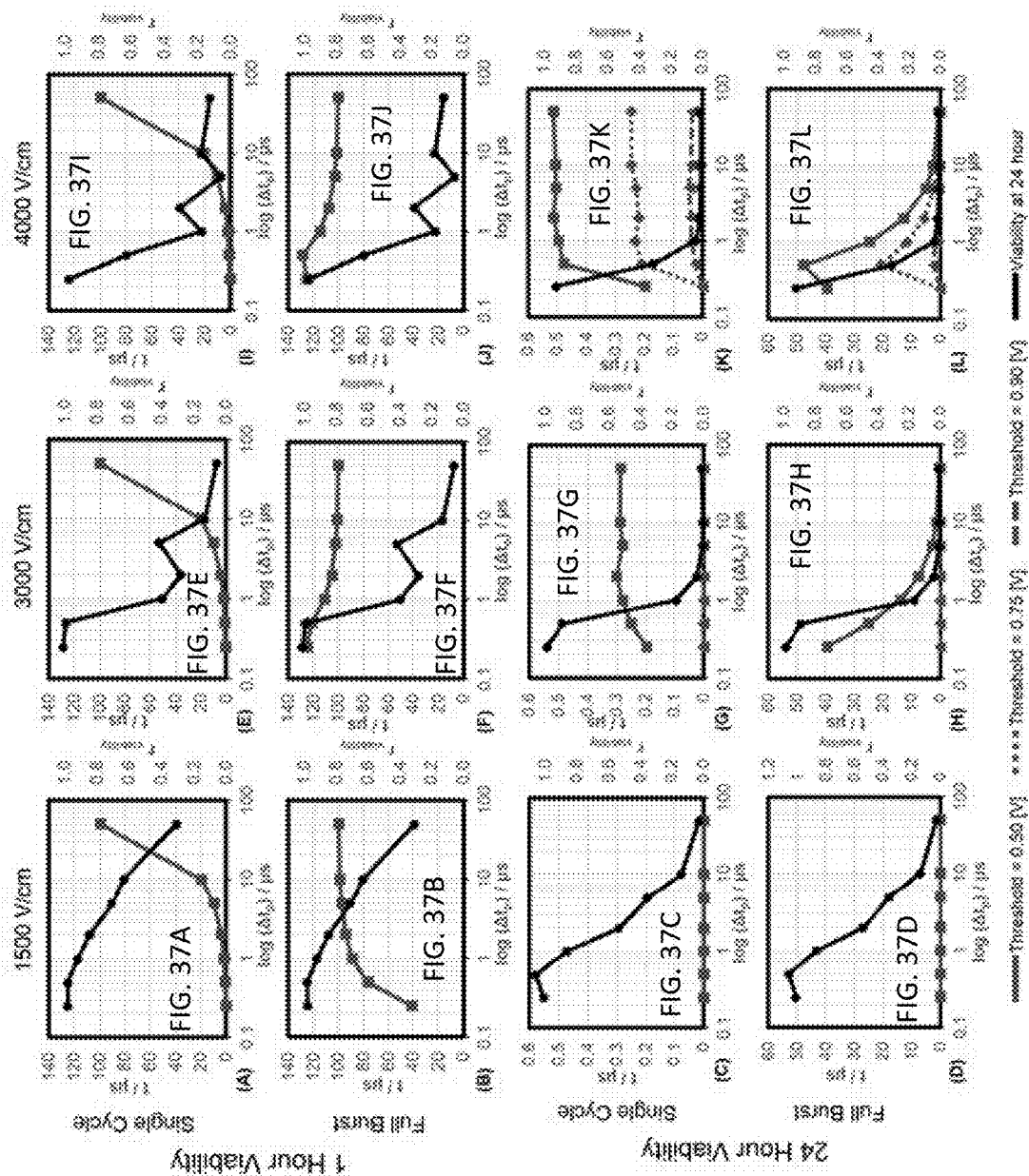

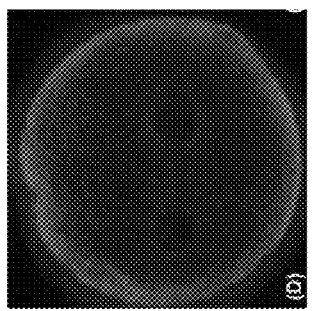
FIG. 38D
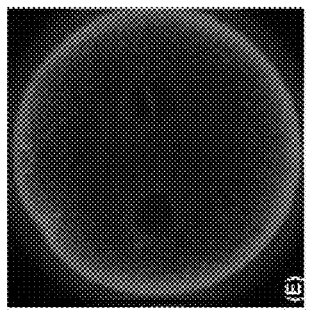
FIG. 38E
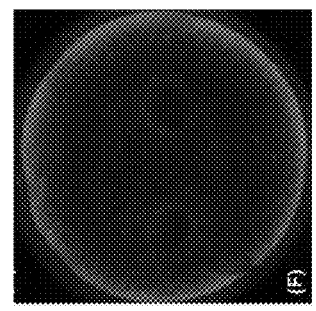
FIG. 38F
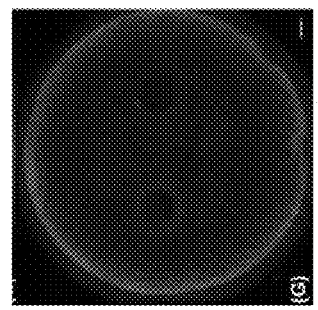
FIG. 38G
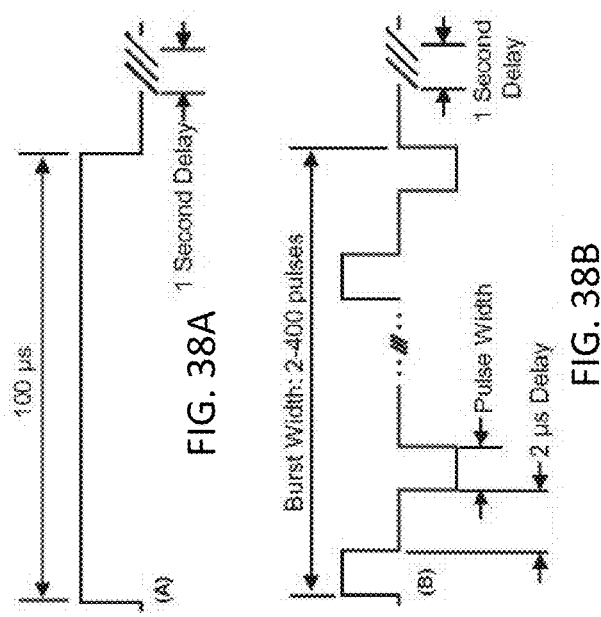
FIG. 38A
FIG. 38B
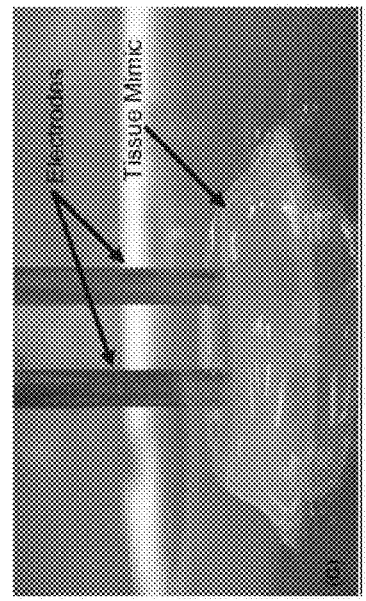
FIG. 38C

| Pulse Width [µs] | Voltage [V] | Pulses per Burst | Delay [µs] | On-Time per Burst [µs] | Bursts | Dose [V²·s] |
|---|---|---|---|---|---|---|
| 0.25 | 650 | 256 | 2 | 64 | 80 | 2163.2 |
| 0.5 | 650 | 128 | 2 | 64 | 80 | 2163.2 |
| 1 | 650 | 64 | 2 | 64 | 80 | 2163.2 |
| 2 | 650 | 32 | 2 | 64 | 80 | 2163.2 |
| 2 | 540 | 50 | 2 | 100 | 80 | 2332.8 |
| 5 | 540 | 20 | 2 | 100 | 80 | 2332.8 |
| 10 | 540 | 10 | 2 | 100 | 80 | 2332.8 |
| 50 | 540 | 2 | 2 | 100 | 80 | 2332.8 |
| 100* | 540 | 1 | - | 100 | 80 | 2332.8 |
| 2 | 540 | 50 | 2 | 100 | 80 | 2332.8 |
| 2 | 650 | 32 | 2 | 64 | 80 | 233.28 |
| 2 | 540 | 2 | 2 | 4 | 8 | 209.7152 |
| 2 | 540 | 24 | 2 | 48 | 8 | 93.312 |
| 2 | 540 | 50 | 200 | 100 | 80 | 1119.744 |
| 2 | 540 | 216 | 2 | 432 | 80 | 2332.8 |
| 2 | 250 | 2 | 2 | 100 | 80 | 2021.1 |
| 50 | 540 | 2 | 2 | 100 | 80 | 233.28 |
| 100 | 540 | 1 | - | 100 | 8 | 233.28 |

FIG. 39

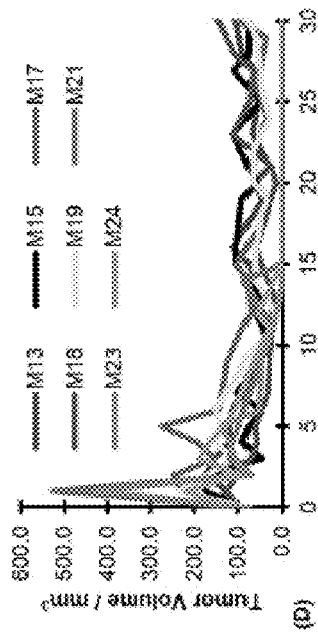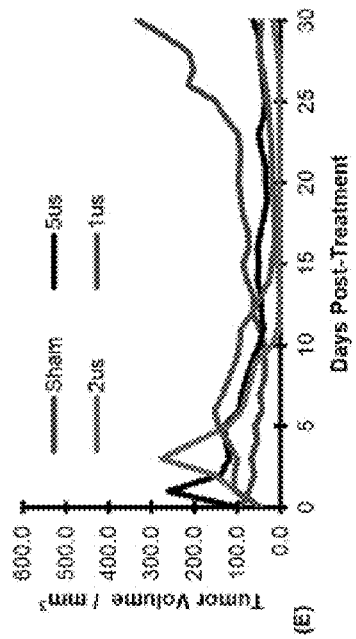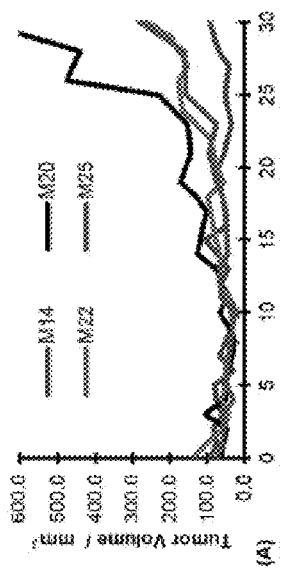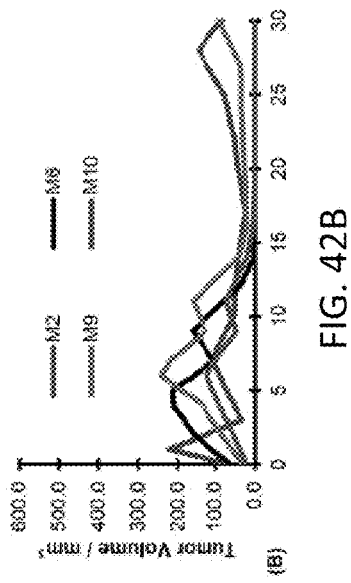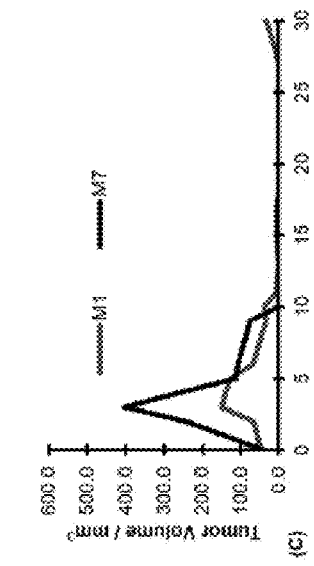

| Group | Pulse Width (µs) | Pulses per Burst | Bursts | Voltage (V) | Dose (V²/s) |
|---|---|---|---|---|---|
| 1 (n=8) | 5 | 20 | 120 | 1000 | 12000 |
| 2 (n=2) | 2 | 50 | 120 | 1000 | 12000 |
| 3 (n=4) | 1 | 100 | 120 | 1000 | 12000 |
| 2 (n=4) | Sham | | | | |

FIG. 44

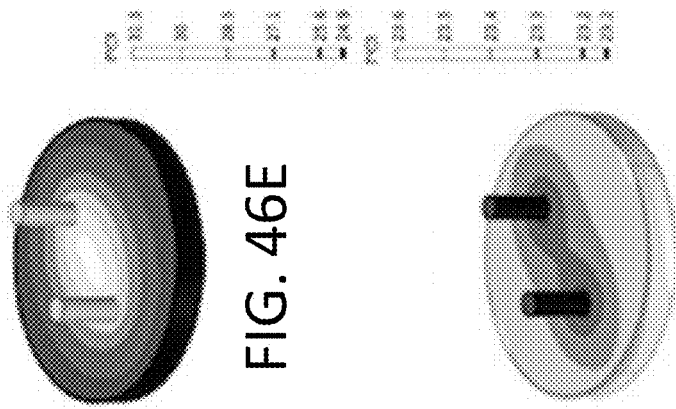
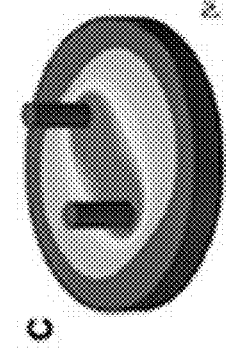
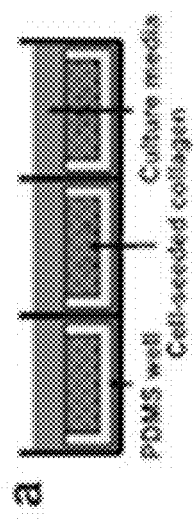
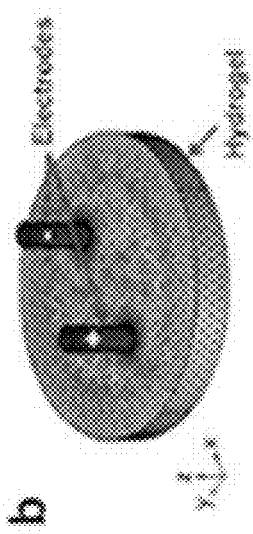
FIG. 46A  FIG. 46C  FIG. 46E
FIG. 46B  FIG. 46D  FIG. 46F

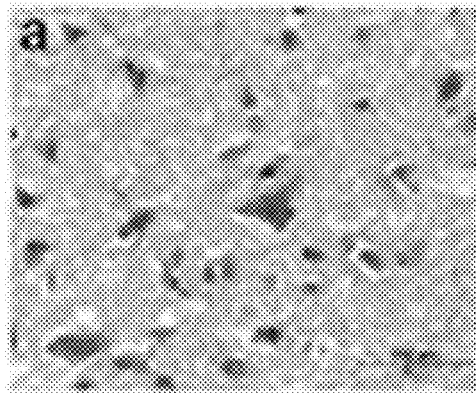
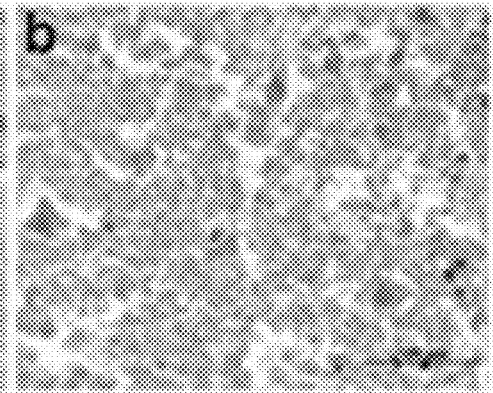
FIG. 49A    FIG. 49B
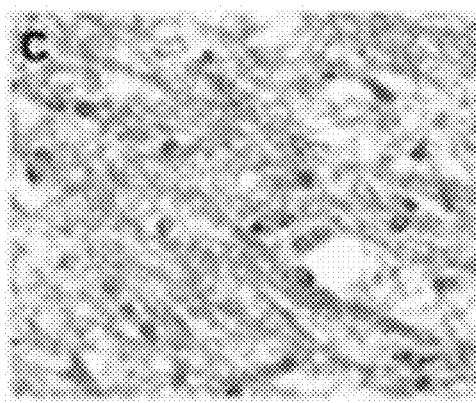
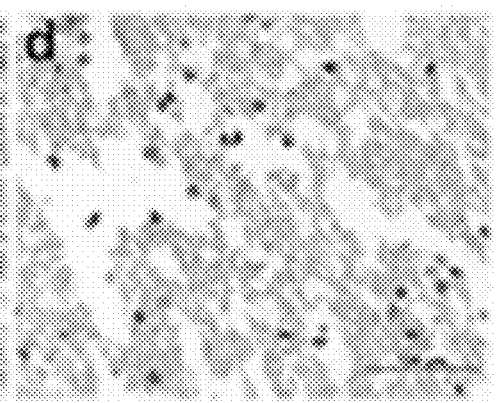
FIG. 49C    FIG. 49D
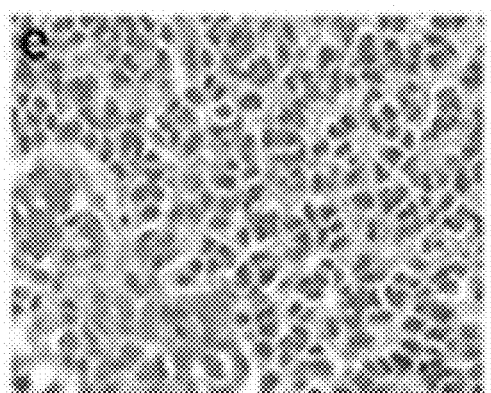
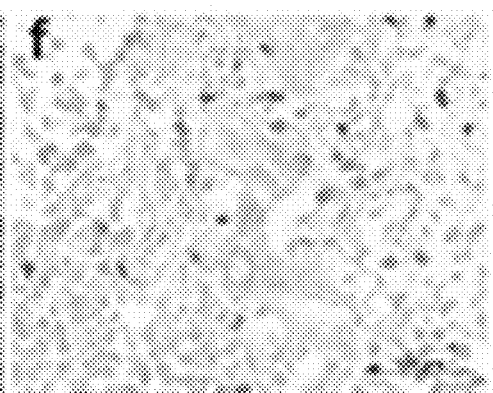
FIG. 49E    FIG. 49F

SELECTIVE MODULATION OF INTRACELLULAR EFFECTS OF CELLS USING PULSED ELECTRIC FIELDS

CROSS-REFERENCE TO RELATED APPLICATIONS

The present application is a National Stage application under 35 U.S.C. § 371 of International Application No. PCT/US15/30429, filed May 12, 2015, which application relies on the disclosure of and claims priority to and the benefit of the filing date of U.S. Provisional Application No. 61/992,023 filed May 12, 2014, the disclosures of each of which are hereby incorporated by reference herein in their entireties.

BACKGROUND OF THE INVENTION

Field of the Invention

The present invention is related to medical therapies involving the administering of electrical treatment energy. Embodiments of the present invention relate to a system and method that produces two treatment zones: a first zone surrounding the electrodes within which cells are killed non-selectively and a second selective treatment zone surrounding the first zone within which cells are killed selectively, such as aberrant cells. In specific embodiments, systems and methods for selectively treating cells, such as cancer cells, through administration of a train of electrical pulses wherein the pulse length and delay between successive pulses is optimized to produce effects on intracellular membrane potentials are provided. Through the systems and methods of the invention, infiltrating tumor cells disposed within a tumor margin can be effectively treated while sparing healthy tissue within the tumor margin.

Description of Related Art

Focal ablation techniques typically attack tumors by destroying cancerous cells within a well-defined region. Typically, these techniques destroy all of the cells and tissue structure within the treated volume, not just the cancerous cells. A major challenge of focal ablation technologies is that there is typically a region surrounding the tumor which contains healthy cells and some infiltrative cancerous cells. These infiltrative cancer cells, if untreated, may lead to recurrence of the tumor. The solution, in traditional surgical resection and focal ablation, is to treat beyond the tumor margin in an attempt to also remove these infiltrative cancer cells. This presents a major challenge for tumors which typically arise near critical structures, such as blood vessels and nerves. Thus, there is a need in the art for new electroporation protocols that overcome these limitations.

SUMMARY OF THE INVENTION

The present invention provides a system and method of treating infiltrative cancer cells in a tumor margin. This bimodal enhanced ablation mechanism (BEAM) platform uses burst of high frequency electric fields which have been specifically optimized to enhance the intracellular effects of the pulse while minimizing effects on healthy tissue. In embodiments, an optimal burst contains constitutive pulses with durations approximately equivalent to the charging time of the cell membrane plus the discharge time of the nuclear envelope. The optimal off-time between pulses is approximately equivalent to the charging time of the cell membrane.

In embodiments, certain cells (malignant) cells can be preferentially targeted based on their biophysical subcellular structure. Cells with a larger nucleus-to-cytoplasm ratio, which is an indication of their malignancy, are more susceptible to these pulses. The mechanism affecting the cells is related to disrupting their nucleus. Although cell size is the primary parameter for determining when a cell dies under an applied field for typical IRE, in contrast according to embodiments of the present invention, cell size does not play a dominant role.

Specific embodiments provide a method of selectively treating cells, comprising: applying to a tissue a plurality of electrical pulses with a delay between successive pulses, wherein the length of each pulse and the delay between successive pulses are optimized to produce a first treatment zone and a second treatment zone; wherein in the first treatment zone target cells, such as cancer cells, and non-target cells, such as non-cancer cells, are killed and in the second treatment zone the target cells are killed or inhibited while the non-target cells are spared. In such methods, the applying can be performed in vitro, in vivo, or ex vivo.

According to embodiments, within the second treatment zone target cells, such as cancer cells, are inhibited by way of slowed or arrested cell division, or target cells (e.g., cancer cells) are inhibited by way of slowed or arrested migration, or target cells (e.g., cancer cells) are inhibited by way of reduced transport of blood and nutrients, or target cells (e.g., cancer cells) are killed by apoptosis, or some target cells (e.g., cancer cells) are killed or inhibited in the second treatment zone and some non-target cells (e.g., non-cancer cells) are spared in the second treatment zone. In embodiments, the second treatment zone surrounds a tumor and the target cancer cells are infiltrative cells originating from the tumor. The tissue can be brain tissue, and/or the tumor glioblastoma. The target cells in any embodiment of this disclosure can be any type of cells, including for example cancer cells, infiltrative cells, or any undesired cells. The non-target cells can be any type of cell as well and are typically healthy cells, normal cells, or non-cancer cells.

According to embodiments, within the first treatment zone target cells and non-target cells (e.g., cancer cells and non-cancer cells) are killed by necrosis, or some cancer cells and some non-cancer cells are killed in the first treatment zone.

Likewise, according to embodiments both target and non-target cells (e.g., cancer cells and non-cancer cells) can be killed within the first treatment zone as a result of an increase of their transmembrane potential to a lethal threshold.

In embodiments, cancer cells are killed within the second treatment zone as a result of an increase in their nuclear transmembrane potential to a lethal threshold.

In embodiments, the delay between successive pulses can be greater than the length of each pulse, or the delay between successive pulses can be a fraction of the length of each pulse, or the length of each pulse can be equivalent to the charging time of the cell membrane of the cancer cells plus the discharge time of the nuclear membrane of the cancer cells, while the delay between successive pulses is equivalent to the charging time of the cell membrane of the cancer cells. Likewise, the charging time of the cell membrane of the cancer cells and the discharge time of the nuclear membrane of the cancer cells can be determined through numerical modeling.

In embodiments, the pulse train comprises an electric field waveform which is a rectangular pulse, ramp, decaying exponential, or sine wave. In embodiments, the electric field waveform is unipolar or bipolar, or can be a superimposed, bimodal signal comprising a first frequency harmonic and a second frequency harmonic, wherein the second frequency harmonic has a frequency higher than that of the first frequency harmonic.

In embodiments, the electric field waveform comprises alternating nanosecond-order pulses with microsecond order pulses in succession. Likewise, the electric field waveform can be symmetric or asymmetric. The electric field waveform in embodiments can have a carrier frequency in the range of 100 kHz to 10 MHz. The carrier frequency or pulse duration of the waveforms can be based on the cross-over frequency of the cancer cells.

In embodiments, the length of each pulse and the delay between successive pulses are optimized based on the physical nucleus to cytoplasm size ratio of the cancer cells.

Embodiments of the invention include a method of treating cancer in a patient, comprising identifying a solid tumor in a patient, inserting at least one electrode into or adjacent to the solid tumor, and applying a pulse train comprising a plurality of electrical pulses with a delay between successive pulses. Such methods are also applicable to treating undesired cells or target cells that are not necessarily cancerous. In embodiments, the length of each pulse and the delay between successive pulses are optimized to produce a first treatment zone within a radius of the at least one electrode and a second treatment zone between the first radius and a within a second radius of the electrode, which second treatment zone lies outside of the first treatment zone. In the first treatment zone cancer cells and healthy cells are killed non-selectively while in the second treatment zone cancer cells are selectively killed or inhibited an healthy cells are spared. Methods of treating cancer in a patient can be performed in vivo, ex vivo, or in vitro.

In embodiments of the invention, selective inhibition of the cancer cells in the second treatment zone comprises slowed or arrested cell division. Alternatively or in addition, selective inhibition of the cancer cells in the second treatment zone comprises slowed or arrested migration. Alternatively or in addition, selective inhibition of the cancer cells in the second treatment zone comprises reduced transport of blood and nutrients.

In embodiments of the invention, cancer cells and healthy cells are killed within the first treatment zone by necrosis. Alternatively or in addition, cancer cells are killed within the second treatment zone by apoptosis.

In embodiments of the invention, cancer cells and healthy cells are killed within the first treatment zone as a result of an increase of their transmembrane potential to a lethal threshold. Alternatively or in addition, cancer cells are killed within the second treatment zone as a result of an increase in their nuclear transmembrane potential to a lethal threshold.

Preferred embodiments of the invention may target the transmembrane potential of the nucleus, such that it reaches a lethal threshold as a result of the optimized pulses of the invention. However, other embodiments may target any membrane-bound intracellular organelle, whether through effects on the transmembrane potential or any other mechanism, including without limitation the mitochondria, smooth endoplasmic reticulum, rough endoplasmic reticulum, the golgi apparatus, endosomes, lysosomes, peroxisomes, storage vesicles, and transport vesicles.

In embodiments of the invention, the delay between successive pulses is greater than the length of each pulse. Alternatively, the delay between successive pulses is a fraction of the length of each pulse.

In embodiments of the invention, the length of each pulse is equivalent to the charging time of the cell membrane plus the discharge time of the nuclear membrane, while the delay between successive pulses is equivalent to the charging time of the cell membrane. Likewise, embodiments can comprise a multiple of such timing or even a fraction of such timing. The charging time of the cell membrane and the discharge time of the nuclear membrane may be determined through numerical modeling.

In embodiments of the invention, the pulse train comprises an electric field waveform which is a rectangular pulse, ramp, decaying exponential, or sine wave. The electric field waveform may be unipolar or bipolar. The electric field waveform may be a superimposed, bimodal signal comprising a first frequency harmonic (such as a low frequency harmonic) and a second frequency harmonic (such as a high frequency harmonic). The electric field waveform may comprise alternating nanosecond-order pulses with microsecond order pulses in succession. The electric field waveform may be asymmetric. The electric field waveform may have a carrier frequency in the range of 100 kHz to 10 MHz. The carrier frequency or pulse duration of the waveforms may be based on the cross-over frequency of the cancer cells, undesired cells, or otherwise referred to as the target cells.

In embodiments, the length of each pulse and the delay between successive pulses are optimized based on the physical nucleus to cytoplasm size ratio of the cancer cells.

In embodiments of the invention, the pulses are bipolar square waves and the length of each pulse is between 250 nanoseconds and 50 microseconds.

Embodiments of the invention include a method of treating a cancer in a patient, comprising identifying a solid tumor in a patient, inserting at least one electrode into or adjacent to the solid tumor, and applying a pulse train comprising a plurality of electrical pulses, wherein the pulses are bipolar square waves and the length of each pulse is between 250 nanoseconds and 50 microseconds.

Embodiments of the invention include a method of treating a cancer in a patient, comprising identifying a solid tumor in a patient, inserting at least one electrode into or adjacent to the solid tumor, and applying a pulse train comprising a plurality of electrical pulses, wherein the pulse train has an electric field waveform which is a superimposed, bimodal signal comprising a first frequency harmonic and a second frequency harmonic, such as a low frequency harmonic and a high frequency harmonic.

Embodiments of the invention include a system for treating a cancer in a subject, comprising at least one electrode, and a voltage pulse generator operatively coupled to the electrode and configured to apply a pulse train comprising a plurality of electrical pulses, wherein the pulse train has an electric field waveform which is a superimposed, bimodal signal comprising a low frequency harmonic and a high frequency harmonic. The voltage pulse generator may comprise solid state switching devices arranged in a multi-level, neutral point clamped, or cascaded H-bridge topology.

Also included is a method of selectively treating cells, comprising: applying a plurality of electrical pulses as a treatment to a substance containing cells, wherein the pulses are bipolar square waves and the length of each pulse is between 250 nanoseconds and 50 microseconds, with a delay between pulses of between 250 nanoseconds and 50 microseconds; wherein one type of cell is treated and another type of cell is not treated by the plurality of electrical pulses. In embodiments, the treated cells are killed and untreated cells are not killed. The substance containing cells for example can be a tissue, a non-living object, a solution, a body part, or a living or non-living patient, human, animal, or tissue.

In embodiments, provided is a method of selectively treating cells, comprising: applying a pulse train comprising a plurality of electrical pulses to a substance containing cells, wherein the pulse train has an electric field waveform which is a superimposed, bimodal signal comprising a first frequency harmonic and a second frequency harmonic with a frequency higher than that of the first. In embodiments, the pulse train selectively kills cells of a selected type and spares cells of another type.

Systems of the invention include any system configured to implement one or more methods of the invention. Included is a system for selectively treating cells, comprising: at least one electrode; and a voltage pulse generator coupled to the electrode and configured to apply a pulse train comprising a plurality of electrical pulses, wherein the pulse train has an electric field waveform which is a superimposed, bimodal signal comprising a first frequency harmonic and a second frequency harmonic, wherein the second frequency harmonic has a frequency higher than that of the first frequency harmonic.

In embodiments, the voltage pulse generator is configured to select the bimodal signal such that the pulse train selectively kills cells of a selected type and spares cells of another type, or the voltage pulse generator comprises solid state switching devices arranged in a multi-level, neutral point clamped, or cascaded H-bridge topology.

Additional methods include a method of selectively treating cells, the method comprising: delivering electrical pulses to a substance containing cells in a manner sufficient to kill only cells having a selected biophysical subcellular structure. In embodiments, the cells having the selected biophysical subcellular structure have a nucleus and the cells are killed by disrupting the nucleus of the cells. The cells having the selected biophysical subcellular structure can have a selected nucleus-to-cytoplasm area ratio.

A method of selectively treating cells, comprising: applying a plurality of electrical pulses to a substance containing cells, wherein the plurality of electrical pulses has a frequency, amplitude, and pulse waveform selected to treat target cells of one type of cell and spare non-target cells of another type of cell is also included within the scope of the invention. Such methods of the invention can be a selective method wherein cancer cells are treated and normal cells are spared. Such methods can be a palliative method wherein cancer cells of a more malignant type are treated and cancer cells of a less aggressive type are spared.

Methods of the invention can further comprise determining a nucleus-to-cytoplasm ratio for the target cells; and selecting the frequency, amplitude, and pulse waveform based on the nucleus-to-cytoplasm ratio for the target cells. In embodiments the nucleus-to-cytoplasm ratio is measured or otherwise determined from cells taken from a biopsy of the substance containing cells.

A method of selectively ablating malignant cells is included in the invention, the method comprises: determining a first death threshold for malignant cells present in a tissue region; determining a second death threshold for non-malignant cells present in the tissue region; administering electrical pulses to the tissue region at or above the first death threshold and below the second death threshold to kill the malignant cells. In embodiments of methods of the invention, the non-malignant cells are not killed. In embodiments, the malignant cells each comprise a cell nucleus and are killed by administering the electrical pulses in a manner sufficient to disrupt the cell nucleus.

Included in embodiments is a method of enhancing the transport of material into an organelle, comprising: applying a plurality of electrical pulses to a substance containing cells, wherein the plurality of electrical pulses has a frequency, amplitude, and pulse waveform selected to optimize the transport of molecules into an organelle.

According to embodiments, the plurality of electrical pulses includes positive and negative pulses having different pulse widths, or the plurality of electrical pulses includes positive and negative pulses having different amplitude. In embodiments, the organelle is the nucleus, mitochondria, endoplasmic reticulum, vacuole, lysosome, or chloroplast.

BRIEF DESCRIPTION OF THE DRAWINGS

The accompanying drawings illustrate certain aspects of embodiments of the present invention, and should not be used to limit the invention. Together with the written description the drawings serve to explain certain principles of the invention.

FIG. 5A is a schematic diagram of cells with two different sized nuclei which serves as a key for FIGS. 5B-5G.

FIG. 5B a graph showing a low frequency bipolar sinusoidal signal.

FIG. 5C is a graph showing a high frequency bipolar sinusoidal signal.

FIG. 5D is a graph showing a bimodal sinusoidal signal comprising the low frequency harmonic of FIG. 5B and a high frequency harmonic of FIG. 5C.

FIG. 5E is a graph showing the nuclear transmembrane potential of cells with two different sized nuclei as a result of the low frequency bipolar sinusoidal signal of FIG. 5B.

FIG. 5F is a graph showing the nuclear transmembrane potential of cells with two different sized nuclei as a result of the high frequency bipolar sinusoidal signal of FIG. 5C.

FIG. 5G is a graph showing the nuclear transmembrane potential of cells with two different sized nuclei as a result of the bimodal sinusoidal signal of FIG. 5D.

FIG. 10 is a table showing parameter values used in parametric studies on the transmembrane potential (TMP).

FIG. 18A shows the nTMP as a result of a 500 nanosecond on −500 nanosecond off pulse regimen and FIG. 18B shows the nTMP as a result of a 4 microsecond on −500 nanosecond off pulse regimen.

FIG. 21A is a schematic diagram of cells with two different sized nuclei which serves as a key for FIGS. 21B and 21C.

FIG. 21B is a graph showing the nuclear transmembrane potential of cells of two different sized nuclei as result of applying a bimodal sinusoidal signal with an electric field strength of 4000 V/cm.

FIG. 21C is a graph showing the nuclear transmembrane potential of cells of two different sized nuclei as result of applying a bimodal sinusoidal signal with an electric field strength of 5000 V/cm.

FIG. 27A shows these zones as a result of 1000 V pulses using in vitro values. FIG. 27B shows these zones as a result of 1000V pulses using equivalent in vivo thresholds.

FIG. 28 is a table showing parameters used in numerical analysis.

FIG. 31A shows a bi-polar square wave with 50 ns rise and fall times was used to simulate the maximum (FIG. 31B) transmembrane potential of the cell membrane (Um) and (FIG. 31C) nuclear envelope (Un).

FIG. 34A shows a 1.5 kV/cm 250 ns impulse and FIG. 34B shows the resulting transmembrane potential of the cell membrane ($U_m$) and nuclear envelope ($U_n$). FIG. 34C shows a 1.5 kV/cm 1 μs impulse and FIG. 34D shows the resulting transmembrane potential of the cell membrane ($U_m$) and nuclear envelope ($U_n$). Dashed lines represent the transmembrane potential of the cell membrane ($U_m$) and solid lines represent the transmembrane potential of the nuclear envelope ($U_n$).

FIGS. 37A-L are graphs showing bursts have cumulative effect on the time membrane potentials are above critical thresholds: The time, t/µs, for which the cell membrane or nuclear envelope is greater than a critical threshold is presented as a function of pulse width, $\Delta t_p$/µs. FIGS. 37A, B, E, F, I, and J represent the time for which the cell membrane has a potential drop ($U_m$) greater than 1 V. FIGS. 37C, D, G, H, K, and L represent the time for which the nuclear envelope has a potential drop ($U_n$) greater than 0.5, 0.75, or 0.9 V.

FIGS. 38A-38B are schematic diagrams showing traditional monopolar IRE pulse (FIG. 38A) and high frequency bipolar burst (FIG. 38B).

FIG. 38C is a photograph showing experimental setup with electrodes inserted into the 3D tissue mimic.

FIGS. 38D-G are images of live [green] and dead [red] regions of a tissue mimic after treatment with 80 bursts containing (FIG. 38D) 2, (FIG. 38E) 24, and (FIG. 38F) 50 bipolar 2 µs pulses with a 2 µs delay between alternating pulses. FIG. 38G shows diffuse treatment of 50 bipolar 2 µs pulses with 20 ms between alternating pulses. Scale bar represents 2 mm.

FIG. 39 is a table showing tissue mimic experimental parameters.

FIG. 41A: 540 V and 100 us energized time per burst with 8 or 80 bursts per treatment. 2 and 50 µs groups contained bipolar pulses, 100 µs group had monopolar pulses. FIG. 41B: 2 µs group at 250, 540, and 650V with equivalent energy per burst. FIG. 41C: 2 µs group at 540V with 4, 48, or 100 µs energized per burst. FIG. 41D: 2 µs group at 540 V where inter-burst delay was 1 s [burst] or 20 ms [diffuse]. FIGS. 41B-D: Treatment groups received 80 bursts of treatment for 80 seconds [diffuse group]. Data labeled ‡ is from Arena et al. 2012.

FIGS. 42A-42D are graphs showing tumor volume as a function of days post treatment for (FIG. 42A) Sham group, (FIG. 42B) 1 µs group, (FIG. 42C) 2 µs group, and (FIG. 42D) 5 µs group. FIG. 42E is a graph showing the volume of tumors averaged across all mice for each treatment group.

FIG. 44 is a table showing a treatment matrix for mouse tumor ablation.

FIG. 45A: Simulated unipolar 100 µs IRE waveform and bipolar 1 µs BEAM waveform. FIG. 45B: Calculated cellular TMP response for two different cell sizes exposed to an IRE waveform applying 500 V/cm shows TMP size dependence. FIG. 45C: BEAM pulse waveform response shows no TMP cell size dependence at 500 V/cm.

FIGS. 46A-F are diagrams showing finite element models to predict the electric field and thermal distributions within hydrogel platforms. FIG. 46A: Engineered 3D collagen hydrogels are made by adding cell-seeded collagen (0.2% or 2% w/w) into PDMS wells of controlled geometry. They are kept in a well plate under cell culture conditions with nutrients supplied by culture media. FIG. 46B: Mesh used to calculate the electric field distribution within the tissue mimics illustrates the experimental setup for therapy testing. FIGS. 46D-E: Electric field (V/cm) iso-contours when 450 V (FIG. 46C) and 700 V (FIG. 46D) pulses are simulated. FIG. 46E: Temperature isocontours immediately post-therapy (50 pulses of 700 V) show a maximum temperature rise of 12° C. above room temperature. FIG. 46F: Temperature isocontours one minute post-therapy confirm that cells are not exposed to any long-term thermal effects as a result of IRE or BEAM pulses.

FIG. 47A: Altered cell morphology and overall cell size results from changing density of hydrogel matrix from 0.2% to 2.0% collagen (n=25, scale bar 20 µm). FIG. 47B: Comparison of IRE treatment for larger cells in 0.2% collagen reveals larger lesion and thus lower death threshold than for smaller cells in 2% collagen (n=20, p<0.001) (scale bar 1 mm) FIG. 47C: Comparison of BEAM treatment in 0.2% and 2% collagen reveals uniform lesions and thus equivalent death thresholds despite cell size differences. (n=20, p≥0.1) (scale bar 1 mm). (p≤0.0005(*) and p≤0.0001(**)).

FIG. 48A: Changing the density of alginate does not change cell morphology due to lack of cell-ECM binding sites, allowing for isolating the effect of stiffness on treatments (n=25) FIG. 48B: IRE lesions and lethal thresholds are equivalent across stiffness differences for equivalent cell morphology (n=20, p≥0.1) (scale bar 1 mm) FIG. 48C: BEAM lesions and lethal thresholds are equivalent across alginate stiffness differences (n=20, p≥0.1) (scale bar 1 mm).

FIGS. 49A-F are microscopic images showing histomorphology of normal and neoplastic canine brain tissues ablated with IRE. a) Normal, untreated cerebrocortical grey matter (FIG. 49A) and white matter (FIG. 49C) of the internal capsule. IRE ablation results in neuronal (FIG. 49B) and glial death (FIGS. 49B and D), as well as vacuolization and axonal loss (FIG. 49D). Biopsy of glioblastoma multiforme before (FIG. 49E) and after (FIG. 49F) IRE ablation.

The IRE treatment causes disruption of tumor and stromal cytoarchitecture, and tumor cell death. All sections stained with hematoxylin and eosin.

Figure 50A:
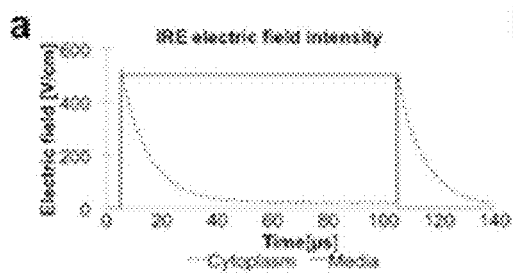

FIG. 50A is a graph showing numerical modeling of the electric field produced by IRE pulses predicts the electric field reaches the cytoplasm inside the cell for only a short duration of the pulse time while the majority of the electric field is retained in the media where it aggregates around the cell membrane.

Figure 50B:
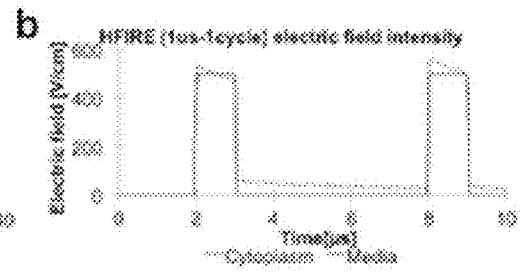

FIG. 50B is a graph showing numerical modeling of the electric field distribution predicts the electric field produced by BEAM pulses penetrates through the plasma membrane into the cytoplasm for the entire duration of the pulse on-time.

Figure 50C:
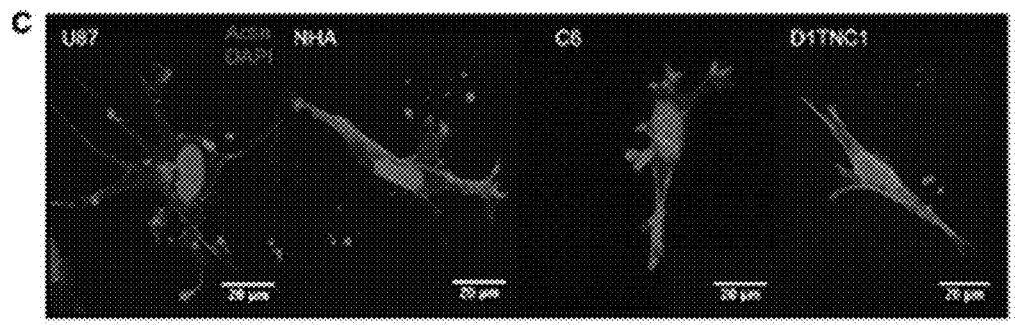

FIG. 50C is a series of fluorescent images of U-87, NHA, C6, and D1TNC1 cells, respectively which allow for determination of shape factors to be used in modeling and to correlate to experimental lesion results.

Figure 50D:
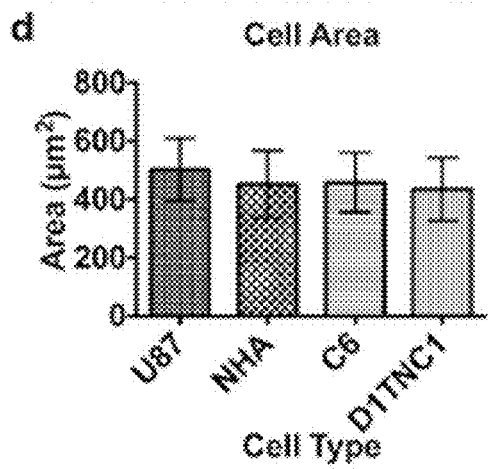

FIG. 50D is a graph showing U-87, NHA, C6, and D1TNC1 cells show no significant difference ($p \geq 0.1$) in overall cell area (n=20).

Figure 50E:
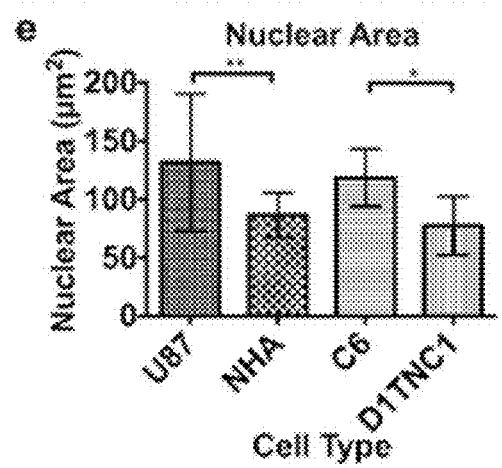

FIG. 50E is a graph showing nuclear area of malignant glioma cells (U-87 and C6) is greater than for non-malignant astrocytes (NHA and D1TNC1) (n=20, $p \leq 0.05$(*) and $p \leq 0.005$ (**)).

Figure 51A:
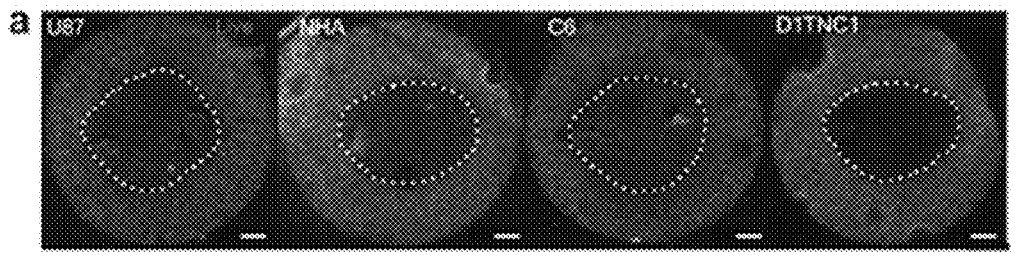

FIG. 51A is a series of images showing IRE lesion sizes have no significant difference across different cell types (n=10, $p \geq 0.1$).

Figure 51B:
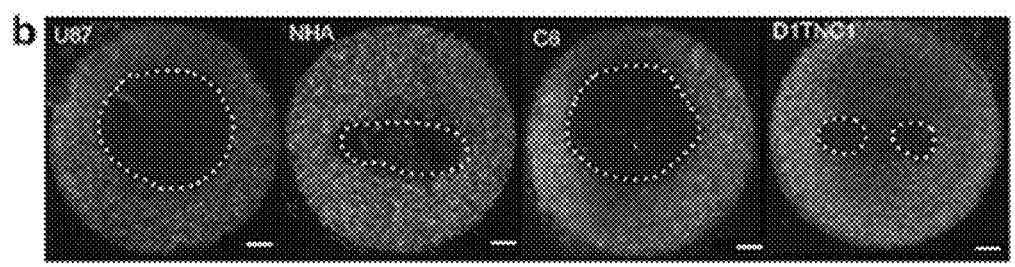

FIG. 51B is a series of images showing BEAM lesion size for malignant glioma cells (U-87 and C6) is greater than non-malignant astrocytes (NHA and D1TNC1) (n=10).

Figure 51C:
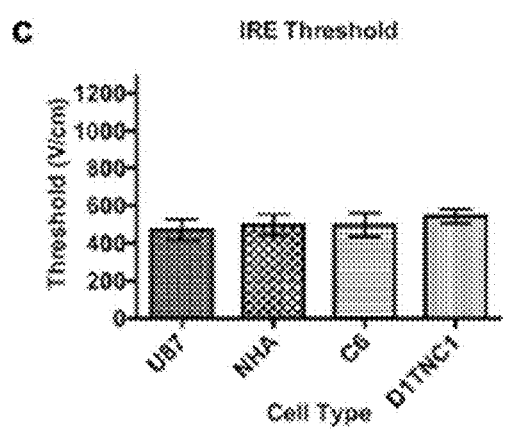

FIG. 51C is a graph showing COMSOL modeling relating lesion size to death thresholds shows no significant difference between IRE thresholds for different cell types (n=10, $p \geq 0.1$), confirming the hypothesis that IRE thresholds are primarily dependent on cell size.

Figure 51D:
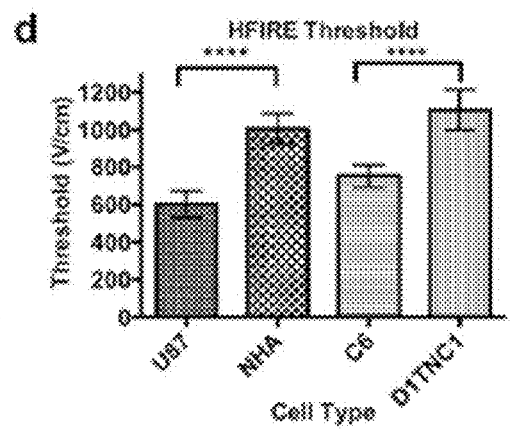

FIG. 51D is a graph showing death thresholds for malignant cells are smaller than normal cells with BEAM treatment, which provides that a range of electric field values will kill malignant cells without killing healthy cells (n=10, $p \leq 0.0001$ (****)).

Figure 52A:
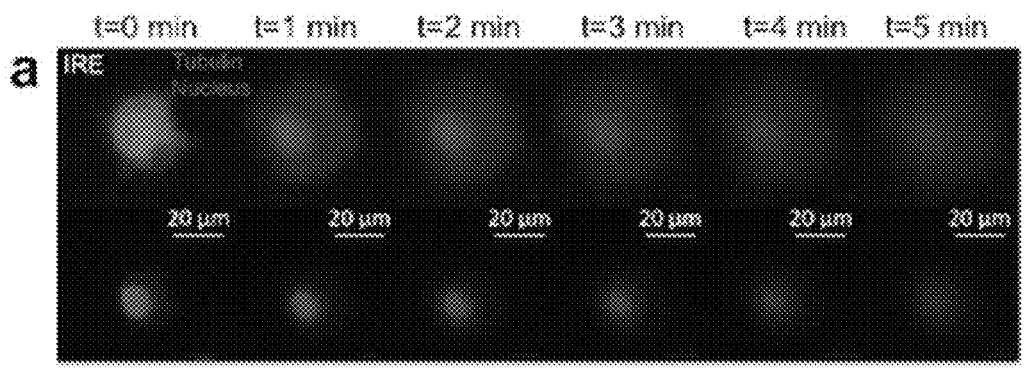

FIG. 52A is a series of images showing a cell exposed to IRE treatment shows a diffusion of stained tubulin from the cell cultured in a 3D hydrogel over a 5-minute time course, suggesting a disruption of the outer cell membrane as a result of pulses.

Figure 52B:
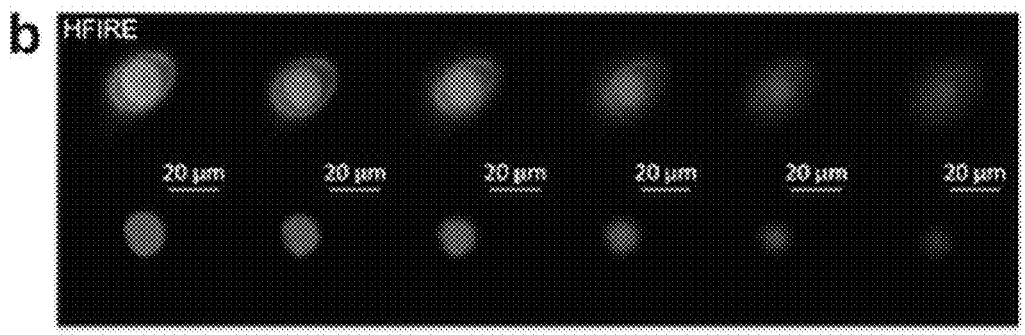

FIG. 52B is a series of images showing a cell exposed to BEAM treatment shows a sharp collapse of the nucleus, and while tubulin staining dims, it does not clearly diffuse outside of original cell membrane area as in the IRE case. This suggests a different effect on both the nucleus and cell membrane between IRE and BEAM.

Figure 52C:
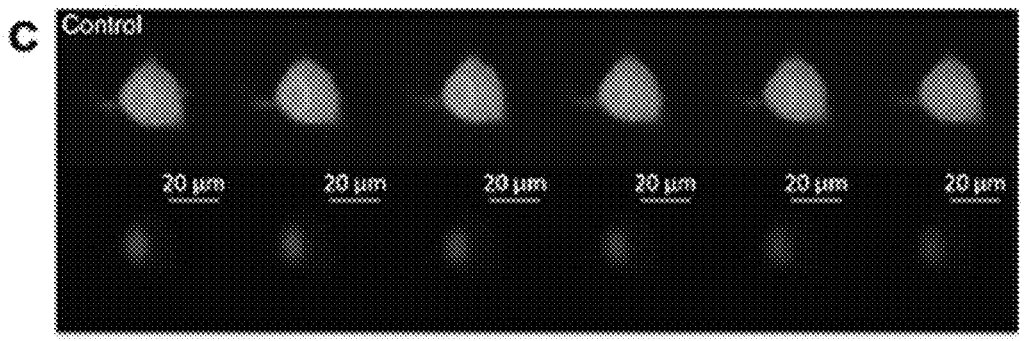

FIG. 52C is a series of images showing cell not exposed to any pulses acts as a control to ensure no photo-bleaching effects from imaging over 5-minute time course.

Figures 53A, 53B:
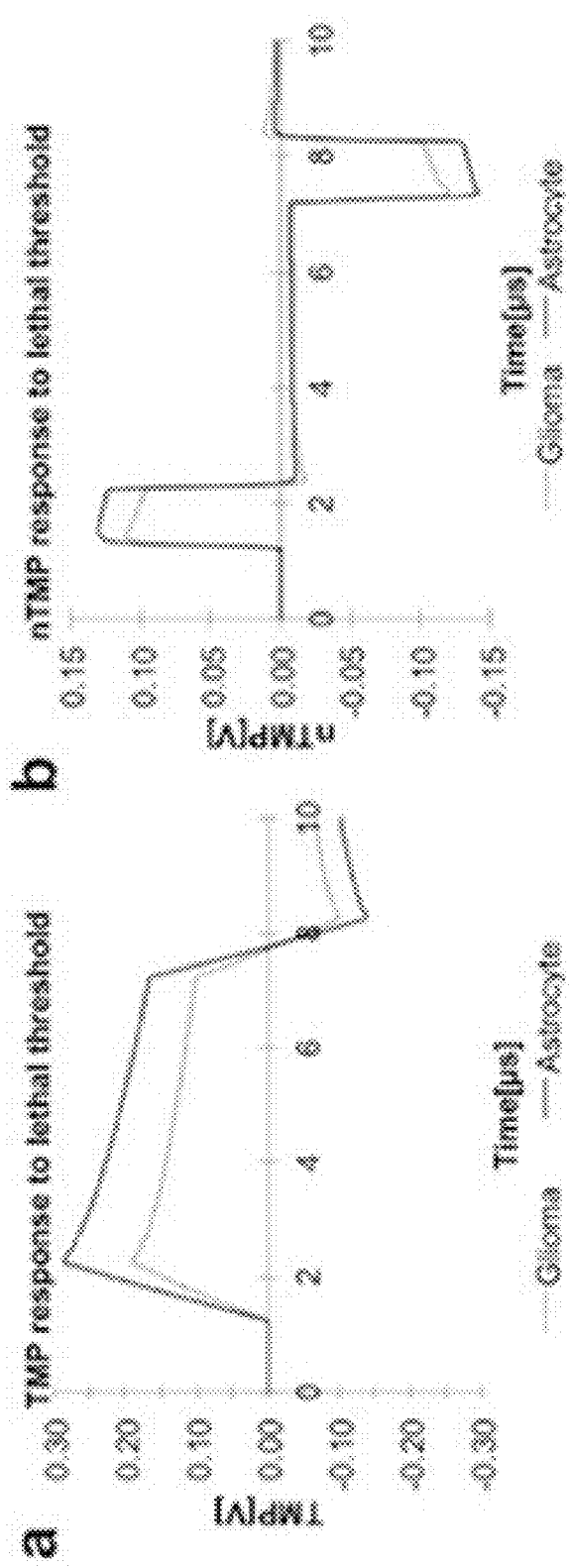

FIGS. 53A-53B are graphs showing the predicted TMP and nTMP response to BEAM experimental lethal thresholds for modeled glioma and astrocyte cells suggests a nTMP effect. FIG. 53A: Modeled cells with experimental geometries for glioma cell and astrocytes exposed to simulated BEAM experimental lethal electric field thresholds for the given cell type show a difference in TMP increase in response. FIG. 53B: Modeled cells with experimental geometries for glioma cell and astrocytes exposed to simulated BEAM experimental lethal electric field thresholds for the given cell type show a similar nTMP increase in response, suggesting a value for nTMP increase that will cause cell death.

Figure 54C:
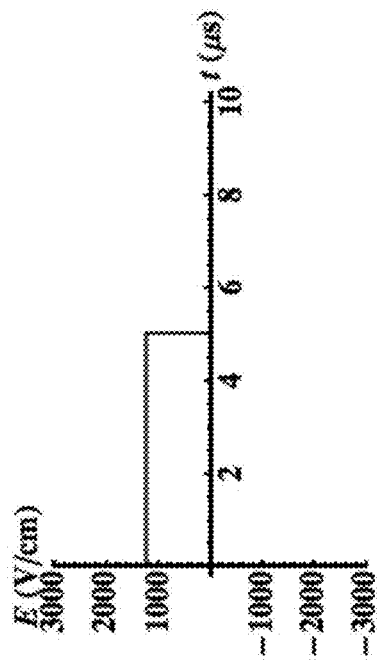
Figure 54A:
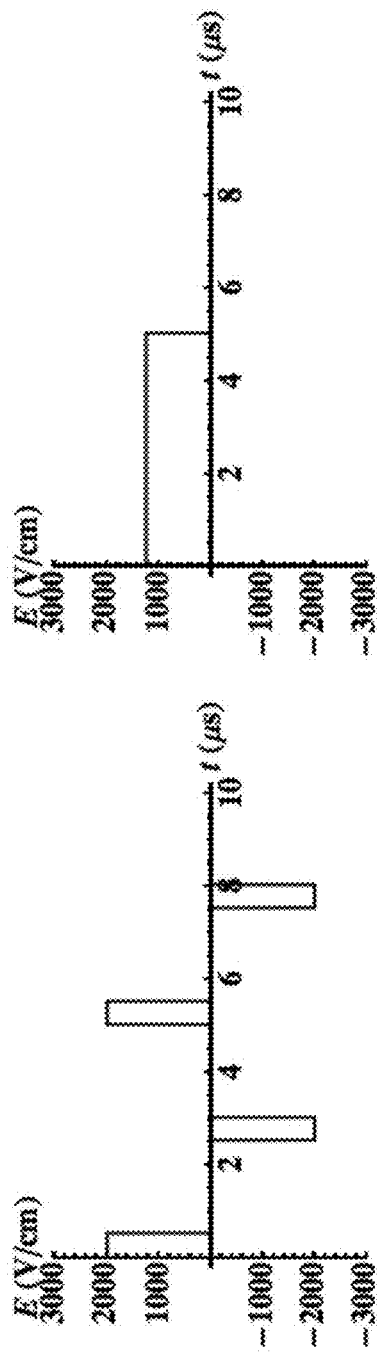
Figure 54D:
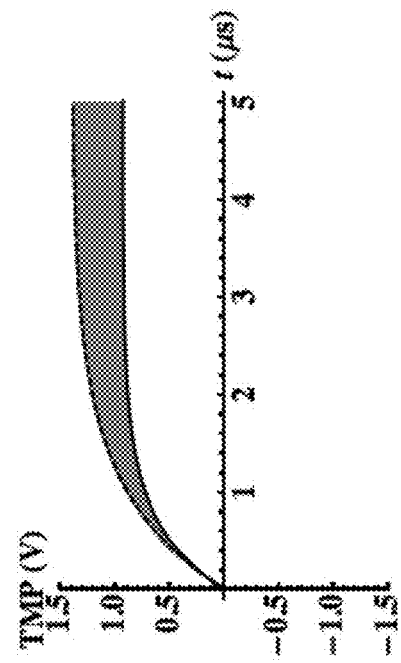

FIGS. 54A-D are graphs showing applied electric field and TMP for a BEAM treatment (FIGS. 54A-B) and applied electric field and TMP for an IRE treatment (FIGS. 54C-D). In the TMP plots, the dotted line represents a cell with a diameter of 15 um, and the solid line represents a cell with a diameter of 10 um. The maximum TMP across the outer membrane is less dependent on cell size during BEAM than during IRE.

DETAILED DESCRIPTION OF VARIOUS EMBODIMENTS OF THE INVENTION

Reference will now be made in detail to various exemplary embodiments of the invention. Embodiments described in the description and shown in the figures are illustrative only and are not intended to limit the scope of the invention. Changes may be made in the specific embodiments described in this specification and accompanying drawings that a person of ordinary skill in the art will recognize are within the scope and spirit of the invention.

Throughout the present teachings, any and all of the features and/or components disclosed or suggested herein, explicitly or implicitly, may be practiced and/or implemented in any combination, whenever and wherever appropriate as understood by one of ordinary skill in the art. The various features and/or components disclosed herein are all illustrative for the underlying concepts, and thus are non-limiting to their actual descriptions. Any means for achieving substantially the same functions are considered as foreseeable alternatives and equivalents, and are thus fully described in writing and fully enabled. The various examples, illustrations, and embodiments described herein are by no means, in any degree or extent, limiting the broadest scopes of the claimed inventions presented herein or in any future applications claiming priority to the instant application.

The present inventors have made the surprising discover that high frequency pulsed electric fields can be manipulated and optimized to target intracellular membranes. More particularly, particular protocols of administering high frequency pulsed electric fields can be used to increase intracellular membrane potentials of the cell in organelles such as the nucleus. By targeting intracellular membrane potentials, cancer cells can be selectively targeted over healthy tissue. In one embodiment, high frequency pulsed electric fields are administered to tumors to create two treatment zones: an ablation zone and a selective therapy zone. In the ablation zone, healthy cells and cancer cells die due to necrotic cell death. Outside the ablation zone, only cancer cells die due to programmed cell death as a result of changes in the membrane potential of intracellular organelles, while healthy cells are spared. Thus, the cell membrane is not the primary target of therapy; resonant additive effects target intracellular components such as the nucleus, mitochondria, and other key membrane-bound organelles. In embodiments, these effects are achieved through an optimization of both pulse length and delay time. In an exemplary embodiment, the pulse length is optimized to be approximately equivalent to the charging time of the cell membrane plus the discharge time of the nuclear envelope, while the delay time is optimized to be approximately equivalent to the charging time of the cell membrane. In embodiments, the delay time is a fraction of the pulse length.

Embodiments of the invention include pulses designed to generate a range of field strengths beyond the tumor margin that results in cell death of aberrant cells while preserving healthy cells. Within the tumor margin, the field strengths are sufficient to kill all cell types. Additionally, embodiments of the invention include pulses designed to generate a range of field strengths beyond the tumor margin that results in enhanced nuclear permeability of aberrant cells while not affecting healthy cells. Within the tumor margin, the field strengths are sufficient to enhance the nuclear permeability of all cell types. Additionally, embodiments of the invention include pulses designed to generate a range of field strengths beyond the tumor margin that slow or arrest the division of aberrant cells while not affecting healthy cells. Within the tumor margin, the field strengths are sufficient to slow the growth rate of all cell types. Additionally, embodiments of the invention include pulses designed to generate a range of field strengths beyond the tumor margin that halts the migration of aberrant cells to prevent metastasis while not affecting healthy cells. Within the tumor margin, the field strengths are sufficient to halt migration of all cell types. Additionally, embodiments of the invention include pulses designed to generate a range of field strengths beyond the tumor margin that prevent the transport of blood and nutrients to aberrant cells. Within the tumor margin, transport of blood and nutrients is prevented to all cell types.

In embodiments, the field strengths generated within the tumor margin are selective to aberrant cells while preserving healthy cells. The electric field waveform may be a rectangular pulse, ramp, decaying exponential, or sine wave and may be unipolar or bipolar. In embodiments, the electric field waveform may be a superimposed, bimodal signal consisting of a low frequency component/harmonic and a high frequency component/harmonic. In embodiments, the electric field waveform may consist of alternating short duration, nanosecond-order pulses with long-duration, microsecond order pulse in succession.

In embodiments, the waveforms are asymmetric to electrophoretically drive exogenous agents, chemical agents, DNA molecules, or nanoparticles through permeabilized membranes. The carrier frequency of the waveforms may be in the range of 100 kHz to 10 MHz. In embodiments, the carrier frequency or pulse duration of the waveforms are chosen based on the cross-over frequency of the cell populations. In other embodiments, the pulses are optimized based on the dielectric properties of the cell populations within the targeted zone of therapy to enable selectivity. In other embodiments, the pulses are optimized based on the physical nucleus to cytoplasm size ratio of the cell populations within the targeted zone of therapy to enable selectivity. In other embodiments, the pulses are designed to generate electro fusion within a select population of cells.

In other embodiments, the pulses are designed to generate simultaneous modulation of the nuclear membrane and outer membrane transmembrane potential. The desired modulatory effect may trigger both reversible electroporation of the nuclear and outer membranes. Alternatively, the desired modulatory effect may trigger reversible electroporation of the outer membrane and irreversible electroporation of the nuclear membrane. Alternatively, the desired modulatory effect triggers both necrosis and apoptosis. Alternatively, the desired modulatory effect slows or arrests cell division. Alternatively, the desired modulatory effect is to prevent metastasis of infiltrative cells.

The treatments may be applied in a single session lasting under 1 hr using an external device. The treatments may be applied over multiple days using an external or implantable device. The resting time between pulses may be varied as part of the optimization routine to select for aberrant cells. The pulses may be delivered in a repetitive manner to lower the required effective field strength and enable the use of solid state switching devices.

In embodiments, the required effective field strength is on the order of 100 to 10,000 V/cm. The solid state switching devices may be arranged in a multi-level, neutral point clamped, or cascaded H-bridge topology.

Embodiments of the invention include an electrical pulse designed to generate a range of field strengths beyond the aberrant cell growth region that results in cell death, slowing the growth rate of, halting the migration of, or preventing the transport of blood and nutrients to aberrant cells while preserving healthy cells, and within the aberrant cell growth region, the field strengths are sufficient to kill, slow the growth rate of, halt migration of, or prevent the transport of blood and nutrients to all cell types. Within the tumor margin, the field strengths are sufficient to enhance the nuclear permeability of all cell types.

Embodiments of the invention include a system for treating a subject suffering from an aberrant cell growth, comprising: at least one electrode configured to be introduced into or adjacent the aberrant cell growth region within the body of a subject, a voltage pulse generator coupled to the electrode and configured to applying multiple electrical pulses to generate an electric field within the growth region with field strengths selective to kill, slow the growth rate of, halt migration of, or preventing the transport of blood and nutrients to aberrant cells while preserving healthy cells.

Embodiments of the invention include a method of treating a subject suffering from an aberrant cell growth, comprising: implanting an electrode into or adjacent the aberrant growth region within the body of a subject, and causing multiple electrical pulses to be emitted from the electrode into the aberrant cell growth region to generate an electric field, wherein the electric field strengths generated within the aberrant cell growth region are selective to kill, slow the growth rate of, halt migration of, or prevent the transport of blood and nutrients to aberrant cells while preserving healthy cells. In embodiments of the method, the electric field has unipolar or bipolar wave form of a rectangular pulse, ramp, decaying exponential, or sine wave. The multiple electrical pulses may take the form of a superimposed, bimodal signal consisting of a low frequency component and a high frequency component. Alternatively, the multiple electrical pulses may consist of alternating short duration, nanosecond-order pulses with long-duration, microsecond order pulse in succession. In embodiments of the method, the frequency of multiple electrical pulses may be in the range of 100 kHz to 10 MHz. In embodiments of the method, the pulses are asymmetric to electrophoretically drive exogenous agents, chemical agents, DNA molecules, or nanoparticles through permeabilized membranes.

In embodiments of the method, the required effective field strength is on the order of 100 to 10,000 V/cm. The carrier frequency or pulse duration of the pulses may be chosen based on the cross-over frequency of the cell populations. Alternatively or additionally, the pulses may be optimized based on the dielectric properties, or the physical nucleus to cytoplasm size ratio of the cell populations within the targeted zone of therapy to enable selectivity. In embodiments of the method, the pulses are designed to generate electro fusion within a select population of cells. In embodiments of the method, the pulses are designed to generate simultaneous modulation of the nuclear membrane and outer membrane transmembrane potential. In embodiments, the desired modulatory effect triggers reversible electroporation of the outer membrane, and irreversible or reversible electroporation of the nuclear membrane. Alternatively or in addition, the desired modulatory effect triggers both necrosis and apoptosis.

In embodiments of the method, the treatments are applied by way of at least one session using an external device or implantable device. The resting time between pulses may be varied as part of the optimization routine to select for aberrant cells. In embodiments, the pulses are delivered in a repetitive manner to lower the required effective field strength and enable the use of solid state switching devices. The solid state switching devices may be arranged in a multi-level, neutral point clamped, or cascaded H-bridge topology.

In embodiments, the pulses, systems, and methods of the invention may have applications in biomedical cancer or tumor treatment.

Figure 1:
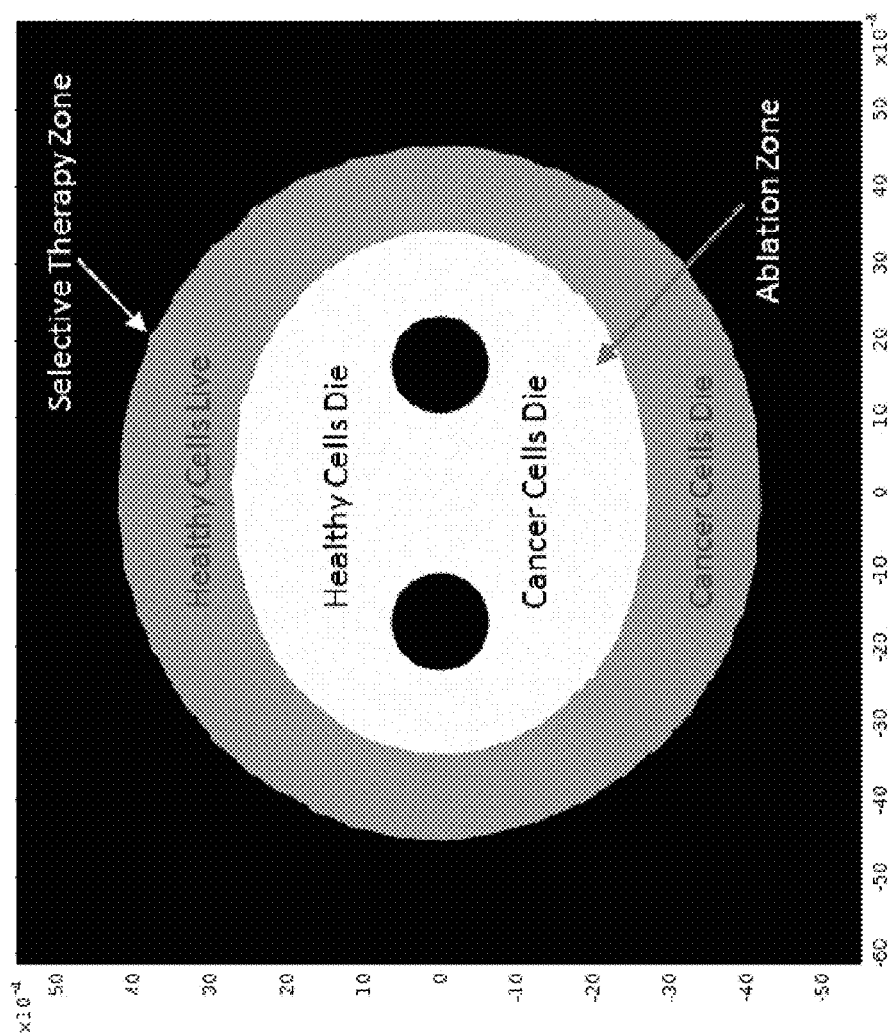
FIG. 1 is a schematic diagram showing an ablation zone and a selective therapy zone according to the invention, with the x- and y-axes showing distance in meters.

The following figures further illustrate the invention. FIG. 1 shows an exemplary dual treatment zone of the invention. The white inner portion surrounding the two black circles represents the ablation zone surrounding a pair of electrodes. In the ablation zone both healthy cells and cancers cells undergo necrosis. The orange zone (grey zone, in black and white figures) outside the perimeter of the ablation zone represents the selective therapy zone, in which cancer cells die and healthy cells are spared. The dual treatment zone results from optimized pulse parameters of the invention, which target the membrane potential of intracellular membranes such as the nuclear envelope.

Figure 2:
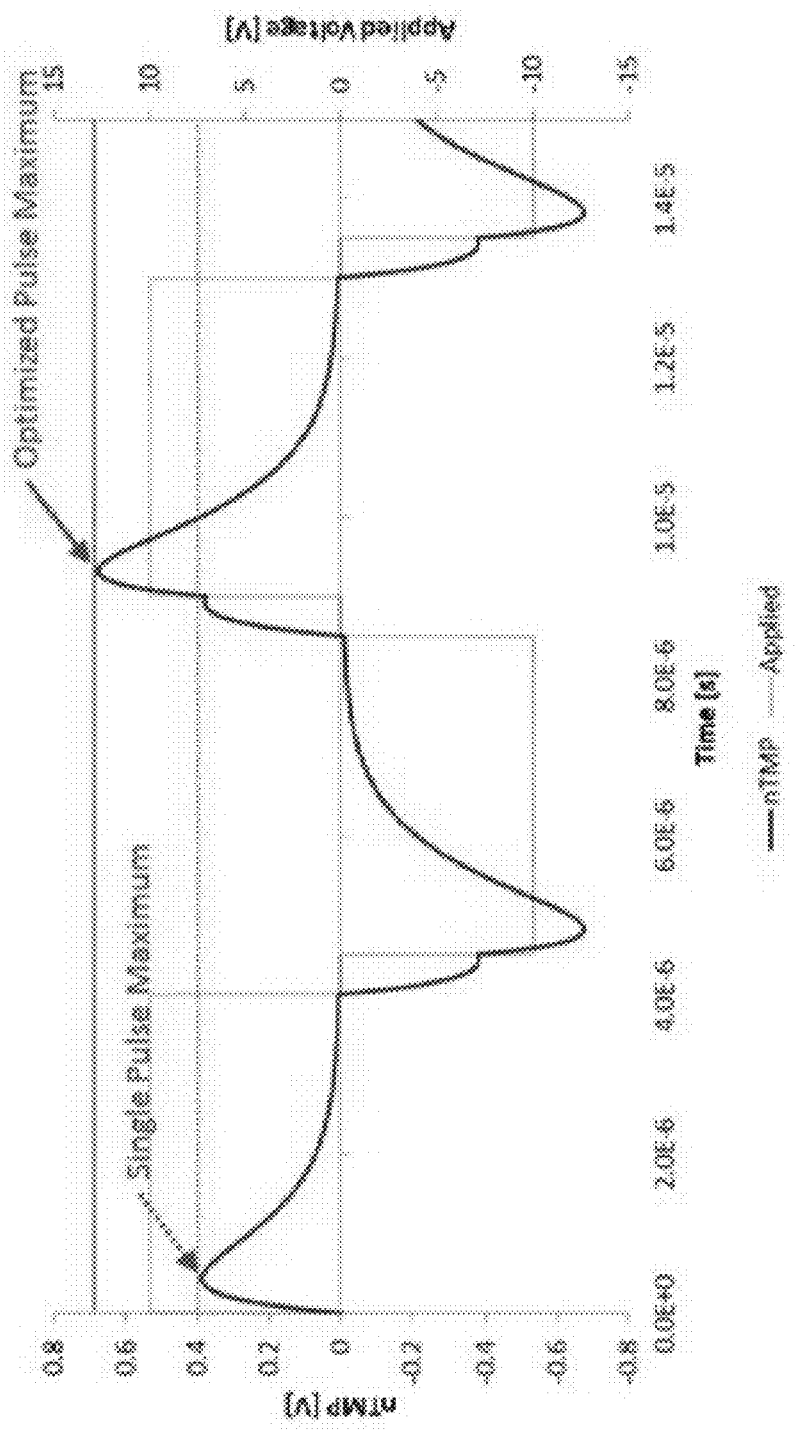
FIG. 2 is a graph showing the effects of an optimized pulse length and pulse delay on the nuclear transmembrane potential.

FIG. 2 shows the effects of optimizing pulse parameters on the nuclear transmembrane potential. As can be seen in the figure, a short delay time between bipolar pulses which is a fraction of the pulse length results in an increase in the nuclear transmembrane potential (optimized pulse maximum) that exceeds that of a single pulse (single pulse maximum).

Figure 3:
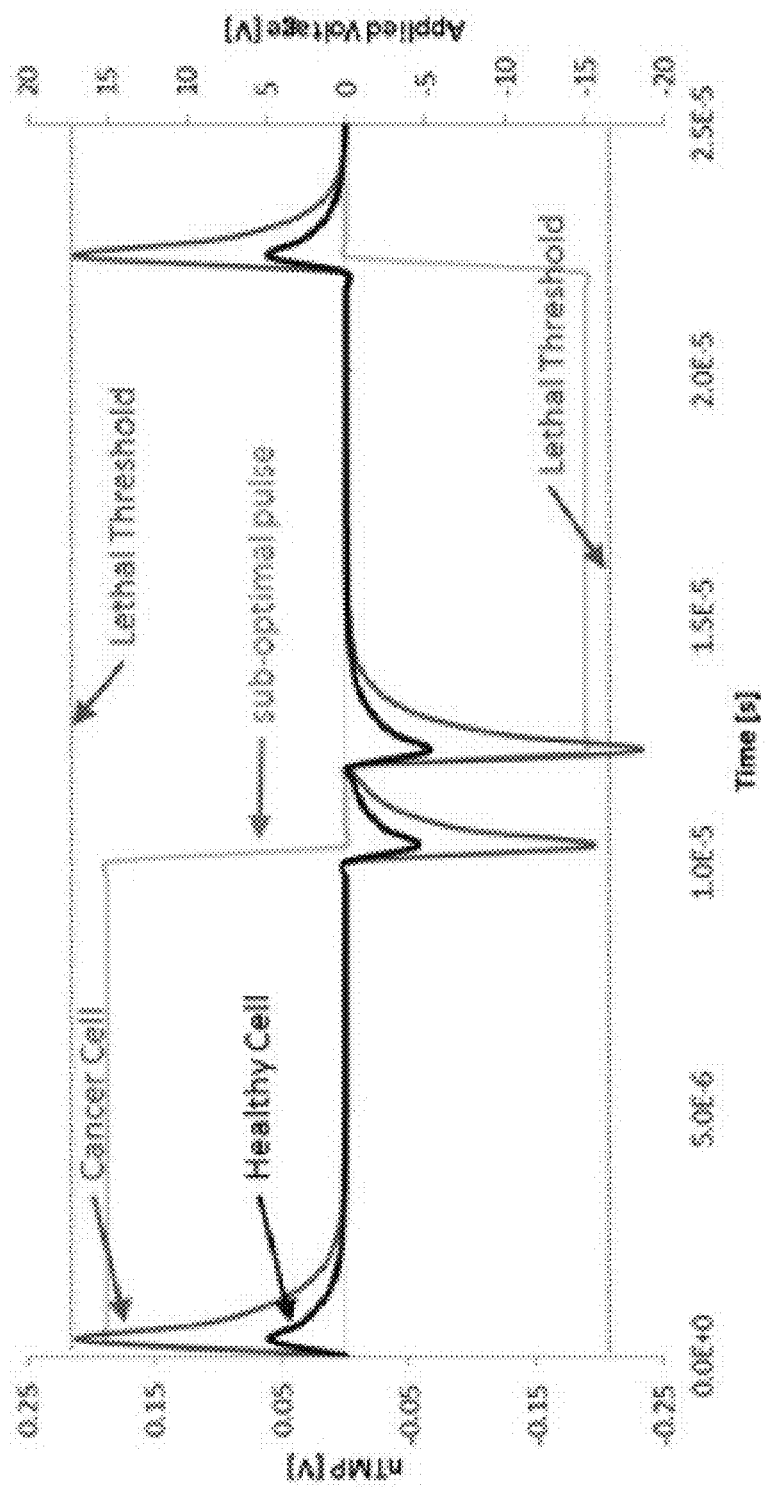
FIG. 3 is a graph showing effects of a suboptimal pulse on the nuclear transmembrane potential in a healthy cell and a cancer cell.

FIG. 3 shows that the nuclear transmembrane potential (nTMP) of cancer cells and healthy cells respond differently to a suboptimal pulse. As shown in the figure, the nuclear transmembrane potential of cancer cells reaches a lethal threshold, while that of a healthy cell is just a fraction of that of a cancer cell. Not wishing to be bound by theory, these differences may be due in part to the larger size of the nucleus in cancer cells. In embodiment, variables were defined as $V_{media}$, $V_{cyto}$, $V_{nuc}$ for the media, cytoplasm, and nucleoplasm domains, respectively. Variables were then defined to calculate the cell membrane (TMP) as ($V_{media}$-$V_{cyto}$) and the nuclear membrane (nTMP) a ($V_{cyto}$-$V_{nuc}$).

Figure 4:
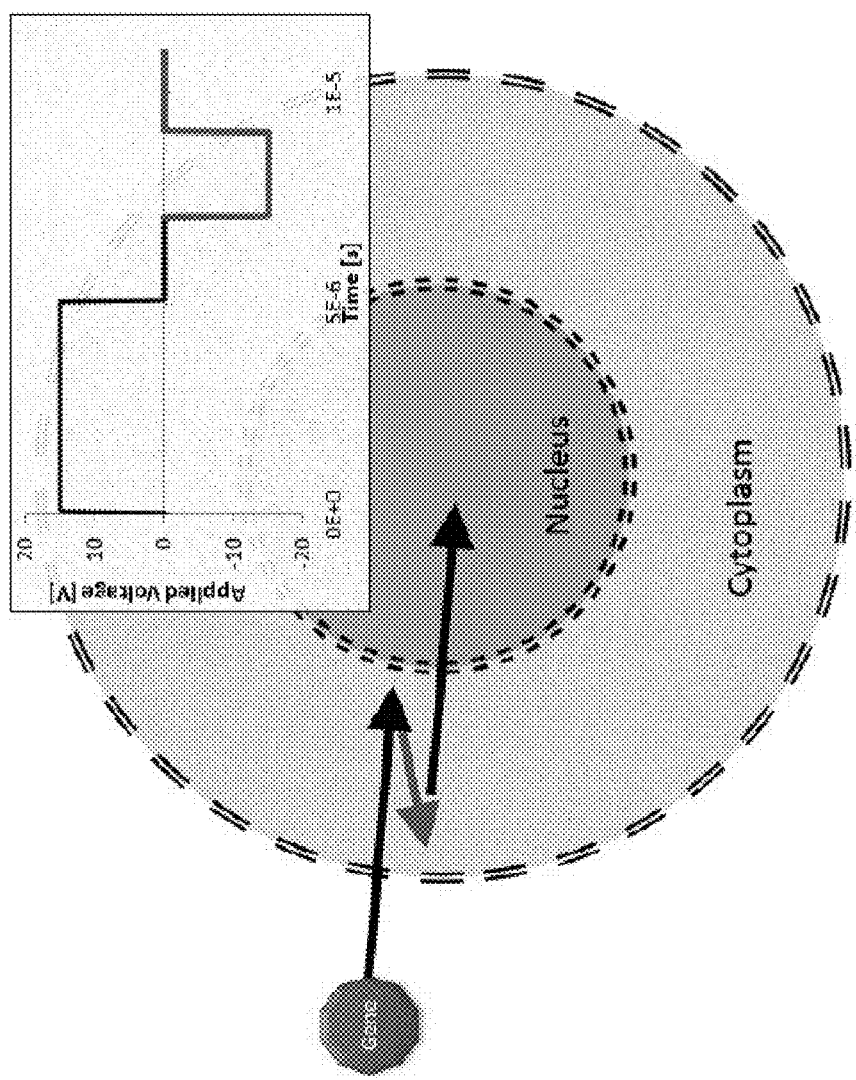
FIG. 4 is a schematic diagram and an overlayed graph showing enhanced electrophoretic transfer of a gene with asymmetric pulses.

In embodiments, the optimized pulse protocol can be used to increase the transport of molecules between the cytoplasm and intracellular organelles. For example, the optimized pulse protocol of the invention can enhance electro-gene and electro-chemo therapy. Additionally, assymetric pulses can enhance electrophoretic transfer. This is shown schematically in FIG. 4.

In embodiments, bimodal sinusoidal signals can be used to achieve an amplification effect. Indeed, any signal with two or more different frequency components can be used, such as a signal with two, three, four, five, or six frequency components. For example, FIG. 5D shows a bimodal sinusoidal signal comprising two different frequency components, a first frequency component (FIG. 5B) and a higher second frequency component (FIG. 5C); their respective effects on the nuclear transmembrane potential are shown in FIGS. 5E-5G. FIG. 5A is a key to FIGS. 5E-5G which shows how the transmembrane potential of two different cells with different nuclei size are plotted, with the dashed line representing an 8 micrometer diameter cell and the solid line representing a 6 micrometer diameter cell.

Figure 6:
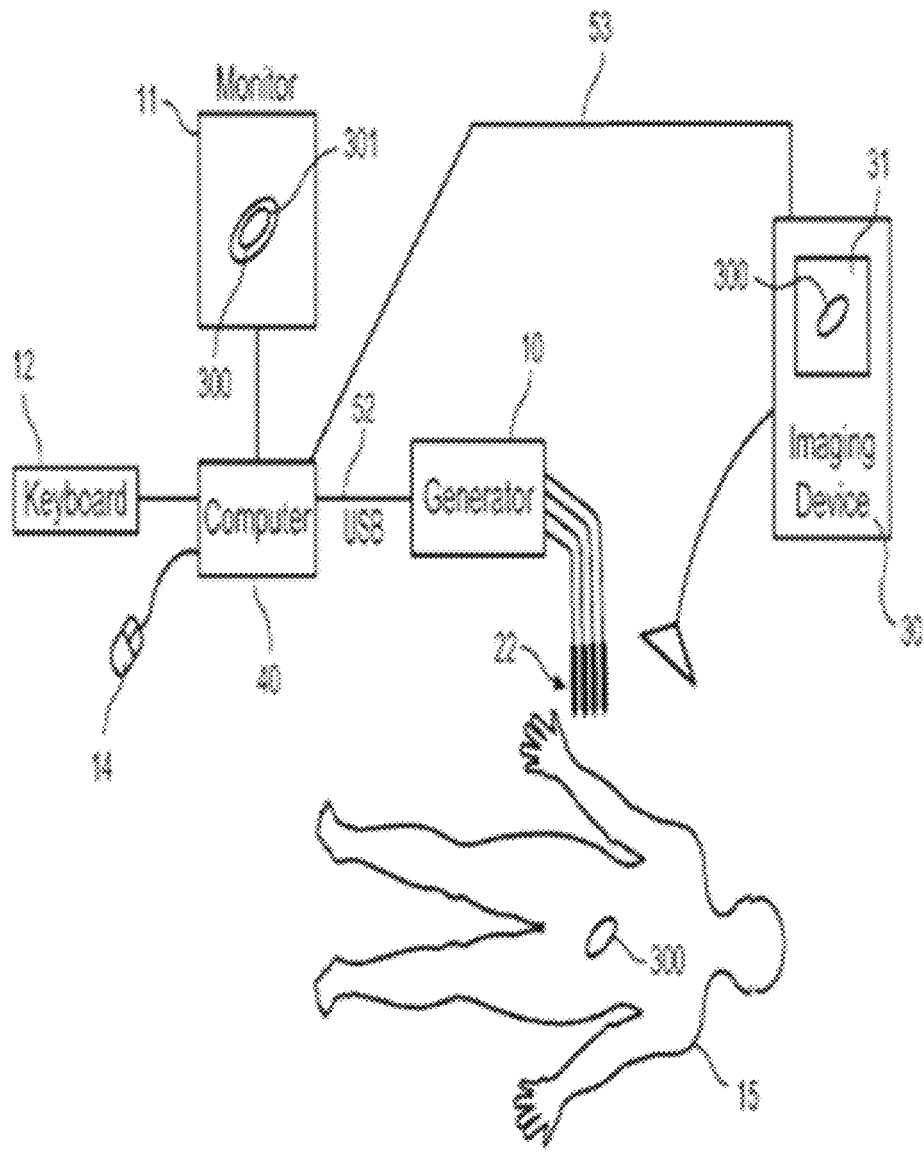
FIG. 6 is a schematic diagram of a representative system of the invention.
Figure 7:
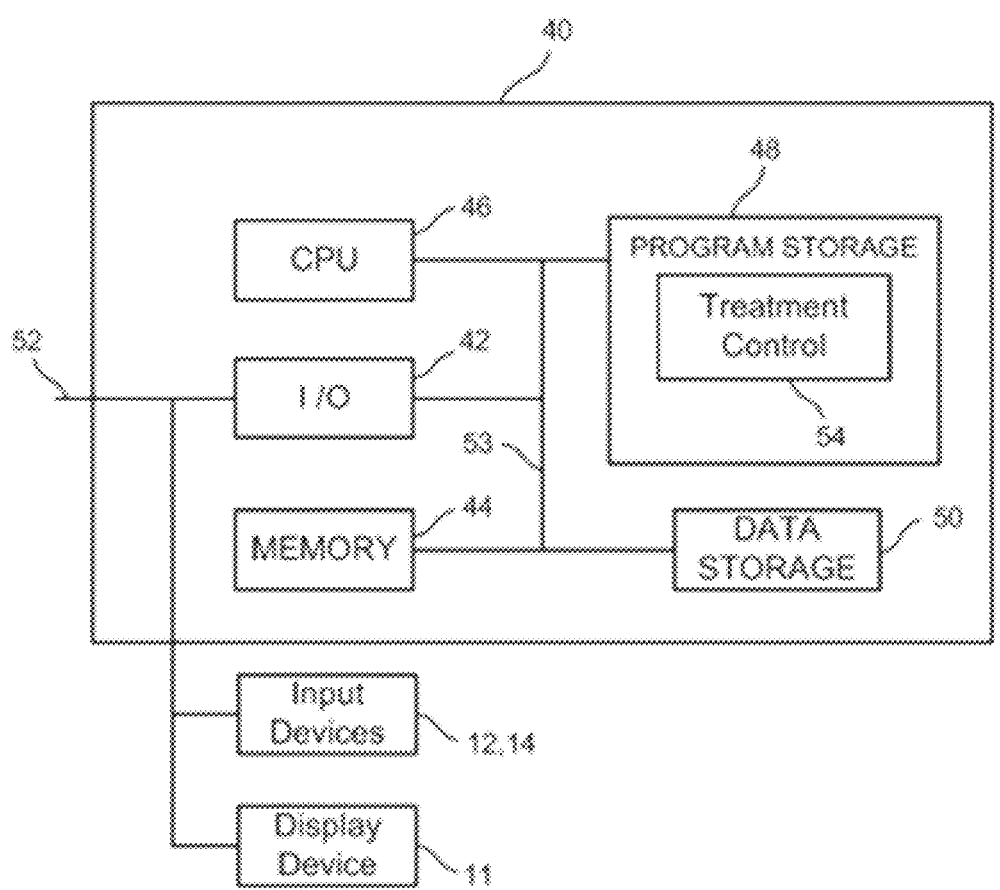
FIG. 7 is a schematic diagram of a representative control computer for implementing a treatment of the invention.

Additionally, embodiments of the invention may include one or more systems capable of performing one or more steps of the method. One embodiment of the present invention is illustrated in FIGS. 6 and 7. Representative components that can be used with the present invention can include one or more of those that are illustrated in FIG. 6. For example, in embodiments, one or more probes 22 can be used to deliver therapeutic energy and are powered by a voltage pulse generator 10 that generates high voltage pulses as therapeutic energy, such as pulses capable of irreversibly electroporating the tissue cells of the target tissue. In the embodiment shown, the voltage pulse generator 10 includes six separate receptacles for receiving up to six individual probes 22 which are adapted to be plugged into the respective receptacle. The receptacles are each labeled with a number in consecutive order. In other embodiments, the voltage pulse generator can have any number of receptacles for receiving more or less than six probes.

For example, a treatment protocol according to the invention could include one or more of a plurality of electrodes. According to the desired treatment pattern, the plurality of electrodes can be disposed in various positions relative to one another. In a particular example, a plurality of electrodes can be disposed in a relatively circular pattern with a single electrode disposed in the interior of the circle, such as at approximately the center. Any configuration of electrodes is possible and the arrangement need not be circular but any shape periphery can be used depending on the area to be treated, including any regular or irregular polygon shape, including convex or concave polygon shapes. The single centrally located electrode can be a ground electrode while the other electrodes in the plurality can be energized. Any number of electrodes can be in the plurality such as from about 1 to 20. Indeed, even 3 electrodes can form a plurality of electrodes where one ground electrode is disposed between two electrodes capable of being energized, or 4 electrodes can be disposed in a manner to provide two electrode pairs (each pair comprising one ground and one electrode capable of being energized). During treatment, methods of treating can involve energizing the electrodes in any sequence, such as energizing one or more electrode simultaneously, and/or energizing one or more electrode in a particular sequence, such as sequentially, in an alternating pattern, in a skipping pattern, and/or energizing multiple electrodes but less than all electrodes simultaneously, for example.

In the embodiment shown, each probe 22 includes either a monopolar electrode or bipolar electrodes having two electrodes separated by an insulating sleeve. In one embodiment, if the probe includes a monopolar electrode, the amount of exposure of the active portion of the electrode can be adjusted by retracting or advancing an insulating sleeve relative to the electrode. See, for example, U.S. Pat. No. 7,344,533, which is incorporated by reference herein in its entirety. The pulse generator 10 is connected to a treatment control computer 40 having input devices such as keyboard 12 and a pointing device 14, and an output device such as a display device 11 for viewing an image of a target treatment area such as a lesion 300 surrounded by a safety margin 301. The therapeutic energy delivery device 22 is used to treat a lesion 300 inside a patient 15. An imaging device 30 includes a monitor 31 for viewing the lesion 300 inside the patient 15 in real time. Examples of imaging devices 30 include ultrasonic, CT, MRI and fluoroscopic devices as are known in the art.

The present invention includes computer software (treatment planning module 54) which assists a user to plan for, execute, and review the results of a medical treatment procedure, as will be discussed in more detail below. For example, the treatment planning module 54 assists a user to plan for a medical treatment procedure by enabling a user to more accurately position each of the probes 22 of the therapeutic energy delivery device 20 in relation to the lesion 300 in a way that will generate the most effective treatment zone. The treatment planning module 54 can display the anticipated treatment zone based on the position of the probes and the treatment parameters. Additionally, the treatment planning module 54 may have a user interface which allows a user to input one or more parameters for IRE.

The treatment planning module 54 can display the progress of the treatment in real time and can display the results of the treatment procedure after it is completed. This information can be displayed in a manner such that it can be used for example by a treating physician to determine whether the treatment was successful and/or whether it is necessary or desirable to re-treat the patient.

For purposes of this application, the terms "code", "software", "program", "application", "software code", "computer readable code", "software module", "module" and "software program" are used interchangeably to mean software instructions that are executable by a processor. The "user" can be any human, including for example, a physician or other medical professional. The treatment planning module 54 executed by a processor outputs various data including text and graphical data to the monitor 11 associated with the generator 10.

Referring now to FIG. 7, the treatment control computer 40 of the present invention manages planning of treatment for a patient. The computer 40 is connected to the communication link 52 through an I/O interface 42 such as a USB (universal serial bus) interface, which receives information from and sends information over the communication link 52 to the voltage generator 10. The computer 40 includes memory storage 44 such as RAM, processor (CPU) 46, program storage 48 such as ROM or EEPROM, and data storage 50 such as a hard disk, all commonly connected to each other through a bus 53. The program storage 48 stores, among others, a treatment planning module 54 which includes a user interface module that interacts with the user in planning for, executing and reviewing the result of a treatment. Any of the software program modules in the program storage 48 and data from the data storage 50 can be transferred to the memory 44 as needed and is executed by the CPU 46.

In embodiments, the user interface may be a graphical user interface which may be used in conjunction with the computer readable code. The user interface may allow a user to enter or input one or more parameters to be used by the treatment planning module 54 in setting a treatment protocol for IRE. The user interface may allow such input through the use of text fields, check boxes, pull-downs, sliders, command buttons, and the like. Based on this input 54, the treatment planning module 54 can calculate a threshold electric field for IRE of the target tissue and one or more parameters of a treatment protocol for administering the IRE in a manner sufficient to produce this threshold electric field.

In embodiments, the treatment planning module 54 provides for numerical modeling capabilities such as those described in the Examples. The model may be used to simulate the nuclear and cellular transmembrane potential of various pulsing parameters prior to treatment. A user interface may allow input of one or more of the parameters listed in the table in FIG. 10 as well as values for pulse length, interpulse delay, electric field strength, etc., and from these a graphic representation of the nuclear and cellular transmembrane potential may be plotted. Additionally, the treatment planning module may allow for a visualization of an ablation zone and surrounding selective treatment zone on the display device 11 based on input of one or more of the parameters.

In one embodiment, the computer 40 is built into the voltage generator 10. In another embodiment, the computer 40 is a separate unit which is connected to the voltage generator through the communications link 52. In a preferred embodiment, the communication link 52 is a USB link. In one embodiment, the imaging device 30 is a stand-alone device which is not connected to the computer 40. In the embodiment as shown in FIG. 6, the computer 40 is connected to the imaging device 30 through a communications link 53. As shown, the communication link 53 is a USB link. In this embodiment, the computer can determine the size and orientation of the lesion 300 by analyzing the data such as the image data received from the imaging device 30, and the computer 40 can display this information on the monitor 11. In this embodiment, the lesion image generated by the imaging device 30 can be directly displayed on the grid (not shown) of the display device (monitor) 11 of the computer running the treatment planning module 54. This embodiment would provide an accurate representation of the lesion image on the grid, and may eliminate the step of manually inputting the dimensions of the lesion in order to create the lesion image on the grid. This embodiment would also be useful to provide an accurate representation of the lesion image if the lesion has an irregular shape.

It should be noted that the software can be used independently of the pulse generator 10. The user can plan the treatment on a different computer as will be explained below and then save the treatment parameters to an external memory device, such as a USB flash drive (not shown). Any non-transitory computer-readable media can be used to store the software and/or the output of the software for a particular treatment protocol. The data from the memory device relating to the treatment parameters can then be downloaded onto the computer 40 to be used with the generator 10 for treatment. Additionally, the software can be used for hypothetical illustration of zones of ablation, temperature thresholds or cutoffs, and electrical field thresholds or cutoffs for training purposes to the user on therapies that deliver electrical energy. For example, the data can be evaluated by a human to determine or estimate favorable treatment protocols for a particular patient rather than programmed into a device for implementing the particular protocol. The treatment protocols can be designed to produce the minimum electrical field threshold for inducing IRE calculated by the treatment planning module 54.

Figure 8:
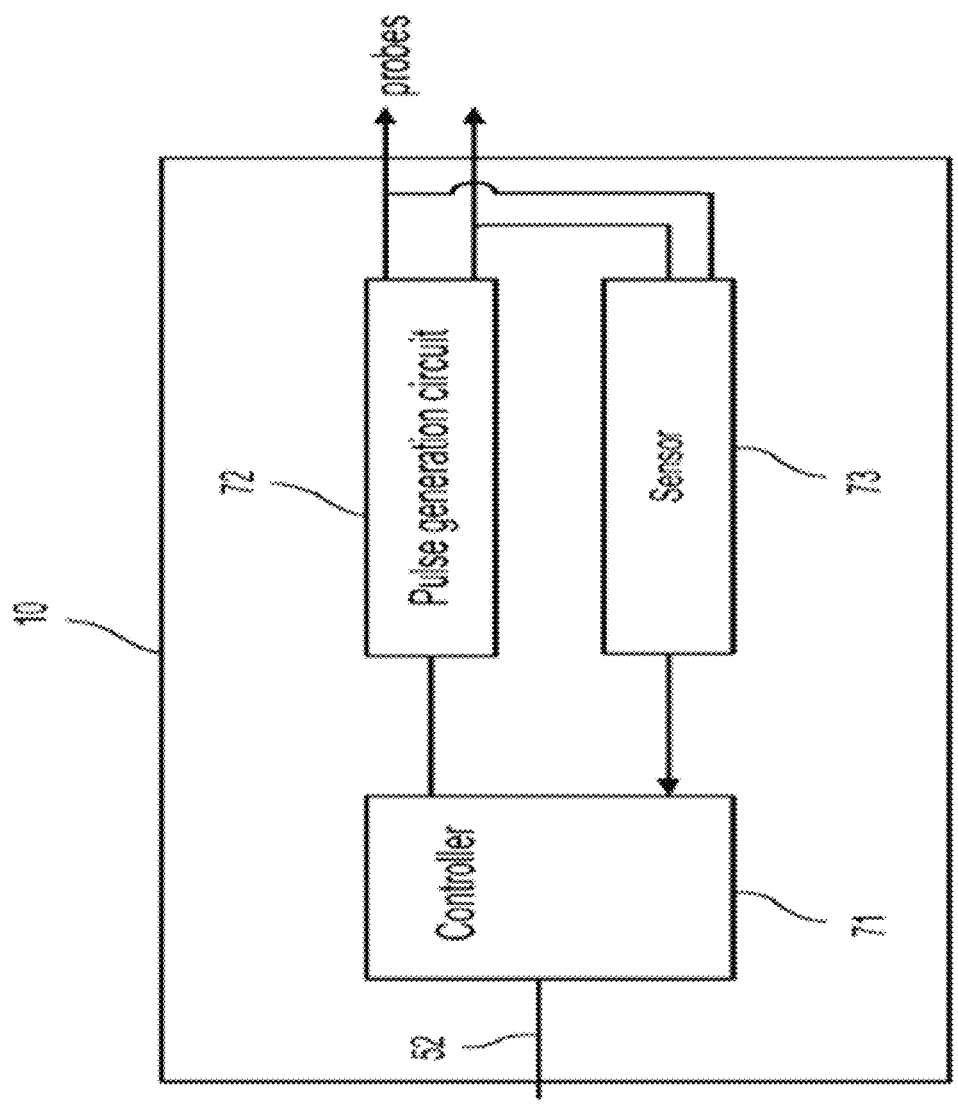
FIG. 8 is diagram illustrating details of the generator shown in the system of FIG. 6, including elements for detecting an over-current condition and/or an under-current.

FIG. 8 illustrates one embodiment of a circuitry to detect an abnormality in the applied pulses such as a high current, low current, high voltage or low voltage condition. This circuitry is located within the generator 10 (see FIG. 6). A USB connection 52 carries instructions from the user computer 40 to a controller 71. The controller can be a computer similar to the computer 40 as shown in FIG. 2. The controller 71 can include a processor, ASIC (application-specific integrated circuit), microcontroller or wired logic. The controller 71 then sends the instructions to a pulse generation circuit 72. The pulse generation circuit 72 generates the pulses and sends electrical energy to the probes. For clarity, only one pair of probes/electrodes is shown. However, the generator 10 can accommodate any number of probes/electrodes (e.g., from 1-10, such as 6 probes) and energizing multiple electrodes simultaneously for customizing the shape of the ablation zone. In the embodiment shown, the pulses are applied one pair of electrodes at a time, and then switched to another pair. The pulse generation circuit 72 includes a switch, preferably an electronic switch that switches the probe pairs based on the instructions received from the computer 40. A sensor 73 such as a sensor can sense the current or voltage between each pair of the probes in real time and communicate such information to the controller 71, which in turn, communicates the information to the computer 40. If the sensor 73 detects an abnormal condition during treatment such as a high current or low current condition, then it will communicate with the controller 71 and the computer 40 which may cause the controller to send a signal to the pulse generation circuit 72 to discontinue the pulses for that particular pair of probes. The treatment planning module 54 can further include a feature that tracks the treatment progress and provides the user with an option to automatically retreat for low or missing pulses, or overcurrent pulses (see discussion below). Also, if the generator stops prematurely for any reason, the treatment planning module 54 can restart at the same point where it terminated, and administer the missing treatment pulses as part of the same treatment. In other embodiments, the treatment planning module 54 is able to detect certain errors during treatment, which include, but are not limited to, "charge failure", "hardware failure", "high current failure", and "low current failure".

General treatment protocols for the destruction (ablation) of undesirable tissue through electroporation are known. They involve the insertion (bringing) electroporation electrodes to the vicinity of the undesirable tissue and in good electrical contact with the tissue and the application of electrical pulses that cause irreversible electroporation of the cells throughout a region of or the entire area of the undesirable tissue. The cells whose membrane was irreversible permeabilized may be removed or left in situ (not removed) and as such may be gradually removed by the body's immune system. Cell death is produced by inducing the electrical parameters of irreversible electroporation in the undesirable area.

Electroporation protocols involve the generation of electrical fields in tissue and are affected by the Joule heating of the electrical pulses. When designing tissue electroporation protocols it is important to determine the appropriate electrical parameters that will maximize tissue permeabilization without inducing deleterious thermal effects. It has been shown that substantial volumes of tissue can be electroporated with reversible electroporation without inducing damaging thermal effects to cells and these volumes have been quantified (Davalos, R. V., B. Rubinsky, and L. M. Mir, Theoretical analysis of the thermal effects during in vivo tissue electroporation. Bioelectrochemistry, 2003. Vol. 61(1-2): p. 99-107).

The electrical pulses used to induce irreversible electroporation in tissue are typically larger in magnitude and duration from the electrical pulses required for reversible electroporation. Further, the duration and strength of the pulses for irreversible electroporation are different from other methodologies using electrical pulses such as for intracellular electro-manipulation or thermal ablation. The methods are very different even when the intracellular (nano-seconds) electro-manipulation is used to cause cell death, e.g. ablate the tissue of a tumor or when the thermal effects produce damage to cells causing cell death.

Typical values for pulse length for irreversible electroporation are in a range of from about 5 microseconds to about 62,000 milliseconds or about 75 microseconds to about 20,000 milliseconds or about 100 microseconds±10 microseconds. This is significantly longer than the pulse length generally used in intracellular (nano-seconds) electro-manipulation which is 1 microsecond or less—see U.S. Published Patent Application No. 2002/0010491.

The pulse is typically administered at voltage such that the local electric field experienced by the tissue is about 100 V/cm to 7,000 V/cm or 200 V/cm to 2000 V/cm or 300V/cm to 1000 V/cm about 600 V/cm for irreversible electroporation. This is substantially lower than that used for intracellular electro-manipulation which is about 10,000 V/cm—see U.S. Published Patent Application No. 2002/0010491.

The voltage expressed above is the voltage gradient (voltage per centimeter). The electrodes may be different shapes and sizes and may be positioned at different distances from each other. The shape may be circular, oval, square, rectangular or irregular etc. The distance of one electrode to another may be in the range of about 0.5 to 10 cm, 1 to 5 cm, or 2-3 cm, for example. The electrode may have a surface area of 0.1-5 sq. cm or 1-2 sq. cm, for example.

The size, shape and distances of the electrodes can vary and such can change the voltage and pulse duration used. Those skilled in the art will adjust the parameters in accordance with this disclosure to obtain the desired degree of electroporation and avoid thermal damage to surrounding cells.

A primary factor in determining the effect of an electroporation procedure is the electric field to which the tissue is exposed. However, IRE protocols have a variety of electrical pulse parameters that may also affect the toxicity of the treatment. In addition to the electric field, these include pulse shape, number of pulses, pulse length, and repetition rate. The thermal effects of an IRE treatment during a pulse are a direct function of the conductivity of the tissue and the voltage to which it is exposed. Therefore, minimizing the thermal effects for a particular tissue type may be done by finding the minimum required electric field, and thus applied voltage, to kill the cells in the tissue.

To this end, pulse parameters and electrode configurations according to embodiments of the invention can include any combination of any of the following: a pulse length in the range of about 1 µs to 1 ms; a number of pulses ranging from 1 to 10,000; an electric field distribution for each conductive wire pair and/or across a treatment region ranging from about 5-5,000 V/cm; a total electrical charge delivered by way of each conductive wire pair and/or across a treatment region of about 0.1 to about 500 mC; a frequency of pulse application ranging from about 0.001-100 Hz; a frequency of pulse signal ranging from about 0-100 MHz; a pulse shape that is square, exponential decay, sawtooth, sinusoidal, or of alternating polarity although the currently favored pulse shape is a biphasic DC pulse; a positive, negative, and neutral electrical charge pulses (changing polarity within the pulse); a resulting current in the treated tissue ranging from about 0 to about 100 amps; from 1-20 electrodes and/or electrically conductive wires; an electrode and/or electrically conductive wire separation distance ranging from about 0.1 mm to about 5 cm; and multiple sets of pulse/electrode parameters for a single treatment, including changing any of the above parameters within the same treatment, such as removing the electrodes and replacing them in different locations within the tissue or changing the number of electrodes, to specialize/customize outcome.

In embodiments treatment protocols can employ a pulse length in the range of about 250 ns and 50 µs, with a delay between pulses on that order. Pulse lengths ranging from about 1 µs to 1 ms are also possible, such as from about 5 µs to about 0.5 ms, or from about 10 µs to about 0.1 ms, or from about 15 µs to about 95 µs. Pulse lengths of 20 µs, 25 µs, 30 µs, 35 µs, 40 µs, 45 µs, 50 µs, 55 µs, 60 µs, 65 µs, 70 µs, 75 µs, 80 µs, 85 µs, 90 µs, 110 µs, 150 µs, or 200 µs, and so on are also acceptable. In some embodiments, the pulse duration of the electroporation-based therapy can exceed 100 µs. Any length pulse or pulse train can be administered in embodiments according to the invention. For example, pulse lengths of about 1 picosecond to 100 seconds can be used, such as from 10 picoseconds to about 10 seconds, or for example from about 100 picoseconds to about 1 second, or from 1 nanosecond to 100 milliseconds, or from about 10 nanoseconds to about 10 milliseconds, or from about 100 nanoseconds to about 1 millisecond, or from about 1 microsecond or 10 microseconds to about 100 microseconds. Some embodiments may have a pulse length ranging from about 100 microseconds to about 1 second, such as a pulse length of about 110, or 120, or 130, or 140, or 150, or 200, or 300, or 350, or 400, or 500, or 600, or 700, or 800 or 900 microseconds, or about 1, 2, 3, 4, 5, 6, 7, 8, 9, or 10 milliseconds, or even 15, 20, 30, 40, 50, 60, 70, 80, 90, or 100 milliseconds, or even for example from about 200, 300, 400, 500, 600, 700, 800, or 900 milliseconds and so on.

In exemplary embodiments, the pulses are monopolar or bipolar and the pulse length may range from about 0.25 microseconds to about 100 microseconds, including 0.5, 1, 2, 3, 4, 5, 6, 7, 8, 9, 10, 20, 30, 40, 50, 60, 70, 80, and 90 µs, or any range in between these values.

In exemplary embodiments, successive pulses, whether monopolar or bipolar may have an interpulse delay between about 0.1 microseconds to about 200 microseconds, including 0.2 microseconds, 0.3 microseconds, 0.4 microseconds, 0.5 microseconds, 0.6 microseconds, 0.7 microseconds, 0.8 microseconds, 0.9 microseconds, 1 microsecond, 1.5 microseconds, 2 microseconds, 2.5 microseconds, 3 microsecond, 3.5 microseconds, 4 microseconds, 4.5 microseconds, 5 microseconds, 5.5 microseconds, 6 microseconds, 6.5 microseconds, 7 microseconds, 7.5 microseconds, 8 microseconds, 8.5 microseconds, 9 microseconds, 9.5 microseconds, 10 microseconds, 20 microseconds, 30 microseconds, 40 microseconds, 50 microseconds, 60 microseconds, 70 microseconds, 80 microseconds, 90 microseconds, 100 microseconds, 120 microseconds, 140 microseconds, 160 microseconds, and 180 microseconds, or any range in between these values.

In exemplary embodiments, the interpulse delay is a portion of the pulse length, including 1%, 2%, 3%, 4%, 5%, 10%, 15%, 20%, 25%, 30%, 35%, 40%, 45%, 50%, 55%, 60%, 65%, 70%, 75%, 80%, 85%, 90%, and 95% of the pulse length, or any range in between these values. In exemplary embodiments, the interpulse delay exceeds the pulse length, including 1.1×, 1.2×, 1.3×, 1.4×, 1.5×, 1.6×, 1.7×, 1.8×, 1.9×, 2.0×, 2.2×, 2.4×, 2.6×, 2.8×, 3.0×, 3.2×, 3.4×, 3.6×, 3.8×, 4.0×, 4.2×, 4.4×, 4.6×, 4.8×, 5.0×, 5.5×, 6.0×, 6.5×, 7.0×, 7.5×, 8.5×, 9.0×, 9.5×, and 10.0× the pulse length, or any range in between these values.

The number of pulses can range for example from 5 to 5,000, or from about 10 to 2,000, or from about 20 to 1,000, or from about 30 to 500, or from about 50 to 200, or from about 75 to 150, or from about 90 to 120, or from about 95 to 110, or about 100 pulses. According to other embodiments, the number of pulses can range from about 5 to about 400 pulses, such as from about 10 to about 350 pulses, or for example from about 15 to about 300 pulses, including from about 20 to about 250 pulses, or from about 25 to about 200 pulses, such as from about 30 to about 150 pulses, for example from about 50 to about 125 pulses, such as from about 75 to about 175 pulses, or from about 90 to 110 pulses, such as about 100 pulses.

Typically, the electric field distribution for each conductive wire pair and/or across a treatment region for IRE is performed using voltages ranging for example between 1500 V/cm to 4,000 V/cm, including 1500 V/cm to 2000 V/cm, 2000 V/cm to 3000 V/cm, 3000 V/cm to 4000 V/cm, 2000 V/cm to 4000 V/cm, 2500 V/cm to 4000 V/cm, and so on. Voltages of much lower power can also be used, including using less than about 1500 V/cm. Applied fields of about 500 V/cm to 1000 V/cm can be used, or even of about 10 V/cm to about 750 V/cm, such as from about 50 V/cm to about 200 V/cm, or an electric field distribution of about 75 V/cm to about 100 V/cm. For example, in the treatment of brain tumors, typically, an applied field of less than 1000 V/cm can be used. Electrical pulse generators that can be used include those capable of delivering from 0 to about 5,000 V, such as the NanoKnife® system of AngioDynamics®, which for example can deliver from 0-3,000 V.

In another embodiment, the amplitude of the pulses of the electroporation-based therapy exceeds 2000 V/cm, including an amplitude of about 2200 V/cm, or 2500 V/cm, such as about 3000 V/cm, or 3500 V/cm, or about 4000 V/cm, such as 4500 V/cm, or about 5000 V/cm, such as about 5500 V/cm, or about 6000 V/cm, or about 6500 V/cm, such as about 7000 V/cm, or about 7500 V/cm, such as 8000 V/cm, or about 8500 V/cm, including 9000 V/cm, or about 9500 V/cm, such as about 10,000 V/cm and so on. Amplitude in the context of this specification refers to the magnitude of the electrical energy being applied using electrical pulses and which pulses can be of either positive or negative polarity.

According to methods of the invention, cycle times for pulses are set generally about 1 Hz. Furthermore, it has been found that alternating polarity of adjacent electrodes minimizes charge build up and provides a more uniform treatment zone. More specifically, in experiments performed by the inventors, a superficial focal ablative IRE lesion was created in the cranial aspect of the temporal lobe (ectosylvian gyms) using the NanoKnife® (Angiodynamics, Queensbury, N.Y.) generator, blunt tip bipolar electrode (Angiodynamics, No. 204002XX) by delivering 9 sets of ten 50 µs pulses (voltage-to-distance ratio 2000 V/cm) with alternating polarity between the sets to prevent charge build-up on the stainless steel electrode surfaces. These parameters were determined from ex-vivo experiments on canine brain and they ensured that the charge delivered during the procedure was lower than the charge delivered to the human brain during electroconvulsive therapy (an FDA approved treatment for major depression). Excessive charge delivery to the brain can induce memory loss, and thus is preferably avoided.

Specific method embodiments may employ administering electroporation based therapy using a pulse rate of about 1 Hz to 20 GHz, such as for example from about 10 Hz to 20 GHz, or about 50 Hz to 500 Hz, or 100 Hz to 1 kHz, or 10 kHz to 100 kHz, or from 250 kHz to 10 MHz, or 500 kHz to 1 MHz, such as from 900 kHz to 2 MHz, or from about 100 MHz to about 10 GHz, including from about 200 MHz to about 15 GHz and so on. In an exemplary embodiment, the pulse rate is between 100 kHz and 10 MHz.

In preferred embodiments, a total electrical charge delivered by way of each conductive wire pair and/or across a treatment region of about 0.5 to about 25 mC can be used, such as about 1 mC to about 20 mC, or from about 1.5 mC to about 15 mC, or from about 2 mC to about 10 mC, or from about 5 mC to about 8 mC, and so on. Similarly, in preferred embodiments, the resulting current in the treated tissue can range for example from about 1 A to about 8 A, or from about 2 A to about 6 A, or from about 3 A to about 5 A, such as 4 A. Indeed, for certain applications the total electrical charge delivered can range from about 0.5 to about 500 mC, such as about 10 mC to about 200 mC, or from about 15 mC to about 150 mC, or from about 20 mC to about 100 mC, or from about 50 mC to about 80 mC, and so on. The resulting current in the treated tissue can range for example from about 1 A to about 80 A, or from about 20 A to about 60 A, or from about 30 A to about 50 A, such as 40 A. It is not uncommon for currents for IRE treatments to reach or exceed 40 and 50 amps, and it is further feasible to operate under even higher current with pulse generators capable of operating under such conditions as well. Currents are expected to be high in certain applications, especially when working in an area where the tissue or the medium is highly conductive, such as with blood present in a blood vessel. Pulse width, pulse shape, number of pulses, and the resultant current in the tissue can be adjusted to achieve specific target goals for limiting the total electric charge, and any of the specific values disclosed in this specification can be used to calculate the target expected charge.

Any number of electrically conductive wires or electrodes can also be used. However, in preferred embodiments 3 to about 18 electrodes are used, such as 3 to 16, or from about 3 to 15, or from 4 to 12, or from 5 to 10, or from 6 to 8. Any one or more of the electrodes/wires can be selectively energized to achieve a particular treatment result. Further, the separation distance between electrically conductive surfaces, such as electrically conductive wires and/or electrodes, can range from about 0.2 mm to about 4 mm, such as ranging from about 0.3 mm to about 3 mm, or from about 0.4 mm to about 2 mm, or from about 0.5 mm to about 1 mm, or from about 0.8 mm to about 4 cm, such as from about 0.9 mm to about 3 cm, or from about 1.2 cm to about 2 cm, or from about 1.5 cm to about 1.8 cm, and so on.

Additional parameters of protocols that can be used in embodiments of the invention are provided in U.S. Published Patent Application Nos. US 2007/0043345, 2009/0269317, 2011/0106221, 2012/0109122, 2013/0184702, 2013/0345697, 2014/0039489, and 2015/0088120, as well as in U.S. Pat. Nos. 8,926,606, 8,992,517, 8,814,860, 8,465,484, the disclosures of each of which are hereby incorporated by reference in their entireties.

EXAMPLES

The following Examples serve to further illustrate the invention.

Example 1 presents a bimodal enhanced ablation mechanism (BEAM) platform that uses one or more bursts of high frequency electric fields which have been specifically optimized to modulate intracellular effects in cancer cells while sparing healthy tissue. An optimal burst contains constitutive pulses with durations approximately equivalent to the charging time of the cell membrane plus the discharge time of the nuclear envelope. This novel concept is expanded upon further in the following sections and has implications for targeting specific cancer types without the need of external markers but with similar specificity to pharmaceutical compounds.

Example 2 presents the in-vitro effects of high frequency bi-polar bursts. Individual pulses within the burst are separated by 2 μs and sequential pulses alternate in polarity. The bursts are repeated once per second for 80 seconds and each burst exposes cells to the applied voltages for 100 μs. To demonstrate the effects of these pulses on the cell membrane and intracellular organelles, the inventors present a finite element model of a cell including a nuclear envelope. The charging behavior of the lipid-bilayer and nuclear envelope is evaluated in response to pulses between 250 ns and 50 μs. A parametric analysis is conducted on the intra- and extracellular conductivity, nucleus-to-cytoplasm ratio, and pulse-to-pulse delay time. In-vitro experiments are presented to confirm the non-thermal nature of the protocol and demonstrate irreversible electroporation within this intermediate pulse-width range.

In Example 3, the inventors explored the pulse-duration space between 250 ns and 100 μs and calculated the lethal electric field intensity for specific bimodal enhanced ablation mechanism (BEAM) protocols using a 3D tumor mimic. The inventors found that the nominal lethal thresholds for bursts containing 0.25, 0.5, 1, 2, 5, 10, and 50 μs pulses were 2022, 1687, 1070, 755, 640, 629, and 531 V/cm, respectively. A murine tumor model was used to investigate the effectiveness of BEAM in vivo. Tumors were exposed to 200 bursts, each energized for 100 μs, containing individual pulses 1, 2, or 5 μs in duration. In all treatment groups, average tumor growth was substantially inhibited versus control. 6 of 14 treated mice had no measurable signs of tumors 30 days after treatment and all protocols were able to achieve complete regressions. This work shows the potential for BEAM to be used as a focal therapy and merits its investigation in larger pre-clinical models.

In Example 4, the inventors report a physical treatment method based on electrical disruption of cells, whose action depends strongly on cellular morphology. Interestingly, numerical modeling suggests that while outer lipid bilayer disruption induced by long pulses (~100 μs) is enhanced for larger cells, short pulses (~1 μs) preferentially result in high fields within the cell interior, which scale in magnitude with nucleus size. Because enlarged nuclei represent a reliable indicator of malignancy, this presents one method for preferentially targeting malignant cells. While the inventors demonstrate killing of both normal and malignant cells using pulsed electric fields (PEFs) to treat spontaneous canine GBM, properly tuned PEFs can be used to provide targeted ablation based on nuclear size. Using 3D hydrogel models of normal and malignant brain tissues, which permit high-resolution interrogation during treatment testing, the inventors confirmed that PEFs could be tuned to preferentially kill cancerous cells. Finally, the inventors estimated the nuclear envelope electric potential disruption needed for cell death from PEFs. The results may be useful in safely targeting the therapy-resistant cell niches that cause recurrence of GBM tumors.

Example 1

Figure 9:
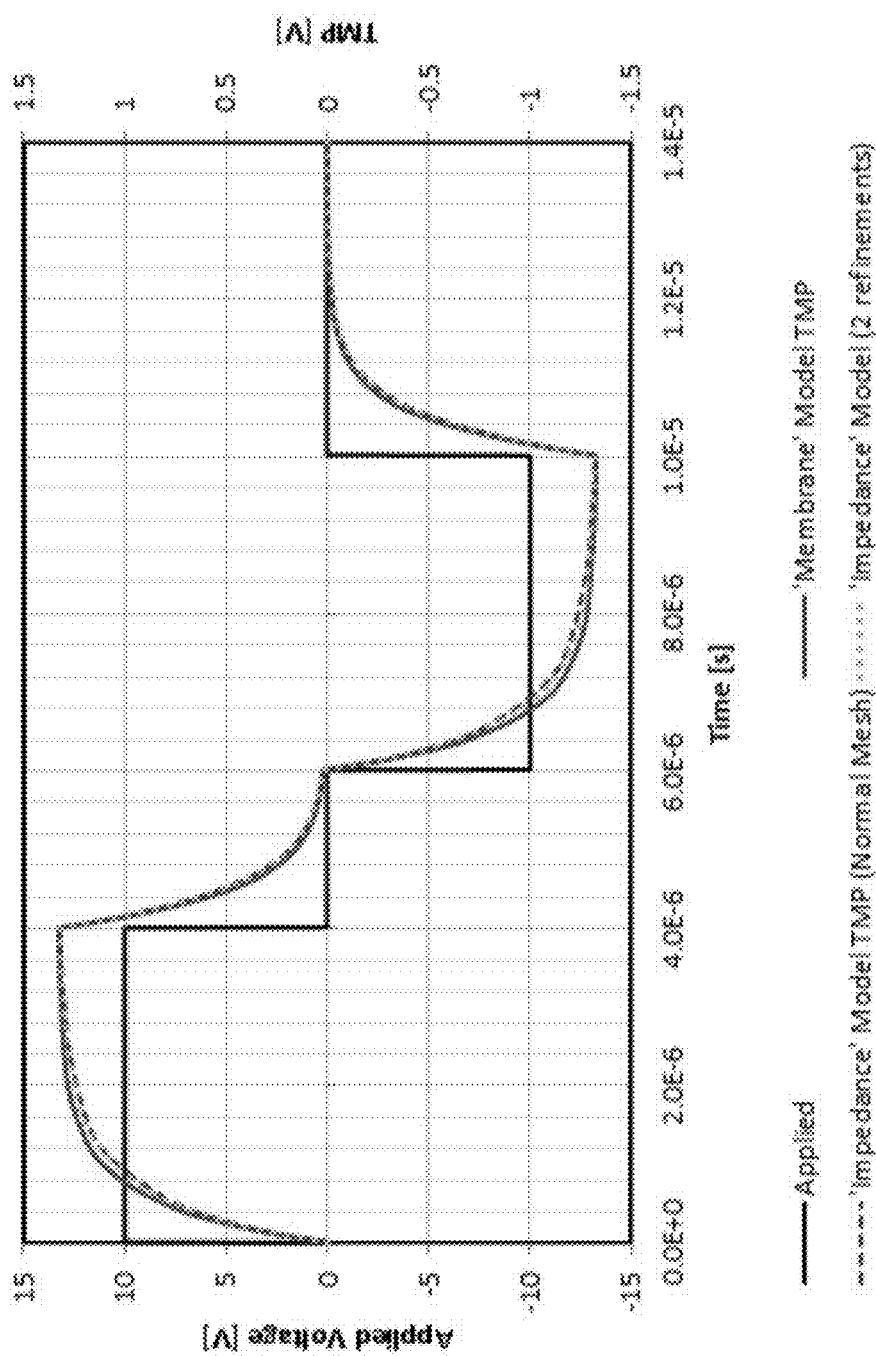
FIG. 9 is a graph showing the results of numerical simulation of the transmembrane potential (TMP) of a cell suspended in 1.0 S/m solution under the influence of a 1000V/cm pulsed electric field.

A numerical model of a cell in suspension was created in Comsol 4.2a. Two schemes were used to model the cell as a membrane covered sphere. In the first model, individual domains were created representing the sample fluid (external to cell), cell membrane, and cytoplasm (internal to cell). The 5 nm thick spherical shell domain representing the cell membrane required significant modification to the default meshing parameters and resulted in a large number of tetrahedral elements. Briefly, the entire geometry was assigned a single mesh with a predefined density of 'Extremely course'. The values for the default parameters were then changed for minimum element size (0.00025), maximum element growth rate (1.2), resolution of curvature (0.04), and resolution of narrow regions (0.0001) to successfully mesh the geometry with 817,184 tetrahedral elements. A computer with a quad core 3.0 GHz processor and 8 GB of ram required 15 hours of computation time to solve a 14 µs transient model with 1,092,902 degrees of freedom (results shown in FIG. 9). This model was presumably the most accurate approach and was used to calculate the frequency, sinusoidal, and pulse response of the TMP for conductivities between 0.01 and 10 S/m. However, it was computationally expensive and limited analysis of transmembrane potentials to the outer cell membrane.

To model the effects of bursts of bipolar square waves and effects on the nuclear membrane, a more efficient impedance boundary condition model was used. In this method, a cubic domain represented the experimental media and two spheres represented the domains for the cytoplasm and nucleoplasm, respectively. For each domain, a separate Electric Currents physics module was used and the dependent voltage variables were defined as $V_{media}$, $V_{cyto}$, $V_{nuc}$ for the media, cytoplasm, and nucleoplasm domains, respectively. Variables were then defined to calculate the cell membrane (TMP) and nuclear membrane (nTMP) as $(V_{media}-V_{cyto})$ and $(V_{cyto}-V_{nuc})$, respectively. In the Electric Currents module, the boundaries representing membranes were defined as impedance boundary conditions with reference voltages prescribed as the voltage in the adjacent domain. In the Media domain, the boundary representing the cell membrane was defined as an impedance boundary with reference voltage of $V_{cyto}$. The layer specification was defined as a 'thin layer' and the electrical conductivity, relative permittivity, and surface thickness were defined using the values presented in the table in FIG. 10.

In the impedance boundary condition model, the mesh was defined as a single Free Tetrahedral group with 'Normal' sized elements resulting in 17,825 tetrahedral elements. In a preliminary study of this model, an additional mesh refinement step (Number of refinements=2) was also taken. With refinement, this computation of the same 14 µs simulation was completed in 27 minutes. Without refinement, the computation time was further reduced to 14 minutes. When compared to the physical boundary model, both impedance boundary configurations sufficiently reproduced similar results. The unrefined impedance boundary condition model was used to conduct the remaining parametric studies.

Analytical Modeling

In order to investigate the effects of a bi-modal sine wave on electroporation, an analytical model was implemented that solved the Laplace equation in the frequency domain for a spherical cell with a concentric nucleus (Yao, C. G., et al., *Study of transmembrane potentials of inner and outer membranes induced by pulsed-electric-field model and simulation*. IEEE Trans Plasma Sci, 2007. 35(5): p. 1541-1549). Each cellular region was characterized by both a dielectric permittivity and conductivity, ensuring TMP and nTMP computational accuracy with frequencies is the MHz range. Briefly, solutions were obtained by merging a low-frequency (250 kHz) and high-frequency (1 MHz) electric field in the time domain, converting the signal to the frequency domain by taking the Laplace Transform, multiplying the signal by a transfer function representing the geometric and dielectric properties of the cell (Kotnik, T. and D. Miklavcic, *Theoretical evaluation of voltage inducement on internal membranes of biological cells exposed to electric fields*. Biophysical Journal, 2006. 90(2): p. 480-491), and converting the result back to the time domain by taking the inverse Laplace transform. To illustrate the clinical benefits of the optimized burst, the Laplace equation was solved for two needle electrodes (Ø 1 mm) in an infinite tissue domain according to standard techniques. The electrodes were spaced 0.1 cm apart and the applied voltage was set to 20 kV.

Cell Preparation and Experimentation

MDA-MB-231 human breast cancer cells were suspended in buffer with conductivity of 0.1 S/m at a concentration of $2.5\times10^6$ cells/ml. A custom pulse generation system capable of delivering 1000 $V_{Peak}$ in each polarity was used to create electric field intensities of approximately 1000, 2000, and 4000 V/cm across cell suspensions in 1 mm or 2 mm electroporation cuvettes. MDA-MB-231 cells were exposed to 90 bursts consisting of 200 bipolar square wave pulses 700 ns wide separated by 1.8 µs of dead time, shown in FIG. 14 (top and middle) at a repetition rate of 1 Hz. Cell viability was assessed 1 and 16 hours post treatment using a Vi-Cell cell viability analyzer (Beckman Coulter). Total viability after 16 hours was quantified as the ratio of live treated cells to live untreated (sham control) cells.

Additional experiments were conducted with PPT8182 murine primary pancreatic tumor cells suspended in a buffer at a concentration of $5\times10^6$ cells/ml with a media conductivity of 0.2 S/m. 100 µL of cell suspension were added to a 2 mm gap cuvette and 80 bursts with 50 microseconds on time in each polarity (100 µs total) were applied. Within each burst, individual pulses had on times of 250 ns, 500 ns, 1 µs, 2 µs, 5 µs, 10 µs, or 50 µs with a 2 µs delay between the end of a pulse and the beginning of the next pulse in the opposite polarity. The cells were exposed to electric fields with magnitudes of 1500 V/cm, 3000 V/cm, and 4000 V/cm.

Numerical Modeling (Outer Membrane)

Figure 11:
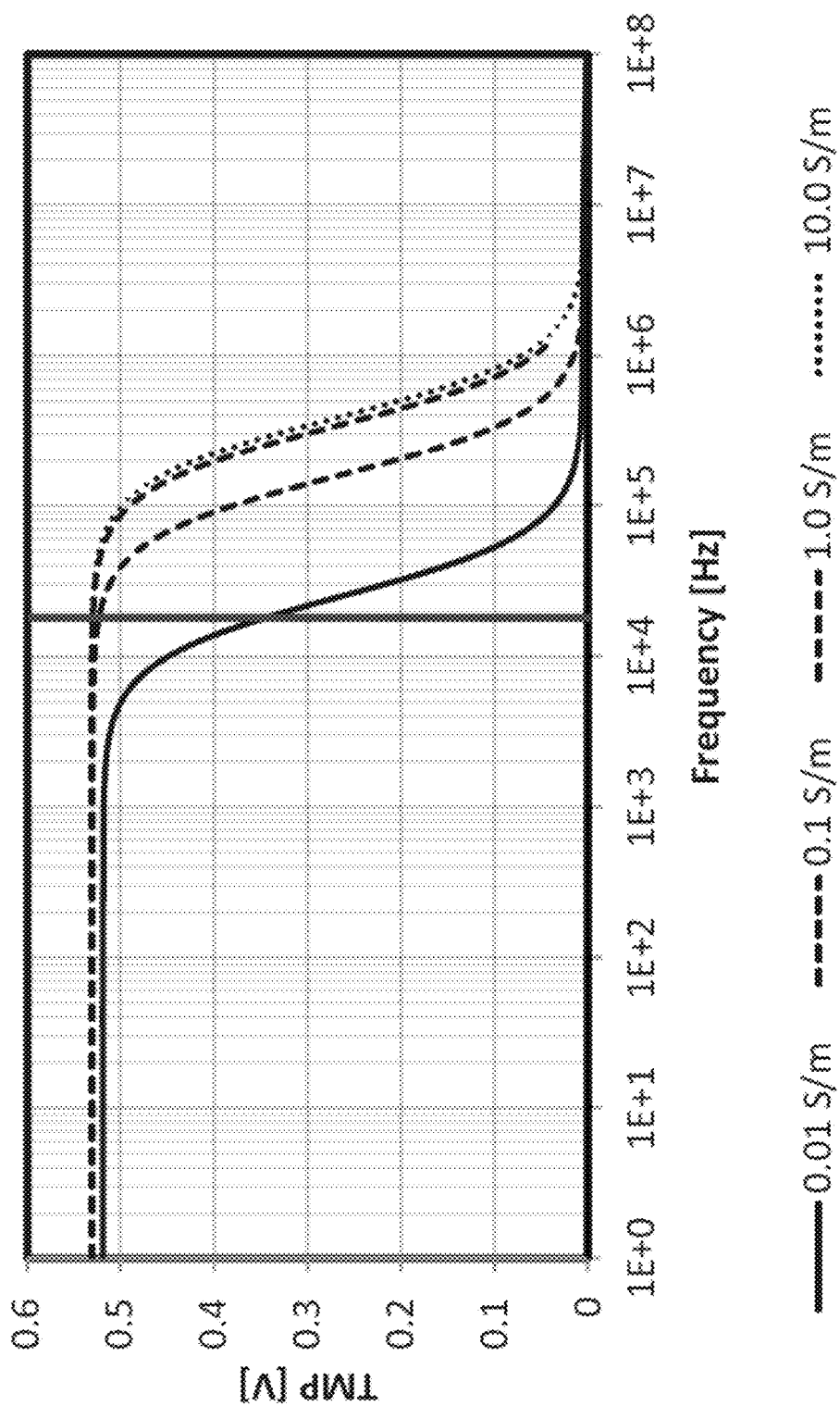
FIG. 11 is a graph showing steady state maximum transmembrane potential (TMP) for a MDA-MB-231 cell under a 400 V/cm electic field verses frequency. The red vertical line represents the first crossover frequency of MDA-MB-231 cells in 0.01 S/m conductivity media.

FIG. 11 shows the maximum TMP for an MDA-MB-231 cell in a 400 V/cm electric field for frequencies between 1 Hz and 100 MHz. DC and low frequency sinusoidal voltages are very effective at increasing the TMP of the cell membrane due to the averaged energized time being much longer than the charging time of the cell membrane. As a result, for a low frequency sinusoidal voltage of 400 V/cm, the TMP is elevated and held at a value greater than the threshold for electroporation independent of the conductivity of the media. In low conductivity solutions, the cell membrane charges more slowly. As the frequency is increased above 1 kHz, the voltage is not on for long enough to fully charge the cell membrane in 0.01 S/m buffer. The results show that the optimal frequency range for interacting with cells without significantly altering their cell membrane occurs above 1 kHz. When operating above 100 kHz, very large magnitude electric fields can be used without significantly increasing the TMP.

Interestingly, previous experimental observations (Sano, M., J. Caldwell, and R. Davalos, *A Low Frequency Contactless Dielectrophoresis Platform for Particle Isolation and Enrichment*. 2011: USA; Sano, M. B., J. L. Caldwell, and R. V. Davalos, *Modeling and Development of a Low Frequency Contactless Dielectrophoresis (cDEP) Platform to Sort Cancer Cells from Dilute Whole Blood Samples*. Biosensors & Bioelectronics, 2011; and Sano, M. B., et al., *Contactless Dielectrophoretic Spectroscopy: Examination of the Dielectric Properties of Cells Found in Blood*. Electrophoresis, 2011. DOI 10.1002/elps.2201100351) showed some degree of electroporation of cells below the first crossover frequency of their Clausius-Mossotti factor, but minimal electroporation above this frequency (i.e. cells were electroporated while experiencing negative DEP, but minimally impacted when experiencing positive DEP). Analysis of the results shown in FIG. 11 shows that the cross-over frequency is collocated with the −3 dB point on the TMP curve. This indicates that at the cross-over frequency, cells are absorbing approximately half of the maximum energy absorbed at lower frequencies and shows the strong dependence of membrane electrical characteristics on DEP and Electroporation effects.

As the conductivity of the media is increased, the charging time of the cell membrane decreases until the media conductivity reaches 1.0 S/m. Above this threshold, increases in media conductivity negligibly impact the TMP charging time. At 0.1 S/m, the −3 dB frequency is not reached until approximately 100 kHz. At 1.0 and 10.0 S/m, this frequency is shifted higher to approximately 300 kHz. If higher conductivity buffers are used in in-vitro experiments, then the frequency range should also be shifted to avoid damaging cell membranes.

Figure 12A:
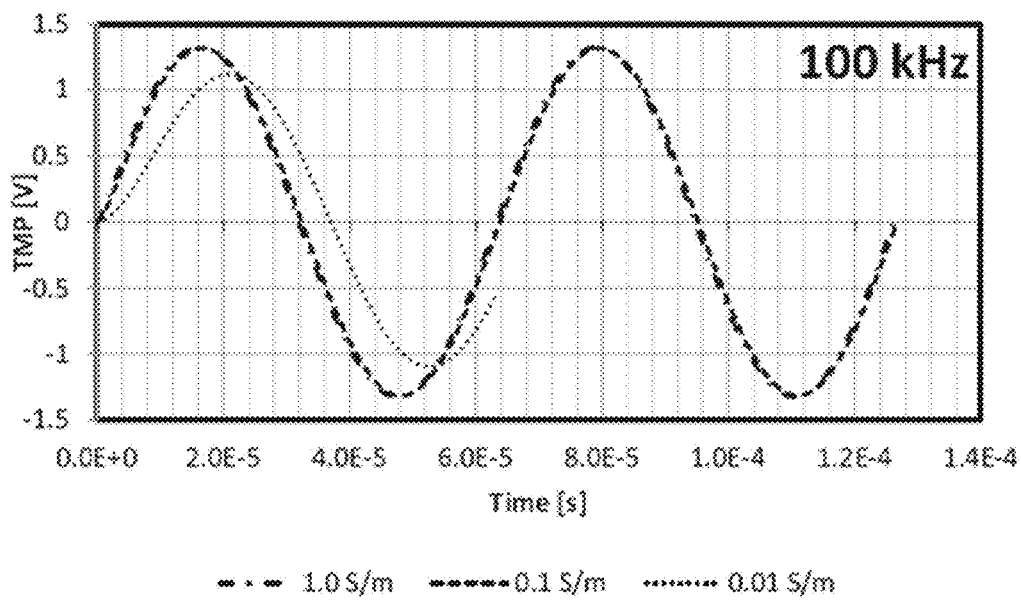
FIGS. 12A and 12B are graphs showing the transmembrane potential (TMP) response to a 1000 V/cm electric field at 100 kHz (FIG. 12A) and 1 MHz (FIG. 12B).
Figure 12B:
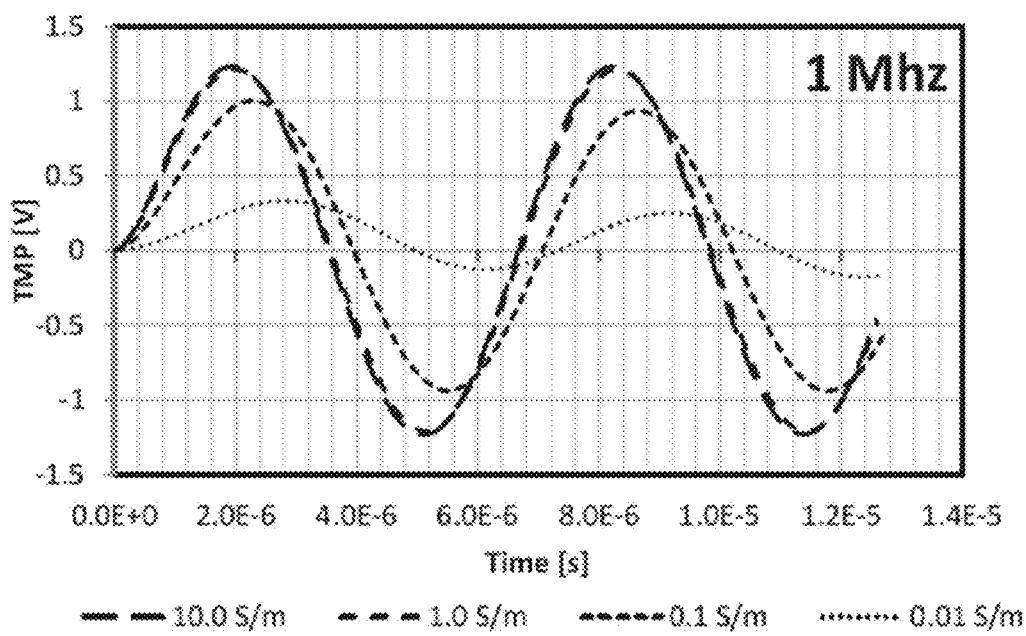

FIGS. 12A and 12B shows the time dependent charging of the TMP for a 1000 V/cm electric field at frequencies of 100 kHz and 1 MHz, respectively. At 100 kHz, the maximum TMP is negligibly affected by media conductivity. At 0.01 S/m there is a slight phase shift and decrease in the maximum value achieved. At 1 MHz, the TMP is drastically affected by media conductivity. A phase shift and decrease is evident for 0.01 and 0.1 S/m conductivity media. This again indicates that low conductivity media provide some measure of protection to cells against lipid bilayer electroporation. In media with conductivity above physiological norms (1.0 S/m), the TMP increases significantly (and in phase) with the applied signal.

Figure 13:
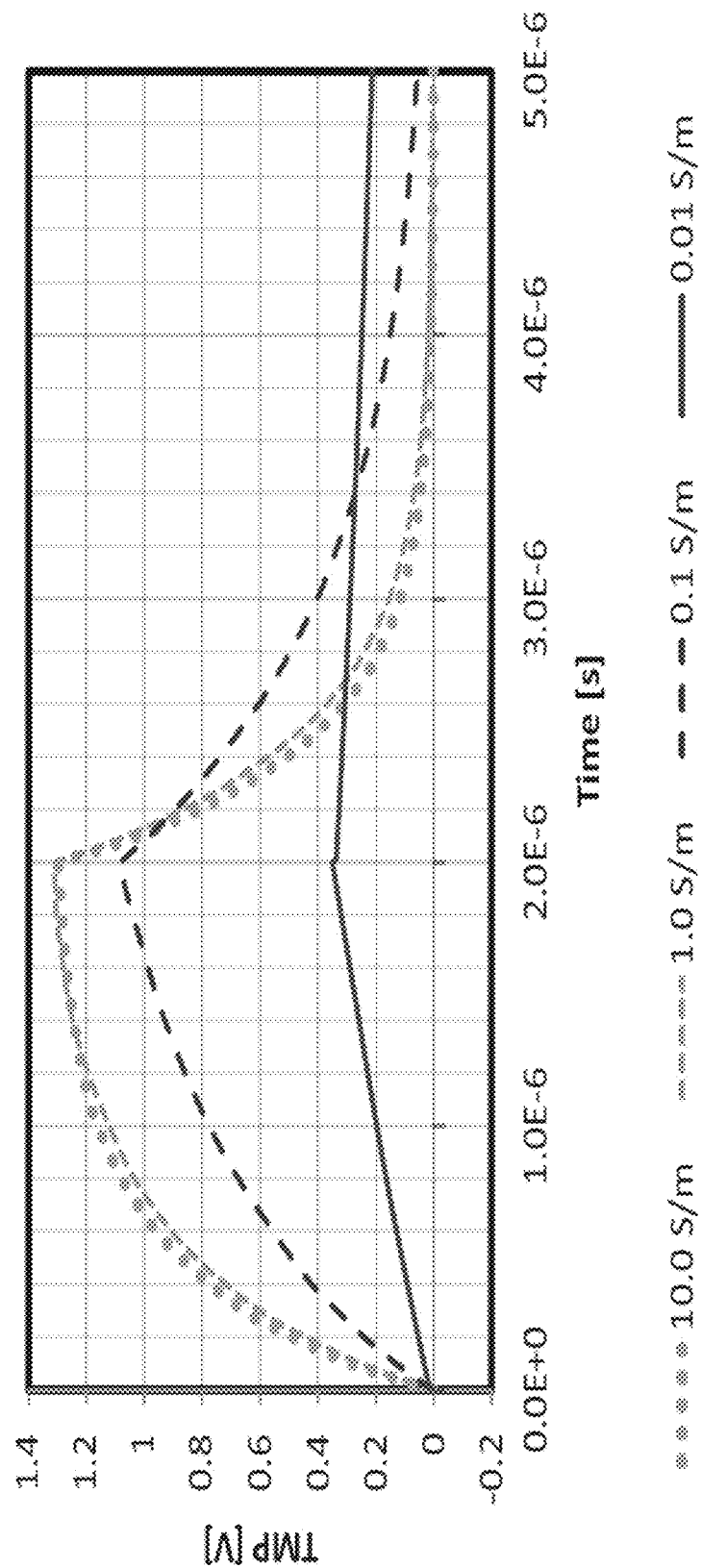
FIG. 13 is a graph showing a transient response to a cell's lipid bilayer to a 1000 V/cm electric field.
Figure 14:
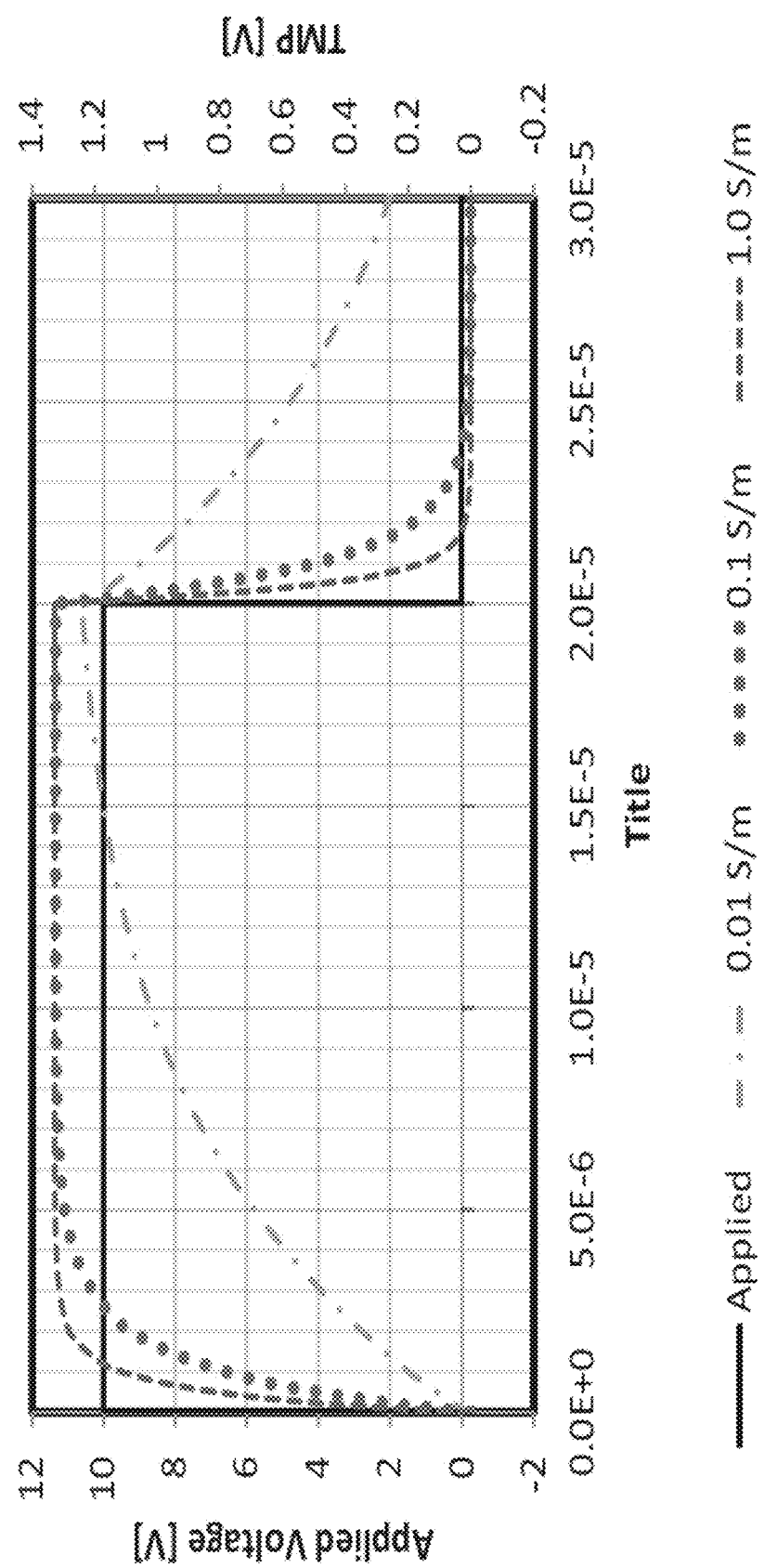
FIG. 14 is a graph of a transient response of a cell to a 1000 V/cm electric field.

FIGS. 13 and 14 show the TMP response to 2 and 20 µs pulsed electric fields with 1000 V/cm magnitudes, respectively. As anticipated from the results with sinusoidal signals, the rate of TMP increase is highly dependent on media conductivity. For the lowest media conductivity (0.01 S/m), it takes longer than 20 µs for the TMP to reach its maximum value. This charging time reduces to approximately 2 µs for conductivities of 1.0 S/m or greater. These results show the exponential increase and decrease in TMP caused by pulsed electric fields. The slower charging rate in physiological conductivities is due to a preference for currents to flow through the cell rather than around it. This highlights the ability to optimize pulse parameters to preferentially impact intracellular components.

Numerical Modeling (Nuclear Membrane)

When a cell is exposed to a pulsed electric field, the capacitive nature of the cell membrane blocks the flow of current through the cell when fully charged. However, the membrane cannot charge instantaneously and there is a brief time when ions and molecules are rearranging and current flows through the cytoplasm of the cell. This displacement current increases the transmembrane potential of membranes surrounding the nucleus and organelles. These cellular components are much smaller than the cell and their theoretical maximum TMP within the same electric filed decreases linearly with their effective radius. Additionally, as a fully charged cell membrane blocks the flow of current through the cytoplasm, these internal membranes can charge for a period less than the TMP charging time.

Figure 15:
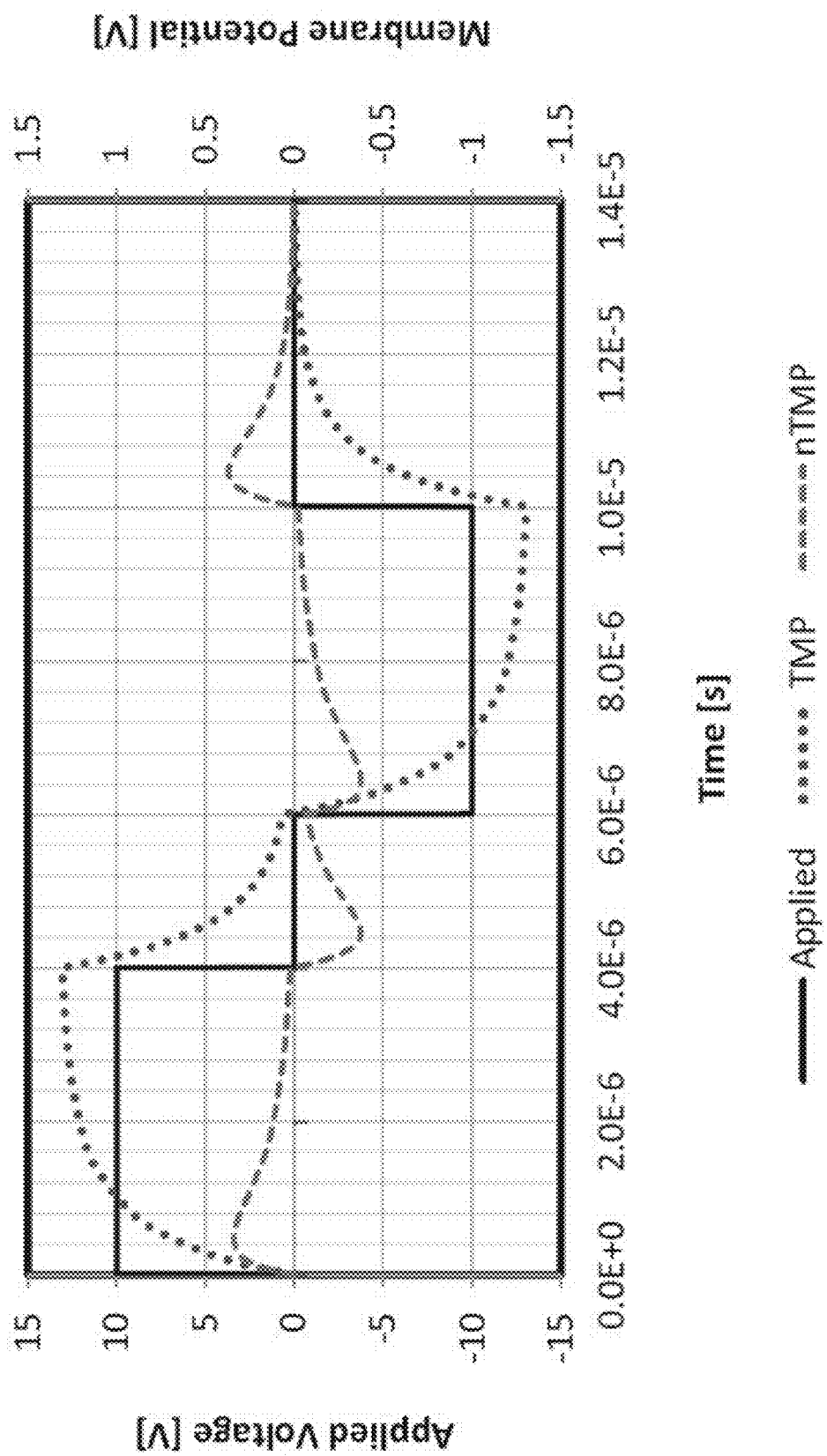
FIG. 15 is a graph showing the transmembrane potential (TMP) and nuclear transmembrane potential (nTMP) for a cell with a 0.5:1 nucleus to cytoplasm ratio.

FIG. 15 shows the charging characteristics of the cell and nuclear membranes for a bipolar pulse with 4 µs on- and 2 µs off-times. For the first 500 ns, current flows through the cytoplasm and the nuclear transmembrane potential (nTMP) increases. After 500 ns, the cell membrane begins to block the flow of current and the nTMP begins to decay back to zero. As the positive going pulse turns off, the charge on the cell membrane begins to dissipate and ions redistributing cause a current to flow in the opposite direction, charging the nuclear membrane in the opposite polarity. This process repeats as the pulse switches polarity. Every bi-polar pulse results in four increases in nTMP with pattern + + − − + +. This pattern of successive nTMP increase in the same polarity suggests that there exists an optimal pulse configuration to increase the maximum nTMP value achievable.

Figure 16:
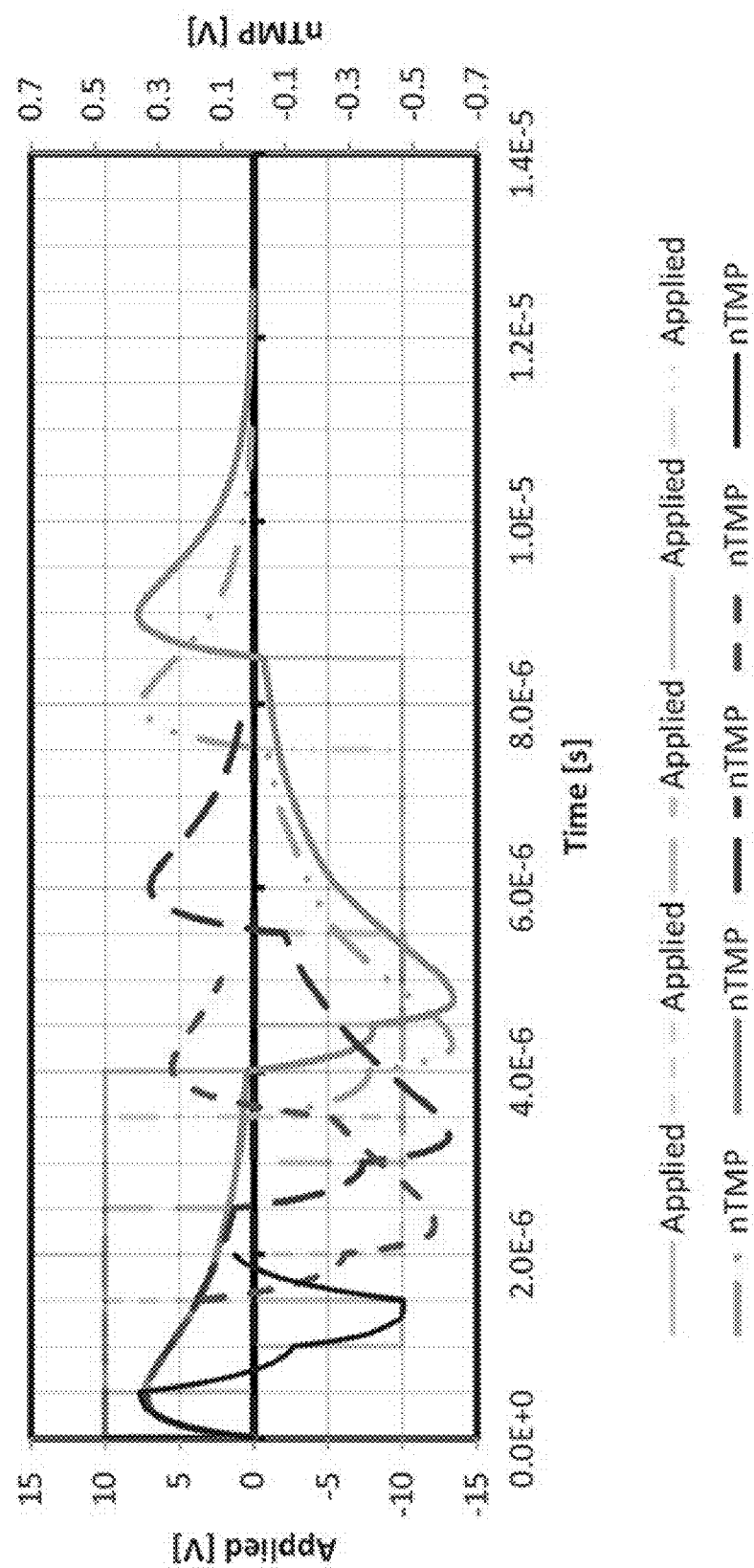
FIG. 16 is a graph showing the effect that pulse time has on the nuclear transmembrane potential (nTMP) when the off time between pulses is held to 500 nanoseconds.

FIG. 16 shows the impact of pulse on time on the nTMP when the pulse off time is held constant at 500 ns. At the onset of the first positive pulse, the nTMP charges up to a maximum of approximately 0.35 V in the first 500 ns before it starts to decay. At the end of the first pulse, displacement currents within the cytoplasm force the nTMP negative. The onset of the negative polarity pulse further increases the magnitude of the nTMP in the negative direction. This additive effect results in a negative nTMP value which is greater in magnitude than the first positive nTMP.

For very short on-time pulses, the nuclear membrane has not fully discharged before the positive pulse returns to zero. This diminishes the maximum negative nTMP achievable. For 500 ns on time pulses, the first positive nTMP reaches 0.35 V while the first negative nTMP reaches −0.47 V. This effect is further enhanced if the positive nTMP is given sufficient time to decay back to zero before the positive pulse is turned off. When the pulse length is increased to 3.5 and 4 µs, the nTMP reaches a maximum magnitude of 0.62 V, nearly double the value achieved by a single mono-polar pulse. FIG. 16 shows the nuclear transmembrane potential can be doubled without increasing the magnitude of the applied field by carefully tuning the pulse parameters.

Figure 17:
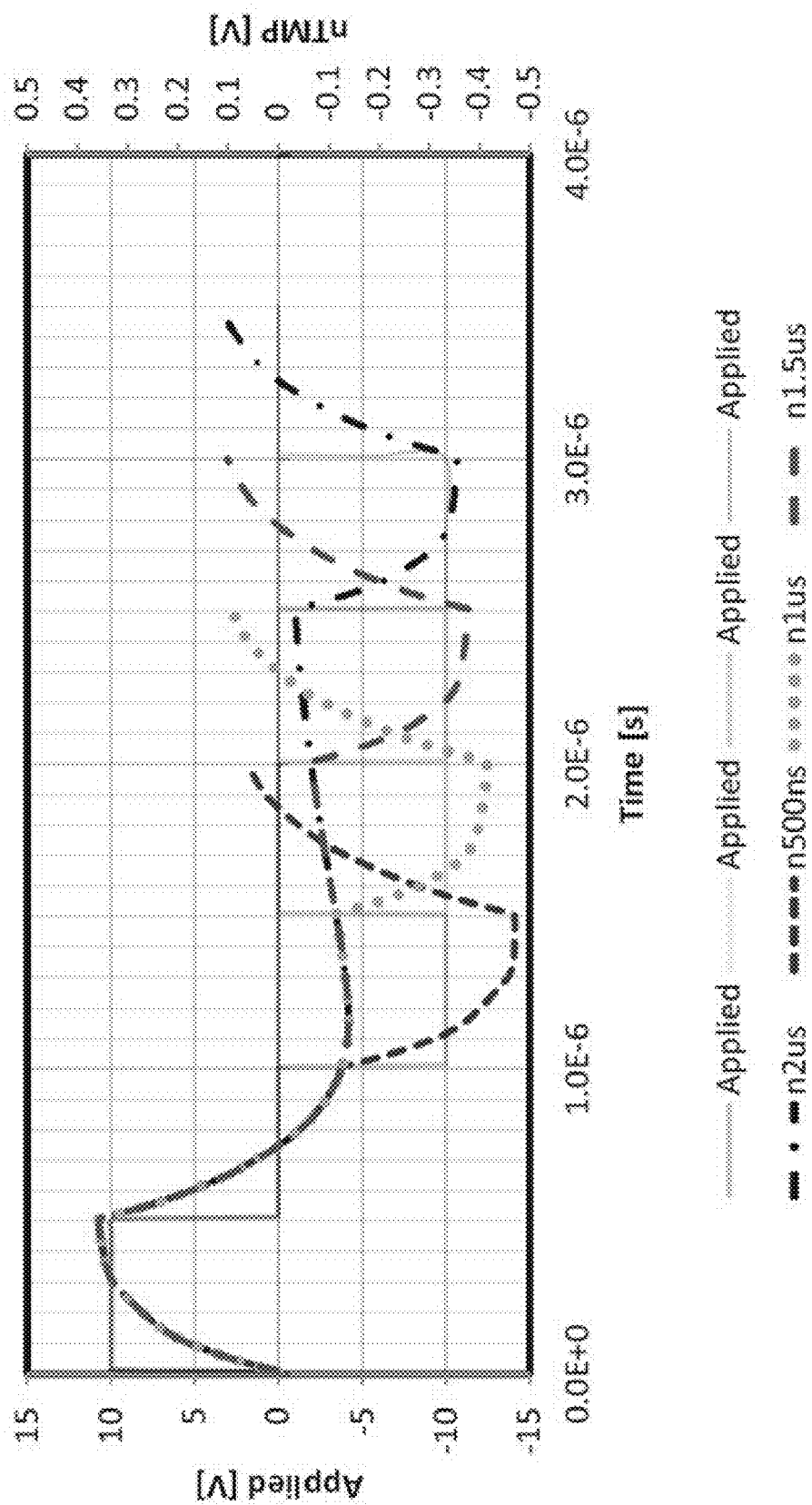
FIG. 17 is a graph showing the effect of pulse delay on the nuclear transmembrane potential (nTMP).

FIG. 17 shows the effect of delay time between pulses. At the end of the first positive pulse, the nTMP decays and becomes negative after approximately 250 ns. It reaches its maximum negative value approximately 500 ns after the end of the first positive pulse before decaying back towards zero. If the negative pulse is initiated before the nTMP can decay back to zero, then the resulting increase in nTMP is greater than that achieved by a single mono-polar pulse. The maximum nTMP value is achieved when the delay between pulses is 500 ns. This optimum time is due to a combination of factors that contribute to the RC time constants for the cell and nuclear membranes. The results shown in FIGS. 16 and 17 show that the pulse characteristics can be optimized to increase the maximum nTMP achievable for high frequency bipolar pulses.

It appears that to maximize the nTMP, the optimal pulse on time is equivalent to the charging time of the cell membrane plus the discharge time of the nuclear membrane. This allows the nTMP to charge up, then return to zero before it is forced negative at the falling edge of the pulse. Similarly, the optimal off time is approximately equivalent to the charging time of the cell membrane. This allows the nTMP to be increased to its maximum opposite polarity value, without decaying, just as the second pulse is initiated.

Figure 18A:
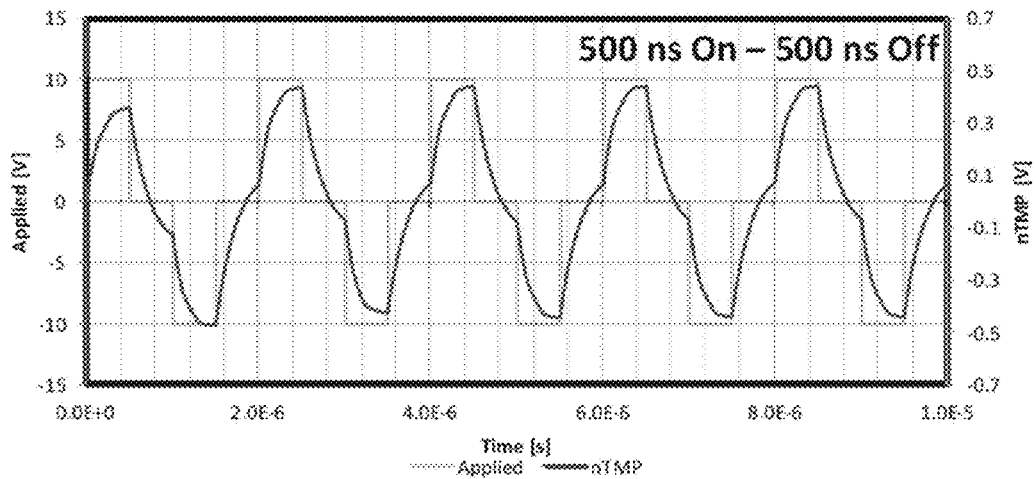
FIGS. 18A and 18B are graphs showing pulse geometry can be optimized to increase the nuclear transmembrane potential (nTMP) above the single pulse maximum, where
Figure 18B:
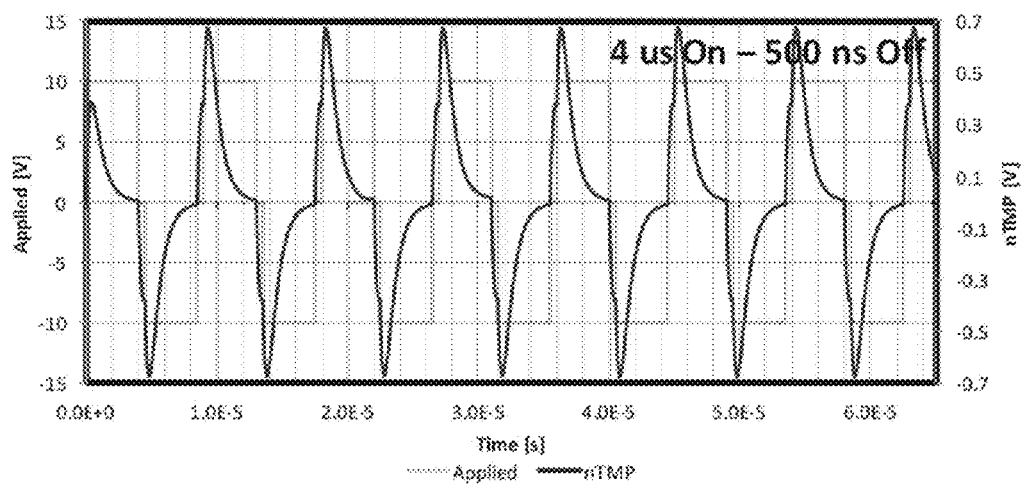

FIGS. 18A and 18B show the effect of following this optimization scheme. In most cases, the use of a train of bipolar pulses will increase the nTMP above the single pulse maximum. For 500 ns pulses with 500 ns off times (FIG. 18A), the first pulse nTMP is approximately 0.33 V. Using a burst of pulses, this value increases to 0.44 V. The use of an optimized pulse with 4 µs on time and 500 ns off time (FIG. 18B) increases the maximum nTMP to almost 0.7 V. This optimized pulse configuration doubles the effect that the electric field has on the nuclear membrane without needing to increase the voltage applied to the system.

Figure 19:
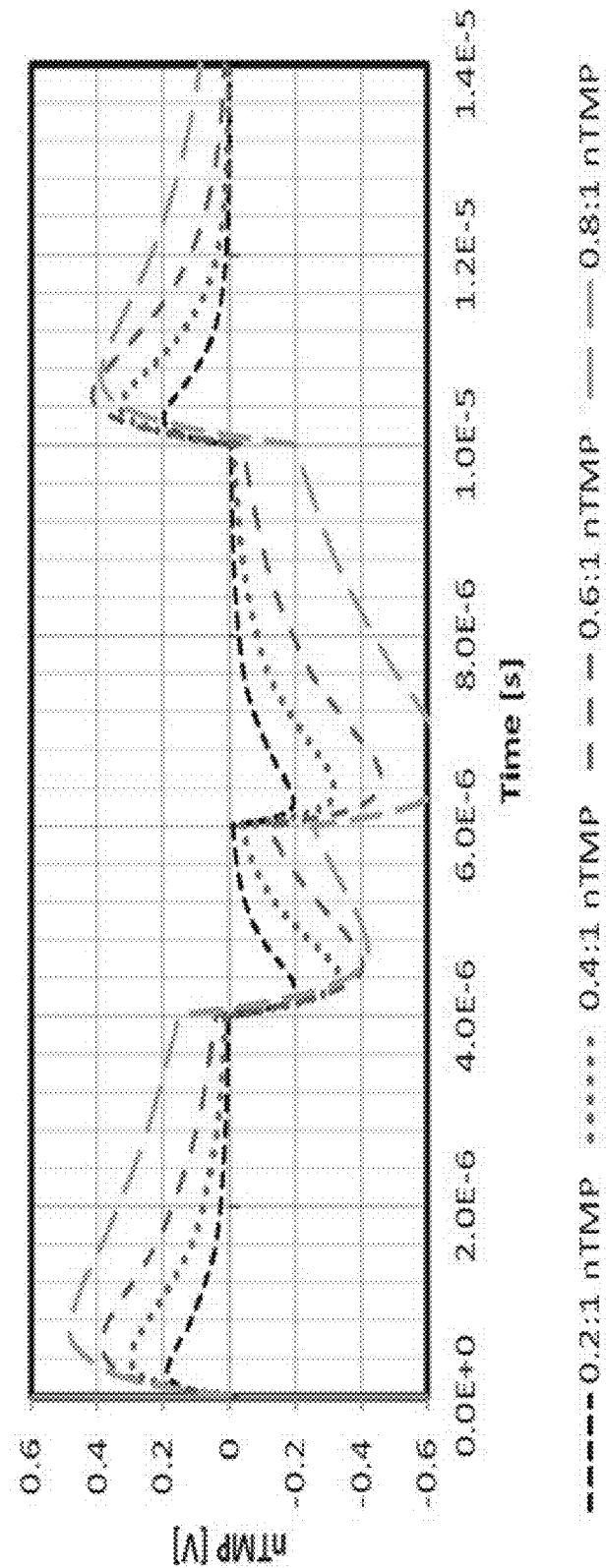
FIG. 19 is a graph showing the effect of nucleus size on the nuclear transmembrane potential.

FIG. 19 shows the effect of nucleus size on nTMP. This has implications for the selectivity of the optimized pulse protocol. Typically, as a cell progresses (normal→benign-→malignant→metastatic) the nucleus to cytoplasm ratio increases. As a result, the cell is more sensitive to the optimized bipolar pulse protocol. This can be seen by the increase in peak nTMP with increasing nucleus to cytoplasm ratio. Clinically this could translate to a zone of ablation that only affects the metastatic, infiltrative cancer cells, and spares the surrounding healthy cells. This example is emphasized in FIG. 21A-C. In another embodiment, this could enable selective nuclear transfection of metastatic cells at sublethal dosages.

According to embodiments of the invention, the nucleus-to-cytoplasm ratio can be determined by obtaining the nuclear area and the cytoplasmic area of selected types of cells and determining the ratio of the areas. One way to obtain the nuclear and cytoplasmic areas is to obtain a biopsy of a substance to be treated, such as a tissue, and measure the nuclear area and the cytoplasmic area of selected cells. The ratio of the nuclear and cytoplasmic areas can then be determined for the selected cells. Treatment protocols can be optimized based on the difference between the nucleus-to-cytoplasm ratio of cells selected as targets for the treatment and other non-target cells. For example, treatment protocols can be designed to apply electrical pulses in a manner that would treat or otherwise have an effect on certain cells but not others. The treatment parameters can be selected such as to have a desired effect (e.g., kill such cells) on target cells that have a certain nucleus-to-cytoplasm ratio or higher but have no effect (e.g., no killing) or a different effect on cells that have a nucleus-to-cytoplasm ratio lower than that of the target cells.

Figure 20:
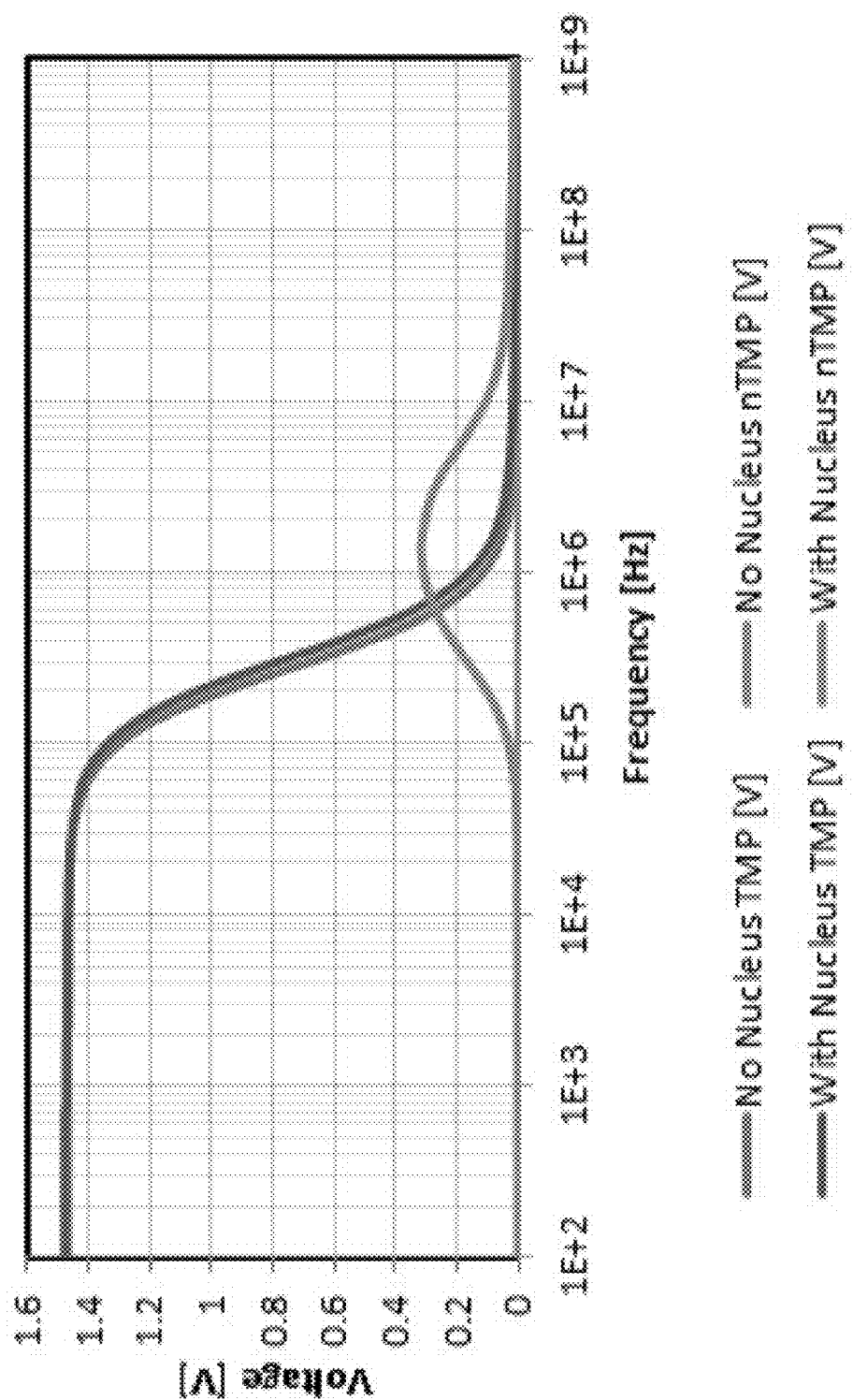
FIG. 20 is a graph showing the steady state maximum membrane potential achievable for a sinusoidal signal.

FIG. 20 shows the relative steady state charging behavior of the cell membrane and nuclear envelope for signals with carrier signals between 100 Hz and 1 GHz. At low frequencies, the cell membrane charges fully, mitigating the steady state maximum membrane potential of intracellular components. As the field oscillates more quickly (frequency increases), the cell membrane can no longer fully charge during a single cycle. This allows the membranes of intracellular components to charge for longer durations resulting in an increased in membrane potentials. Above approximately 500 kHz, the nuclear envelope develops a higher membrane potential than the cell membrane. As the frequency is increased above 100 MHz, the internal components cannot effectively charge during a single cycle resulting in a decreased maximum potential. This shows that there is a frequency-band over which pulses can be optimized to maximize the effect on intracellular components while minimizing effects to the cell membrane.

Analytical Modeling

FIGS. 21B-C shows the effect a bi-modal sine wave on nTMP for two cells with different nucleus to cytoplasm ratios; FIG. 21A is a key to FIGS. 21B and 21C which shows how the nuclear transmembrane potential of the two different cells is plotted. As mentioned in the methods, the applied signal consists of a superimposed low frequency (250 kHz) and high-frequency (1 MHz) electric field. The peak electric field of each individual signal is 2000 V/cm. However, when superimposed, the oscillations increase up to 4000 V/cm when the two signals are in phase. At 4000 V/cm, only the cell with the larger nucleus experiences nuclear electroporation (dotted line). An electric field of 5000 V/cm is required to achieve an equivalent level of electroporation in the cell with the smaller nucleus.

Figure 22:
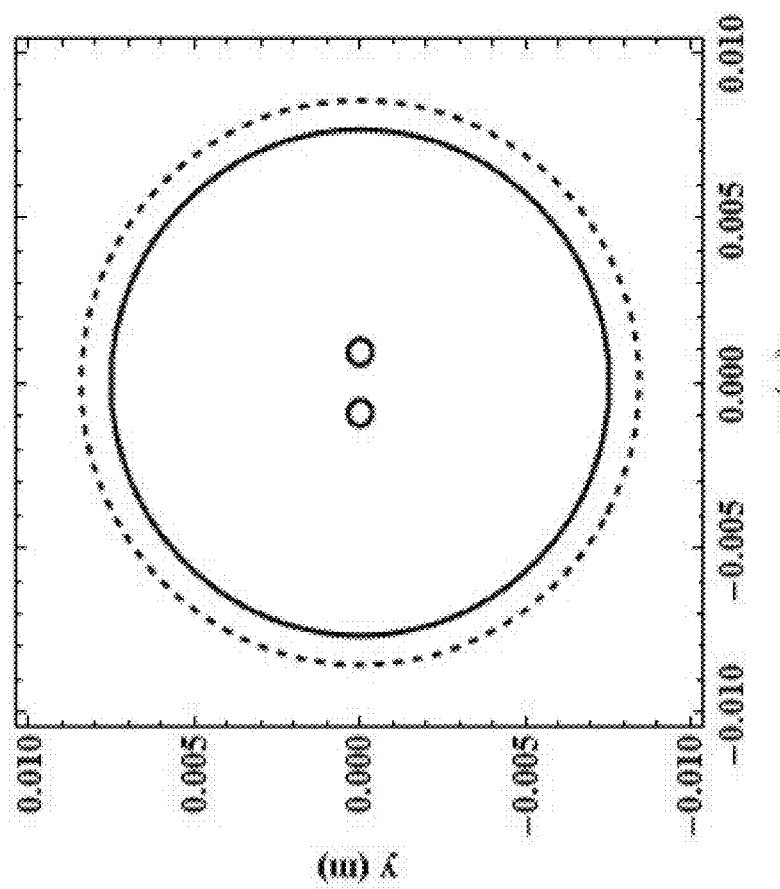
FIG. 22 is a graph which illustrates the selective zone of nuclear electroporation. The electric field contours shown are 4000 V/cm (solid line) and 5000 V/cm (dashed line).

The clinical benefit of the bi-modal sine wave presented above is illustrated in FIG. 22. The two needle electrodes were spaced 0.1 cm apart and the applied voltage was set to 20 kV. The solid line (5000 V/cm electric field contour) indicates the boundary of the zone were all cells are affected by the treatment. The zone between the solid and dashed line (4000 V/cm contour) represents the region where only the infiltrate cancer cells with a larger nucleus to cytoplasm ratio would be affected. The healthy cells within this region would not be affected.

Experimental Results

Figure 23A:
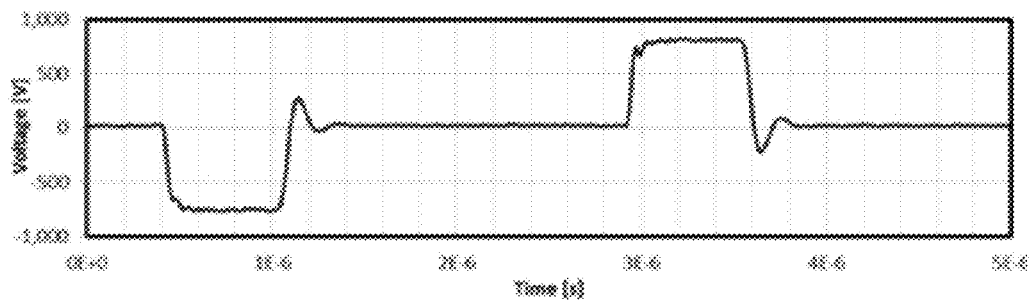
FIG. 23A is a graph showing a single sub-microsecond pulse waveform.
Figure 23B:
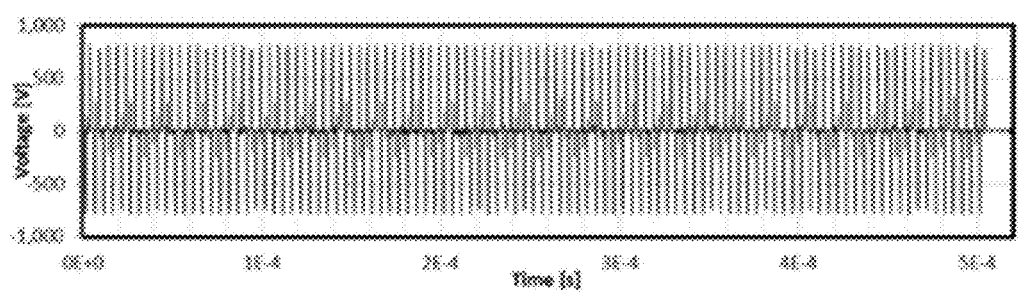
FIG. 23B is a graph showing the single sub-microsecond pulse waveform of FIG. 23A repeated 200 times to create an irreversible electroporation pulse train.
Figure 23C:
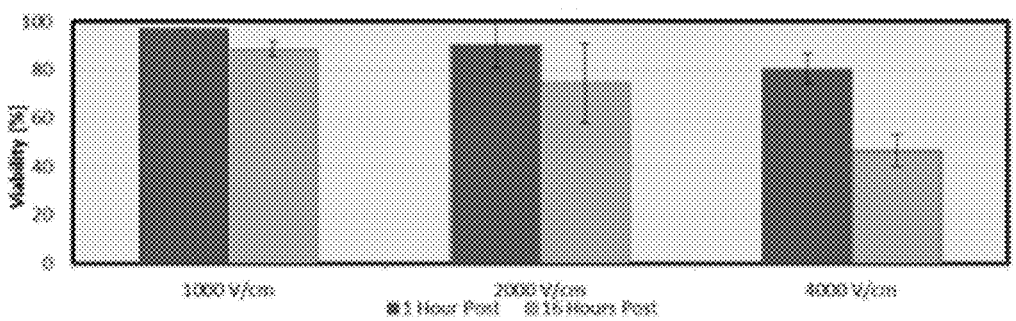
FIG. 23C is a graph of the effect of the pulse train of FIG. 23B on cell viability for 1000 V/cm, 2000 V/cm, and 4000 V/cm pulses at 1 hour and 16 hours post-treatment.

FIG. 23C shows the viability of MDA-MB-231 cells exposed to bursts of 700 ns wide pulses (FIG. 23A) repeated 200 times to create an irreversible electroporation pulse train (FIG. 23B) in 0.1 S/m buffer. Viability was assessed by comparing the number of cells attached and floating in suspension to control at 1 and 16 hours post treatment. At 1000 V/cm there was minimal effect on the viability of the cells immediately and 16 hours post treatment. At 2000 V/cm and 4000 V/cm the viability reduced to 50% and 10% when considering only cells that attached to the well plates. Examination of the supinate revealed that for 4000 V/cm there was a large number of cells that failed to attach to the well plate surface, an indication that the cytoskeletal network of the cells became damaged or they were in various stages of apoptosis.

An extensive parametric study (FIGS. 24-26) was conducted on PPT8182 murine pancreatic cancer cells in media with conductivity of 0.2 S/m. Eighty bursts with total on time of 100 µs consisting of pulses with widths between 250 ns and 50 µs were delivered at field strengths of 1500 V/cm (FIG. 24), 3000 V/cm (FIG. 25), and 4000 V/cm (FIG. 26). At 1500 V/cm, pulse widths of 2 µs or greater were able to reduce the total viability to less than 50 percent after 24 hours. For pulses of 5 microseconds or greater, the viability after 24 hours was significantly reduced indicating that the cells were undergoing some form of apoptosis or delayed cell death. At 3000 V/cm pulses 1 µs or greater were reduced cell viability below 50 percent with 2 µs pulses and greater almost completely eliminating signs of cellular metabolic activity after 24 hours. At 4000 V/cm, 500 nanosecond pulses appear to induce immediate cell death (60% viability) after 1 hour and delayed cell death (30% viability) after 24 hours. Pulses greater than this induce immediate cell death (<30% viability) at one hour and further delayed cell death (<10% viability) at 24 hours. Cell viability was negligibly impacted by 250 ns pulse widths for all field strengths.

Figure 24:
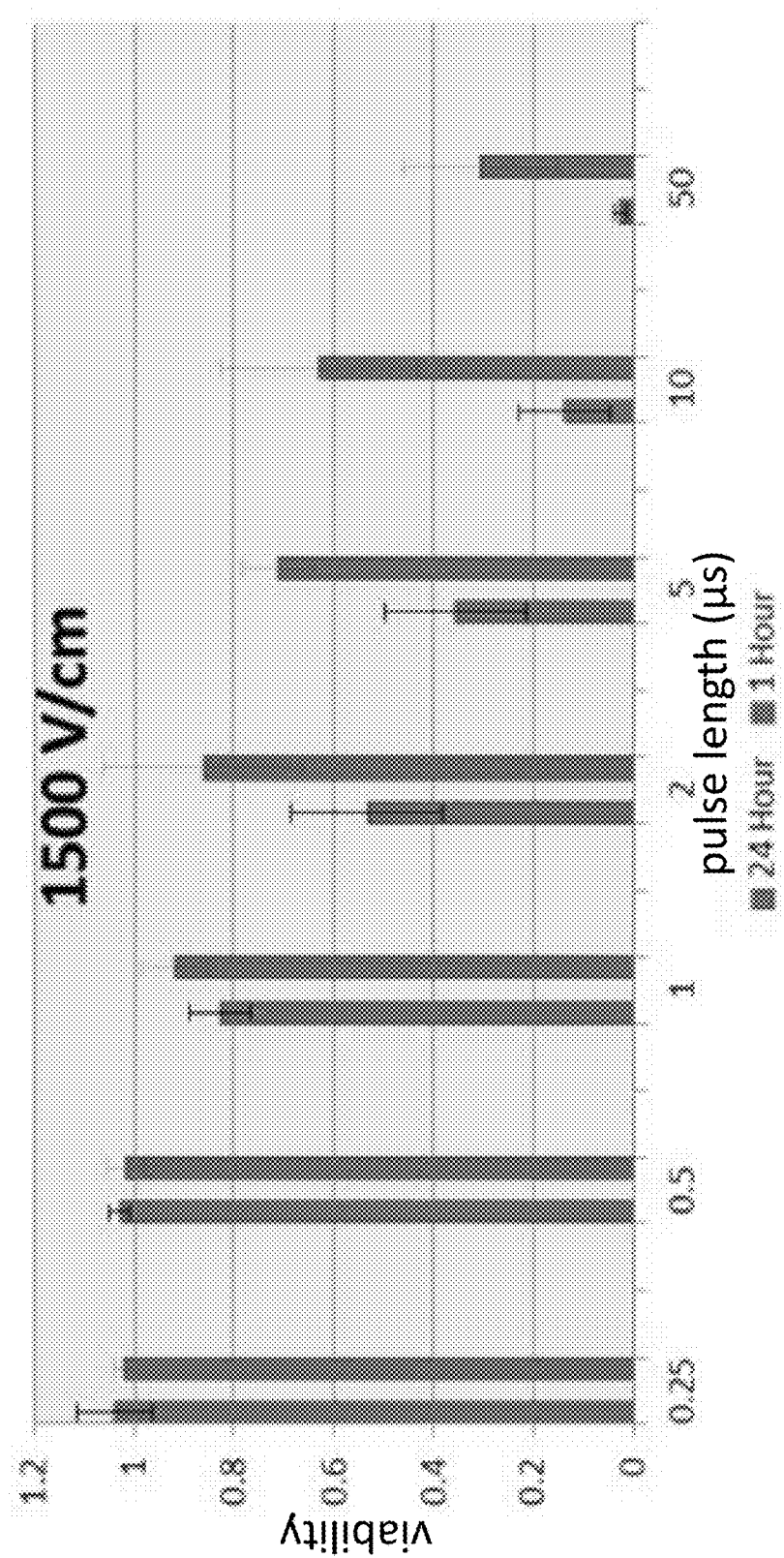
FIG. 24 is a graph showing viability of cells treated with 1500 V/cm pulses as a function of pulse length.
Figure 25:
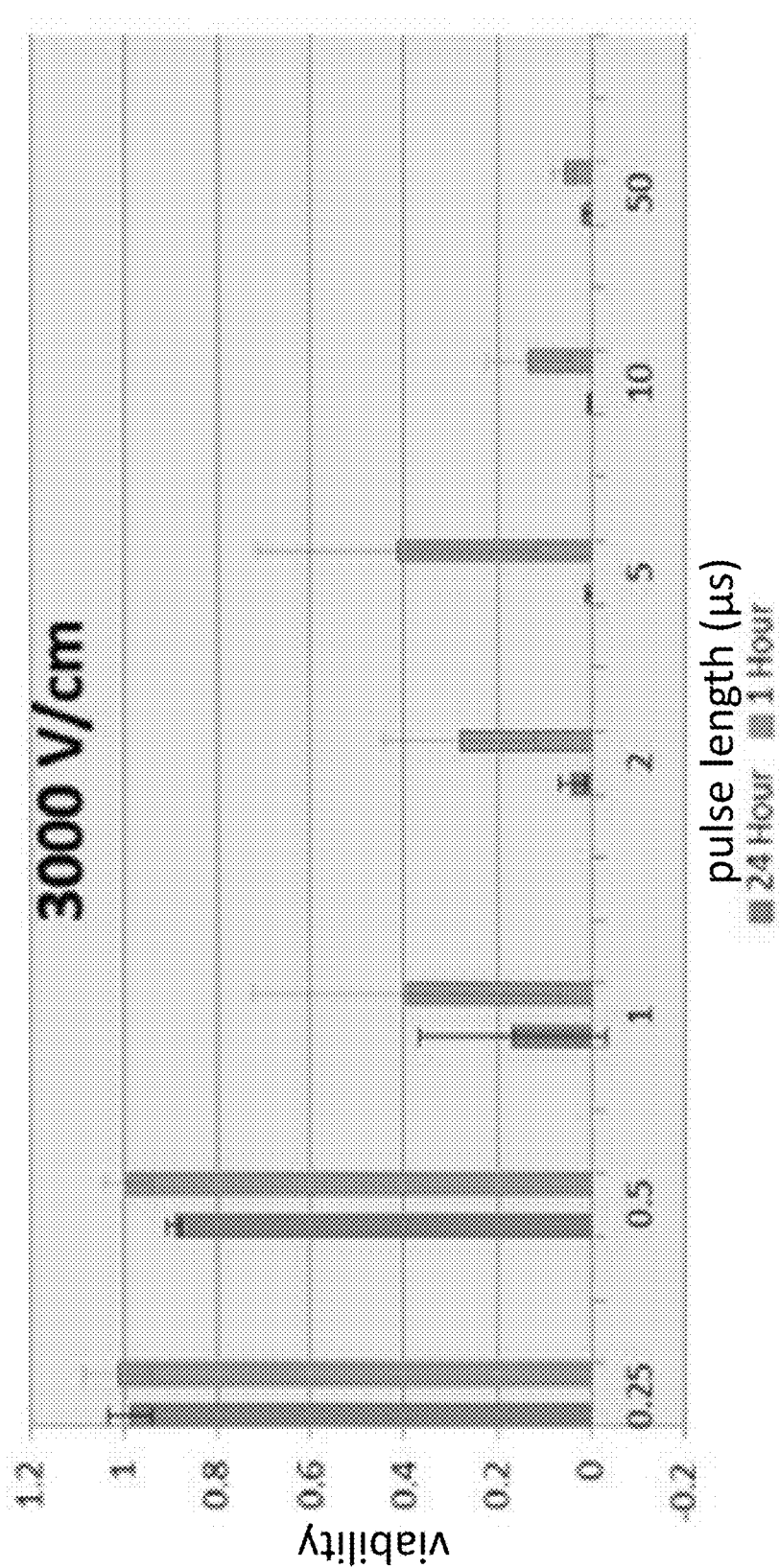
FIG. 25 is a graph showing viability of cells treated with 3000 V/cm pulses as a function of pulse length.
Figure 26:
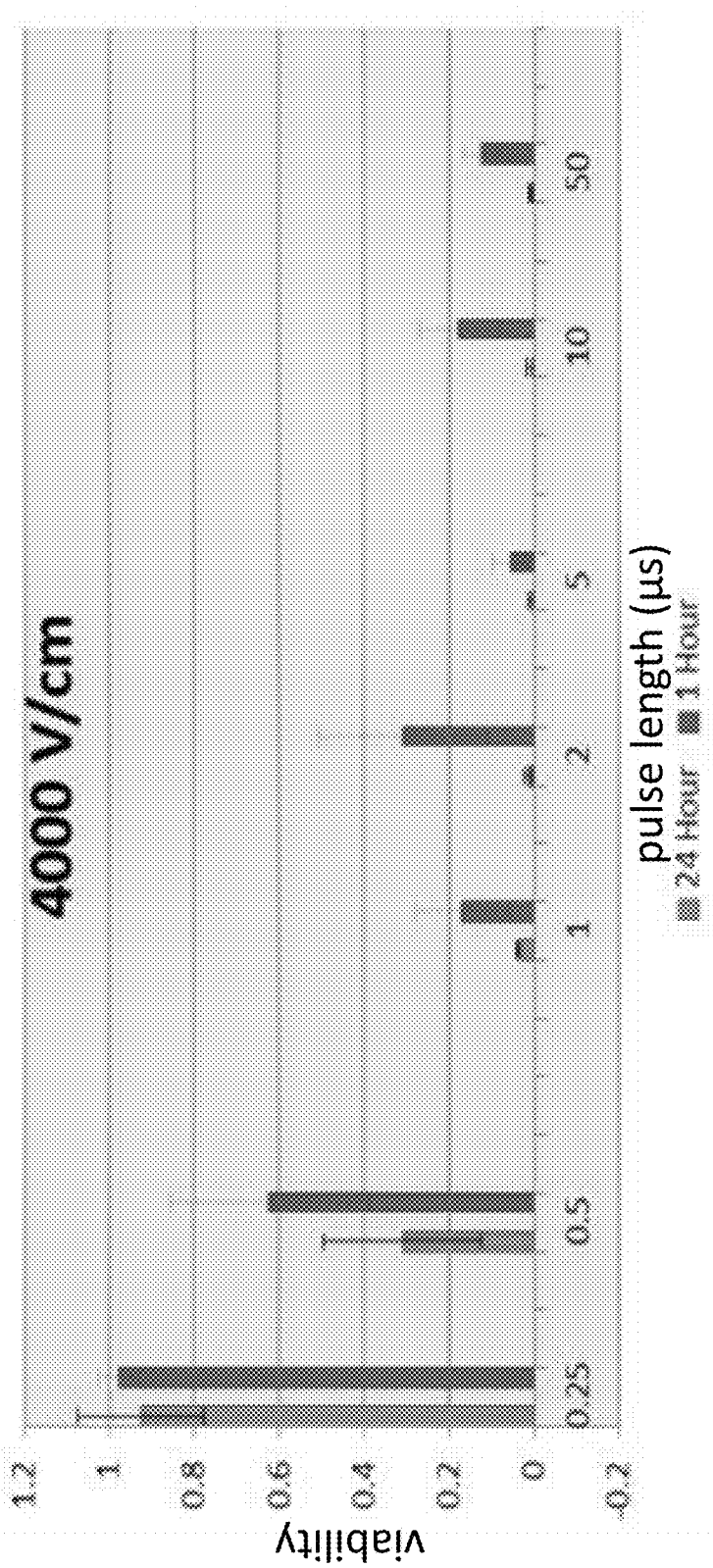
FIG. 26 is a graph showing viability of cells treated with 4000 V/cm pulses as a function of pulse length.
Figure 27A:
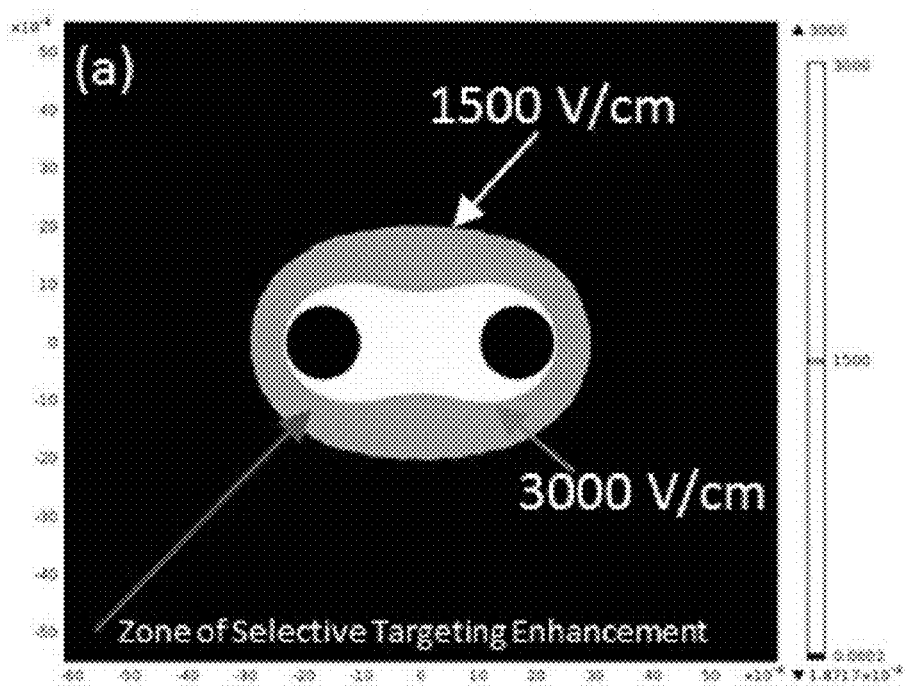
FIGS. 27A and 27B are diagrams showing ablation enhancement due to selective targeting, with the x- and y-axes showing distance in meters and with the ablation zone shown in white and the zone of selective targeting enhancement shown in orange (grey, in black and white figures).
Figure 27B:
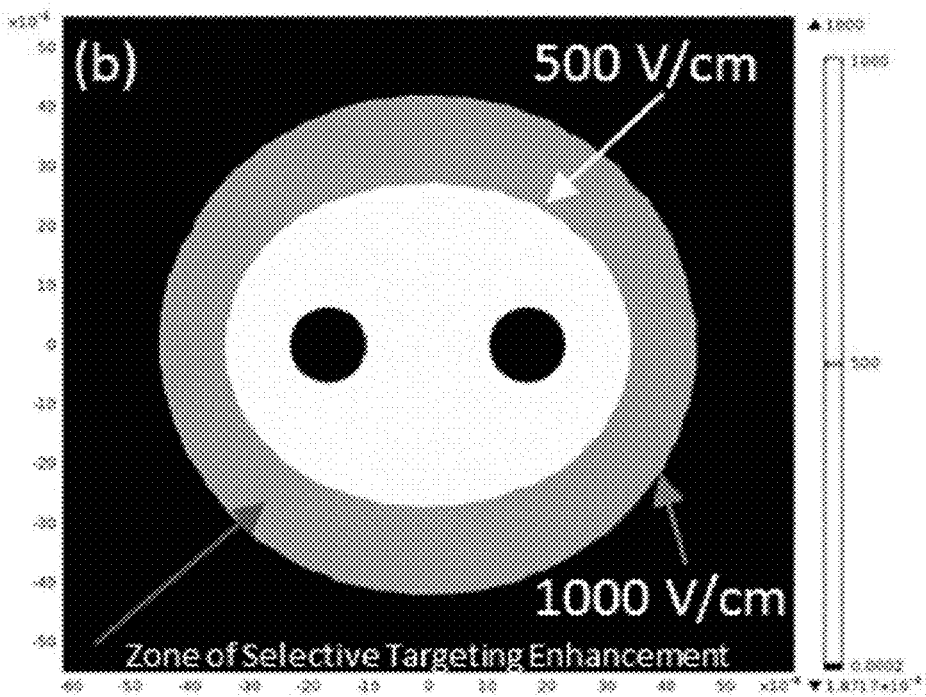

Analysis of FIGS. 24-26 show that for bursts with pulses longer than 2 µs, the viability at 1 hour and 3000 V/cm is equivalent to the viability at 24 hours and 1500 V/cm. For 1 and 2 µs pulses, the viability at 1 hour and 4000 V/cm is equivalent to the viability at 24 hours and 3000 V/cm. When applied in-vivo this will result in a zone of selective targeting enhancement in which infiltrative cancer cells will be selectively targeted. FIG. 27A shows the anticipated ablation and enhancements based on thresholds established in in-vitro experiments. The selective zone sweeps out an oval which is approximately 2 cm greater in height and width than the ablation zone, indicating that infiltrative cells within a 1 cm margin will be treated. Larger volumes, but similar enhancement zones are achieved when the field thresholds are adjusted to account for the ~3× decrease in field thresholds observed in-vivo (FIG. 27B).

Conclusion

The present inventors showed that the frequency of the applied field and the conductivity of the suspending medium play a large role in the buildup of the TMP. In the case where electroporation is not desirable, the lowest conductivity physiologically suitable buffer should be used. Even at 0.01 S/m, the TMP will increase if continuous sine wave voltages are applied between DC and approximately 10 kHz. The extent of electroporation (both reversible and irreversible) diminishes significantly above this frequency if the field strength is held constant. This allows for significant optimization of the temporal properties of the applied electric field to maximize the effect on intracellular components.

If electroporation is desirable, as in the case of tissue ablation, it is advantageous to operate within a sufficiently conductive media. Numerical analysis of the charging times for the cell membrane indicates that 1.0 S/m is a critical conductivity. Above this, the charging time does not increase significantly, while below this, the cell may not reach its maximum TMP for short pulses. However, physiological tissue typically has conductivity between 0.1 and 0.7 S/m. The result is that short duration pulses have a mitigated effect on the cell membrane while having an enhanced effect on intracellular components. Theoretically, bursts of 4 µs pulses with 500 ns off time will result in the largest effect on the nuclear transmembrane potential and may help to further increase the lethality of the high frequency pulses.

Cells form a complex resistor-capacitor (RC) network with the fluid/media surrounding the cell. The capacitive nature of the cell membrane (C) couples with the resistance of the extracellular material (R), limiting the rate at which the cell membrane will charge to its theoretical maximum potential. In general, smaller cells have a smaller net capacitance. This in turn allows them to charge more quickly than larger cells. This charging behavior blocks the flow of current through the intracellular cytoplasm. The smallest cells in a volume of tissue will experience the smallest intracellular effects of any pulsed field. It has been shown that highly metastatic cells have a higher membrane capacitance, due to changes in the morphology of the cell membrane, even when compared to non-cancerous cell of the same size. The result of this biophysical change is that infiltrative cancerous cells will exhibit a larger net capacitance than the surrounding healthy cells. This in turn results in a longer time constant associated with the charging of the cell membranes of infiltrative cells. This lag in cell membrane charging results in an increase in charge build up on intracellular components leading to an amplified electroporation effect on the nucleus and organelles.

The result of this is that a therapeutic electric field can be applied to a volume of tissue containing healthy and cancerous cells such that only the cancerous cells in the tissue will receive the therapeutic effect. This can be selective electroporation of intracellular components for drug, gene, or protein delivery or specific triggering of an apoptotic cascade. These pulses can also be designed such that a specific volume of tissue experiences irreversible electroporation and an additional external volume will experience a targeted cancer-cell-only apoptosis inducing dose. This later scenario allows for selective targeting of infiltrative cells, such as microscopic disease, embedded in healthy tissue surrounding a tumor.

Example 2

Methods:
Numerical Modeling

A numerical model of a cell in suspension was created in COMSOL 4.2 using an impedance boundary condition scheme (G. Pucihar, T. Kotnik, B. Valič, D. Miklavčič, *Numerical determination of transmembrane voltage induced on irregularly shaped cells*, Annals of Biomedical Engineering, 34 (2006) 642-652). The solution domain consisted of a three dimensional cube with edge-lengths of 0.1 mm. At the center of this domain, two spheres were created representing the cytoplasm and nucleoplasm. Within the solution domain, the Electric Currents module was used to solve for following equations:

$$\nabla \cdot J = Q_j /(A/m^3) \quad [1]$$

$$J = \left(\sigma + \varepsilon_0 \varepsilon_r \frac{\partial}{\partial t}\right) E /(A/m^2) \quad [2]$$

$$E = -\nabla U /(V/m) \quad [3]$$

where U is the electric potential, E is the electric field, J is the current density, and Q is the current source. One boundary was assigned a time dependent electrical potential $$U = U(t)/V \quad [4]$$

The opposing boundary was assigned as the relative ground $$U = 0 V \quad [5]$$

The remaining boundaries were defined as electrical insulation $$n \cdot J = 0/(A/m) \quad [6]$$

where n is the normal vector to the surface, J is the electrical current.

For each domain (media, cytoplasm, nucleoplasm), a separate Electric Currents physics module was used and the dependent electric potential variables $U_{media}$, $U_{cyto}$, $U_{nuc}$ for the media, cytoplasm, and nucleoplasm domains were defined, respectively. These variables were then defined to calculate the voltage across the cell membrane ($U_m$) and nuclear envelope ($U_n$)

$$U_m = U_{media} - U_{cyto}/V \quad [7]$$

$$U_n = U_{cyto} - U_{nuc}/V \quad [8]$$

In each Electric Currents module, the boundaries representing membranes were defined as impedance boundary conditions with reference voltages prescribed as the electric potential in the adjacent ($U_{ref}$) domain $$n \cdot (J_1 - J_2) = \frac{1}{d}\left(\sigma(U - U_{ref}) + \varepsilon_0 \varepsilon_m \frac{\partial}{\partial t}(U - U_{ref})\right)(A/m^2) \quad [9]$$

where σ is the conductivity, ε is the permittivity, and d is the thickness of the cell membrane or nuclear envelope. For example, in the Media domain, the boundary representing the cell membrane was defined as an impedance boundary with reference potential of $U_{cyto}$. In the Cytoplasm domain, the same boundary representing the cell membrane was defined as an impedance boundary with a reference potential of $U_{media}$. The boundary was defined as a 'thin layer' and the electrical conductivity, relative permittivity, and surface thickness were defined using the values presented in Table 1. The nuclear envelope consists of two individual lipid membranes separated by the perinuclear space. To limit the complexity of the model and avoid improperly assessing the electrical properties of these individual components (not readily available in the literature), the inventors lumped these biological features into a single 40 nm membrane for which electrical properties representing their combined features are available.

The mesh was defined as a single free tetrahedral group with the elements between 1.8 and 10 μm on edge, resulting in 19353 tetrahedral elements. In a preliminary study of this model, finer and courser meshes were used. Simulation times more than doubled between successive refinements. The average deviation between the mesh presented here and the next successive refinement was less than 2.0% and 5.5% for the cell membrane and nuclear envelope potentials, respectively. For each parameter, solutions were found in approximately 22 minutes on a on a quad core 3.0 GHz processor with 8 GB of RAM. Results of the numerical simulations, using the values in the table in FIG. 28, were compared to those found using the analytical method presented by Kotnik and Miklavcic (T. Kotnik, D. Miklavčič, *Theoretical evaluation of voltage inducement on internal membranes of biological cells exposed to electric fields*, Biophysical Journal, 90 (2006) 480-491). When calculating the maximum/minimum potentials across the cell membrane and nuclear envelope, the error between the numerical and analytical solution was 0.15%/0.15% and 1.97%/0.89%, respectively.

Cell Preparation and Experimentation

In all experiments, cells were suspended in a buffer consisting of a 5.5:1 ratio of culture media (DMEM) to low conductivity sucrose buffer (85 g sucrose, 3.0 g glucose, 7.25 mL RPMI, and 992.75 mL DI water) (L. A. Flanagan, J. Lu, L. Wang, S. A. Marchenko, N. L. Jeon, A. P. Lee, E. S. Monuki, *Unique dielectric properties distinguish stem cells and their differentiated progeny*, Stem Cells, 26 (2008) 656-665). The electrical conductivity of the cell suspension was measured with a conductivity meter prior to experimentation (Horiba B-173, Cole-Parmer, Vernon Hills, Ill.) to ensure a final conductivity of 0.2 S/m. Clark et al. reported that the conductivity of pancreatic tissue varied between 0.097 and 0.44 S/m for frequencies between 1 kHz and 2 MHz, respectively (D. Clark, J. Greenwell, A. Harper, A. M. Sankey, T. Scratcherd, *The electrical properties of resting and secreting pancreas*, The Journal of Physiology, 189 (1967) 247-260). A media conductivity of 0.2 S/m was chosen to minimize the current delivered through the sample while maintaining a conductivity value within the range of those found in in-vivo tissue. Due to limitations in the inventors' pulse generation system, higher conductivity buffers would drive the pulse delivery system outside of its safe operating region.

PPT8182 murine primary pancreatic tumor cells (J. von Burstin, S. Eser, M. C. Paul, B. Seidler, M. Brandl, M. Messer, A. von Werder, A. Schmidt, J. Mages, P. Pagel, *E-cadherin regulates metastasis of pancreatic cancer in vivo and is suppressed by a SNAIL/HDAC1/HDAC2 repressor complex*, Gastroenterology, 137 (2009) 361; von Burstin, 2009) were used in all experiments. These cells have been shown to replicate human pancreatic cancer in terms of histology, metastasis, and genetic alterations (von Burstin, 2009; B. Seidler, A. Schmidt, U. Mayr, H. Nakhai, R. M. Schmid, G. Schneider, D. Saur, *A Cre-loxP-based mouse model for conditional somatic gene expression and knockdown in vivo by using avian retroviral vectors*, Proceedings of the National Academy of Sciences, 105 (2008) 10137-10142; D. Saur, B. Seidler, G. Schneider, H. Algül, R. Beck, R. Senekowitsch-Schmidtke, M. Schwaiger, R. M. Schmid, *CXCR4 expression increases liver and lung metastasis in a mouse model of pancreatic cancer*, Gastroenterology, 129 (2005) 1237-1250; and M. J. PaszeK, N. Zahir, K. R. Johnson, J. N. Lakins, G. I. Rozenberg, A. Gefen, C. A. Reinhart-King, S. S. Margulies, M. Dembo, D. Boettiger, *Tensional homeostasis and the malignant phenotype*, Cancer cell, 8 (2005) 241-254).

Figure 29A:
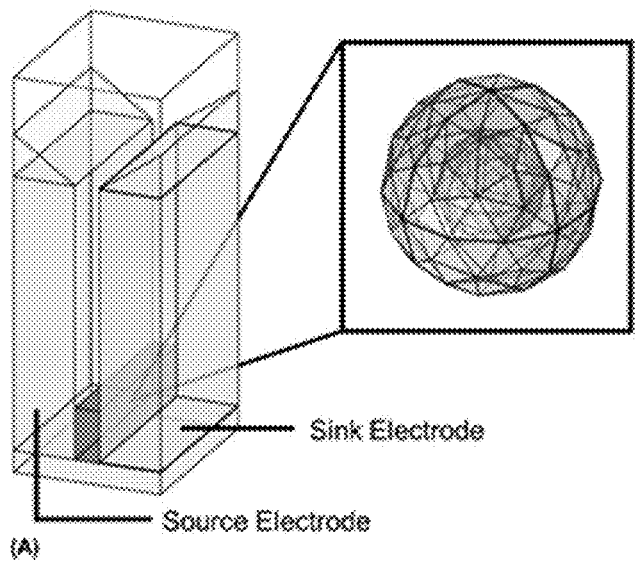
FIG. 29A is a schematic of an experimental setup used in Example 2. 100 uL of cell suspension was added to a 2 mm electroporation cuvette. The inset represents mesh used to simulate the cell membrane and nuclear envelope.

Cells were cultured in DMEM (supplemented with L-glutamine, ATCC, Manassas, Va.) containing 10% fetal bovine serum (Sigma Aldrich, St. Louis, Mo.) and 1% stock solution of penicillin/streptomycin (Invitrogen, Carlsbad, Calif.) at 37° C. in 5% $CO_2$ in a humidified atmosphere. All cells were harvested for experiments by trypsinization at 80% confluence. Suspensions were centrifuged twice and resuspended in an experimental buffer at a concentration of $5 \times 10^6$ cells/mL. 100 μL of cell suspension were injected into a 2 mm gap cuvette (Model 620, Harvard Apparatus, Holliston, Mass.) immediately prior to pulse delivery. A schematic of the experimental setup is shown in FIG. 29A.

Figure 29B:
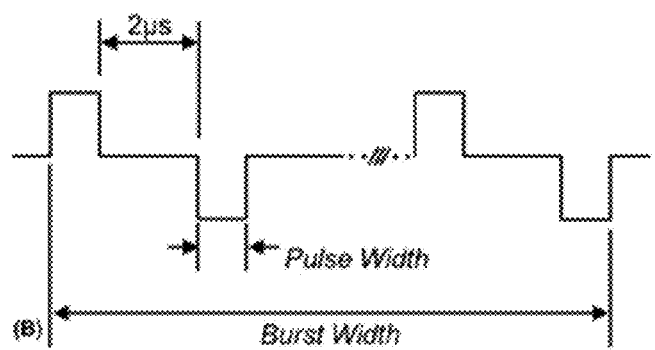
FIG. 29B is a schematic of the experimental burst containing a cycling of positive and negative polarity pulses which represents the protocol used for all experiments in Example 2.
Figure 30A:
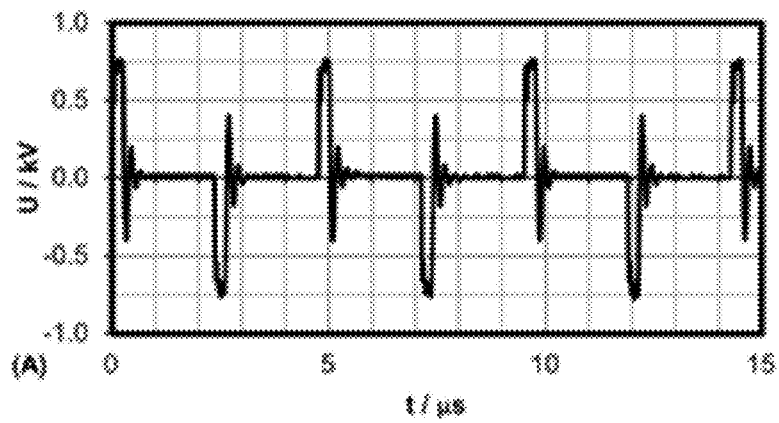
FIGS. 30A-30C are graphs showing exemplary waveforms of pulses of different lengths using the experiments in Example 2 which plot applied voltage, U/kV, i as a function of time, t/μs. Each burst has a total on time of 100 μs, with 50 μs energized in each polarity. Representative segments from bursts with 250 ns (FIG. 30A) and 1 μs (FIG. 30B) and 5 μs (FIG. 30C) constitutive pulses.
Figure 30B:
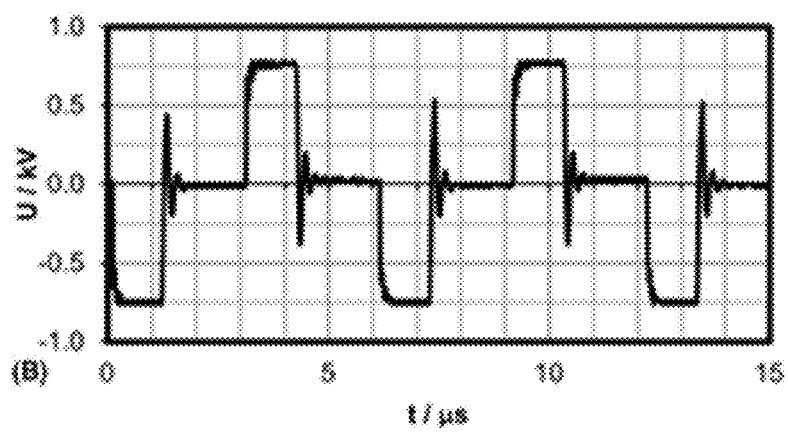
Figure 30C:
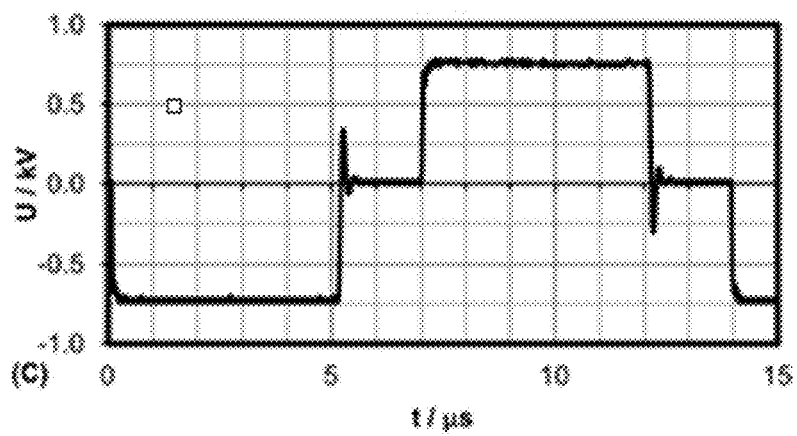

The protocol for all experiments used the waveform presented in FIG. 29B. The schematic depicts an example burst which contains a repeated sequence of individual pulses. The burst begins with a positive polarity pulse followed by a 2 μs pause, then a negative polarity pulse followed by another 2 μs pause. This cycling is immediately repeated until the voltage has been delivered for a total of 100 μs (50 μs in each polarity). Eighty Bursts were delivered with a frequency of 1 Hz. Within each burst, individual pulses had a single duration of 250 ns, 500 ns, 1, 2, 5, 10, or 50 μs and therefore bursts contained 400, 200, 100, 50, 20, 10, or 2 pulses, respectively to result in equivalent energized time. The 2 μs delay time was programmed between sequential opposite polarity pulses to protect the electronics from over-voltages due to ringing. Representative examples of the bursts are shown in FIGS. 30A-30C. The cells were exposed to electric potentials with voltage-to-distance ratios (E) of 1500, 3000, and 4000 V/cm. The temperature change in the cell suspension due to pulsing was measured using fiber optic temperature probes (Luxtron FOT Lab Kit, LumaSense Technologies, Santa Clara, Calif.) inserted directly into the cell suspension.

For the in vitro studies, each of the treatment groups was repeated a minimum of three times (n=3) add experiment for each group were conducted on at least two different days. For each treatment, different experimental parameters, including sham exposure, were alternated in a random sequence. After treatment, samples were split into two equal 50 μL samples to be evaluated at 1 and 24 hour time points. The samples were kept at room temperature for approximately 20-30 minutes prior to being placed on ice (1 hour group) or moved to the incubator (24 hour group) while the remaining experimental groups were completed. Approximately one hour post exposure, viability was assessed using a trypan blue exclusion assay. Cells which had been irreversibly electroporated were unable to exclude the dye and were stained blue. Cells were counted visually using a hemocytometer and the percentage viability was determined as $$Viability_{1\ hour} = \frac{N_{live}}{N_{total}} \cdot 100 / \% \qquad [10]$$

$$r_{viability-1\ hour} = \frac{Viability_{1\ hour-treatment}}{Viability_{1\ hour-control}} \qquad [11]$$

The average viability of sham control samples in the 1 hour time group was greater than 85%. Samples to be analyzed at 24 hours were placed in separate wells in a 12-well pate containing a total of 1 mL of culture media and maintained at room temperature until the well plate was full (approximately 30 minutes). At this point the well plate was placed in an incubator at 37° C. and 5% $CO_2$ for 24 hours. Viability was then assessed using an Alamar blue metabolism assay (Life Technologies, Grand Island, N.Y.) using the manufactures recommended procedure. Briefly, 100 µL/mL stock Alamar blue solution was added to each well. After 4 hours, the samples were read using a spectrophotometer at 570/600 nm wavelengths. For each sample, the absorbance was measured in three separate wells and averaged. Additional measurements were taken for sample media without cells and for control cell samples which were not exposed to an electric field. The percentage viability was determined as $$r_{viability-24\ hour} = \frac{I_{sample} - I_{media}}{I_{control} - I_{media}} \quad [12]$$

where I is the relative intensity measurement from the spectrophotometer. In general, trypan blue analysis and metabolism assays complement each other quite well. They et al. previously showed that metabolism assays mirrored those from trypan blue analysis after nano-second pulsed electric field exposure (B. L. they, A. G. Pakhomov, B. W. Gregory, V. A. Khorokhorina, C. C. Roth, M. A. Rassokhin, J. A. Bernhard, G. J. Wilmink, O. N. Pakhomova, *Selective cytotoxicity of intense nanosecond-duration electric pulses in mammalian cells*, Biochimica Et Biophysica Acta-General Subjects, 1800 (2010) 1210-1219). The Alamar blue assay used in this study is well established for measuring cytotoxicity in mammalian cells (J. O'Brien, I. Wilson, T. Orton, F. Pognan, *Investigation of the Alamar Blue (resazurin) fluorescent dye for the assessment of mammalian cell cytotoxicity*, European Journal of Biochemistry, 267 (2000) 5421-5426). Reduction rates for cells seeded between 2.5× $10^3$ and 2×$10^6$ cells/mL were measured to ensure that the sham population did not completely reduce the Alamar blue solution (results not shown) and a 4 hour incubation time with 2.5×$10^5$ cells/mL was determined to be optimal. Viability data for both the 1 hour and 24 hour groups were normalized to the sham control groups. Statistical analysis of the data was completed using JMP Pro V. 10.0 (SAS Institute Inc., Cary, N.C.).

Electronics

Waveforms were generated using an arbitrary function generator (AFG3021C, Tektronix Inc., Beaverton, Oreg.), which were amplified by a custom built high voltage pulse generator capable of +/−1000V outputs through high impedance loads (Applied Energetics, Tucson, Ariz., USA). Output waveforms were visualized using an oscilloscope (DPO2002B, Tektronix Inc., Beaverton, Oreg.) after the voltage was attenuated using a 50 MHz 1000× high voltage probe (P5210A, Tektronix Inc., Beaverton, Oreg.) and the current was measured using an active clamp on 50 MHz current probe (TCP305, Tektronix Inc., Beaverton, Oreg.). Short circuit protection resistors on the output limited the maximum output voltage through the 2 mm cuvettes to approximately 800 V (4000 V/cm).

Results and Discussion

Numerical Modeling

Figure 31A:
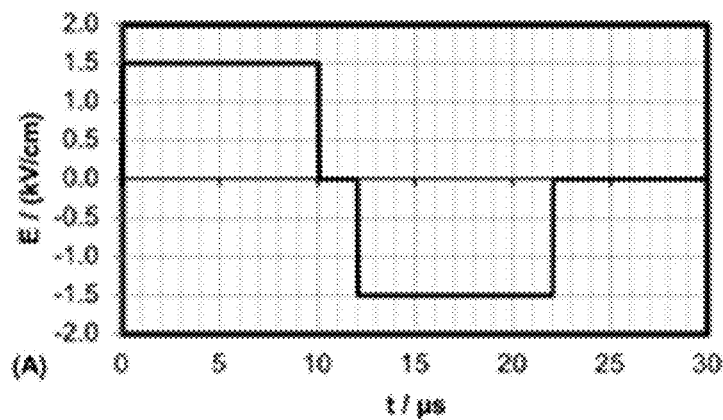
FIGS. 31A-31C are graphs showing the results of finite element simulations. The applied electric field, E/(kV/cm), voltage drop across the cell membrane, Um/V, and nuclear envelope, Un/V, are presented as a function of time, t/μs.
Figure 31B:
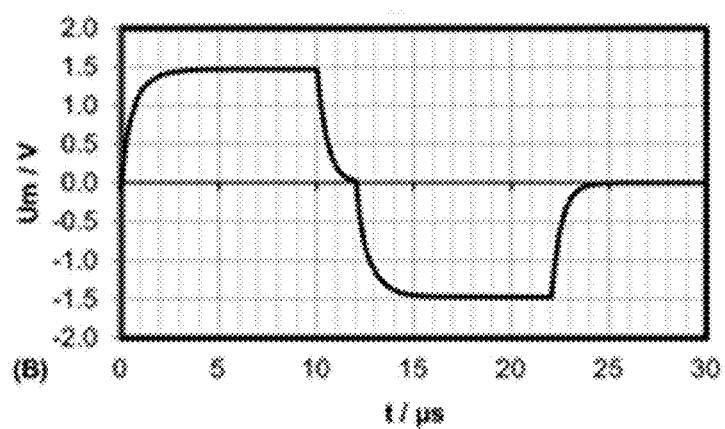
Figure 31C:
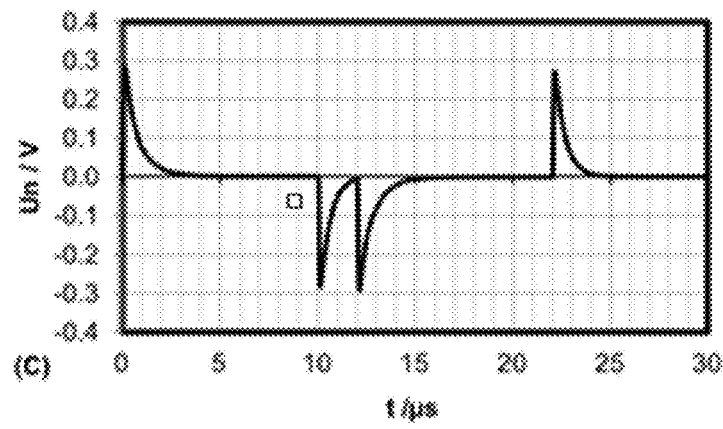

As shown in FIGS. 31A-31C, under the influence of a 1500 V/cm electric field (FIG. 31A), the potential drop across the cell membrane ($U_m$) (FIG. 31B) and nuclear envelope ($U_n$) (FIG. 31C) reaches maximums of 1.47 V and 0.28 V, respectively. $U_m$ reaches 50% of the maximum value in 0.34 µs, 70.7% in 1.11 µs, and 99.99% maximum in 7.92 µs. $U_n$ reaches 99.99% max in 145 ns and falls back below 70 mV in approximately 0.94 µs. This brief charging and discharging of the nuclear envelope is due to current that flows within the cytoplasm as the cell membrane is charging. This transient current increases the potential across membranes surrounding the nucleus and organelles. These intracellular components are smaller than the cell and their exposure to currents is brief resulting in a smaller potential increase.

As the positive polarity pulse falls, the cell membrane begins to discharge resulting in a second current flow within the cytoplasm in the opposite direction, as compared to the rising pulse edge. This results in the formation of a negative potential across the nuclear envelope. This negative potential reaches a minimum of −0.28 V and falls below −70 mV in a similar 0.94 µs. The rising edge of the negative polarity pulse creates a similar decrease in $U_n$ creating an interesting double peak in the membrane potential of the nuclear envelope. This second peak reaches a value of −0.29 V. Though this peak is only 10 mV different than the maximum achieved by the initial pulse, it suggests that optimization of the pulse length and delay time between pulses could result in an increased effect on intracellular membranes.

In this Example, the inventors elected to disregard the effects of electroporation on the cell membrane to simplify their analysis. However, in the case of electroporation, current would be allowed to flow through the cytoplasm and a sustained potential would be induced across the intracellular membranes.

Analysis of Experimental Parameters

Figure 32A:
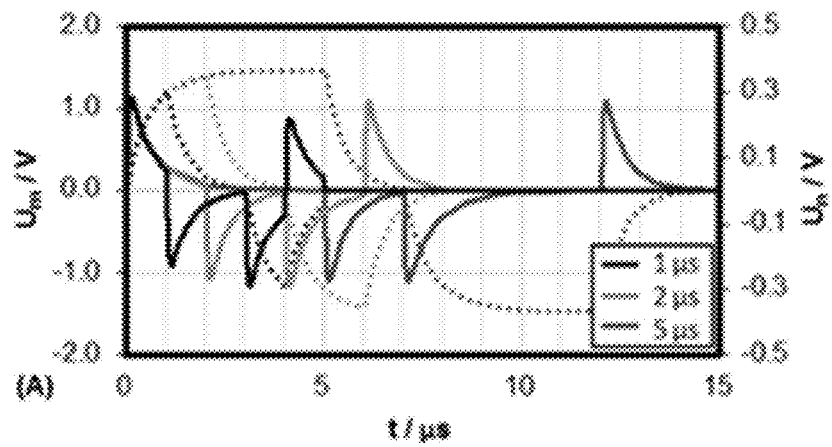
FIGS. 32A-C are graphs showing the results of a parametric analysis on the cell membrane potential. The voltage drop across the cell membrane, Um/V, and nuclear envelope, Un/V, are presented as a function of time, t/μs. The effect of varying the (FIG. 32A) Pulse Width, (FIG. 32B) Media Conductivity, (FIG. 32C) Pulse-to-Pulse Delay Time are shown. Dashed lines represent the transmembrane potential of the cell membrane (Um) and solid lines represent the transmembrane potential of the nuclear envelope (Un). Note that the axis for Um and Un have different scales.
Figure 32B:
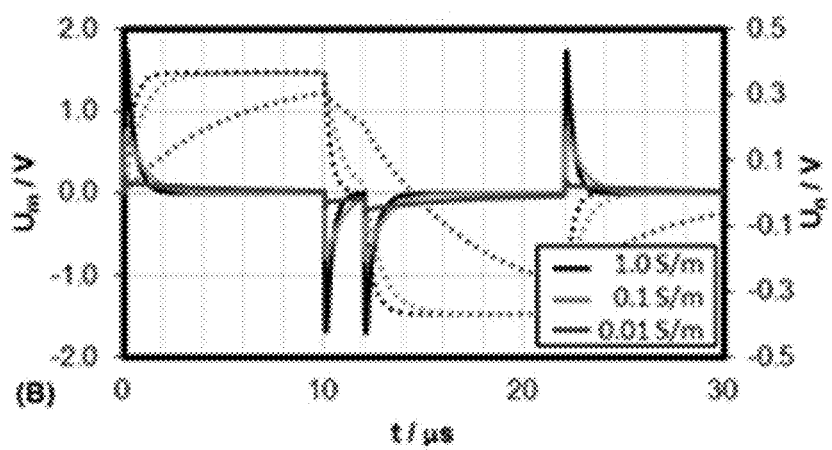
Figure 32C:
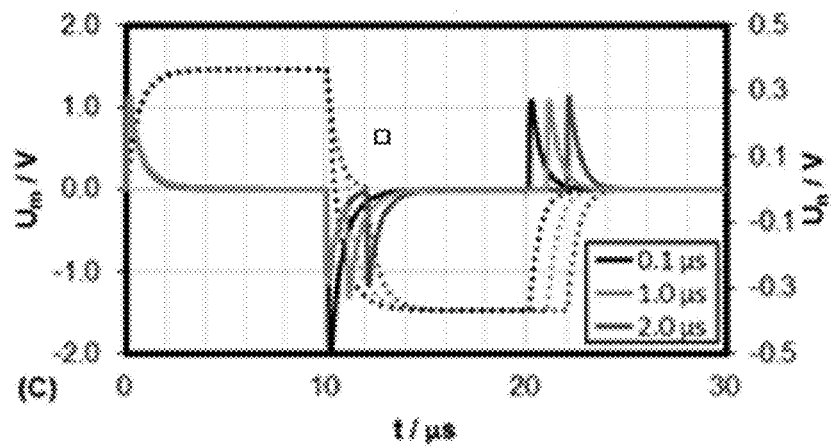

FIGS. 32A-C presents a parametric analysis of variables which can be controlled experimentally. The pulse duration, shown in FIG. 32A, directly impacts the maximum $U_m$ achieved and the duration that $U_m$ is elevated above the 1V critical threshold. Pulses that are shorter than 1 µs do not elevate the $U_m$ above this threshold. As pulse duration increases beyond 1 µs, $U_m$ saturates to a maximum value of 1.47 V. In contrast, because $U_n$ rises rapidly in comparison to the $U_m$, the effects on the nuclear envelope are minimally impacted by the pulse duration. Regardless of pulse width, the $U_n$ reaches a maximum value within 145 ns. For pulses 1 µs or less, the $U_n$ does not completely return to zero before the falling edge of the positive pulse, muting the negative $U_n$ response.

It has been observed that pore formation behavior occurs within 1 µs after $U_m$ is elevated above 1V, quenching further increases in potential (K. Kinosita, I. Ashikawa, N. Saita, H. Yoshimura, H. Itoh, K. Nagayama, A. Ikegami, *Electroporation of cell membrane visualized under a pulsed-laser fluorescence microscope*, Biophysical Journal, 53 (1988) 1015-1019), after which new pore formation is limited and pore expansion takes over as the dominant phenomena (K. Kinosita, T. Y. Tsong, Formation and resealing of pores of controlled sizes in human erythrocyte membrane, (1977); K. Kinosita, T. Y. Tsong, Voltage-induced pore formation and hemolysis of human erythrocytes, Biochimica et Biophysica Acta (BBA)-Biomembranes, 471 (1977) 227-242). At the field strengths presented here, pulses 1 µs in duration and shorter may not efficiently result in pore expansion within the cell membrane (O. M. Nesin, O. N. Pakhomova, S. Xiao, A. G. Pakhomov, *Manipulation of cell volume and membrane pore comparison following single cell permeabiliza-* tion with 60- and 600-ns electric pulses, Biochimica et Biophysica Acta (BBA)-Biomembranes, 1808 (2011) 792-801).

The conductivity of the sample media, FIG. 32B, contributes significantly to the charge-discharge behavior of the cell membrane and the nuclear envelope. At low media conductivities (0.01 S/m), the media presents a significant resistance to current flow and the cell membrane charges slowly. This low conductivity media minimizes the current which can flow through the cytoplasm, muting the maximum $U_n$ achieved. As the media conductivity increases, the cell membrane charges more quickly, saturating as the conductivity is increased above 1 S/m. Based on these simulations, a media conductivity of 0.2 S/m experimentally is a compromise between membrane charging times and current output required from the pulse generator. Increasing media conductivity may have resulted in slightly faster membrane charging times.

The delay between positive and negative polarity pulses, FIG. 32C, has a negligible effect on the transmembrane potential ($U_m$); though, it has a significant impact on the nuclear envelope ($U_n$). The falling edge of the positive pulse results in a negative potential build up on the nuclear envelope. $U_n$ reaches a relative maximum approximately 100 ns after the falling edge of each pulse. For long delays between pulses, this potential decays back to zero. In contrast, as the delay is contracted, $U_n$ is compounded by the rising edge of the negative polarity pulse. Ultimately, as the delay is decreased to 0.1 µs, an effective doubling of the $U_n$ is achieved. Based on these simulations, bursts with a 100 ns delay between changes in pulse polarity will achieve the greatest potential across the nuclear envelope. Counterintuitively, including zero inter-pulse delay results in a lower $U_n$ than the 100 ns case (results not shown). To achieve a doubling in $U_n$, the potential across the nuclear envelope must be allowed to decay back to zero before the applied voltage is turned off. In this scenario, all pulses which are 0.94 µs in duration or longer resulted in approximately a 2× increase in $U_n$ versus the single pulse maximum.

The role of DNA damage in the PEF apoptotic cascade is not fully understood and the nucleus is not typically the target for PEF therapy. However, intrinsic and extrinsic apoptotic cell death processes are associated with field strength dependent effects on mitochondria and the endoplasmic reticulum. If waveform optimization can be used to double the increase in the transmembrane potential of these organelles, as shown in FIG. 32C, then a lower amplitude electric field would be needed to induce the associated apoptotic cascades. Alternatively, by finely tuning the pulse widths and inter-pulse delays it may be possible to enhance DNA damage processes allowing for further study of this mechanism in the PEF apoptotic cascade. Unfortunately, experimental investigation of well controlled 100-500 ns inter-pulse delay scenarios was inhibited by ringing in the output voltages of the inventors' current system and are left as the subject of future work.

Analysis of Cell Electrical Properties

Electrical properties for the cell membrane, nuclear envelope, cytoplasm, and nucleoplasm are readily available in the literature (B. Alberts, D. Bray, J. Lewis, M. Raff, K. Roberts, J. D. Watson, *Molecular Biology of the Cell*, 3rd edition, Garland Science, New York, 1994; P. R. Gascoyne, R. Pethig, J. P. Burt, F. F. Becker, *Membrane changes accompanying the induced differentiation of Friend murine erythroleukemia cells studied by dielectrophoresis*, Biochimica et Biophysica Acta (BBA)-Biomembranes, 1149 (1993) 119-126; J. Yang, Y. Huang, X. J. Wang, X. B. Wang, F. F. Becker, P. R. C. Gascoyne, *Dielectric properties of human leukocyte subpopulations determined by electrorotation as a cell separation criterion*, Biophysical Journal, 76 (1999) 3307-3314; I. Ermolina, Y. Polevaya, Y. Feldman, B.-Z. Ginzburg, M. Schlesinger, *Study of normal and malignant white blood cells by time domain dielectric spectroscopy*, Dielectrics and Electrical Insulation, IEEE Transactions on, 8 (2001) 253-261; J. Gimsa, T. Müller, T. Schnelle, G. Fuhr, *Dielectric spectroscopy of single human erythrocytes at physiological ionic strength: dispersion of the cytoplasm*, Biophysical Journal, 71 (1996) 495-506; and K. Asami, Y. Takahashi, S. Takashima, *Dielectric properties of mouse lymphocytes and erythrocytes*, Biochimica et Biophysica Acta (BBA)-Molecular Cell Research, 1010 (1989) 49-55). Subuncu et al. report that a cytoplasmic conductivity of between 0.3 and 0.6 S/m (A. C. Sabuncu, J. A. Liu, S. J. Beebe, A. Beskok, *Dielectrophoretic separation of mouse melanoma clones*, Biomicrofluidics, 4 (2010) 021101). Labeed et al. report increases in conductivity from 0.28 S/m to 0.45 S/m as cells begin to undergo apoptosis (F. H. Labeed, H. M. Coley, M. P. Hughes, *Differences in the biophysical properties of membrane and cytoplasm of apoptotic cells revealed using dielectrophoresis*, Biochimica et Biophysica Acta (BBA)-General Subjects, 1760 (2006) 922-929). Ron et al. report a conductivity of 0.724 S/m and 0.93 S/m for pre-osteoblast cells and normal canine kidney cells, respectively (A. Ron, R. R. Singh, N. Fishelson, I. Shur, R. Socher, D. Benayahu, Y. Shacham-Diamand, *Cell-based screening for membranal and cytoplasmatic markers using dielectric spectroscopy*, Biophysical chemistry, 135 (2008)) 59-68. Mulhall el al. found cytoplasm conductivities of 0.71, 0.42, 0.26, and 0.25 S/m for normal keratinocytes, abnormal keratinocytes, for two different malignant keratinocytes, respectively (H. Mulhall, F. Labeed, B. Kazmi, D. Costea, M. Hughes, M. Lewis, *Cancer, pre-cancer and normal oral cells distinguished by dielectrophoresis*, Analytical and Bioanalytical Chemistry, 401 (2011) 2455-2463). Additionally, Chen et al. show that drug resistant cells have a lower cytoplasmic conductivity than non-drug resistant cells (J. Chen, Y. Zheng, Q. Tan, E. Shojaei-Baghini, Y. L. Zhang, J. Li, P. Prasad, L. You, X. Y. Wu, Y. Sun, *Classification of cell types using a microfluidic device for mechanical and electrical measurement on single cells*, Lab on a Chip, 11 (2011) 3174-3181). These results provide evidence of decreasing cytoplasmic conductivity as cells transition from benign to malignant.

Yuan et al. show an increase in nucleus-to-cytoplasm (NCR) ratio from 0.45 to 0.49 and from 0.40 to 0.49 as cancer cells achieve drug resistance. Similarly, Helczynska et al. show histologically, that the NCR increases from 0.3 to 0.8 as a function of tumor grade, with higher NCRs for increasingly malignant cancers (K. Helczynska, Å. Kronblad, Å. Jögi, E. Nilsson, S. Beckman, G. Landberg, S. Påhlman, *Hypoxia promotes a dedifferentiated phenotype in ductal breast carcinoma in situ*, Cancer Research, 63 (2003) 1441-1444). Salmanzadeh et al. showed that the specific membrane capacitance of a syngeneic cell line increased from 15.39 mF/m$^2$ to 26.42 mF/m$^2$ as the cells became successively more malignant (A. Salmanzadeh, M. B. Sano, R. C. Gallo-Villanueva, P. C. Roberts, E. M. Schmelz, R. V. Davalos, *Investigating dielectric properties of different stages of syngeneic murine ovarian cancer cells*, Biomicrofluidics, 7 (2013) 011809). This translates into an increase in relative membrane permittivity from 8.70 to 14.92.

A parametric analysis was conducted using cytoplasmic conductivity values of 0.7, 0.475, and 0.25 S/m, an NCR of 0.3, 0.55, and 0.8, and a membrane permittivity of 9, 12, and 15 to represent this transition from benign to intermediate to metastatic, respectively. The present inventors modeled the response of a 'benign' cell having cytoplasmic conductivity of 0.7 S/m, NCR of 0.3, and membrane permittivity of 8.7. A 'metastatic' cell was modeled as having cytoplasmic conductivity of 0.25 S/m, NCR of 0.8, and a membrane permittivity of 15. All other values (Table 1) were held constant.

Figure 33A:
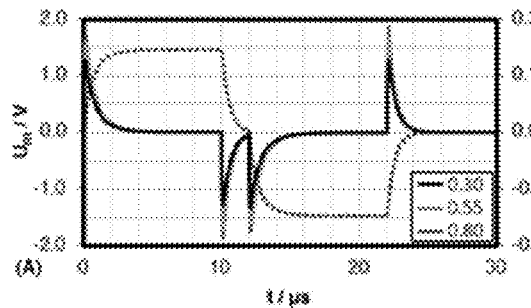
FIGS. 33A-33E are graphs showing a cell property parametric analysis. The voltage drop across the cell membrane, Um/V, and nuclear envelope, Un/V, are presented as a function of time, t/μs. The effect of varying the (FIG. 33A) Nucleus-Cytoplasm Ratio, (FIG. 33B) Cytoplasm Conductivity, and (FIG. 33C) Cell Membrane Permittivity are shown. The voltage drop across the cell membrane, Um/V, and nuclear envelope, Un/V, of a benign and cancerous cell are shown in FIGS. 33D and 33E. Note that the axis for Um and Un have different scales.
Figure 33D:
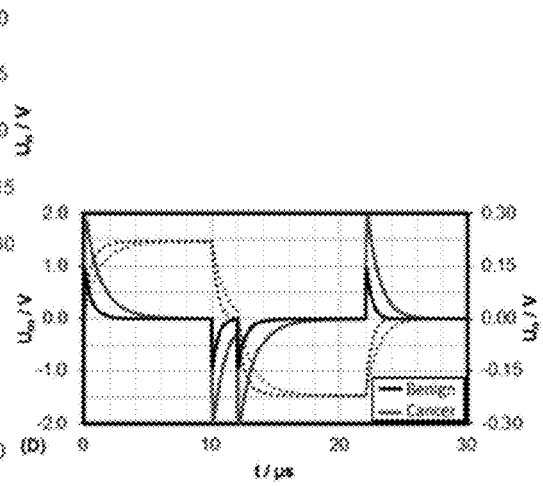
Figure 33B:
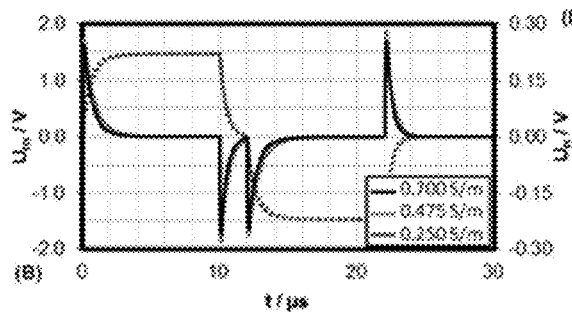
Figure 33E:
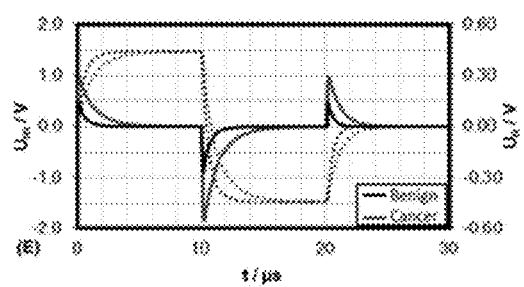
Figure 33C:
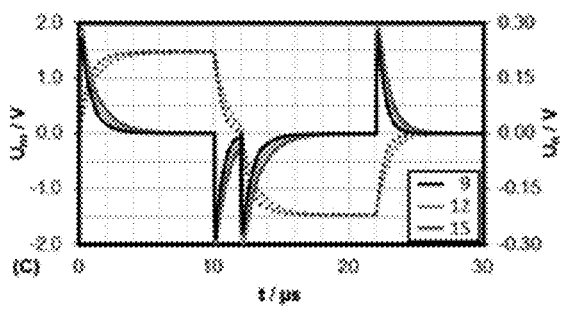

The nucleus-to-cytoplasm ratio (NCR), FIG. 33A, has a negligible effect on $U_m$ and a measurable effect on $U_n$. As expected from electromagnetic theory (P. Marszalek, D. Liu, T. Y. Tsong, *Schwan equation and transmembrane potential induced by alternating electric field*, Biophysical Journal, 58 (1990) 1053-1058), the potential across the nuclear envelope is related to the equation $$\Delta U = 1.5 r E \cos \theta / V \quad [13]$$

where r is the radius of the nucleus and E is the electric field which the cell is exposed to. However, other dielectric properties of the nucleus may affect the membrane charging time (T. Kotnik, D. Miklavčič, Theoretical evaluation of voltage inducement on internal membranes of biological cells exposed to electric fields, Biophysical Journal, 90 (2006) 480-491; K. H. Schoenbach, S. J. Beebe, E. S. Buescher, Intracellular effect of ultrashort electrical pulses, Bioelectromagnetics, 22 (2001) 440-448). As the NCR increases in FIG. 33A, $U_n$ also increases. The cytoplasm conductivity, FIG. 33B, has a negligible impact on the maximum amplitude of $U_m$ and $U_n$, however lower conductivity values result in a slightly higher $U_n$ values. The permittivity of the cell membrane, FIG. 33C, impacts the charge and discharge of the cell membrane and the nuclear envelope. A higher permittivity causes the $U_m$ to increase slightly slower than the lower permittivity cells. This slower charging time of the cell membrane results in the nuclear envelope reaching a slightly higher transmembrane potential.

Numerical Simulation of Experimental Pulses

Figure 34A:
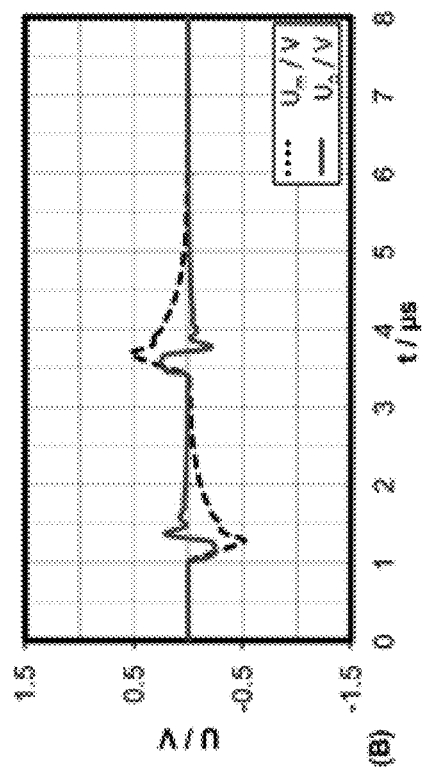
FIGS. 34A-34D are graphs showing simulation of membrane potentials due to 250 ns and 1 μs experimental pulses. The applied electric field, E/(kV/cm), voltage drop across the cell membrane, $U_m$/V, and nuclear envelope, $U_n$/V, are presented as a function of time, t/μs.
Figure 34B:
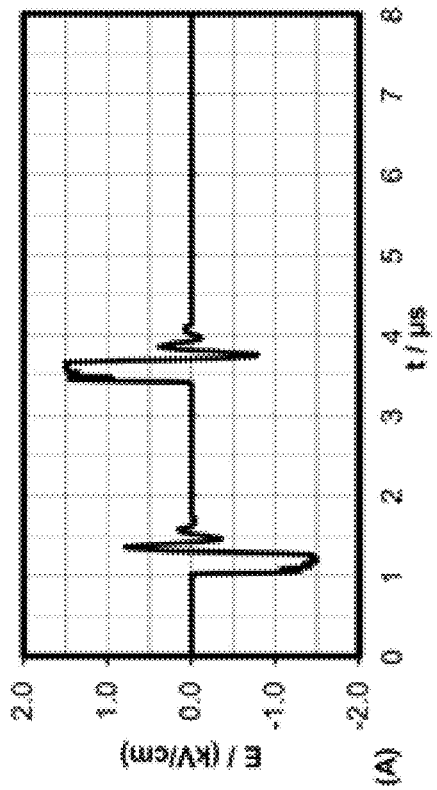
Figure 34C:
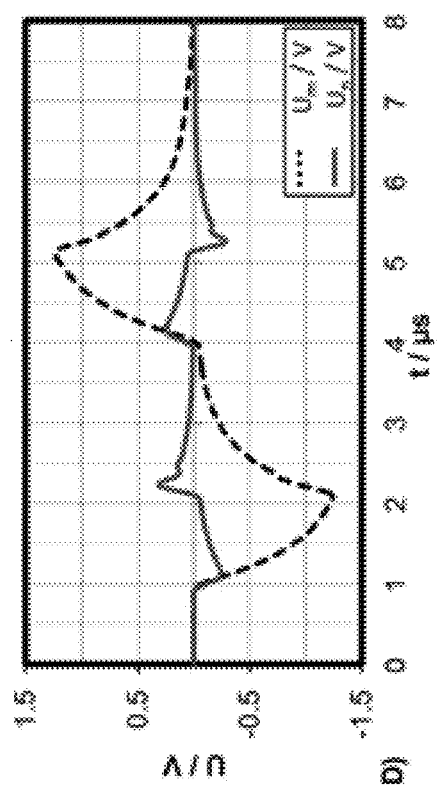
Figure 34D:
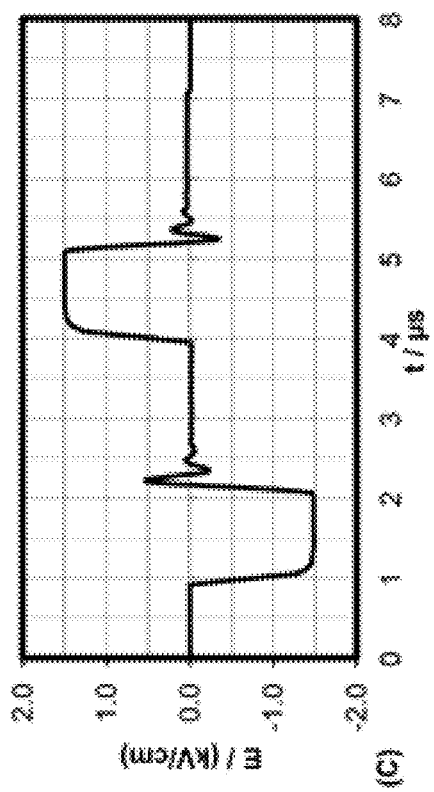

The simulation results of FIGS. 31A-33C represent the idealized response to a perfect square wave with 10 ns rise and fall times. The waveforms exhibited ringing effects on the rising edge and after the falling edge as shown in FIGS. 34A and 34C. FIGS. 34B and 34D shows the transmembrane potential ($U_m$) and trans-nuclear membrane potential ($U_n$) resulting from experimental 250 ns and 1 µs pulses, respectively. As in the idealized case, the falling edge of the pulses results in an increased $U_n$ in the opposite polarity. The ringing in the output waveform causes an additional minor increase in $U_n$. At 1500 V/cm the first rising edge of a 250 ns pulse results in an $U_n$ amplitude maximum of 0.21 V. The falling edge and ringing of the same pulse results in a maximum $U_n$ amplitude of 0.25 V, a 19% increase.

For a 1 µs experimental pulse, $|U_m|$ reaches a maximum of 1.24 V while $|U_n|$ reaches a maximum of 0.32 V. The magnitude of $U_m$ for this experimental pulse is approximately equal to the ideal value predicted in FIG. 32A (1.21V). However, the magnitude of $U_n$ for this experimental pulse (0.32 V) is greater than the value predicted in FIG. 32A (0.29 V). This is due to the ringing which occurs after the experimental pulses fall back to zero.

As the pulse length increases, the initial $U_n$ response is allowed to fall back towards zero. The result is that for longer pulses, the negative going edge and subsequent ringing have an increased effect. For similar field strengths, a 5 µs pulse results in $U_n$ amplitude change from 0.24 V to 0.36 V, a 50% increase (not shown). For these cases, the peak amplitude of the ringing is 46-52% that of the pulse amplitude and lasts for less than 200 ns.

Experimental Results

Figure 35:
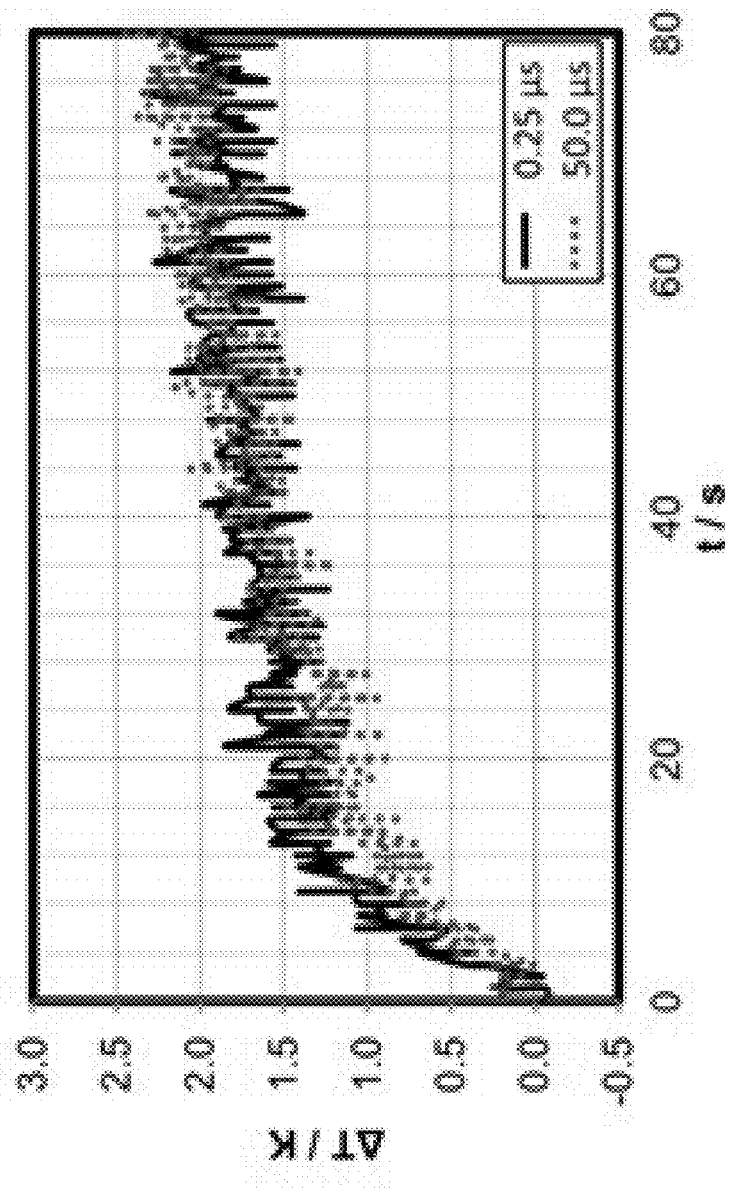
FIG. 35 is a graph showing change in media temperature during exposure to 4000 V/cm. The change in temperature, ΔT/K, is presented as a function of time, t/s. Bursts with 50 us and 250 ns constitutive pulses resulted in similar temperature rises. $\Delta T=T-T_{ref}$, where $T_{ref}=20°$ C.

Experiments were conducted with an initial sample temperature between 22 and 25° C. At 4000 V/cm all experimental groups resulted in a temperature rise less than 3.5° C. Representative temperature profiles for experiments with 50 µs and 250 ns constitutive pulses are shown in FIG. 35. The temperature increase for bursts with 250 ns pulses is similar to the increase for longer duration pulses. This is likely due to the delivery of an equivalent quantity of energy in each burst regardless of the duration of the constituent pulses. The starting temperature of the experiments ensured that the temperature never rose above 37° C., mitigating the possibility of temperature as a confounding factor, affecting the viability of cells.

Figure 36A:
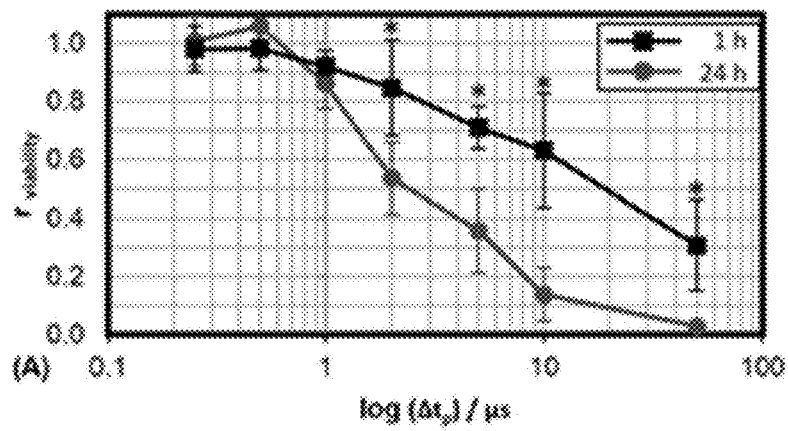
FIGS. 36A-36C are graphs showing cell death occurs due to immediate and delayed mechanisms. The relative viability, $r_{viability}$, is presented as a function of pulse width, $\Delta t_p$/μs. Relative viability of cells 1 and 24 hours after exposure to (FIG. 36A) 1500 V/cm, (FIG. 36B) 3000 V/cm, (FIG. 36C) 4000 V/cm bursts. $r_{viability}=N_{surviving}/N_{total}$, normalized to controls, where N is the number of cells. In all experiments cells were exposed to 80 bursts each with an energized time of 100 µs. Error bars represent the standard deviation after a minimum of three (n=3) randomized experiments. Stars (*) denote statistical significance between 1 and 24 hour time points ($\alpha \leq 0.1$).
Figure 36B:
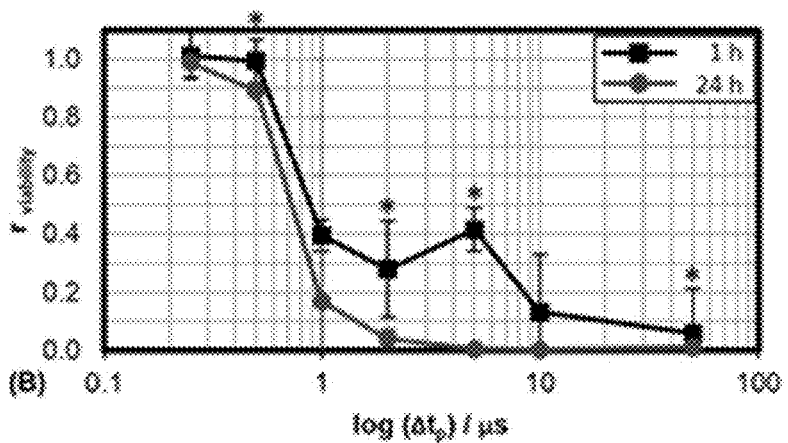
Figure 36C:
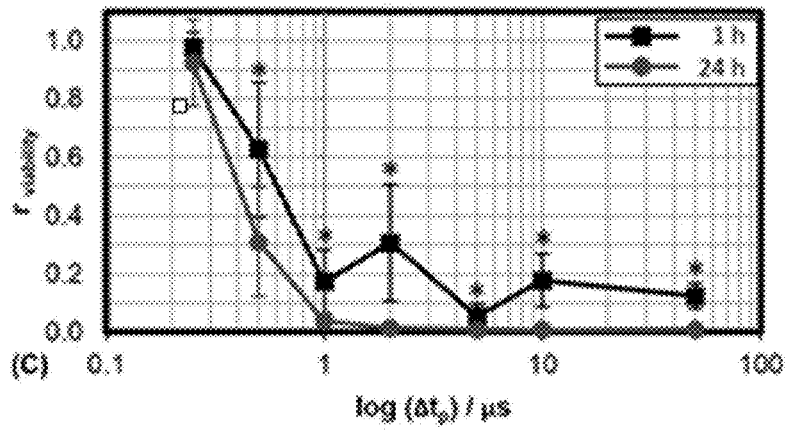

FIGS. 36A-36C show the viability of the samples 1 and 24 hours after treatment for field strengths of (FIG. 36A) 1500 V/cm, (FIG. 36B) 3000 V/cm, and (FIG. 36C) 4000 V/cm. There is a clear inverse relationship between constituent pulse length and viability, with longer duration pulses resulting in a lower viability for both the 1 and 24 hour viability studies.

Specifically, at 1500 V/cm, bursts containing 50 µs pulse (2×) resulted in a 1 hour post-treatment viability of 31% which reduced to 3% after 24 hours. The 1500 V/cm bursts containing pulses between 250 ns (400×) and 10 µs (10×) resulted in 1 hour viabilities above 50% and notably, pulses 2 µs (5×) and shorter had viabilities of 85% or greater, similar to sham treatments. In between the 1 and 24 hour time-points, the viability fell by an average of 20% for cells exposed to 1500 V/cm over all constituent pulses. For this field strength, bursts containing 10 µs pulses had the largest change in viability over 24 hours, 49%, while 250 and 500 ns pulses resulted in a negligible change in viability compared to controls. Significant changes in viability occurred between the 1 and 24 hour time points for bursts with pulses 2 µs and longer. It is interesting that 10 and 50 µs pulses resulted in delayed cell death, however, the mechanism of action is unclear.

Cell viability was significantly lower for 3000 V/cm versus 1500 V/cm bursts when the pulse duration was 1 µs or longer. After 24 hours, the viability for 2 to 50 µs pulses reduced to less than 5% at 3000 V/cm. Between 3000 V/cm and 4000 V/cm, the most significant impact on viability occurred for 500 ns pulses. For all field strengths, 250 ns pulses have a minimal impact on cell viability.

For bursts containing 250 ns pulses, the difference in viability after 1500, 3000, and 4000 V/cm treatments was not statistically significant ($\alpha \leq 0.1$). All other pulse-widths had a statistically significant difference between the 1500 V/cm and 3000 V/cm treatments at each timepoint ($\alpha \leq 0.06$). Between the 3000 and 4000 V/cm treatments, 5 µs (1 hour), 500 ns (1 hour), and 500 ns (24 hour) groups had statistically different viabilities ($\alpha \leq 0.03$)

Interestingly, this study shows that viability is not directly correlated to the energy dose delivered. This conforms to the results presented by others that electropermeabilization (A. Maček-Lebar, D. Miklavčič, *Cell electropermeabilization to small molecules in vitro: control by pulse parameters*, Radiology and Oncology, 35 (2001)) and lethal (B. L. Ibey, A. G. Pakhomov, B. W. Gregory, V. A. Khorokhorina, C. C. Roth, M. A. Rassokhin, J. A. Bernhard, G. J. Wilmink, O. N. Pakhomova, *Selective cytotoxicity of intense nanosecond-duration electric pulses in mammalian cells*, Biochimica Et Biophysica Acta-General Subjects, 1800 (2010) 1210-1219) effects of mono-polar pulses of different pulse widths exhibit a complex relationship that cannot be correlated to the quantity of energy delivered alone. The inverse correlation between pulse length and toxicity presented may be related to the cell membrane charging time, calculated here as between 1.11 and 7.92 μs. FIGS. 37A-L shows the effect of multiple pulses within each burst on the time in which $U_m$ and $U_n$ are elevated above critical thresholds. A single cycle of 1500 V/cm 250 ns pulses, one positive and one negative, increases $U_m$ above 1 V for only 200 ns total. However, the cumulative effect of 200 cycles per burst (400 total pulses) increases $U_m$ above 1 V for approximately 40 μs. At 1500 V/cm (FIG. 9A-B) time above the 1 V threshold increases as constitutive pulse width ($\Delta t_p$) is increases. This process reaches a maximum of approximately 99.8 μs for bursts with 50 μs constitutive pulse widths, which only have one cycle. At 3000 and 4000 V/cm, FIGS. 37E-F, I-J, bursts of shorter pulses elevate $U_m$ above 1 V for a longer duration than those with longer pulse durations, however, this appears to have a negligible impact on cell viability. Though not examined here, pulses energized for less than the membrane charging time may result in limited pore expansion, minimizing lethal effects.

At 1500 V/cm, none of the pulse durations elevated $U_n$ above thresholds of 0.5, 0.75, or 0.9 V (FIGS. 37C-D). 0.7 and 0.9 V are shown a surrogates for the 1.0 V threshold which was not reached for any simulation at the highest voltage (4000 V) and 0.5 V is used to approximate the onset of reversible electroporation (A. M. Lebar, G. C. Troiano, L. Tung, D. Miklavcic, *Inter-pulse interval between rectangular voltage pulses affects electroporation threshold of artificial lipid bilayers*, NanoBioscience, IEEE Transactions on, 1 (2002) 116-120; A. Polak, D. Bonhenry, F. Dehez, P. Kramar, D. Miklavčič, M. Tarek, *On the Electroporation Thresholds of Lipid Bilayers: Molecular Dynamics Simulation Investigations*, The Journal of membrane biology, 246 (2013) 843-850). At 3000 V/cm (FIGS. 37G-H), all pulse durations are able to increase $U_n$ above the 0.5 V threshold. The cumulative impact of a full burst results in $U_n$ increasing above the 0.5 V threshold for a substantially longer duration for shorter constitutive pulses. At 4000 V/cm (FIGS. 37K-L), some pulse durations are able to elevate $U_n$ above the 0.75 and 0.9 V thresholds. Interestingly, 500 ns pulses result in greater cumulative time above all of the thresholds than any other pulse durations. This may help explain why 500 ns bursts resulted in significant changes in viability between 1 and 24 hours and 250 ns did not.

For all bursts containing pulses 1 μs in duration or longer, the viability at 3000 V/cm after 24 hours is lower than the corresponding viability at 4000 V/cm after one hour. This has interesting implications for in-vivo applications as it indicates that ablation sizes may grow over time and that immediate observation may be inadequate to predict the total volume treated. From the numerical simulations, it is anticipated that cells with a larger cytoplasm-nucleus ratio will achieve higher $U_n$ amplitudes than cells of similar size with a smaller ratio. A high nucleus-cytoplasmic ratio (NCR) has been associated with the aggressiveness of malignant cells and is used as a parameter in grading cancers (K. Seibert, S. M. Shafie, T. J. Triche, J. J. Whang-Peng, S. J. O'Brien, J. H. Toney, K. K. Huff, M. E. Lippman, *Clonal variation of MCF-7 breast cancer cells in vitro and in athymic nude mice*, Cancer research, 43 (1983) 2223-2239; Y. Shimizu, S. Kamoi, S. Amada, F. Akiyama, S. G. Silverberg, *Toward the development of a universal grading system for ovarian epithelial carcinoma*, Cancer, 82 (1998) 893-901; A. Malpica, M. T. Deavers, K. Lu, D. C. Bodurka, E. N. Atkinson, D. M. Gershenson, E. G. Silva, *Grading ovarian serous carcinoma using a two-tier system*, The American journal of surgical pathology, 28 (2004) 496-504; and S. G. Silverberg, *Histopathologic grading of ovarian carcinoma: A review and proposal*, Inter. J. of Gynecological Pathology, 19 (2000) 7-15).

Additionally, it has been shown that an increase in invasiveness and metastatic potential has been correlated to cell membrane ruffling, which leads to higher membrane capacitances in aggressive cells (A. Salmanzadeh, M. B. Sano, R. C. Gallo-Villanueva, P. C. Roberts, E. M. Schmelz, R. V. Davalos, *Investigating dielectric properties of different stages of syngeneic murine ovarian cancer cells*, Biomicrofluidics, 7 (2013) 011809; A. Salmanzadeh, H. Kittur, M. B. Sano, P. C. Roberts, E. M. Schmelz, R. V. Davalos, *Dielectrophoretic differentiation of mouse ovarian surface epithelial cells, macrophages, and fibroblasts using contactless dielectrophoresis*, Biomicrofluidics, 6 (2012) 024104; and A. Salmanzadeh, E. S. Elvington, P. C. Roberts, E. M. Schmelz, R. V. Davalos, *Sphingolipid Metabolites Modulate Dielectric Characteristics of Cells in a Mouse Ovarian Cancer Progression Model*, Integr. Biol., (2013)). In numerical simulations (FIG. 33D), a normal cell model experiences a $|U_n|\approx 0.14V$ while a cancer cell model reaches $|U_n|\approx 0.32V$. The nucleus in the cancer cell model reaches a potential approximately 2 time higher than the normal cell model as a result of changes in NCR. This effect is amplified further if the delay between pulses is reduced to 100 ns (FIG. 33E) where $|U_n|\approx 0.6$ V for the cancer cell model. It is anticipated that malignant cells will experience an increased response to bi-polar pulses due the increase in lipid-bilayer charging time, resulting from an increased membrane capacitance, coupled with increased nucleus-cytoplasm ratio. However, future work will be required to determine if these burst have an increased efficiency at targeting aggressive cells.

Conclusions

The present inventors found, through finite element simulations, that the charge-discharge behavior of the cell membrane impacts the electric field experienced by intracellular components. This simplified model has some limitations. Cells were modeled as simple spheres to reflect the shape of the cells in their non-adhered state. In vivo, cells typically take on more complex, elongated, or spindled shapes which can alter the effects of pulsed electric fields on transmembrane potential. Additionally, cells in tissue are affected by local inhomogeneity and the responses of cells in their immediate vicinity which was not accounted for here.

Cytoplasm-nucleus ratio, cytoplasm conductivity, and cell membrane permittivity play a significant role in the charging characteristics of the nuclear envelope. Experimentally the inventors found that bursts of bi-polar square waves increased the media temperature less than 3.5° C. when the total energized time per burst was held constant at 100 μs and eighty bursts were delivered. The resulting cellular responses are therefore limited to those related directly to non-thermal phenomena. For the bursts of bi-polar pulses presented, there exists an inverse correlation between pulse-width and toxicity despite the delivery of equal quantities of energy. The changes in cellular viability over 24 hours post treatment show presence of both instantaneous and delayed cell death processes, however, the exact mechanisms are unknown.

To the best of the inventors' knowledge, this is the first experimental parametric analysis on the effects of bi-polar square wave bursts with pulses between 0.25 and 50 μs. In the 3000 V/cm treatment groups, cell viability was reduced to 4.0%, 0.5%, 0.3%, and 1.0% for bursts containing 2, 5, 10, and 50 µs pulses, respectively. In the 4000 V/cm treatment groups, cell viability was reduced to 3.8%, 1.4%, 0.9%, 0.8%, and 0.8% for bursts containing 1, 2, 5, 10 and 50 µs pulses, respectively. Rubinsky et al. (J. Rubinsky, G. Onik, P. Mikus, B. Rubinsky, *Optimal Parameters for the Destruction of Prostate Cancer Using Irreversible Electroporation*, The Journal of Urology, 180 (2008) 2668-2674) showed that ten 100 µs monopolar pulses at 2000 V/cm resulted in a viability of 70%. In the same study, they showed that seventy-five 100 µs monopolar pulses at 250 V/cm resulted in a viability of 10-20% while ninety 100 µs monopolar pulses at 250 V/cm reduced viability to 0-10%. Arena et al. (C. B. Arena, C. S. Szot, P. A. Garcia, M. N. Rylander, R. V. Davalos, *A Three-Dimensional In vitro Tumor Platform for Modeling Therapeutic Irreversible Electroporation*, Biophysical Journal, 103 (2012) 2033-2042 ("Arena et al., 2012")) showed that after eighty 100 µs monipolar pulses at 1500 V/cm, cell viability was approximately 8% and this protocols is consistent with those currently being employed successfully in clinical applications of irreversible electroporation in the prostate (G. Onik, B. Rubinsky, *Irreversible Electroporation: First Patient Experience Focal Therapy of Prostate Cancer*, in: B. Rubinsky (Ed.) Irreversible Electroporation, Springer Berlin Heidelberg, 2010, pp. 235-247), pancreas (R. C. Martin II, K. McFarland, S. Ellis, V. Velanovich, Irreversible electroporation therapy in the management of locally advanced pancreatic adenocarcinoma, Journal of the American College of Surgeons, 215 (2012) 361-369), and liver (R. Cannon, S. Ellis, D. Hayes, G. Narayanan, R. C. Martin, *Safety and early efficacy of irreversible electroporation for hepatic tumors in proximity to vital structures*, Journal of Surgical Oncology, (2012)). The comparable level of toxicity resulting from the bi-polar burst protocol presented here indicates that it may be advantageous in in-vivo therapies where muscle contractions due to longer duration mono-polar pulses are undesirable.

Example 3

Materials and Methods
Collagen Hydrogel Tumor Mimics
PPT8182 murine primary pancreatic tumor cells (von Burstin, 2009), shown to replicate human pancreatic cancer in terms of histology, metastasis, and genetic alterations (von Burstin, 2009; Seidler, B., et al. *A Cre-loxP-based mouse model for conditional somatic gene expression and knockdown in vivo by using avian retroviral vectors*. Proceedings of the National Academy of Sciences 105, 10137-10142 (2008); Saur, D., et al. *CXCR4 expression increases liver and lung metastasis in a mouse model of pancreatic cancer*. Gastroenterology 129, 1237-1250 (2005); PaszeK, M. J., et al. *Tensional homeostasis and the malignant phenotype*. Cancer cell 8, 241-254 (2005); and Szot, C. S., Buchanan, C. F., Freeman, J. W. & Rylander, M. N. *3D in vitro bioengineered tumors based on collagen I hydrogels*. Biomaterials 32, 7905-7912 (2011)) were used in the 3D tumor platform experiments. Cells were cultured in Dulbecco's Modified Eagle Medium (DMEM) supplemented with L-glutamine (ATCC, Manassas, Va.) containing 10% fetal bovine serum (FBS; Sigma Aldrich, St. Louis, Mo.) and 1% penicillin/streptomycin (Invitrogen, Carlsbad, Calif.) at 37° C. in 5% $CO_2$ in a humidified atmosphere. All cells were harvested for experiments by trypsinization at 80% confluence.

FIGS. 38A-B show that high-frequency BEAM treatment replaces the single monopolar pulse (FIG. 38A) with a burst of higher frequency bi-polar pules (FIG. 38B). Collagen I hydrogels, shown in FIG. 38C, were produced as described previously (Szot, C. S., Buchanan, C. F., Freeman, J. W. & Rylander, M. N. *3D in vitro bioengineered tumors based on collagen I hydrogels*. Biomaterials 32, 7905-7912 (2011)). Briefly, Sprague Dawley rat tail tendons were excised and allowed to dissolve under agitation overnight in 10 mM HCl at room temperature. The resulting monomeric collagen suspension was centrifuged at 22,500×g for 30 min, and the supernatant was decanted and stored at 4° C. until later use. The collagen hydrogels were formed by neutralizing the collagen I in HCl with a buffer containing 10× concentrated DMEM (supplemented with 4.5 g/L glucose, L-glutamine, sodium pyruvate, and sodium bicarbonate; Mediatech Inc., Manassas, Va.), 1N NaOH, and deionized $H_2O$ to obtain a final concentration of 8 mg/mL at a pH of 7.4. The PPT8182 cells were suspended in the neutralizing buffer at a final seeding density of $1\times10^6$ cells/mL and then mixed with the collagen I solution. The collagen-cell suspension was pipetted into 10 mm diameter cylindrical molds to achieve a thickness of 3 mm after polymerization. Following a 20 min gelation period at 37° C., the hydrogels were removed from the molds and cultured in complete media for 18 hours prior to pulse delivery.

Electronics and Protocols
A custom pulse generation system was used to deliver bursts of bi-polar pulses with constitutive pulse widths of 250 ns, 500 ns, 1 µs, 2 µs, 5 µs, 10 µs, and 50 µs. A 500Ω resistor was placed in parallel with the load to ensure proper pulse shaping and to protect against delivering pulses to an open circuit. Custom electrodes were made from hollow 1.27 mm diameter dispensing needles (Howard Electronic Instruments Inc., El Dorado, Kans.) with a 2.0 mm edge-to-edge separation distance.

A pilot study was conducted at 540 $V_{peak}$ and a total energized time of 100 µs for all pulse widths. This protocol used 400, 200, 100, 50, 20, 5, or 2 pulses to comprise a burst, with individual pulse durations of 250 ns, 500 ns, 1 µs, 2 µs, 5 µs, 10 µs, or 50 µs, respectively. The ablation zones at 540 $V_{peak}$ for bursts containing pulses 1 µs or less were not well formed ovals surrounding the electrodes. Instead, dead cells occupied small triangular zones which extended, but did not connect between the two electrodes. The electric field intensity changed rapidly in this zone resulting in large variations in the calculation of electric field thresholds. To avoid this, a higher voltage of 650 V was used for the 250 ns, 500 ns, 1 µs and 2 µs groups. To facilitate comparison between groups, a simplified electrical dose formula was used.

$$\text{Dose}=V^2 * T_p * n * N[V^2 s] \qquad [14]$$

where V is the applied voltage, $T_p$ is the pulse width, n is the number of pulses per burst, and N is the number of bursts per treatment which was held a constant 80. The 540 $V_{peak}$ group had an approximate dose of 2300 $V^2$s. At 650 $V_{peak}$, 256, 128, 64, and 32 pulses were used for the 250 ns, 500 ns, 1 µs, and 2 µs groups, respectively. This resulted in an approximate dose of 2200 $V^2$s. An additional 2 µs group at 250 $V_{peak}$ with 216 pulses an approximate dose of 2000 $V^2$s was also conducted to compare effects of energy and lethal electric field threshold.

To explore the effect of burst energized time, a set of experiments were conducted with 80 bursts containing 2 µs pulses at 540V. Pulses were repeated 2, 24, or 50 times per burst with a 2 µs inter-pulse delay. To compare 'diffuse' and 'burst' delivery of pulses an additional group of 50 pulses per second was tested. In this group, one positive and one negative pulse were delivered, with a 2 µs inter-pulse delay, every 20 ms for a total of 80 seconds. This is the only group presented in which a 1 second inter-burst delay was not used.

To explore the effect of treatment time, a set of experiments were conducted with eight bursts. These groups had 2 μs, 50 μs, and 100 μs pulses which were repeated 50, 2, and 1 times per burst, respectively. The experimental parameters are summarized in the table in FIG. 39. All parameters were repeated a minimum of three (n=3) times.

Sample Processing

At 24 hours after treatment, normal culture media was replaced with 2.5 mL of media supplemented with 4 μM Calcein AM (live stain, $\lambda_{em}$=515 nm, Invitrogen, Eugene, Oreg.) and incubated at 37 C for 30 minutes. Five minutes prior to visualization, the media was supplemented with 75 μL of 1.5 mM propidium iodide (PI; dead stain, $\lambda_{em}$=617 nm, Invitrogen, Eugene, Oreg.) for 5 minutes. Finally, the hydrogels were rinsed with PBS to flush out any unabsorbed dyes and increase the signal to noise ratio. A Leica DMI 6000 fluorescent microscope with a 20× objective (Leica Microsystems Inc., Buffalo Grove, Ill.) was used to tile a set of images and reconstruct an entire plane of the treated scaffolds just under the surface.

Analysis of Electric Field Thresholds in Tissue Mimics

Finite element models were created in COMSOL Multiphysics (Version 4.2a, COMSOL Inc., Burlington, Mass.). The collagen hydrogels were modeled as a 3 mm thick cylinder with a 5 mm radius and conductivity of 1.2 S/m. Cylinders representing the 1.27 mm outer diameter electrodes were offset such that their edge-to-edge distance was equal to 2 mm. Within the solution domain, the Electric Currents module was used to solve for the following equations:

$$\nabla \cdot J = Q_j/(A/m^3) \quad [1]$$

$$J = \left(\sigma + \varepsilon_0 \varepsilon_r \frac{\partial}{\partial t}\right) E / (A/m^2) \quad [2]$$

$$E = -\nabla U / (V/m) \quad [3]$$

where U is the electric potential, E is the electric field, J is the current density, Q is the current source, a is the conductivity, $\in_r$ is the relative permittivity, and $\in_0$ is the permittivity of free space. The boundaries surrounding one electrode were assigned a constant electrical potential $$U=U[V] \quad [15]$$

The boundaries of the other electrode were assigned as a relative ground $$U=0/V \quad [5]$$

The remaining boundaries were defined as electrical insulation $$n \cdot J = 0/(A/m) \quad [6]$$

where n is the normal vector to the surface, J is the electrical current.

Changes in temperature due to Joule heating were calculated for 540 V and 100 energized time over 80 seconds using a modified duty cycle approach (Arena, C. B., et al. *High-Frequency Irreversible Electroporation (H-FIRE) for Non-thermal Ablation without Muscle Contraction*. Biomed Eng Online 10(2011); Neal, R. E., 2nd, Garcia, P. A., Robertson, J. L. & Davalos, R. V. *Experimental Characterization and Numerical Modeling of Tissue Electrical Conductivity during Pulsed Electric Fields for Irreversible Electroporation Treatment Planning*. IEEE Trans Biomed Eng 59, 1076-1085 (2012)). The temperature distribution (T) was obtained by transiently solving a modified heat conduction equation:

$$\rho c \frac{\partial T}{\partial t} = \nabla \cdot (k \nabla T) + \frac{\tau(\sigma |E|^2)}{P} \left[\frac{J}{m^3 \cdot s}\right] \quad [16]$$

where τ is the pulse duration, P is the period of the pulses, k is the thermal conductivity, c is the specific heat at constant pressure, and p is the density. Outer boundaries were treated as convective cooling $$-n \cdot (-k \nabla T) = h(T_{ext} - T)\left[\frac{W}{m}\right] \quad [17]$$

with an exterior temperature ($T_{ext}$) of 22° C. and a heat transfer coefficient (h) of 25 (W m$^{-2}$ K$^{-1}$). Intermediate time stepping was used to ensure that at least one time step was taken each second. Simulations at 540 V showed that thermal effects resulted in a negligible impact on the electric field distribution and changes in conductivity due to temperature increases were neglected in subsequent models to minimize computational time. Changes in conductivity due to electroporation were similarly neglected due to the low concentration of cells within the scaffold. To replicate the values measured experimentally, the voltage on one electrode was swept between 470-700V, in steps of 10V, and the other was held at ground.

Tiled images near the surface of the hydrogels (representative examples in FIGS. 38D-G) were examined using ImageJ (version 1.43u, National Institutes of Health, USA). The width and height of the region of cells that had taken up PI (dead region) was measured. These values were then correlated to the electric field intensity from the numerical simulations to determine the electric field threshold required for cell death (Arena et al., 2012). Statistical analysis of the data was completed using JMP (Version 10.0 Pro, SAS Institute Inc., Cary, N.C.) with a confidence level of 99% (α=0.01).

Murine Tumor Model

This study was approved by the Virginia Tech Institutional Animal Care and Use Committee. 6-7 week old Hsd:Athymic Nude-Foxn1$^{nu}$ male mice (Harlan, Dublin, Va.) were inoculated subcutaneously in the dorsolateral flank region with human glioblastoma cells (DBTRG-05MG) while anesthetized by inhalation of 3% isoflurane (Abbott Laboratories, Abbott Park, Ill.). Mice were housed in individually ventilated cages in groups of five under specific pathogen free conditions and allowed access to sterilized water and food ad libitum. Prior to inoculation, cells were cultivated using standard techniques in DMEM (High-glucose supplemented with L-glutamine; Thermo Scientific, Logan, Utah) containing 10% FBS and 1% penicillin/streptomycin. Upon reaching 80% confluence, cells were suspended at a concentration of 5×10$^6$ cells/mL in an 85/15 mixture of PBS and Matrigel (BD Biosciences, San Jose, Calif.). 200 μL aliquots of this final suspension was used for each injection (1×10$^6$ cells total).

Tumor growth was measured over time using calipers, and volumes (v) were calculated according to the modified ellipsoid formula (Jensen, M. M., Jorgensen, J. T., Binderup, T. & Kjaer, A. *Tumor volume in subcutaneous mouse xenografts measured by microCT is more accurate and repro-* ducible than determined by 18FFDG-microPET or external caliper. BMC medical imaging 8, 16 (2008)):

$$v = l * \frac{w^2}{2} [mm^3] \quad [18]$$

where l is the length of the longitudinal diameter and w is the width of the transverse diameter. Tumors were treated when the greatest diameter reached approximately 5 mm; treatment groups are shown in the table in FIG. 44. Mice were anesthetized following the same isoflurane inhalation protocol, and the skin over the tumor was prepped with 70% isopropyl alcohol. Then, custom steel needle electrodes (0.4 mm Ø) were advanced into the center of the tumor. A 0.4 cm spacing (center-to-center) was used in all treatments. In all treatment groups, the pulse generation system was set to deliver its maximum 1000 Vpeak output. The energized time per burst was fixed to 100 μs and bursts were delivered with a repetition rate of 1 Hz for 2 minutes.

Following treatment, topical antibiotic ointment was applied to the needle insertion wounds. Mice were removed from anesthesia and provided 5 mg/kg ketoprofen analgesic diluted in 1 mL sterile saline solution for recovery. The mice were euthanized 30 days post-treatment or earlier for humane reasons if the tumor volume reached 800 mm3.

Samples of any present tumor tissue were excised and sectioned for processing. Representative tissues were preserved in 10% neutral buffered formalin and embedded in paraffin. Formalin preserved paraffin embedded samples were sectioned and processed for histology using hematoxylin and eosin (H&E) staining. All photomicrographs were obtained with a Leica DMI 6000 inverted microscope.

Results

Figure 40A:
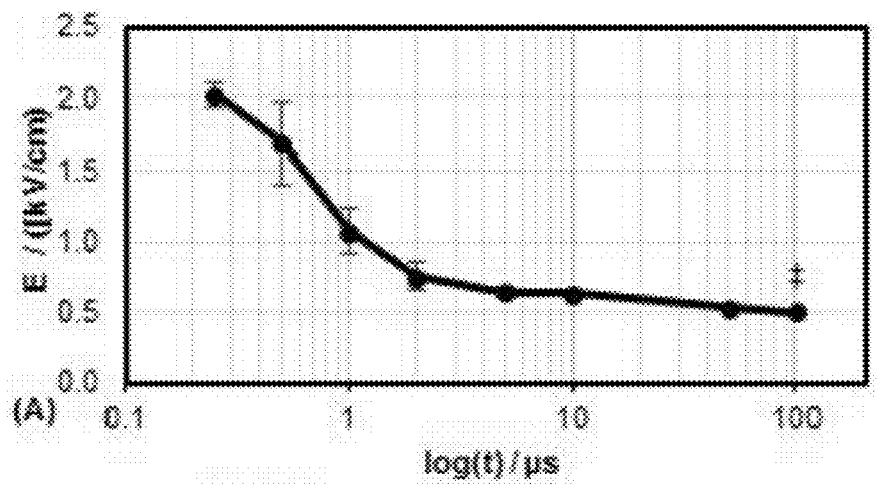
FIG. 40A is a graph showing lethal electric field threshold for PPT cells in tissue mimic for 2200 V2s dose.

BEAM Treatment Pulse Width, Pulse Number, and Total Energized Time Affect the Lethal Electric Field Threshold Typical IRE treatments involve the delivery of 80 monopolar pulses, each 100 μs in duration at a repetition rate of 1 Hz. Using the PPT8182 cell line and the same tissue mimic, Arena et al (Arena et al., 2012) found that the lethal threshold for this standard protocol is 501 V/cm. FIG. 40A shows the lethal threshold when the monopolar pulse is replaced by a burst of bipolar pulses with an equivalent electrical dose. The lethal electric field thresholds were found to be 2022, 1687, 1070, 755, 640, 629, and 531 V/cm for bursts containing 0.25, 0.5, 1, 2, 5, 10 and 50 μs pulses, respectively.

Figure 40B:
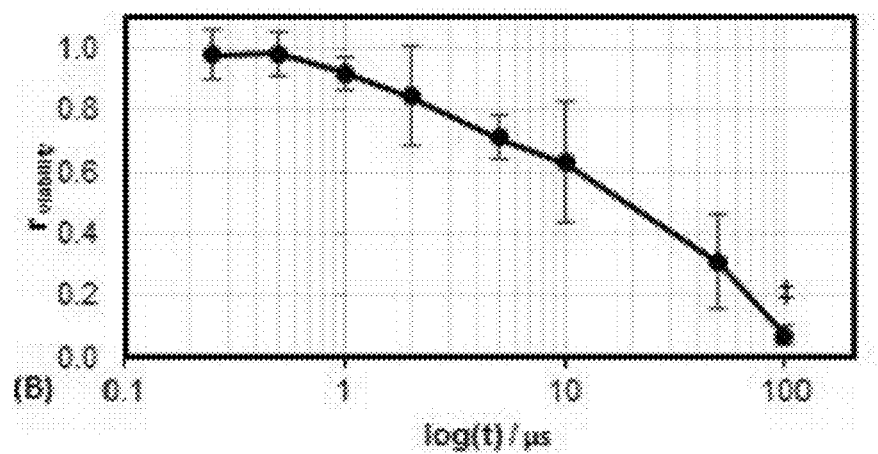
FIG. 40B is a graph showing relative viability of PPT cells in media suspension after treatment with 1500 V/cm. Data in FIG. 40B is from Sano et al. 2014 and data labeled ‡ in FIGS. 40A and B is from Arena et al. 2012.
Figure 40C:
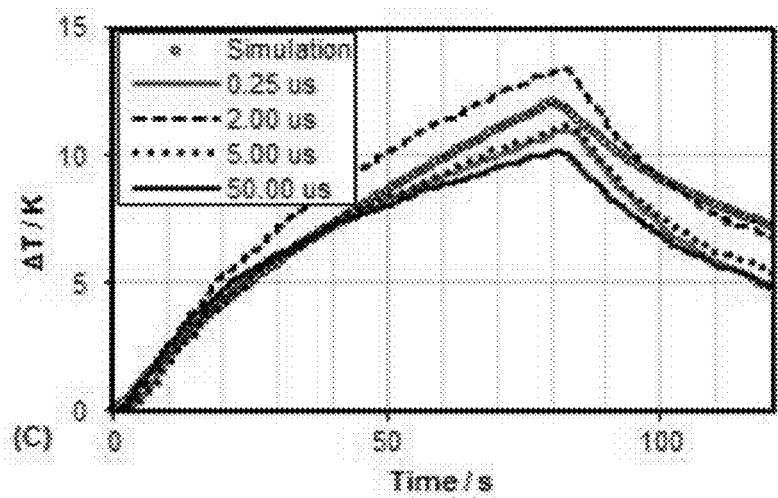
FIG. 40C is a graph showing the temperature profile at center of tissue mimic as measured experimentally and predicted numerically.

The temperature profiles measured were well correlated to those predicted numerically (FIG. 40C). Simulations of these pulses predict a temperature increase of approximately 12° C. at the center of the tissue mimic after 80 pulses were delivered. Experimentally, the average temperature increase across all groups was 14.4±2.2° C. Experiments were conducted at room temperature and the maximum temperature measured experimentally was 34.8° C. The largest variation in maximum temperature, 3.2° C., occurred between the 2 μs and 50 μs groups.

Figure 41B:
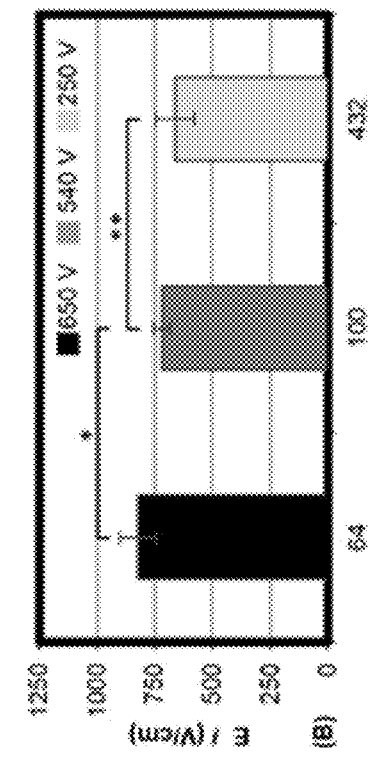
FIGS. 41A-41D are graphs showing the lethal electric field threshold for the following treatments.

Treatments with 8 and 80 bursts were conducted for bursts with 2 and 50 μs pulses. For comparison, treatments with either 8 or 80 monopolar pulses 100 μs in duration were conducted (FIG. 41A). The thresholds for 8 pulses were found to be 1675, 1211, and 820 V/cm, for the 2, 50, and 100 μs groups, respectively. The corresponding thresholds for 80 pulses were found to be 756, 531, and 501 V/cm.

To explore the limitations of the inventors' equivalent dose approximation, eighty bursts held constant with 2 μs pulses were delivered at three different voltages: 250, 540, and 650 V. For these cases, each burst contained 216, 50, and 32 pulses, resulting in approximate doses of 2000, 2300, and 2200 V²s, respectively. The threshold for cell death for these treatments were 663, 718, and 822 V/cm (FIG. 41B). The 250 and 650 V groups were found to be statistically different with a 99% confidence level (α=0.01).

Figure 41D:
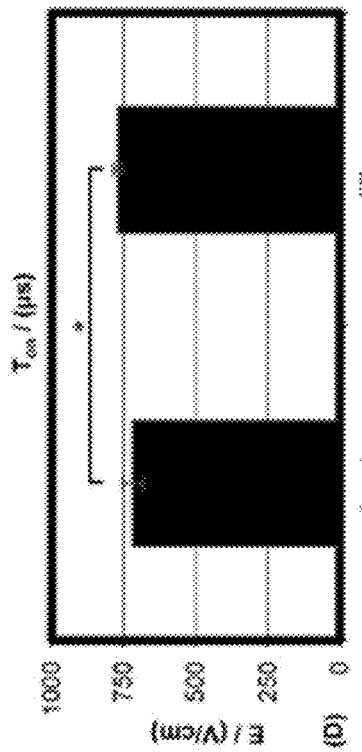
Figure 41A:
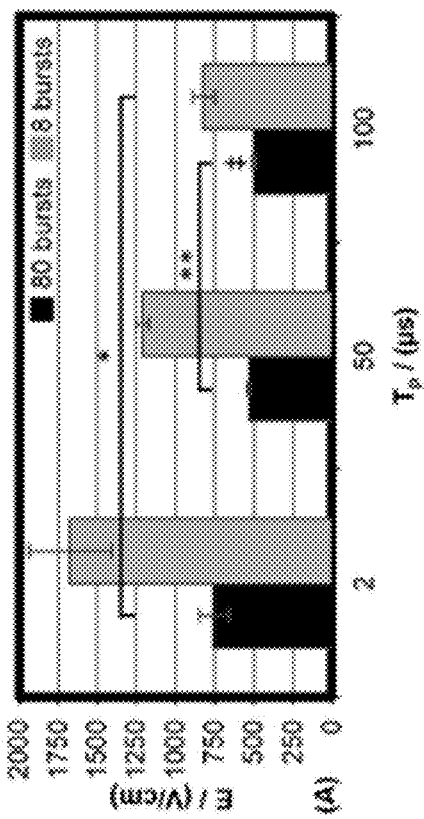
Figure 41C:
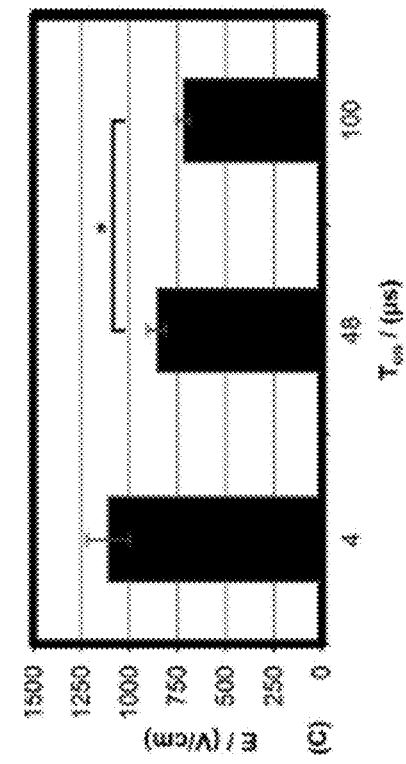

For bursts with 2 μs pulses, when the voltage was held constant at 540 V, but the energized time per burst was decreased from 100 to 48 or 4 μs, the electric field threshold was found to increase from 718 V/cm to 855 and 1110 V/cm, respectively (FIG. 41C). The difference between 100 and 48 μs was not statistically significant.

FIG. 41D shows the effect of inter-pulse delay on lethal electric field threshold. At 540 V, the inter-pulse delay between 2 μs pulses was increased from 2 μs to 200 μs. Similar to the 'burst', this 'diffuse' treatment was energized for 100 μs per second and this waveform was delivered for 80 seconds. This change in inter-pulse delay resulted in an increase in electric field threshold from 718 V/cm to 770 V/cm; this difference was not statistically different.

BEAM Treatment Inhibits Tumor Growth In Vivo

At the time of treatment, tumors were on average 91, 101, 45, and 44 mm³ for the sham, 5 μs, 2 μs, and 1 μs groups. Thirty days post-treatment, these averages had changed to 332, 62, 16, and 44 mm³ (FIG. 42E). Three of the four sham tumors more than doubled in size by day 30 (FIG. 42A). The fourth did not significantly increase in size and measured 92 mm³ at the conclusion of the study. Tumors in the 1, 2, and 5 μs group (FIGS. 42B-D) exhibited varying increases in size over days 1-5 before regression was observed. The 1 μs group had two complete regressions at the end of the study. The other two tumors measured 85 and 91 mm³ on day 30. The 2 μs group had 1 complete regression and the other tumor measured 32.9 mm³ on day 30 (FIG. 42C). The 5 μs group had 3 complete regressions. The remaining tumors had volumes of 77, 77, 97, 106, and 144 mm³. FIG. 4E shows the average tumor volumes for each treatment group over the 30 day trial.

Figure 43C:
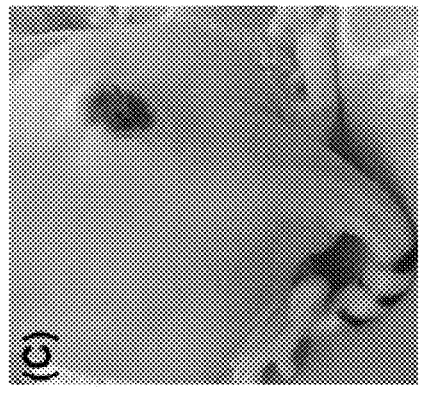
FIG. 43B is a photograph showing immediate tumor whitening and FIG. 43C is a photograph showing scab formation after 24 hours that was observed after most treatments.
Figure 43B:
Figure 43A:
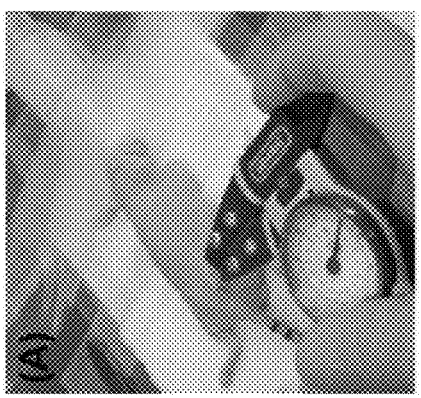
FIG. 43A is a photograph showing pulses being delivered through needles inserted into the tumor.
Figure 43G:
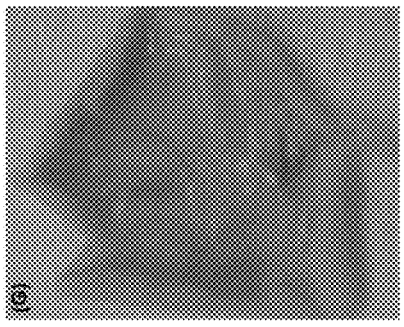
FIGS. 43E and 43G are photographs showing representative end point images from the 5 µs group. The photographs show the existence and absence of subcutaneous tumor 30 days post-treatment. Numbers written on the surface of the skin are for tissue orientation during histological preparation.
Figure 43F:
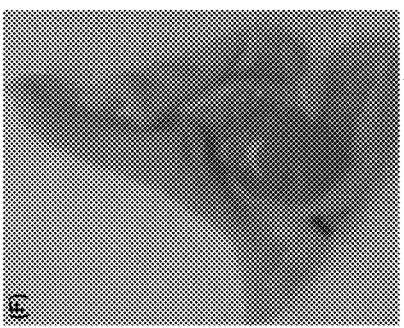
FIGS. 43D and 43F are photographs showing representative end point images from the sham group.
Figure 43E:
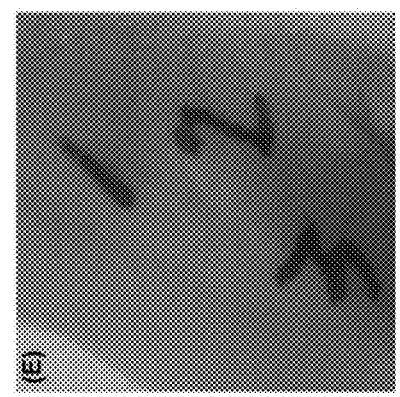
Figure 43D:
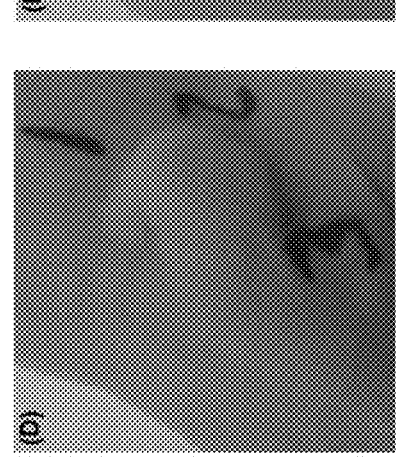

Immediately following in vivo treatment, whitening of the tumor occurred. This is associated with reduced blood flow and the beginning stages of edema (FIG. 43B). This characteristic anti-vascular effect of electroporation-based therapies has been utilized in electro-chemotherapy (ECT) to treat bleeding metastasis (Jarm, T., Cemazar, M., Miklavcic, D. & Sersa, G. *Antivascular effects of electrochemotherapy: implications in treatment of bleeding metastases*. Expert Rev Anticancer Ther 10, 729-746 (2010)). Due to the use of uninsulated electrodes, the skin overlying the tumor was killed in conjunction with the tumor. This resulted in scab formation (FIG. 43C) within 1 day post treatment which typically resolved within two weeks. Endpoint images taken immediately prior to and following tissue harvesting show evidence of complete tumor regression 30 days after BEAM treatment (FIGS. 43D-G).

Figure 43I:
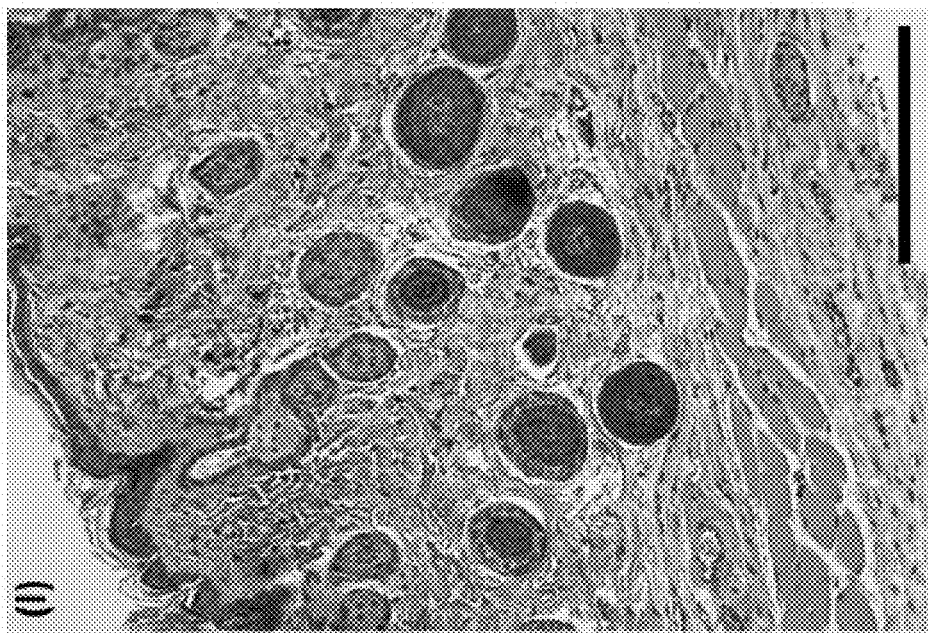
FIG. 43I is a microscopic image showing treated mouse superficial skin (top of image) and underlying musculature (bottom of image). Scale bars represent 250 µm.
Figure 43H:
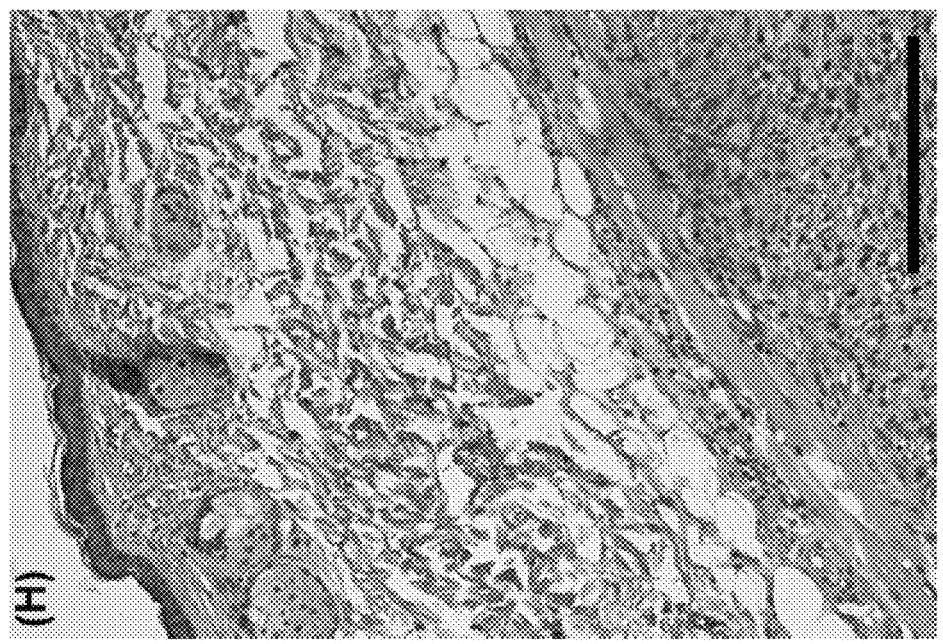
FIG. 43H is a microscopic image showing sham mouse superficial skin (top of image) and underlying tumor (bottom of image). Scale bars represent 250 µm.

FIG. 43H-I shows histological sections from the study endpoint of a mouse in the sham group (FIG. 43H) and 5 μs treatment group (FIG. 43I). Despite the fact that no measurable tumor was observed in the treated mouse, pockets of viable glioblastoma cells were present surrounding blood vessels located above the musculature. Similar features were seen in the sham mouse, with the addition of a viable tumor mass beneath the muscle layer. Cells comprising the viable tumor display a large nucleus surrounded by a well-marked cytoplasm and well-defined cell membrane. Additionally, there is evidence of healthy vasculature along the margin of the tumor at the interface between the muscle and fat layer.

Discussion

For bursts of bipolar pulses, the electric field threshold required to induce cell death is inversely correlated to the duration of the constitutive pulses (FIG. 40A). The lethal threshold increases slightly as pulse duration is decreased from 50 μs to 2 μs. The threshold for cell death for bursts with 1 μs pulses is approximately double the threshold for bursts with 50 μs pulses and 250 ns pulses have a threshold approximately four times greater than the 50 μs treatments. The treatments shown in FIG. 40A all received equivalent doses in 80 bursts.

FIG. 40B shows data adapted from Sano et al. (Sano, M. B., Arena, C. B., DeWitt, M. R., Saur, D. & Davalos, R. V. *In-vitro bipolar nano- and microsecond electro pulse bursts for irreversible electroporation therapies.* Bioelectrochemistry 100, 69-79 (2014) and Arena et al. (Arena et al., 2012) for PPT8182 cells suspended in media and exposed to 80 monopolar 100 μs pulses or 80 bi-polar bursts with pulses between 250 ns and 50 μs (100 μs energized per burst) with a 1500 V/cm voltage-to-distance ratio. In suspension, bursts with 2 μs or shorter pulses do not affect cell viability. In contrast, 1500 V/cm is sufficient to kill all of the cells in the tissue mimics for bursts with pulses 1 μs or longer.

When the cells are in suspension, they take on a more spherical appearance. In contrast, when grown in the 3D tissue mimics they begin to stretch out and obtain a more natural phenotype. In vivo, IRE is typically observed in regions which are exposed to approximately 500-750 V/cm (Garcia, P. A., et al. *Intracranial Nonthermal Irreversible Electroporation: In vivo Analysis.* Journal of Membrane Biology 236, 127-136 (2010); Miklavčič, D., Šemrov, D., Mekid, H. & Mir, L. M. *A validated model of in vivo electric field distribution in tissues for electrochemotherapy and for DNA electrotransfer for gene therapy.* Biochimica et Biophysica Acta (BBA)-General Subjects 1523, 73-83 (2000); and Edd, J. F., Horowitz, L., Davalos, R. V., Mir, L. M. & Rubinsky, B. *In vivo results of a new focal tissue ablation technique: irreversible electroporation.* Biomedical Engineering, IEEE Transactions on 53, 1409-1415 (2006)) and the field strengths predicted in these 3D tissue mimics are more likely to represent the in vivo thresholds for bipolar bursts. However, extensive in vivo evaluation is still needed to determine how these thresholds compare to those necessary to ablate complex heterogeneous tissues such as pancreatic tumors which contain healthy and malignant cells, vasculature, ductile systems, and connective tissue.

Electro-gene (EGT) and ECT protocols typically employ 8 pulses with the goal of permeabilizing the cell membrane, but not inducing cell death. FIG. 41A shows that there is a significant difference between 8 monopolar 100 μs pulses and bipolar 50 μs bursts. This is interesting because these groups were not significantly different when the burst number was increased to 80. Increasing the number of pulses reduced the lethal electric field threshold significantly for all groups. Between 8 and 80 pulses, the thresholds drop by 920 V/cm (55%), 679 V/cm (56%), and 319 V/cm (39%) for the 2 μs bipolar, 50 μs bipolar, and 100 μs monopolar groups, respectively. Interestingly, the lethal thresholds for 80 bursts with 2 μs pulses was the same as 8 monopolar 100 μs pulses. Though not investigated here, the use of bi-polar pulses may allow investigators to treat larger volumes using EGT or ECT without deleterious lethal effects.

Protocols with 1 μs, 500 ns, and 250 ns failed to produce connected lesions in the tissue mimics when the voltage was set to 540 V and the energized time per burst was 100 μs. This made it difficult to accurately calculate the lethal electric field threshold. In the inventors' initial pilot study, the inventors found that increasing the voltage to 650 V while delivering 80 pulses with 100 μs energized time resulted in thermal denaturing of the collagen matrix. Arena et al. (Arena et al., 2012) associated collagen denaturation during IRE with temperatures greater than 45° C. Reducing the energized time to 64 μs at 650 V, a similar dose to 540 V and 100 μs, resulted in well-formed oval shaped lesions for all groups. The present inventors used this higher voltage, equivalent dose protocol for all groups with 1 μs pulses and shorter.

In FIG. 41B the inventors investigated the validity of this equivalent dose hypothesis using bursts with 2 μs pulses, which formed connected lesions at the lowest voltage tested, 250 V. There is no statistical difference between equivalent dose protocols at 650 V and 540 V nor between 540 V and 250 V protocols with a 99% confidence level ($\alpha=0.01$) and there is no statistical difference between the three groups with a 95% confidence level ($\alpha=0.05$). This indicates that in the 3D tumor mimic model, an equivalent dose approximation is sufficient for comparing protocols.

It is unclear how far outside this range (250-650 V) the equivalent dose hypothesis is valid. However, clinical IRE systems are currently limited to outputs of 2700 V. At this voltage, a burst energized for 4 μs would have an equivalent dose and a lethal threshold of approximately 750 V/cm (the average of values from FIG. 41B). FIG. 41C shows that when bursts are energized for 100 μs versus 4 μs, there is 35% reduction in the lethal threshold. If these two effects are additive, a protocol with 80 burst of 2 μs pulses, energized for 100 μs per burst (Dose≈58,000 V2s), is expected to have a lethal threshold of approximately 460 V/cm. This indicates that BEAM treatments should be capable of creating similar ablation volumes as the clinical systems currently employed. However, extensive in vivo testing and measurement of ablation volumes will be required to validate this.

Previous in vivo IRE experiments on murine tumor models required the application of pulses with 1000 $V_{peak}$ amplitude or greater to obtain complete regression of similar sized tumors. Neal et al. (Neal II, R. E., et al. *Treatment of breast cancer through the application of irreversible electroporation using a novel minimally invasive single needle electrode.* Breast cancer research and treatment 123, 295-301 (2010)) achieved complete regression in 5 of 7 mice when 100 monopolar pulses, each 100 μs in duration and 1300 $V_{peak}$ (5600 V/cm) were applied through a bi-polar probe with a 2.3 mm electrode spacing. Al-Sakere et al. (Al-Sakere, B., et al. *Tumor ablation with irreversible electroporation.* PloS one 2, e1135 (2007)) achieved complete regression in 12 of 13 mice when 80 pulses, each 100 μs in duration and 1000 (2500 V/cm) were applied between plate electrodes spaced 4 mm apart.

To mimic the clinical protocol, treatments in this study were applied through two needle electrodes. A spacing of 0.4 mm was used to maximize coverage of the tumors while accounting for the 1000 $V_{peak}$ limit of the inventors' pulse generation system. The 0.4 mm diameter electrodes used in these in vivo experiments were significantly smaller than the 1 mm diameter electrodes used clinically and the 1.27 mm electrodes used in the tumor mimics. Electrode diameter is closely linked to the electric field distribution and smaller electrodes will produce a smaller ablation zone. To account for this, the number of bursts delivered was increased to 120 to provide the best possible outcomes while avoiding extensive thermal heating effects. Gross and histological examination did not indicate any scar formation from thermal damage.

In the treated groups, the measured tumor volume increased over the first 1-5 days post treatment. The formation of a scab along with the occurrence of edema may have led to an overestimation of tumor volumes during short-term follow-up. Within two weeks after treatment delivery, scabs resolved and evidence of tumor regression was observable.

This treatment protocol inhibited tumor growth. The average tumor volumes in the treatment groups were significantly smaller than control at the end of the study. Due to the limited time-span of the IACUC protocol, it is unclear if the tumors would have entered an exponential growth period post-treatment and the inventors were unable to obtain Kaplan-Meier survival curves. In total, 6 of 14 treated mice had no measurable signs of tumors 30 days after treatment and all protocols were able to achieve some complete regressions. Future work should include a long-term study to monitor tumor regression over the lifetime of the animals.

Histological examination of some treated animals revealed pockets of neoplastic cells superficial to the muscle fascia in the dermal layers, which is indicative of under treatment. It is possible that better regression results can be obtained by using a protocol with a higher applied voltage, increased number of bursts, and/or higher energized time per burst. It is noted that the work presented by Al-Sakere did not obtain a 100% regression rates, however, their protocol has been successfully adapted to human clinical applications with promising results.

Conclusion

This study shows the differences in lethal threshold for IRE and BEAM protocols. Despite delivering equivalent doses, bursts with shorter constituent pulses typically require higher electric field strengths for ablation. The number of bursts, energized time per burst, and pulse duration are all significant factors affecting the lethal threshold. Using 80 bursts the inventors found that 1, 2, and 5 µs pulses had electric field thresholds of 1070, 755, and 640 V/cm. When 200 bursts were delivered in vivo, these pulses had similar effects on tumor volume. All mice treated with BEAM tolerated the therapy well and experienced a significant reduction in tumor volume when compared to untreated controls. Each group attained at least one complete regression. This study provides strong evidence that BEAM can be used for tumor ablation and future investigation is warranted.

Example 4

Methods

Cell Culture

U-87 MG primary human glioblastoma cells (ATCC), D1TNC1 rat astrocyte cells (ATCC), and C6 rat glioblastoma cells (ATCC) were cultured in Dulbecco's Modified Eagle Medium (DMEM) containing 10% fetal bovine serum (FBS) and 1% penicillin/streptomycin (PS) at 37° C. in 5% $CO_2$ in a humidified incubator. Normal Human Astrocyte (NHA) cells (Lonza) were cultured in Astrocyte Growth Media (Lonza) at 37° C. in 5% $CO_2$ in a humidified incubator. Cells were seeded in hydrogels at a density of $1\times10^6$ cells/mL. The hydrogels were submerged in appropriate growth media for the cell type at 37° C. in 5% $CO_2$ in a humidified incubator and cell viability was maintained within hydrogels for up to 7 days (FIG. 46A).

Construction of 3D Collagen Scaffolds

Stocks of type I collagen were prepared by dissolving rat tail tendon in acetic acid, followed by freezing and lyophilization as described previously (Arena et al. 2012). Two different stock solution concentrations of collagen were created: 4.5 mg/mL and 30 mg/mL. Scaffolds with a final concentration of 2 mg/mL and 20 mg/mL were made from concentrated collagen stocks to create collagen gels of 0.2% (w/w) and 2% (w/w). Neutralized collagen solutions were created by mixing acid-dissolved collagen with 10×DMEM (10% of total collagen solution volume) and sufficient volumes of 1N NaOH until a pH in the range of 7.0-7.4 was achieved. The neutralized collagen was mixed with cells suspended in DMEM to achieve a cell density of $1\times10^6$ cells/mL in the final collagen mixture. Solutions were mixed carefully with a spatula to ensure homogenous distribution throughout the gel without damaging cells. Collagen solutions were then dispensed into a polydimethylsiloxane (PDMS) mold with a cut-out of 10 mm diameter and 1 mm depth and molded flat to ensure consistent scaffold geometry. The inventors' previous mathematical modeling and experiments on oxygen ($O_2$) consumption rates by tumor cells (Verbridge, S. S. et al. *Oxygen-Controlled Three-Dimensional Cultures to Analyze Tumor Angiogenesis. Tissue Engineering.* Part A 16, 2133-2141, doi:10.1089/ten.tea.2009.0670 (2010) ("Verbridge et al., 2010")) confirms that at this cell density and scaffold thickness, $O_2$ concentration is uniform throughout the scaffold depth. Collagen was allowed to polymerize at 37° C. and 5% $CO_2$ for 45 minutes.

Construction of 3D Alginate Scaffolds

Calcium alginate gels were created using the same PDMS molds as for collagen, creating discs 10 mm in diameter and 1 mm in thickness. Two alginate gel stock concentrations (0.4% and 4.0% (w/v)) were prepared using powdered alginate (Protanal LF 10/60, FMC BioPolymer) that was dissolved in buffer, dialyzed, frozen and lyophilized, followed by re-constitution in serum-free DMEM, as the inventors have previously reported (Verbridge, S. S. et al. *Oxygen-Controlled Three-Dimensional Cultures to Analyze Tumor Angiogenesis.* Tissue Engineering. Part A 16, 2133-2141, doi:10.1089/ten.tea.2009.0670 (2010)). Alginate concentrations were chosen to span a wide range in mechanical stiffness, similar to the collagen concentrations used. Alginate solutions were mixed with cells at a density of $1\times10^6$ cells/mL and dispensed into PDMS molds and molded flat with a porous membrane. Alginate hydrogels were crosslinked by submerging under 0.1M $CaCl_2$ dispensed over a porous membrane cover for 45 min. The alginate hydrogels were then cultured in 24 well plates with DMEM supplemented with 10% FBS and 1% PS at 37° C., 5% $CO_2$.

Determination of Shape Factors

U-87, NHA, D1TNC1, and C6 cells were individually seeded in hydrogels of one of the four conditions described previously (0.2%, 2% collagen, 0.4%, 4% alginate). After culturing the cells for 24 hours, the hydrogels were fixed using 4% formalin and blocked and permeabilized using 40 mg/mL bovine serum albumin (BSA) and 0.5% Triton-X. Cellular actin was stained with Alexa Flour 568 phalloidin (Life Technologies, Carlsbad, Calif.) while cell nuclei were stained with diaminophenylindole (DAPI; Sigma-Aldrich, St. Louis, Mo.). Cells were visualized using a Zeiss LSM510 (Carl Zeiss Microscopy LLC, Thornwood, N.Y.) laser scanning confocal microscope. The stained cells were then used to determine cellular shape factors for cells in each of the four conditions. Image analysis was done in Image J (NIH, Bethesda, Md.) to determine the nuclear area, nuclear perimeter, cytoplasmic area, cytoplasmic perimeter, and longest and shortest diameter of the cell. Measurements were made on at least four cells per hydrogel and at least 5 hydrogels were analyzed for each condition.

Live Fluorescent Imaging

U-87 cells were cultured under normal culture conditions and incubated for 16 hours with CellLight Nucleus-RFP, Bacman 2.0 (Molecular Probes, Eugene, Oreg.) and CellLight Tubulin-GFP (Molecular Probes, Eugene, Oreg.) added to the media at a concentration of 10 particles per cell. Cells were then passaged and seeded into hydrogels of a final concentration of 0.2% collagen at a density of $1 \times 10^6$ cells/mL. After cells were cultured in collagen hydrogels for 24 hours, electroporation of hydrogels was performed on the stage of a Zeiss Observer Z1 microscope (Carl Zeiss Microscopy LLC, Thornwood, N.Y.) to allow for imaging during treatment. Images were taken of single cells immediately before pulsing treatments were started and then every 30 seconds for 5 minutes after pulsing began. Cells were imaged upon exposure to IRE treatment or BEAM treatment. Cells that were not exposed to pulses were also imaged as a control.

Electroporation of 3D Scaffolds

Pulsed electroporation experiments were performed in hydrogels with constant electrical properties. The electrical conductivities of each of the gel-cell mixtures were measured with a conductivity meter to ensure similar electrical properties (0.98±0.04 S/m). The IRE pulses were generated using an ECM 830 pulse generator (Harvard apparatus, Holliston, Mass.) and delivered to the tissue through custom electrodes. High-frequency pulses were delivered using a custom-built pulse generation system (INSPIRE 2.0, VoltMed Inc., Blacksburg, Va.). Two solid stainless steel cylinders with diameters of 0.87 mm, separated 3.3 mm edge-to-edge, were used as electrodes.

Treatments were performed delivering a total of 50 square pulses (IRE) or 50 bursts of 1 µs pulses (BEAM). The IRE protocol delivered 100 µs pulses with a repetition rate of 1 pulse per second. In the BEAM protocol, a burst consisting of 100×1 µs pulses with a 5 µs inter-pulse delay was delivered with a repetition rate of 1 burst per second. For IRE treatments, the pulse amplitude was set to 450 $V_{peak}$ while for BEAM treatments 700 $V_{peak}$ was used to produce ablations of approximately the same volume as the IRE group.

Finite Element Analysis in Hydrogels

Finite element models using COMSOL Multiphysics (Version 4.3, COMSOL Inc., Palo Alto, Calif.) were used to solve the Laplace equation to find the electric field distribution within the hydrogels for each different voltage used. COMSOL Multiphysics was also used to solve the Joule heating equation to calculate the temperature distribution in the hydrogel as a result of each treatment. The simulation geometry was modeled as a 10 mm diameter and 1 mm thick cylinder with two steel electrode cylinders (d=0.87 mm) spanning the depth of the hydrogel. The mesh was refined until error between successive refinements was less than 1%. The final mesh contained 47,438 elements and solutions were found in approximately 3 minutes on a Pentium i3 processor.

Finite Element Analysis of Individual Cells

The transmembrane potentials across the cell membrane and nuclear envelope were modeled using a finite element model with an impedance boundary condition scheme (Sano, M. B., Arena, C. B., DeWitt, M. R., Saur, D. & Davalos, R. V. *In-vitro bipolar nano- and microsecond electro pulse bursts for irreversible electroporation therapies*. Bioelectrochemistry 100, 69-79, doi:DOI 10.1016/j.bioelechem.2014.07.010 (2014)). These finite element models were used to numerically investigate the response of representative cell geometries to simulated IRE and BEAM pulses. Cell geometry was determined based on average measurements made in ImageJ image analysis software (NIH, Bethesda, Md.) from confocal microscopy images. Geometries for U-87 cells in two different collagen densities (0.2%, 2%) as well as four different cell types (U-87, NHA, C6, D1TNC1) in a 0.2% collagen matrix were used. All models were solved using a 2D-axisymmetric platform in COMSOL Multiphysics. A separate electric currents physics module was used for each domain (media, cytoplasm, nucleoplasm). A large media domain, with sides of 300 µm, was used to avoid any significant boundary effects. The cell and the nucleus were modeled as half-ovals where their lengths and widths were varied according to measurements from confocal microscopy images.

Simulations were solved in the time-domain using an electric currents module. To account for the resistance and capacitance posed by the cell membrane and the nuclear envelope the boundaries of the nucleus and cytoplasm were assigned impedance properties based on the existing literature.

Determination of Lethal Thresholds

The thresholds for cell death were determined by first performing a live-dead stain on the hydrogels 24 hours after delivering treatment. Live cells were stained with Calcein AM (Biotium, Hayward, Calif.) and fluoresced as green while dead cells were stained with ethidium homodimer III (Biotium, Hayward, Calif.) and fluoresced as red. The diameter of the red-stained dead region was measured using ImageJ image analysis software. Geometric measurements of the ablation zones were mapped to a finite element model to calculate the electric field during treatments of the scaffolds (FIG. 46C). The electric field magnitude at the edge of the live and dead regions was considered the electric field threshold for cell death for the given cell type.

In Vivo Canine Treatment

All canine in vivo studies were approved by the institutional animal care and use committee (08-218-CVM). IRE treatments were performed in the brains of anesthetized normal canine subjects, and in dogs with spontaneous malignant gliomas according to previously described methods (Edd, J. F. & Davalos, R. V. *Mathematical Modeling of Irreversible Electroporation for Treatment Planning*. Technology in Cancer Research & Treatment 6, 275-286, doi: 10.1177/153303460700600403 (2007) ("Edd and Davalos, 2007"); Garcia, P. A. et al. *Non-Thermal Irreversible Electroporation (N-TIRE) and Adjuvant Fractionated Radiotherapeutic Multimodal Therapy for Intracranial Malignant Glioma in a Canine Patient*. Technology In Cancer Research & Treatment 10, 73-83 (2011); Rossmeisl, J. H., Garcia, P. A., Roberston, J. L., Ellis, T. L. & Davalos, R. V. *Pathology of non-thermal irreversible electroporation (N-TIRE)-induced ablation of the canine brain*. Journal of Veterinary Science 14, 433-440, doi:10.4142/jvs.2013.14.4.433 (2013) ("Rossmeisl et al., 2013")). In tumor-bearing dogs, biopsy of the brain lesion was performed prior to IRE ablation to allow for histopathological diagnosis and grading of tumors, and an additional biopsy of the ablated region obtained within 24 hours of the IRE to characterize the effects of the IRE treatment.

Histomorphological Staining

Archived, paraffin embedded, transversely oriented brain sections from normal and tumor-bearing dogs treated with IRE were retrieved, cut at 5 µm thickness, mounted on positively charged slides, and stained routinely with hematoxylin and eosin (Edd and Davalos, 2007; Rossmeisl et al., 2013). Digital photomicrographs of regions of interest representing IRE ablated regions of cerebral cortex, subcortical white matter, contralateral homologous cortical and white matter controls, and a canine GBM pre- and post-IRE treatment were captured with charge-coupled device digital camera (Nikon DS-Filc, Nikon, Japan) and commercial imaging analysis software system (NIS Elements AR, Nikon, Japan).

Statistical Analysis

Statistical significance was determined by a two-tailed t-test performed in Prism Statistical Software (Version 6, Graphpad, La Jolla, Calif.). A 95% confidence interval was used with significance defined as $p<0.05$. All numerical results are reported as the mean and the standard deviation of all experimental measurements. No outliers were excluded.

Results

Cell Size Selectivity of Pulsed Electric Fields

Figure 45A:
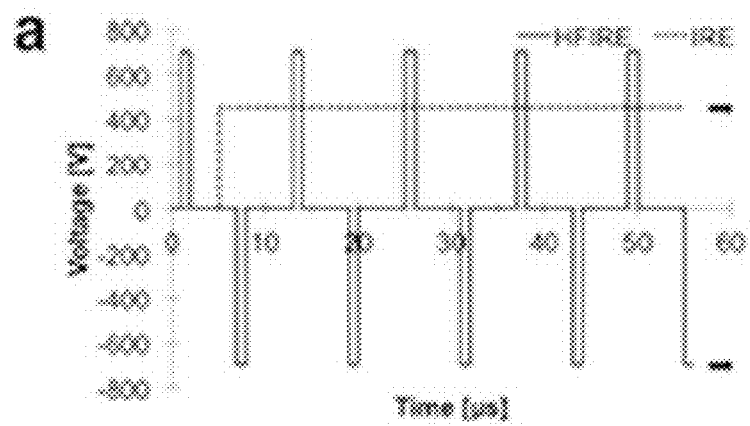
FIGS. 45A-C are graphs showing finite element modeling using two pulse waveforms which predicts IRE is cell size dependent while BEAM is cell size independent.
Figure 45B:
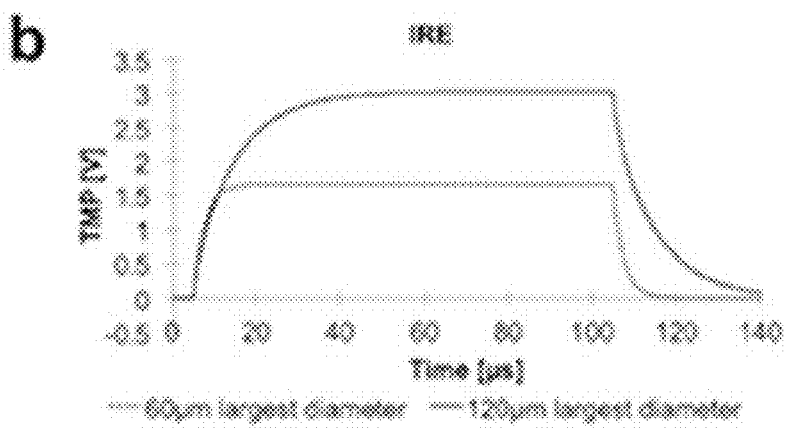
Figure 45C:
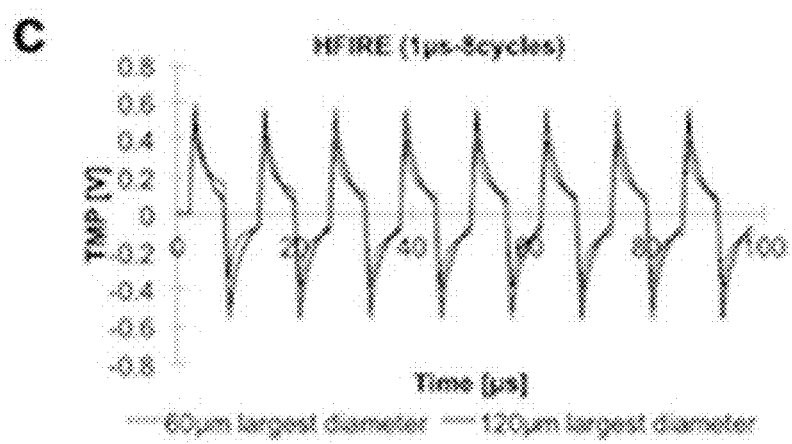

Single cell responses to electric field pulses were simulated with finite element modeling. Simulated TMP changes in response to modeled IRE pulses (FIG. 45A) are highly dependent on cell size (FIG. 45B). In contrast, cells exposed to BEAM pulses do not show significant TMP variation with cell size in these models (FIG. 45C).

To experimentally explore the effect of cell size on electric field thresholds for cell death, the inventors tuned the mechanical and chemical structure of the tumor microenvironment using a three-dimensional GBM hydrogel tumor model (FIG. 46A) to then be used as a therapy-testing platform (FIG. 46B). The inventors determined the lethal electric field threshold by simulating the electric field within the hydrogels during pulse exposure, at the two experimental voltages, using finite element modeling (FIGS. 46C and 46D). These simulations reveal the change in expected lesion shape as a function of voltage, evolving from a peanut to a circular shape as the electric field magnitude increases. Finite element modeling of treatment-induced temperature distribution in the hydrogel demonstrates that cellular damage does not occur through thermal effects, as cells are not exposed to temperatures above physiological levels (FIG. 46E), with no long-term temperature increases evident (FIG. 46F).

Figure 47A:
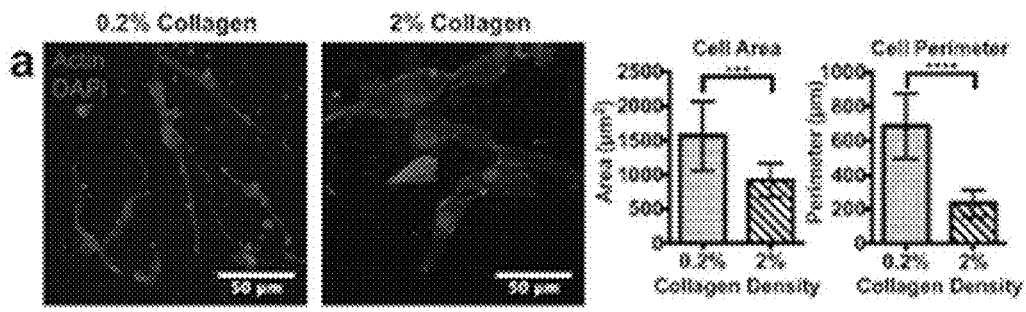
FIGS. 47A-C are images and graphs showing ECM-tuned hydrogels which reveal cell size dependent IRE lesions and cell size independent BEAM lesions.
Figure 47B:
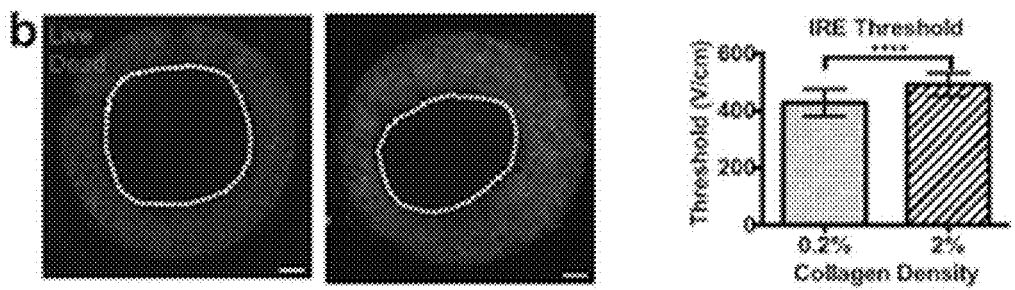
Figure 47C:
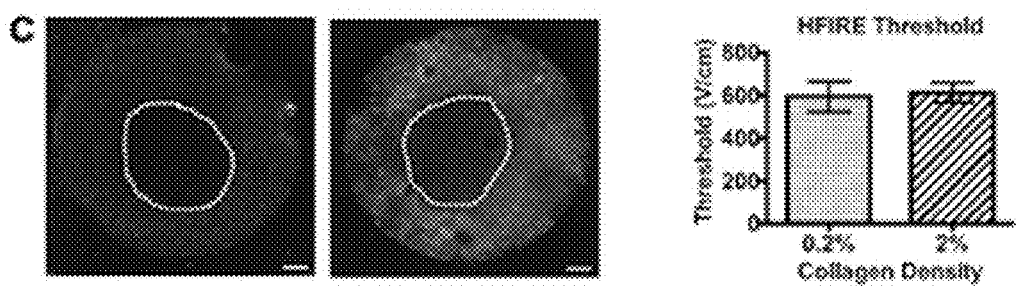

Cell size and shape within hydrogel scaffolds are functions of scaffold density; by varying collagen density in the tissue model the inventors were able to control cell size and outer membrane perimeter for a single cell type. U-87 MG human GBM cells exhibited a significantly smaller area ($p=0.005$) in the higher density (2% w/w) collagen (920±249 µm2) as compared with lower density (0.2% w/w) collagen (1572±503 µm2) (FIG. 47A). Using this in vitro model the inventors then determined that these cell geometries determined lethal thresholds for IRE but not for BEAM pulses. As predicted by the model, IRE lesions for cells in 0.2% collagen were larger than the lesions for cells in 2.0% collagen (FIG. 47B, $p<0.0001$). The larger cells were killed by IRE pulses with amplitude exceeding 428±47 V/cm, while the smaller cells required a larger field for cell death (492±41 V/cm). In contrast, BEAM treatments did not result in statistically significant differences in lesion size, corresponding to an average lethal threshold of 601±65 V/cm that was independent of collagen density (FIG. 47C). The electrical conductivity for the two scaffolds was experimentally comparable, and cell densities were identical in the two conditions.

Figure 48A:
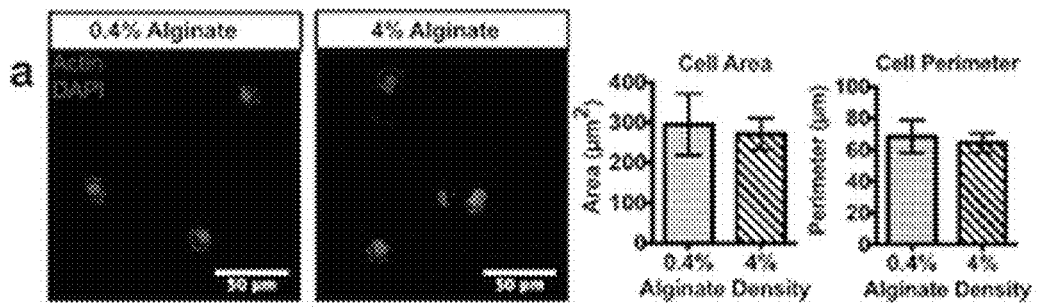
FIGS. 48A-C are images and graphs showing constant cell morphology with changing stiffness results in equivalent lethal thresholds for IRE and BEAM.
Figure 48B:
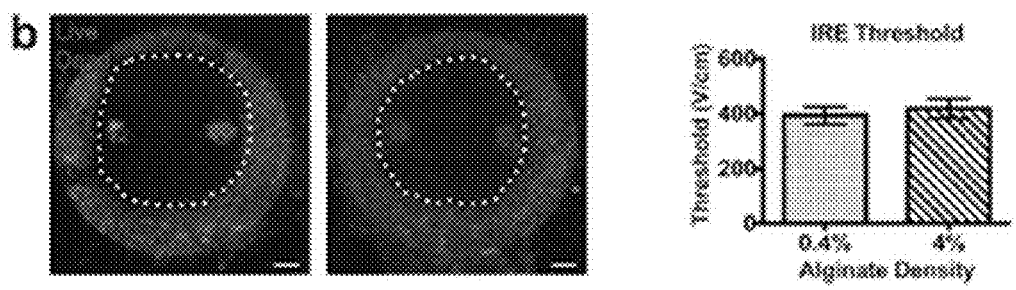
Figure 48C:
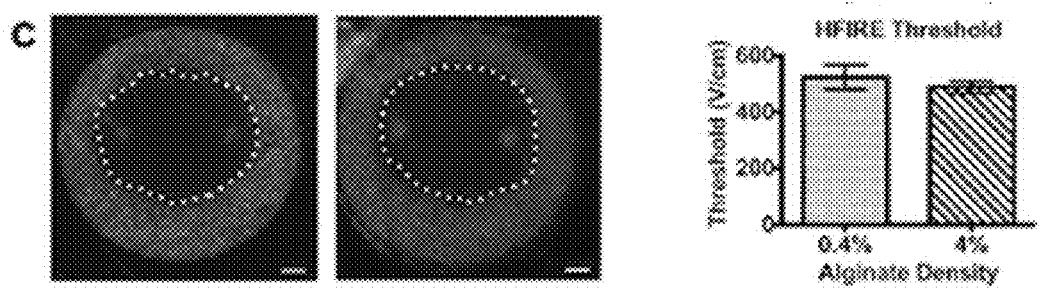

The inventors performed additional experiments in calcium alginate hydrogels, in which cell morphology is relatively constant for different scaffold densities due to the lack of cell-ECM binding sites (FIG. 48A). In alginate hydrogels, lesion sizes and lethal thresholds were independent of polymer concentration for both IRE (FIG. 48B) and BEAM (FIG. 48C).

In Vivo Selectivity of IRE

The inventors previously treated canine patients with naturally occurring malignant gliomas using IRE29. Histology from this treatment provides an important comparison point between the inventors' 3D in vitro ablation results presented here, and the in vivo outcome in a context that is highly representative of the human GBM phenotype. When untreated cerebrocortical grey matter (FIG. 49A) was exposed to IRE treatment, non-discriminate cell death occurred as both neuronal and glial cells were ablated (FIG. 49B). Similarly, untreated white matter of the internal capsule (FIG. 49C) treated with IRE resulted in glial death in addition to vacuolization and axonal loss. Though malignant glioblastoma cells (FIG. 49E) were ablated with IRE treatment (FIG. 49F), so too is the stromal cytoarchitecture. Based on these in vivo results demonstrating the relatively non-selective nature of IRE ablation in canine GBM, combined with the inventors' in vitro studies demonstrating statistically significant yet small differences in IRE threshold based on cell size, the inventors next focused on the potential for pulsed electric fields to exert cell-specific targeting. Histology images from canine patients illustrate the well-known tumor cell phenotype characterized by the enlarged nuclei of GBM cells (FIG. 49E) compared to healthy tissue (FIGS. 49A, C), therefore motivating the inventors' hypothesis that intracellular localization of treatment electric fields may enable tumor cell targeting due to nuclear size differences.

Intracellular Effect of Pulsed Electric Fields

To examine the potential for BEAM pulses to exert their effect via intracellular localization of electric fields, the inventors performed finite element modeling of field distribution across a single cell. This model predicts that for a simulated IRE pulse with an electric field magnitude of 500 V/cm applied for 100 µs, only 14% of the external electric field traverses the cell membrane and is present in the cytoplasm (FIG. 50A). In contrast, BEAM pulses deliver most of their energy to the inside of the cell (FIG. 50B). The cytoplasm is charged over 400 V/cm for the entire duration of each 1 µs BEAM pulse while the same is true for only 8% of each 100 µs IRE pulse. To test the implications of effects on tumor cell nuclei for this prediction of a strong intracellular field created by BEAM, the inventors constructed 3D models using four different cell types (FIG. 50C), chosen to include multiple malignant versus normal cell comparisons. These 3D cultured cells exhibited no significant difference in cell area (FIG. 50D), but did exhibit significant differences in nuclear area (FIG. 50E). A human malignant glioma cell line (U-87) showed significantly greater nuclear area than normal human astrocytes (NHA) ($p=0.0048$) while a rat glioblastoma line (C6) exhibited increased nuclear area when compared to normal rat astrocytes (D1TNC1) ($p=0.0140$).

Consistent with model predictions of IRE cell size dependence and nuclear size independence, the four cell types exhibited similar IRE lesions (FIG. 51A). In contrast, BEAM lesions in the tissue mimics with GBM cells were significantly larger than lesions with normal astrocytes (FIG. 51B). The similar lethal IRE thresholds across cell types (FIG. 51C) is consistent with the fact that all four cell types have similar outer membrane areas. BEAM experimental results, however, reveal a lower lethal threshold for malignant cells (FIG. 51D), which have larger nuclei compared with their normal cell counterparts. For BEAM treatments on human cells, U87 glioblastoma cells were killed at a threshold of 601+/−71 V/cm while NHAs were killed at a threshold of 1006+/−81 V/cm (p<0.0001). For rat cell lines, C6 cells had a lethal threshold of 752+/−58 V/cm while D1TNC1 cells had a lethal threshold of 1107+/−106 V/cm (p<0.0001).

Death Mechanisms of IRE and BEAM

To investigate the differences between the mechanism of death with IRE and BEAM the inventors performed single cell imaging upon exposure to each treatment regime. Cell nuclei and tubulin were stained by live fluorescent stain and cultured in 3D collagen hydrogels. Fluorescent imaging in situ within these hydrogels was performed directly before, and then at 30-second intervals after exposure to IRE, revealing an outward diffusion of dye from the cell membrane within 1 minute after pulsing (FIG. 52A). By 5 minutes after treatment the tubulin dye had diffused almost entirely out of the cell while the nuclear dye showed a disruption of the integrity of the nucleus. In contrast, cells exposed to BEAM showed a strong inward collapse of the nucleus followed by a collapse of the tubulin stained cytoplasm on the 5-minute timescale (FIG. 52B). A control cell that was not exposed to either treatment imaged over the same time course confirms that treatment-induced changes are not related to photo-bleaching (FIG. 52C).

Estimate of Lethal Threshold for Nuclear Disruption

The inventors explored the relationship between BEAM lethal thresholds and nuclear size, leveraging the experimental data as input for subsequent mathematical models. Based on this data, it would appear that cell death occurs at a critical nTMP disruption that is independent of cell type, whereas the external field required for this nuclear disruption scales inversely with nucleus size. Using experimental findings for lethal thresholds, nuclear geometries, and idealized cell geometries for glioma cells and astrocytes, the inventors performed finite element modeling of single cell response to minimum lethal electric fields for each cell type. Simulating cell exposure to these lethal conditions, 1006 V/cm for NHA cells and 601 V/cm for U-87 cells, the inventors found a larger increase in TMP for the glioma cell than for the astrocyte (FIG. 53A), however these TMPs were significantly below the anticipated 1 V instantaneous lethal threshold for IRE. In contrast, simulation of nTMP response predicts similar increases in nTMP for both cell types, indicating that cell death is occurring at a common value of nTMP for both cells, at ~130 mV disruption (FIG. 53B).

Discussion

The overall goal was to leverage tissue engineered models of tumor versus normal brain microenvironments, based on previously published methods (Verbridge, S. S. et al. *Oxygen-Controlled Three-Dimensional Cultures to Analyze Tumor Angiogenesis*. Tissue Engineering. Part A 16, 2133-2141, doi:10.1089/ten.tea.2009.0670 (2010)), to investigate the response of representative cell geometries to IRE and BEAM pulses. These platforms critically provide a three-dimensional physiological tissue context in which to explore the effects of 3D cell morphology on response to electric fields, not possible with 2D experiments, while eliminating other confounding variables found in vivo. Hydrogels have been previously established as a relevant platform to test tissue responses to IRE pulses (Arena et al., 2012), while such models have also been demonstrated to better recapitulate human tumor physiology and therapy response as compared with 2D models (Fischbach, C. et al. *Engineering tumors with 3D scaffolds*. Nat Meth 4, 855-860, (2007); Fong, E. L. S. et al. *Modeling Ewing sarcoma tumors in vitro with 3D scaffolds*. Proceedings of the National Academy of Sciences 110, 6500-6505, doi:10.1073/pnas.1221403110 (2013)). With the ability to easily tune targeting parameters and microenvironment, these models provide a valuable tool for measuring the impact of cell morphology and tissue physics on therapy response broadly, and more specifically on response to therapeutic electric fields.

It is important to note that the inventors' work is informed by, and builds on their experience in treating spontaneous GBM in canine patients. Spontaneous, primary brain tumors are only relatively common in two species—dogs and humans. Human and canine brain tumors share many features, including histopathologic and diagnostic imaging characteristics, which allows application of World Health Organization pathologic classification and imaging based therapeutic response assessment schemes used in human clinical practice. Canine and human brain tumors have also been demonstrated to have similar expression patterns of growth factor receptors, chromosomal deletions, and losses of function of tumor suppressor genes. As tumors progress 5- to 7-fold faster in dogs relative to humans, dogs with spontaneous brain tumors are an attractive model for the faithful and rapid evaluation and translation of novel brain tumor therapeutics (Rossmeisl, J. H. *New Treatment Modalities for Brain Tumors in Dogs and Cats*. Veterinary Clinics of North America: Small Animal Practice 44, 1013-1038, doi:http://dx.doi.org/10.1016/j.cvsm.2014.07.003 (2014)).

Size selective ablation using PEFs has been previously reported for cell suspensions, differentiating tumor from blood cells based on large differences in size (Eppich, H. M. et al. *Pulsed electric fields for selection of hematopoietic cells and depletion of tumor cell contaminants*. Nature Biotechnology 18, 882-887, doi:http://dx.doi.org/10.1038/78504 (2000) ("Eppich et al., 2000")), but has yet to be demonstrated for cells cultured in physiologically-relevant tissues. The inventors' experiments support the concept that IRE results in cell size-selective lethal thresholds into 3D tissues. The bulk electrical resistance properties of the cell-seeded hydrogels did not vary as a function of collagen density, and the inventors therefore believe differences measured are a result of cell morphology rather than altered tissue electrical properties. Control experiments performed in alginate further support this hypothesis that the differences observed in collagen resulted from cell size variations rather than additional factors such as direct sensing of matrix density. Although this finding does not eliminate the possibility that variation in binding ligand density may also impact lesion size, this size dependence is consistent with previously published data on cells in solution (Eppich et al., 2000). Furthermore this correlation of threshold with cell size is absent for BEAM. The inventors hypothesize that this is due to the BEAM field primarily interacting with the inner organelles of the cell. The inventors' finite element modeling confirms this hypothesis as a single BEAM burst applied to a single cell model produces a much higher field inside the cell than a simulated IRE burst. BEAM treatment delivers a rapid burst of over 100 of these 1 µs pulses. This allows BEAM pulses to preferentially charge intracellular membranes, which the inventors anticipated would have profound effects on cell death as a function of cell type.

The inventors' in vitro 3D model results demonstrate a statistically significant dependence of field threshold on cell size, however the cell size heterogeneity observed in vivo may prevent this dependence from being leveraged for targeting specificity. A much more obvious difference between cell types, clearly evident in the inventors' H&E staining of tumorous and healthy canine brain samples, is the enlarged nuclei of cancer cells compared to healthy brain tissue. Used as a pathological indicator of cancer, enlarged nuclei compared with their non-malignant counterparts is one of the most reliable distinguishing characteristics of tumor cells (Zink, D., Fischer, A. H. & Nickerson, J. A. *Nuclear structure in cancer cells*. Nat Rev Cancer 4, 677-687 (2004)), however the targeting of anti-cancer therapy against this hallmark has never been demonstrated.

The nucleus is typically the largest contiguous intracellular feature and a likely target for damage by the high intracellular fields produced by BEAM. To experimentally test the effect of nuclear area on treatments, the inventors chose different cell types, which exhibited differences in nuclear sizes without significant differences in plasma membrane area, eliminating confounding effects due to cell size. Numerical simulations identified increased nuclear size as an important variable for increased nTMP. An increase in nTMP could trigger cell death above a specific threshold, and therefore malignant cells should have a lower BEAM lethal threshold than normal cells, in contrast with IRE, which would not exhibit nuclear selectivity. The similarity of IRE thresholds is consistent with the fact that there was no significant difference in plasma membrane areas. The differences in BEAM lesion sizes supports that BEAM threshold differences are related to nucleus area as opposed to overall cell area, with lower lethal thresholds corresponding to larger nuclei. The intracellular field produced from BEAM seems to affect the intercellular nucleus membrane in a way at least partially analogous to the way IRE affects the plasma membrane, as a larger membrane exposed to the majority of the electric field is easier to affect than a smaller membrane.

Time-course images of single cells exposed to each treatment show a distinct difference in mechanism of killing between BEAM and IRE, consistent with the findings that different cellular characteristics are important variables with the two treatments. The time-course of cell death after IRE treatment strongly implicates the immediate disruption of the cell membrane as a cause of cell death, as tubulin proteins originally confined in the cell by the cell membrane begin diffusing out of the cell upon exposure to IRE. In contrast, cells exposed to BEAM show no diffusion from the outer cell membrane but rather a nuclear collapse while the tubulin is retained within the original cell area. These finding suggest that the outer membrane does not play as much of a role in the mechanism of cell death in BEAM, but rather that the primary effect is on the nucleus.

Given the inventors' results, it appears BEAM is acting on the biophysical structure of the cells in a way that nuclear area becomes a key variable. When glioma and astrocyte cells were simulated at their respective lethal BEAM thresholds (601 V/cm vs. 1006 V/cm), the inventors found similar TMP and nTMP ranges of approximately 150-250 mV and 100-130 mV, respectively. These simulations did interestingly predict a small difference in outer TMP as a function of nuclear size. However the magnitude of this TMP, approximately 150 mV, was significantly lower than the anticipated instantaneous threshold (1 V) for cell death by irreversible electroporation. Thus, it would appear that the primary mechanism of death with BEAM is not an increase in cell TMP, but rather is related to intracellular effects. For glioma and astrocyte cells, the maximum simulated nTMP of 130 mV is also well below the lethal threshold for death resulting from outer membrane disruption, suggesting that small disruptions of nTMP may significantly impact cell survival. It is unclear whether the pathway to cell death is dominated by effects on the nuclear envelope alone, versus in combination with cell membrane disruption, or a separate cascade of intracellular effects. However, the correlation of nTMP values between the two different cell types, at different lethal electric field strengths, indicates that nuclear area impacts the cell death process after BEAM treatment.

The inventors' mathematical model does have limitations, as outer cell membranes are approximated as elliptical, and do not account for the irregular shape of physiological cells, or heterogeneity in electrical properties of individual cells. Inclusion of membrane conductivity changes due to electroporation effects is expected to enhance the accuracy of the inventors' simulations. While experimental evidence also suggests that outer membrane electroporation is occurring during BEAM (at time-points beyond those in FIGS. 52A-C, data not shown), the inventors' experimental results and model findings strongly suggest an active role for nTMP effects in the BEAM mechanism of action. It is widely recognized that the mechanism of death in irreversible electroporation using short pulses is complex, poorly understood, and can follow multiple different pathways (Weaver, J. C., Smith, K. C., Esser, A. T., Son, R. S. & Gowrishankar, T. R. *A brief overview of electroporation pulse strength-duration space: A region where additional intracellular effects are expected*. Bioelectrochemistry 87, 236-243, doi: http://dx.doi.org/10.1016/j.bioelechem.2012.02.007 (2012)). Furthermore, nuclear poration may be aided not only by increased nuclear size of cancer cells but also other abnormalities of the nucleus such as reduced nucleus stiffness necessary for invasion (Dahl, K. N., Ribeiro, A. J. S. & Lammerding, J. Nuclear shape, mechanics, and mechanotransduction. Circulation research 102, 1307-1318, doi: 10.1161/CIRCRESAHA.108.173989 (2008)). Another possibility is an amplification of the electric field applied to the cytoplasm caused by distortion around an enlarged nucleus. This may result in other inner organelles, such as mitochondria, being disrupted by BEAM pulses. The inventors' results highlight the importance of TMP increases in both IRE and BEAM and nTMP increases specifically associated with BEAM, in determining cell death PEF thresholds.

It is important to note, the death mechanism of IRE and BEAM are not based on targeting the highly proliferative phenotype that is leveraged by many current GBM therapies including chemotherapy and tumor treating fields (Kirson, E. D. et al. *Alternating electric fields arrest cell proliferation in animal tumor models and human brain tumors*. Proceedings of the National Academy of Sciences 104, 10152-10157, doi:10.1073/pnas.0702916104 (2007)). While these therapies leave behind quiescent tumor initiating cells that cause recurrence, IRE and BEAM should elicit a death response through membrane disruption for both bulk tumor cells and tumor initiating cells. It is unlikely that this physical death mechanism would select for the emergence of resistant subpopulations on short timescales, because a large number of genetic mutations would likely be required to render a cell resistant to electric field-induced damage.

Though the exact mechanism of cell killing with BEAM is not yet known, the inventors' modeling and experimental data suggest a mechanism that is different than that of long IRE pulses which target the plasma membrane, and that, unlike for IRE, is cell type dependent among cells of similar size. The BEAM killing mechanism is such that the biophysical structure of malignant cells allows for the selective targeting of these cells using a range of electric field distributions that induce no damage to the healthy cells studied but elicit a death response in malignant cells. Because malignant cells that comprise the bulk tumor have a lower death threshold (~530-810 V/cm) than normal astrocytes (~930-1200 V/cm) surrounding the tumor, it follows that a treatment regime delivering a voltage between these two thresholds to the edge of the tumor may result in ablation of tumor cells while sparing healthy astrocytes. A threshold in such a range at the edge of the tumor may be effective at killing the invasive glioblastoma cells that render surgery to be an ineffective treatment for GBM, and infiltrative tumors more broadly.

Example 5

Individual pulses with durations one to two orders of magnitude shorter than IRE pulses can kills cells in such a way that is less dependent on the outer cell diameter (assuming a similar size nucleus). The individual pulses are applied in alternating polarity to reduce muscle contractions. Additionally, the individual pulses are repeated to form a high-frequency burst, and multiple bursts are typically necessary to induce cell death. This is similar to how multiple, longer duration pulses are applied during an IRE treatment. This form of BEAM treatment typically requires a higher e-field threshold, but there is less dependence on cell size. Therefore, treatment planning is significantly reduced, as different cell types, regardless of their morphology, have the same e-field threshold.

Figure 54B:
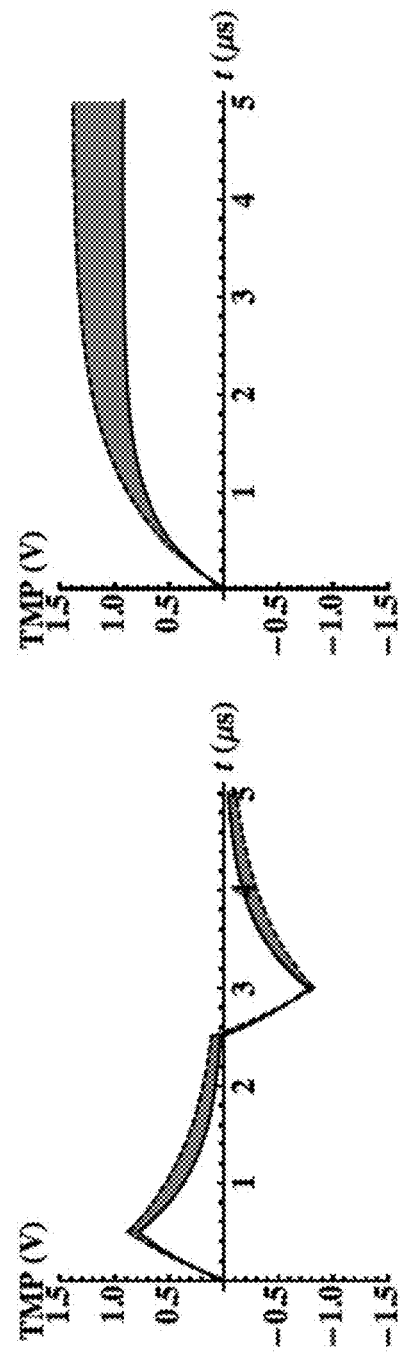

In the theoretical example provided in FIGS. 54A-D, the cells are assumed to be spherical, and the conductivities $\lambda o$ and $\lambda i$ are set to 0.1 S/m and km is set to 3e-7 S/m. The plots of FIGS. 54A-D show the TMP at the cell pole ($\theta$=0) for a cell with a diameter of 10 um (solid line) and a cell with a diameter of 15 um (dotted line). As shown in FIGS. 54A-B, the cells are exposed to BEAM with 500 ns long pulses applied at 2000 V/cm. As shown in FIGS. 54C-D, the cells are exposed to IRE with 5 us long pulses applied at 1250 V/cm. Because the BEAM pulses are shorter than the membrane charging time, the peak TMP reach at the end of the pulses is nearly the same for both cell diameters. During IRE, the outer membrane is fully charged and the TMP reaches a plateau that is significantly different for each.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A method of selectively treating cells, comprising:
applying to a tissue a plurality of electrical pulses with a delay between successive pulses, wherein the length of each pulse and the delay between successive pulses are optimized to produce a first treatment zone and a second treatment zone;
wherein only selected cells are affected in the second treatment zone, such that the selected cells are cancer cells which are inhibited:
by way of slowed or arrested cell division, or
by way of slowed or arrested migration, or
by way of reduced transport of blood and nutrients.

2. The method of claim 1, wherein the applying is performed in vitro.

3. The method of claim 1, wherein the applying is performed in vivo.

4. The method of claim 1, wherein the applying is performed ex vivo.

5. The method of claim 1, wherein the first treatment zone comprises cancer cells and non-cancer cells which are killed by necrosis.

6. The method of claim 5, wherein the first treatment zone comprises cancer cells and non-cancer cells which are killed as a result of an increase of their transmembrane potential to a lethal threshold.

7. The method of claim 1, wherein the second treatment zone comprises cancer cells which are killed by apoptosis.

8. The method of claim 1, wherein the first treatment zone comprises some cancer cells and some non-cancer cells which are killed.

9. The method of claim 1, wherein the second treatment zone comprises cancer cells and non-cancer cells and some of the cancer cells in the second treatment zone are killed or inhibited and some of the non-cancer cells in the second treatment zone are spared.

10. The method of claim 1, wherein the second treatment zone comprises cancer cells which are killed as a result of an increase in their nuclear transmembrane potential to a lethal threshold.

11. The method of claim 1, wherein the delay between successive pulses is greater than the length of each pulse.

12. The method of claim 1, wherein the delay between successive pulses is a fraction of the length of each pulse.

13. The method of claim 1, wherein the length of each pulse is equivalent to the charging time of the cell membrane of the cancer cells plus the discharge time of the nuclear membrane of the cancer cells, while the delay between successive pulses is equivalent to the charging time of the cell membrane of the cancer cells.

14. The method of claim 13, wherein the charging time of the cell membrane of the cancer cells and the discharge time of the nuclear membrane of the cancer cells are determined through numerical modeling.

15. The method of claim 1, wherein the plurality of electrical pulses comprises an electric field waveform which is a rectangular pulse, ramp, decaying exponential, or sine wave.

16. The method of claim 15, wherein the electric field waveform is unipolar or bipolar.

17. The method of claim 15, wherein the electric field waveform is a superimposed, bimodal signal comprising a first frequency harmonic and a second frequency harmonic, wherein the second frequency harmonic has a frequency higher than that of the first frequency harmonic.

18. The method of claim 15, wherein the electric field waveform comprises alternating nanosecond-order pulses with microsecond order pulses in succession.

19. The method of claim 15, wherein the electric field waveform is asymmetric.

20. The method of claim 15, wherein the electric field waveform has a carrier frequency in the range of 100 kHz to 10 MHz.

21. The method of claim 15, wherein carrier frequency or pulse duration of the waveforms are based on the cross-over frequency of the cancer cells.

22. The method of claim 1, wherein the length of each pulse and the delay between successive pulses are optimized based on the physical nucleus to cytoplasm size ratio of the cancer cells.

23. The method of claim 1, wherein the pulses are bipolar square waves and the length of each pulse is between 250 nanoseconds and 50 microseconds.

24. The method of claim 1, wherein the cells affected by the plurality of electrical pulses in the second treatment zone have a higher nucleus-to-cytoplasm ratio than cells not affected by the plurality of electrical pulses in the second treatment zone.

25. A method of selectively treating cells, comprising:
applying a plurality of electrical pulses to a substance containing cells, wherein the plurality of electrical pulses has a frequency, amplitude, and pulse waveform selected to treat target cells of one type of cell and spare non-target cells of another type of cell;
determining a nucleus-to-cytoplasm ratio for the target cells; and
selecting the frequency, amplitude, and pulse waveform based on the nucleus-to-cytoplasm ratio for the target cells;
wherein the method is selective such that cancer cells are treated and normal cells are spared; or
wherein the method is palliative such that cancer cells of a more malignant type are treated and cancer cells of a less aggressive type are spared.

26. The method of claim 25, wherein the substance containing cells is a tissue.

27. The method of claim 25, wherein the applying is performed in vitro.

28. The method of claim 25, wherein the applying is performed in vivo.

29. The method of claim 25, wherein the applying is performed ex vivo.

30. A method of selectively ablating malignant cells, the method comprising:
determining a first death threshold for malignant cells present in a tissue region;
determining a second death threshold for non-malignant cells present in the tissue region;
administering electrical pulses to the tissue region at or above the first death threshold and below the second death threshold to kill the malignant cells.

31. The method of claim 30, wherein the non-malignant cells are not killed.

32. The method of claim 30, wherein the malignant cells each comprise a cell nucleus and are killed by administering the electrical pulses in a manner sufficient to disrupt the cell nucleus.

33. A method of selectively treating cells, comprising:
applying to a tissue a plurality of electrical pulses with a delay between successive pulses, wherein the length of each pulse and the delay between successive pulses are optimized to produce a first treatment zone and a second treatment zone;
wherein only selected cells are affected in the second treatment zone;
wherein the second treatment zone surrounds a tumor and the selected cells are infiltrative cancer cells originating from the tumor.

34. The method of claim 33, wherein the tissue is brain tissue and the tumor is glioblastoma.

35. A method of selectively treating cells, comprising:
applying a plurality of electrical pulses to a substance containing cells, wherein the plurality of electrical pulses has a frequency, amplitude, and pulse waveform selected to treat target cells of one type of cell and spare non-target cells of another type of cell;
determining a nucleus-to-cytoplasm ratio for the target cells; and
selecting the frequency, amplitude, and pulse waveform based on the nucleus-to-cytoplasm ratio for the target cells, wherein the nucleus-to-cytoplasm ratio is measured from cells taken from a biopsy of the substance containing cells.

* * * * *